(12) United States Patent
Igawa et al.

(10) Patent No.: US 11,485,790 B2
(45) Date of Patent: Nov. 1, 2022

(54) IMMUNOACTIVATING ANTIGEN-BINDING MOLECULE

(71) Applicant: Chugai Seiyaku Kabushiki Kaisha, Kita-ku (JP)

(72) Inventors: Tomoyuki Igawa, Gotemba (JP); Taro Miyazaki, Kamakura (JP); Kenji Taniguchi, Kamakura (JP); Naoka Hironiwa, Gotemba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 159 days.

(21) Appl. No.: 15/302,439

(22) PCT Filed: Apr. 7, 2015

(86) PCT No.: PCT/JP2015/060794
§ 371 (c)(1),
(2) Date: Oct. 6, 2016

(87) PCT Pub. No.: WO2015/156268
PCT Pub. Date: Oct. 15, 2015

(65) Prior Publication Data
US 2017/0022287 A1 Jan. 26, 2017

(30) Foreign Application Priority Data

Apr. 7, 2014 (JP) .............................. JP2014-078457
Dec. 26, 2014 (JP) .............................. JP2014-264589

(51) Int. Cl.
| C07K 16/28 | (2006.01) |
| C07K 16/30 | (2006.01) |
| A61K 39/395 | (2006.01) |
| C07K 16/46 | (2006.01) |
| A61K 39/00 | (2006.01) |

(52) U.S. Cl.
CPC ........ *C07K 16/30* (2013.01); *A61K 39/39558* (2013.01); *C07K 16/2809* (2013.01); *C07K 16/2878* (2013.01); *C07K 16/303* (2013.01); *C07K 16/3023* (2013.01); *C07K 16/3038* (2013.01); *C07K 16/3046* (2013.01); *C07K 16/3061* (2013.01); *C07K 16/468* (2013.01); *A61K 2039/505* (2013.01); *A61K 2039/507* (2013.01); *A61K 2039/545* (2013.01); *C07K 2317/21* (2013.01); *C07K 2317/24* (2013.01); *C07K 2317/30* (2013.01); *C07K 2317/31* (2013.01); *C07K 2317/52* (2013.01); *C07K 2317/71* (2013.01); *C07K 2317/73* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 5,585,097 A | 12/1996 | Bolt et al. |
| 5,595,756 A | 1/1997 | Bally et al. |
| 5,601,819 A | 2/1997 | Wong et al. |
| 5,624,821 A | 4/1997 | Winter et al. |
| 5,648,260 A | 7/1997 | Winter et al. |
| 6,025,165 A | 2/2000 | Whitlow et al. |
| 6,143,297 A | 11/2000 | Bluestone |
| 6,805,869 B2 * | 10/2004 | Guo .................. A61K 35/13 424/277.1 |
| 7,183,076 B2 | 2/2007 | Arathoon et al. |
| 7,563,869 B2 | 7/2009 | Honjo et al. |
| 7,659,384 B2 | 2/2010 | Jure-Kunkel et al. |
| 7,728,114 B2 | 6/2010 | Mach et al. |
| 8,058,399 B2 | 11/2011 | Jung |
| 8,080,250 B1 | 12/2011 | Govindan et al. |
| 8,263,073 B2 | 9/2012 | Korman et al. |
| 8,298,801 B2 | 10/2012 | Kink et al. |
| 8,398,956 B2 | 3/2013 | Mcbride et al. |
| 8,586,713 B2 | 11/2013 | Davis et al. |
| 8,592,562 B2 | 11/2013 | Kannan et al. |

(Continued)

FOREIGN PATENT DOCUMENTS

| CA | 2819530 A1 | 6/2012 |
| CA | 2830972 A1 | 10/2012 |

(Continued)

OTHER PUBLICATIONS

Jefferis et al. (Immunology Letters 82 (2002) 57-65) (Year: 2002).*
Melero et al., Clin Cancer Res; 19(5); 1044-53. (2013) (Year: 2013).*
Palazon et al. (Cancer Discov; 2(7); 608-23. (2012)) (Year: 2012).*
Clayton et al. (Biochemistry 2007, 46, 4589-4597). (Year: 2007).*
Muller et al. (J Immunother 2008;31:714-722) (Year: 2008).*
Ho et al. (EurJ Cancer, Feb. 2011;47(3):333-8). (Year: 2011).*
Wang et al. (J Membr Biol. Sep. 1, 2002;189(1):35-43). (Year: 2002).*
Li et al. (Proc Natl Acad Sci USA, Nov. 26, 2013;110(48):19501-6, S1-S6). (Year: 2013).*

(Continued)

*Primary Examiner* — Zachary S Skelding
(74) *Attorney, Agent, or Firm* — Nixon & Vanderhye P.C.

(57) ABSTRACT

It was discovered that the use of an antigen-binding molecule having a cancer-specific antigen-binding domain, and a TNF superfamily-binding domain or a TNF receptor superfamily-binding domain enables agonist activity against a factor belonging to the TNF superfamily or the TNF receptor superfamily to be exhibited only in the presence of cancer-specific antigen-expressing cells, thus leading to activation of immune cells and thereby maintain anti-tumor activity while avoiding side effects such as hepatotoxicity. It was also discovered that concomitant use of the antigen-binding molecule with an antigen-binding molecule having a cancer-specific antigen-binding domain and a T cell receptor complex-binding domain can avoid side effects while increasing the anti-tumor activity.

8 Claims, 20 Drawing Sheets

Specification includes a Sequence Listing.

(56) References Cited

U.S. PATENT DOCUMENTS

| | | |
|---|---|---|
| 8,735,545 B2 | 5/2014 | Lazar et al. |
| 8,796,424 B2 | 8/2014 | Croasdale et al. |
| 8,871,912 B2 | 10/2014 | Davis et al. |
| 9,017,676 B2 | 4/2015 | Lindhofer |
| 9,067,986 B2 | 6/2015 | Gurney et al. |
| 9,150,663 B2 | 10/2015 | Labrijn et al. |
| 9,212,230 B2 | 12/2015 | Schuurman et al. |
| 9,228,017 B2 | 1/2016 | Igawa et al. |
| 9,315,567 B2 | 4/2016 | Chang et al. |
| 9,527,926 B2 | 12/2016 | Ho et al. |
| 9,587,036 B2 | 3/2017 | Kufer et al. |
| 9,637,557 B2 | 5/2017 | Scheer et al. |
| 9,688,762 B2 | 6/2017 | Igawa et al. |
| 9,834,604 B2 | 12/2017 | Zhu et al. |
| 9,975,966 B2 | 5/2018 | Nezu et al. |
| 10,011,858 B2 | 7/2018 | Igawa et al. |
| 10,435,458 B2 | 10/2019 | Kuramochi et al. |
| 10,759,870 B2 | 9/2020 | Teranishi et al. |
| 11,066,483 B2 | 7/2021 | Nezu et al. |
| 2003/0078385 A1 | 4/2003 | Arathoon et al. |
| 2003/0232049 A1 | 12/2003 | Jung |
| 2004/0002587 A1 | 1/2004 | Watkins et al. |
| 2005/0118174 A1 | 6/2005 | Presta |
| 2006/0177896 A1 | 8/2006 | Mach et al. |
| 2006/0235208 A1 | 10/2006 | Lazar et al. |
| 2006/0275282 A1 | 12/2006 | Moore et al. |
| 2007/0178092 A1 | 8/2007 | Bolt et al. |
| 2007/0224188 A1 | 9/2007 | Allan et al. |
| 2007/0231329 A1 | 10/2007 | Lazar et al. |
| 2007/0248602 A1 | 10/2007 | Lazar et al. |
| 2007/0254831 A1 | 11/2007 | Mezo et al. |
| 2007/0287170 A1 | 12/2007 | Davis et al. |
| 2008/0025979 A1 | 1/2008 | Honjo et al. |
| 2008/0095755 A1 | 4/2008 | Kink et al. |
| 2008/0220000 A1 | 9/2008 | Moore et al. |
| 2008/0317758 A9 | 12/2008 | Presta |
| 2009/0068192 A1 | 3/2009 | Jure-Kunkel et al. |
| 2009/0274649 A1 | 11/2009 | Qu et al. |
| 2009/0324589 A1 | 12/2009 | Igawa et al. |
| 2010/0015133 A1 | 1/2010 | Igawa et al. |
| 2010/0105874 A1 | 4/2010 | Schuurman et al. |
| 2010/0178298 A1 | 7/2010 | Lindhofer |
| 2010/0221252 A1 | 9/2010 | Bigler et al. |
| 2010/0286374 A1 | 11/2010 | Kannan et al. |
| 2010/0298542 A1 | 11/2010 | Igawa et al. |
| 2010/0322935 A1 | 12/2010 | Croasdale et al. |
| 2010/0331527 A1 | 12/2010 | Davis et al. |
| 2011/0021755 A1 | 1/2011 | Lazar et al. |
| 2011/0059076 A1 | 3/2011 | Mcdonagh et al. |
| 2011/0081354 A1 | 4/2011 | Korman et al. |
| 2011/0123532 A1 | 5/2011 | Gurney et al. |
| 2011/0150892 A1 | 6/2011 | Thudium et al. |
| 2011/0236374 A1 | 9/2011 | Shitara et al. |
| 2011/0287009 A1 | 11/2011 | Scheer et al. |
| 2011/0293513 A1 | 12/2011 | Govindan et al. |
| 2012/0034228 A1 | 2/2012 | Kufer et al. |
| 2012/0065379 A1 | 3/2012 | Igawa et al. |
| 2012/0076727 A1 | 3/2012 | Mcbride et al. |
| 2012/0100140 A1* | 4/2012 | Reyes ............... C07K 16/00 424/134.1 |
| 2012/0149876 A1 | 6/2012 | Von Kreudenstein et al. |
| 2012/0184718 A1 | 7/2012 | Bruenker et al. |
| 2012/0213781 A1 | 8/2012 | Hilbert |
| 2012/0269826 A1 | 10/2012 | Mckee et al. |
| 2013/0039913 A1 | 2/2013 | Labrijn et al. |
| 2013/0058937 A1 | 3/2013 | Auer et al. |
| 2013/0101581 A1 | 4/2013 | Kuramochi et al. |
| 2013/0115208 A1 | 5/2013 | Ho et al. |
| 2013/0129730 A1 | 5/2013 | Kufer et al. |
| 2014/0050660 A1 | 2/2014 | Chang et al. |
| 2014/0112914 A1 | 4/2014 | Nezu et al. |
| 2014/0294759 A1 | 10/2014 | Chu et al. |
| 2014/0302037 A1 | 10/2014 | Borges et al. |
| 2014/0348832 A1 | 11/2014 | Zhu et al. |
| 2014/0370020 A1 | 12/2014 | Kuramochi et al. |
| 2015/0166661 A1* | 6/2015 | Chen ............... C07K 16/2809 424/135.1 |
| 2015/0337053 A1 | 11/2015 | Janssen |
| 2016/0152722 A1 | 6/2016 | Sharp et al. |
| 2016/0229915 A1* | 8/2016 | Igawa ............... C07K 16/00 |
| 2016/0333095 A1* | 11/2016 | Van Den Brink . C07K 16/1063 |
| 2017/0022287 A1 | 1/2017 | Igawa et al. |
| 2017/0260271 A1 | 9/2017 | Igawa et al. |
| 2017/0267783 A1 | 9/2017 | Nezu et al. |
| 2018/0171017 A1 | 6/2018 | Taniguchi et al. |
| 2018/0192623 A1 | 7/2018 | Jishage et al. |
| 2018/0244805 A1 | 8/2018 | Kaisha |
| 2018/0326058 A1 | 11/2018 | Tsunenari et al. |
| 2019/0077872 A1 | 3/2019 | Igawa et al. |
| 2019/0352421 A1 | 11/2019 | Adams et al. |
| 2020/0048361 A1 | 2/2020 | Kinoshita et al. |
| 2020/0087380 A1 | 3/2020 | Kuramochi et al. |
| 2020/0123256 A1 | 4/2020 | Kaisha |
| 2020/0223940 A1 | 7/2020 | Teranishi et al. |
| 2020/0354473 A1 | 11/2020 | Teranishi et al. |

FOREIGN PATENT DOCUMENTS

| | | |
|---|---|---|
| CN | 1763097 A | 4/2006 |
| CN | 1842540 A | 10/2006 |
| CN | 1763097 B | 4/2011 |
| CN | 1842540 B | 7/2012 |
| CN | 102574921 A | 7/2012 |
| CN | 102574921 B | 5/2016 |
| EP | 1378520 A1 | 1/2004 |
| EP | 1674111 A1 | 6/2006 |
| EP | 1674111 A1 | 6/2006 |
| EP | 1870459 A1 | 12/2007 |
| EP | 2194006 A1 | 6/2010 |
| EP | 2194066 A1 | 6/2010 |
| EP | 1674111 B1 | 11/2010 |
| EP | 2270051 A2 | 1/2011 |
| EP | 2445936 A1 | 5/2012 |
| EP | 2543730 A1 | 1/2013 |
| EP | 2576621 A1 | 4/2013 |
| EP | 2647707 A1 | 10/2013 |
| EP | 2194006 B1 | 1/2014 |
| EP | 2698431 A1 | 2/2014 |
| EP | 1272647 B1 | 11/2014 |
| EP | 1870459 B1 | 6/2016 |
| EP | 3130606 A1 | 2/2017 |
| EP | 2647707 B1 | 9/2018 |
| EP | 3378488 A1 | 9/2018 |
| EP | 2543730 B1 | 10/2018 |
| EP | 2576621 B1 | 4/2019 |
| EP | 2270051 B1 | 5/2019 |
| EP | 3130606 B1 | 10/2021 |
| JP | 2002521053 A | 7/2002 |
| JP | 2002540771 A | 12/2002 |
| JP | 2004508036 A | 3/2004 |
| JP | 2007532095 A | 11/2007 |
| JP | 2008523783 A | 7/2008 |
| JP | 2009526823 A | 7/2009 |
| JP | 2009527499 A | 7/2009 |
| JP | 2010532369 A | 10/2010 |
| JP | 4616838 B2 | 1/2011 |
| JP | 2012515556 A | 7/2012 |
| JP | 2012224631 A | 11/2012 |
| JP | 2012528092 A | 11/2012 |
| JP | 2012531439 A | 12/2012 |
| JP | 2013505732 A | 2/2013 |
| JP | 2013508392 A | 3/2013 |
| JP | 2013528569 A | 7/2013 |
| JP | 5376759 B2 | 12/2013 |
| JP | 5695059 B2 | 4/2015 |
| JP | 5719354 B2 | 5/2015 |
| JP | 5816170 B2 | 11/2015 |
| JP | 2015535828 A | 12/2015 |
| JP | 2016538275 A | 12/2016 |
| JP | 2017504314 A | 2/2017 |
| JP | 6153862 B2 | 6/2017 |
| JP | 6449295 B2 | 1/2019 |
| KR | 20080013875 A | 2/2008 |
| KR | 101374454 B | 3/2014 |

(56) References Cited

FOREIGN PATENT DOCUMENTS

| | | |
|---|---|---|
| KR | 101374454 B1 | 3/2014 |
| KR | 101960109 B1 | 3/2019 |
| MX | 2013006100 A | 7/2013 |
| MX | 349057 B | 7/2017 |
| RU | 2003130072 A | 4/2005 |
| RU | 2005137578 A | 6/2007 |
| RU | 2005137578 A | 6/2007 |
| RU | 2337107-02 | 10/2008 |
| RU | 2337107 C2 | 10/2008 |
| RU | 2355705 C2 | 5/2009 |
| WO | WO-9627011 A1 | 9/1996 |
| WO | WO-9850431 A2 | 11/1998 |
| WO | WO-9958572 A1 | 11/1999 |
| WO | WO-9961057 A2 | 12/1999 |
| WO | WO-0006605 A2 | 2/2000 |
| WO | WO-0018806 A1 | 4/2000 |
| WO | WO-0042072 A2 | 7/2000 |
| WO | WO0177342 A1 | 10/2001 |
| WO | WO-0190192 A2 | 11/2001 |
| WO | WO 0220615 A2 | 3/2002 |
| WO | WO-03035835 A2 | 5/2003 |
| WO | WO-2004003019 A2 | 1/2004 |
| WO | WO-2004035607 A2 | 4/2004 |
| WO | WO-2004099249 A2 | 11/2004 |
| WO | WO-2005035584 A1 | 4/2005 |
| WO | WO 2005061547 A2 | 7/2005 |
| WO | WO-2005063815 A2 | 7/2005 |
| WO | WO-2005092927 A1 | 10/2005 |
| WO | WO-2005115451 A2 | 12/2005 |
| WO | WO-2005118635 A2 | 12/2005 |
| WO | WO-2006020114 A2 | 2/2006 |
| WO | WO2006074399 A2 | 7/2006 |
| WO | WO-2006105338 A2 | 10/2006 |
| WO | WO-2006106905 A1 | 10/2006 |
| WO | WO-2007093630 A1 | 8/2007 |
| WO | WO-2007145941 A2 | 12/2007 |
| WO | WO-2007147901 A1 | 12/2007 |
| WO | WO-2008051424 A2 | 5/2008 |
| WO | WO-2008090960 A1 | 7/2008 |
| WO | WO-2009041613 A1 | 4/2009 |
| WO | WO-2009053368 A1 | 4/2009 |
| WO | WO-2009080252 A1 | 7/2009 |
| WO | WO-2009080253 A1 | 7/2009 |
| WO | WO-2009089004 A1 | 7/2009 |
| WO | WO-2009095478 A1 | 8/2009 |
| WO | WO-2009120922 A2 | 10/2009 |
| WO | WO-2009126920 A2 | 10/2009 |
| WO | WO-2009134776 A2 | 11/2009 |
| WO | WO-2010034441 A1 | 4/2010 |
| WO | WO-2010037395 A2 | 4/2010 |
| WO | WO-2010085682 A2 | 7/2010 |
| WO | WO-2010102251 A2 | 9/2010 |
| WO | WO-2010120561 A1 | 10/2010 |
| WO | WO-2010120561 A1 | 10/2010 |
| WO | WO 2010136172 A1 | 12/2010 |
| WO | WO-2010151792 A1 | 12/2010 |
| WO | WO-2011039126 A1 | 4/2011 |
| WO | WO-2011050106 A2 | 4/2011 |
| WO | WO2011108714 A1 | 9/2011 |
| WO | WO 2011121110 A1 | 10/2011 |
| WO | WO-2011147986 A1 | 12/2011 |
| WO | WO-2012073985 A1 | 6/2012 |
| WO | WO-2012095412 A1 | 7/2012 |
| WO | WO-2012115241 A1 | 8/2012 |
| WO | WO-2012145183 A2 | 10/2012 |
| WO | WO-2012175751 A2 | 12/2012 |
| WO | WO-2013026833 A1 | 2/2013 |
| WO | WO-2013070468 A1 | 5/2013 |
| WO | WO-2013072523 A1 | 5/2013 |
| WO | WO-2013092001 A1 | 6/2013 |
| WO | WO-2014047231 A1 | 3/2014 |
| WO | WO-2014089113 A1 | 6/2014 |
| WO | WO-2014108483 A1 | 7/2014 |
| WO | WO-2014116846 A2 * | 7/2014 ......... A61K 39/3955 |
| WO | WO 2014116846 A2 | 7/2014 |
| WO | WO-2014138306 A1 | 9/2014 |
| WO | WO-2014145907 A1 | 9/2014 |
| WO | WO-2014165818 A2 * | 10/2014 |
| WO | WO-2015046467 A1 * | 4/2015 ......... C07K 16/2866 |
| WO | WO-2015063339 A1 | 5/2015 |
| WO | WO-2015095392 A1 | 6/2015 |
| WO | WO2015103072 A1 | 7/2015 |
| WO | WO-2015124715 A1 | 8/2015 |
| WO | WO-2015149077 A1 | 10/2015 |
| WO | WO-2015156268 A1 | 10/2015 |
| WO | WO-2015174439 A1 | 11/2015 |
| WO | WO-2016194992 A1 | 12/2016 |
| WO | WO-2017086367 A1 | 5/2017 |
| WO | WO-2017086419 A1 | 5/2017 |

OTHER PUBLICATIONS

Fisher et al. (Cancer Immunol Immunother (2012) 61:1721-1733, and Supplemental Data pp. 1-9). (Year: 2012).*
Bruhns et al. (Blood. 2009; 113:3716-3725). (Year: 2009).*
NCT01307267, pp. 1-11, available on clinicaltrials.gov as of Mar. 3, 2014. (Year: 2014).*
Chan et al., Ann Rheum Dis 2000;59(suppl I):i50-i53, at page i51-i52. (Year: 2000).*
Shao et al. (Molecular Immunology 45 (2008) 3990-3999). (Year: 2008).*
Genbank NP_001070977.1, murine CD137/TNFRSF9 precursor, Mar. 23, 2014, pp. 1-3. (Year: 2014).*
Genbank NP_001552.2, human CD137/TNFRSF9 precursor, Mar. 16, 2014, pp. 1-3. (Year: 2014).*
Ascierto, P.A., et al., "Clinical Experiences With Anti-CD137 and Anti-PD1 Therapeutic Antibodies," *Seminars in Oncology* 37(5/508-516, Elsevier Inc., United States (2010).
Brandl, C., et al., "The effect of dexamethasone on polyclonal T cell activation and redirected target cell lysis as induced by a CD19/CD3-bispecific single-chain antibody construct," *Cancer Immunology, Immunotherapy* 56(10):1551-1563, Springer-Verlag, Germany (2007).
Dubrot, J., et al., "Treatment with anti-CD137 mAbs causes intense accumulations of liver T cells without selective antitumor immunotherapeutic effects in this organ," *Cancer Immunology, Immunotherapy* 59(80):1223-1233, Springer-Verlag, Germany (2010).
Filmus, J. and Selleck, S.B., "Glypicans: proteoglycans with a surprise," *The Journal of Clinical Investigation* 108(4)497-501, American Society for Clinical Investigation, United States (2001).
Guo, H., et al., "Extracellular domain of 4-1BBL enhanced the antitumoral efficacy of peripheral blood lymphocytes mediated by anti-CD3 x anti-Pgp bispecific diabody against human multidrug-resistant leukemia," *Cellular Immunology* 251(2):102-108, Elsevier Inc., United States (2008).
Hanahan, D. and Weinberg, R.A., "Hallmarks of Cancer: The Next Generation," *Cell* 144(5)646-674, Elsevier Inc., United States (2011).
Houot, R., et al., "Therapeutic effect of CD137 immunomodulation in lymphoma and its enhancement by $T_{reg}$ depletion," *Blood* 114(16):3431-3438, American Society of Hematology, United States (2009).
International Preliminary Report on Patentability for International Application No. PCT/JP2015/060794, The International Bureau of WIPO, Geneva, Switzerland, dated Oct. 12, 2016, 5 pages.
International Search Report and Written Opinion for International Application No. PCT/JP2015/060794, Japan Patent Office, Tokyo, Japan, dated Jun. 9, 2015, 15 pages.
Li, F. and Ravetch, J.V., "Antitumor activities of agonistic anti-TNFR antibodies require differential FcγRIIB coengagement in vivo," *Proceedings of the National Academy of Sciences of the USA* 110(48):19501-19506, National Academy of Sciences, United States (2013).
Prieto, P.A., et al., "CTLA-4 Blockade With Ipilimumab: Long-term Follow-up of 177 Patients With Metastatic Melanoma," *Clinical Cancer Research* 18(7):2039-2047, American Association for Cancer Research, United States (2012).

(56) References Cited

OTHER PUBLICATIONS

Schabowsky, R-H., et al., "A novel form of 4-1 BBL has better immunomodulatory activity than an agonistic anti-4-1BB Ab without Ab-associated severe toxicity," *Vaccine* 28(2):512-522, Elsevier Ltd., England (2009).

Summers Deluca, L. and Gommerman, J.L., "Fine-tuning of dendritic cell biology by the TNF superfamily," *Nature Reviews Immunology* 12(5):339-351, Nature Publishing Group, England (2012).

Vinay, D.S. and Kwon, B.S., "TNF superfamily: Costimulation and clinical applications," *Cell Biology International* 33(4):453-465, Elsevier Ltd., England (2009).

Yamauchi, N., et al., "The glypican 3 oncofetal protein is a promising diagnostic marker for hepatocellular carcinoma," *Modern Pathology* 18(12):1591 -1598, USCAP, Inc., United States (2005).

Yorita, K., et al., "Prognostic significance of circumferential cell surface immunoreactivity of glypican-3 in hepatocellular carcinoma," *Liver International* 31(1):120-131, John Wiley & Sons A/S, United States (2011).

Zhu, Z-W., et al., "Enhanced glypican-3 expression differentiates the majority of hepatocellular carcinomas from benign hepatic disorders," *Gut* 48(4):558-564, British Medical Association, England (2001).

Co-pending U.S. Appl. No. 15/310,162, inventor Igawa, T., filed May 13, 2015 (Not Published).

Alarcon, B., et al., "The CD3-gamma and CD3-delta Subunits of the T Cell Antigen Receptor Can Be Expressed Within Distinct Functional TCR/CD3 Complexes," The EMBO Journal, 10(4):903-912, Wiley Blackwell, London (Apr. 1991).

Amann, M., et al., "Therapeutic Window of an EpCAM/CD3-specific BiTE Antibody in Mice is Determined by a Subpopulation of EpCAM-expressing Lymphocytes That is Absent in Humans," Cancer Immunology, Immunotherapy, 58(1):95-109, Springer Verlag, Germany (Jan. 2009).

Armour, K.L., et al., "Recombinant Human IgG Molecules Lacking Fcgamma Receptor I Binding and Monocyte Triggering Activities," European Journal of Immunology, 29(8):2613-2624, Wiley-VCH, Germany (Aug. 1999).

Asano, R., et al., "Highly Effective Recombinant Format of a Humanized IgG-like Bispecific Antibody for Cancer Immunotherapy With Retargeting of Lymphocytes to Tumor Cells," The Journal of Biological Chemistry, 282(38):27659-27665, American Society for Biochemistry and Molecular Biology, United States (Sep. 2007).

Barach, Y. S., et al., "T Cell Coinhibition in Prostate Cancer: New Immune Evasion Pathways and Emerging Therapeutics," Trends in Molecular Medicine, 17(1):47-55, Elsevier Science Ltd, England (Jan. 2011).

Bargou, R., et al., "Tumor Regression in Cancer Patients by Very Low Doses of a T Cellengaging Antibody," Science, 321(5891):974-977, American Association for the Advancement of Science, United States (Aug. 2008).

Bastid, J., et al., "ENTPD1/CD39 is a Promising Therapeutic Target in Oncology," Oncogene, 32(14):1743-1751, Nature Publishing Group, England (Apr. 2013).

Bates, G. J., et al., "Quantification of Regulatory T Cells Enables the Identification of High-risk Breast Cancer Patients and Those at Risk of Late Relapse," Journal of Clinical Oncology, 24(34):5373-5380, American Society of Clinical Oncology, United States (Dec. 2006).

Bekeredjian-Ding, I and Jego, G., "Toll-like Receptors—sentries in the B-cell Response," Immunology, 128(3):311-323, Blackwell Scientific Publications, England (Nov. 2009).

Bendig, M.M., "Humanization of Rodent Monoclonal Antibodies by CDR Grafting," Methods: a Companion to Methods in Enzymology, 8(2):83-93, Jan. 1995).

Bokemeyer, C., "Catumaxomab—trifunctional Anti-EpCAM Antibody Used to Treat Malignant Ascites," Expert Opinion on Biological Therapy, 10(8):1259-1269, Taylor & Francis, England (Aug. 2010).

Borch, T.H., et al., "Reorienting the Immune System in the Treatment of Cancer by Using Anti-PD-1 and Anti-PD-L1 Antibodies," Drug Discovery Today, 20(9):1127-1134, Elsevier Science Ltd, England (Sep. 2015).

Buszko, M., et al., "Differential Depletion of Total T Cells and Regulatory T Cells and Prolonged Allotransplant Survival in CD3ε Humanized Mice Treated With Polyclonal Anti Human Thymocyte Globulin," PLoS One, 12(3):e0173088, Public Library of Science, United States (Mar. 2017).

Campoli, M., et al., "Immunotherapy of Malignant Disease With Tumor Antigen (TA)-specific Monoclonal Antibodies: Does its Therapeutic Efficacy Require Cooperation With TA-specific CTL?," Clinical Cancer Research, 16(1):11-20, The Association, United States (Jan. 2010).

Chandramohan, V., et al., "Antibody, T-cell and Dendritic Cell Immunotherapy for Malignant Brain Tumors," Future Oncology, 9(7):977-990, Future Medicine Ltd, England (Jul. 2013).

Chen, S., et al., "Bispecific Antibodies in Cancer Immunotherapy," Human Vaccines & Immunotherapeutics, 12(10):2491-2500, Taylor & Francis, United States (Oct. 2016).

Cheng, L., et al., "Interleukin-6 Induces Gr-1+CD11b+ Myeloid Cells to Suppress CD8+ T Cell-mediated Liver Injury in Mice," PLoS One, 6(3):e17631, Public Library of Science, United States (Mar. 2011).

U.S. Appl. No. 15/776,587, Tsunenari, T., et al., filed May 16, 2018, related application, now published.

U.S. Appl. No. 15/776,541, Igawa, T., et al., filed Nov. 18, 2016, related application, now published.

Dall'Acqua, W.F., et al., "Modulation of the Effector Functions of a Human IgG1 Through Engineering of its Hinge Region," Journal of Immunology, 177(2):1129-1138, American Association of Immunologists, United States (Jul. 2006).

D'Arena, G., et al., "Regulatory T-cell Number is Increased in Chronic Lymphocytic Leukemia Patients and Correlates With Progressive Disease," Leukemia Research, 35(3):363-368, Pergamon Press, England (Mar. 2011).

De Gast, G.C., et al., "CD8 T Cell Activation After Intravenous Administration of CD3 X CD19 Bispecific Antibody in Patients With Non-hodgkin Lymphoma," Cancer Immunology, Immunotherapy, 40(6):390-396, Springer Verlag, Germany (Jun. 1995).

De Vos Van Steenwijk, P.J., et al., "Tumor-infiltrating CD14-positive Myeloid Cells and CD8-positive T-cells Prolong Survival in Patients With Cervical Carcinoma," International Journal of Cancer, 133(12):2884-2894, Wiley-Liss, United States (Dec. 2013).

Drake, C. G., "Combined Immune Checkpoint Blockade," Seminars in Oncology, 42(4):656-662, Elsevier Inc. (Aug. 2015).

El Andaloussi, A., et al., "Prolongation of Survival Following Depletion of CD4+CD25+ Regulatory T Cells in Mice With Experimental Brain Tumors," Journal of Neurosurgery, 105(3):430-437, American Association of Neurological Surgeons, United States (Sep. 2006).

Fischer, N. and Léger O., "Bispecific Antibodies: Molecules that Enable Novel Therapeutic Strategies," Pathobiology: Journal of Immunopathology, Molecular and Cellular Biology, 74(1):3-14, S. Karger, Switzerland (Jan. 2007).

French, J.D., et al., "Tumor-associated Lymphocytes and Increased FoxP3+ Regulatory T Cell Frequency Correlate With More Aggressive Papillary Thyroid Cancer," The Journal of Clinical Endocrinology and Metabolism, 95(5):2325-2333, Oxford University Press, United States (May 2010).

Furness, A. J., et al., "Impact of Tumour Microenvironment and Fc Receptors on the Activity of Immunomodulatory Antibodies," Trends in Immunology, 35(7):290-298, Elsevier Science Ltd, England (Jul. 2014).

Gajewski, T.F., et al., "Innate and Adaptive Immune Cells in the Tumor Microenvironment," Nature Immunology, 14(10):1014-1022, Nature America Inc., United States (Oct. 2013).

Gerber, A.L., et al., "High Expression of FOXP3 in Primary Melanoma is Associated With Tumour Progression," British Journal of Dermatology, 170(1):103-109, Blackwell Scientific Publications, England (Jan. 2014).

Gobert, M., et al., "Regulatory T Cells Recruited Through CCL22/CCR4 are Selectively Activated in Lymphoid Infiltrates Surround-

(56) References Cited

OTHER PUBLICATIONS ing Primary Breast Tumors and Lead to an Adverse Clinical Outcome," Cancer Research, 69(5):2000-2009, American Association for Cancer Research, United States (Mar. 2009).

Goldstein, M. J., et al., "Adoptive Cell Therapy for Lymphoma With CD4 T Cells Depleted of CD137-expressing Regulatory T Cells," Cancer Research, 72(5):1239-1247, American Association for Cancer Research, United States (Mar. 2012).

Hamid, O. and Carvajal, R.D., "Anti-programmed Death-1 and Anti-programmed Death-ligand 1 Antibodies in Cancer Therapy," Expert Opinion on Biological Therapy, 13(6):847-861, Taylor & Francis, England (Jun. 2013).

Hiraoka, N., et al., "Prevalence of FOXP3+ Regulatory T Cells Increases During the Progression of Pancreatic Ductal Adenocarcinoma and its Premalignant Lesions," Clinical Cancer Research, 12(18):5423-5434, The Association, United States (Sep. 2006).

Hornig, N., et al., "Combination of a Bispecific Antibody and Costimulatory Antibody-ligand Fusion Proteins for Targeted Cancer Immunotherapy," Journal of Immunotherapy, 35(5):418-429, Lippincott Williams & Wilkins, United States (Jun. 2012).

Hornig, N., et al., "Evaluating Combinations of Costimulatory Antibody-ligand Fusion Proteins for Targeted Cancer Immunotherapy," Cancer Immunology, Immunotherapy, 62(8):1369-1380, Springer Verlag, Germany (Aug. 2013).

Jacobs, J.F., et al., "Dendritic Cell Vaccination in Combination with anti-CD25 Monoclonal Antibody Treatment: A Phase I/II Study in Metastatic Melanoma Patients," Clinical Cancer Research, 16(20):5067-5078, The Association, United States (Oct. 2010).

Jefferis, R. and Lund, J., "Interaction sites on human IgG-Fc for FcγR: current models," Immunol Letters, 82:57-65 (2002).

Jure-Kunkel, M., et al., "Synergy Between Chemotherapeutic Agents and CTLA-4 Blockade in Preclinical Tumor Models," Cancer Immunology, Immunotherapy, 62(9):1533-1545, Springer Verlag, Germany (Sep. 2013).

Kawaida, H., et al., "Distribution of CD4(+)CD25 high Regulatory T-cells in Tumor-draining Lymph Nodes in Patients With Gastric Cancer," The Journal of Surgical Research, 124(1):151-157, Academic Press, United States (Mar. 2005).

Khan, A.R., et al., "Tumor Infiltrating Regulatory T Cells: Tractable Targets for Immunotherapy," International Reviews of Immunology, 29(5):461-484, Informa Healthcare, England (Oct. 2010).

Klein, C., et al., "Progress in Overcoming the Chain Association Issue in Bispecific Heterodimeric IgG Antibodies," mAbs, 4(6):653-663, Taylor & Francis, United States (Nov.-Dec. 2012).

Kobayashi, N., et al., "FOXP3+ Regulatory T Cells Affect the Development and Progression of Hepatocarcinogenesis," 13(3):902-911, The Association, United States (Feb. 2007).

Kono, K., et al., "CD4(+)CD25 high Regulatory T Cells Increase With Tumor Stage in Patients With Gastric and Esophageal Cancers," Cancer Immunology, Immunotherapy, 55(9):1064-1071, Springer Verlag, Germany (Sep. 2006).

Koristka, S., et al., "Retargeting of Human Regulatory T Cells by Single-chain Bispecific Antibodies," Journal of Immunology, 188(3):1551-1558, American Association of Immunologists, United States (Feb. 2012).

Kufer, P., et al., "A Revival of Bispecific Antibodies," Trends in Biotechnology, 22(5):238-244, Elsevier Science Publishers, England (May 2004).

Kumagai et al., "Humanized Bispecific Antibodies that Recognize Lymphocytes and Cancer Cells," Drug Delivery System, 23(5):518-552, (2008) With English Translation.

Lazar, G.A., et al., "Engineered Antibody Fc Variants With Enhanced Effector Function," Proceedings of the National Academy of Sciences of the United States of America, 103(11):4005-4010, National Academy of Sciences, United States (Mar. 2006).

Li, B., et al., "Construction and Characterization of a Humanized Anti-human Cd3 Monoclonal Antibody 12f6 With Effective Immunoregulation Functions," Immunology, 116(4):487-498, Blackwell Scientific Publications, England (Dec. 2005).

Li, Y., et al., "Phosphorylated ERM is Responsible for Increased T Cell Polarization, Adhesion, and Migration in Patients With Systemic Lupus Erythematosus," Journal of Immunology, 178(3):1938-1947, American Association of Immunologists, United States (Feb. 2007).

Liotta, F., et al., "Frequency of Regulatory T Cells in Peripheral Blood and in Tumour-infiltrating Lymphocytes Correlates With Poor Prognosis in Renal Cell Carcinoma," BJU International, 107(9):1500-1506, Blackwell Science, England (2 010).

Liu, R., et al., "Efficient Inhibition of Human B-cell Lymphoma in SCID Mice by Synergistic Antitumor Effect of Human 4-1 BB ligand/anti-CD20 Fusion Proteins and Anti-CD3/anti-CD20 Diabodies," Journal of Immunotherapy, 33(5):500-509 (Jun. 2010), Abstract.

Mack, M., et al., "A Small Bispecific Antibody Construct Expressed as a Functional Single-chain Molecule With High Tumor Cell Cytotoxicity," Proceedings of the National Academy of Sciences of the United States of America, 92(15):7021-7025, National Academy of Sciences, United States (Jul. 1995).

McDermott, D. and Atkins, M., "PD-1 as a Potential Target in Cancer Therapy," Cancer Medicine, 2(5):662-673, John Wiley & Sons Ltd, United States (Oct. 2013).

McEarchern, J.A., et al., "Engineered Anti-cd70 Antibody With Multiple Effector Functions Exhibits in Vitro and in Vivo Antitumor Activities," Blood, 109(3):1185-1192, American Society of Hematology, United States (Feb. 2007).

Melero, I., et al., "Multi-layered Action Mechanisms of CD137 (4-1BB)-targeted Immunotherapies," Trends in Pharmacological Sciences, 29(8):383-390, Elsevier in Association With The International Union of Pharmacology, England (Aug. 2008).

Merchant, A.M., et al., "An Efficient Route to Human Bispecific IgG," Nature Biotechnology, 16(7):677-681, Nature America Publishing, United States (Jul. 1998).

Mezzanzanica, D., et al., "Human Ovarian Carcinoma Lysis by Cytotoxic T Cells Targeted by Bispecific Monoclonal Antibodies: Analysis of the Antibody Components," International Journal of Cancer, 41(4):609-615, Wiley-Liss, United States (Apr. 1988).

Molhoj, M., et al., "CD19-/CD3-bispecific Antibody of the BiTE Class is Far Superiorto Tandem Diabody With Respect to Redirected Tumor Cell Lysis," Molecular Immunology, 44(8):1935-1943, Pergamon Press, England (Mar. 2007).

Nakano, K., et al., "Anti-glypican 3 Antibodies Cause Adcc Against Human Hepatocellular Carcinoma Cells," Biochemical and Biophysical Research Communications, 378(2):279-284, Elsevier, United States (Jan. 2009).

Natsume, A., et al., "Improving Effector Functions of Antibodies for Cancer Treatment: Enhancing ADCC and CDC," Drug Design, Development and Therapy, 3:7-16, Dove Press Limited, New Zealand (Sep. 2009).

Nishikawa, W., et al., "Perspectives on Clinical Applications of Regulatory T Cells," Inflammation & Immunology, Jan. 2013, 21(1):66-72 (with English Translation).

Pastor, F., et al., "Targeting 4-1BB Costimulation to Disseminated Tumor Lesions With Bispecific Oligonucleotide Aptamers," Molecular Therapy, 19(10):1878-1886, Cell Press, United States (Oct. 2011).

Paul, Fundamental Immunology, 3rd Edition, 1993, pp. 292-295 (Year: 1993).

Pavlou, A.K and Belsey, M.J, "The Therapeutic Antibodies Market to 2008," European Journal of Pharmaceutics and Biopharmaceutics, 59(3):389-396, Elsevier Science, Netherlands (Apr. 2005).

Percival-Alwyn, J.L., et al., "Generation of Potent Mouse Monoclonal Antibodies to Self-proteins Using T-cell Epitope "Tags"," mAbs, 7(1):129-137, aylor & Francis, United States (2015).

Pere, H., et al., "Comprehensive Analysis of Current Approaches to Inhibit Regulatory T Cells in Cancer," Oncoimmunology, 1(3):326-333, Taylor & Francis, United States (May 2012).

Porter, D. L., et al., "Chimeric Antigen Receptor-modified T Cells in Chronic Lymphoid Leukemia," The New England Journal of Medicine, 365(8):725-733, Massachusetts Medical Society, United States (Aug. 2011).

(56) References Cited

OTHER PUBLICATIONS

Postow, M. A., et al., "Nivolumab and Ipilimumab versus Ipilimumab in Untreated Melanoma," The New England Journal of Medicine, 372(21):2006-2017, Massachusetts Medical Society, United States (May 2015).
Presta, L. G., "Molecular Engineering and Design of Therapeutic Antibodies," Current Opinion in Immunology, 20(4):460-470, Elsevier, England (Aug. 2008).
Reichert, J.M., et al., "Monoclonal Antibody Successes in the Clinic," Nature Biotechnology, 23(9):1073-1078, Nature America Publishing, United States (Sep. 2005).
Remer, M., et al., "Abstract B046: Therapeutic Mechanisms of Anti-4-1bb Antibodies in Cancer: Agonism Versus Regulatory T Cell Depletion," Translating Science into Survival, 4(11) (Nov. 2016).
Ruf, P., and Lindhofer, H., "Induction of a Long-lasting Antitumor Immunity by a Trifunctional Bispecific Antibody," Blood, 98(8):2526-2534, American Society of Hematology, United States (Oct. 2001).
Salfeld, J. G., "Isotype Selection in Antibody Engineering," Nature Biotechnology, 25(12):1369-1372, Nature America Publishing, United States (Dec. 2007).
Sandin, L. C., "Local CTLA4 blockade Effectively Restrains Experimental Pancreatic Adenocarcinoma Growth in Vivo," Oncoimmunology, 3:e27614, Taylor & Francis, United States (2014).
Sato, E., et al., "Intraepithelial Cd8+ Tumor-infiltrating Lymphocytes and a High Cd8+/regulatory T Cell Ratio Are Associated With Favorable Prognosis in Ovarian Cancer," Proceedings of the National Academy of Sciences of the United States of America, 102(51):18538-18543, National Academy of Sciences, United States (Dec. 2005).
Schlereth, B., et al., "T-cell Activation and B-cell Depletion in Chimpanzees Treated With a Bispecific Anti-cd19/anti-cd3 Single-chain Antibody Construct," Cancer Immunology, Immunotherapy, 55(5):503-514, Springer Verlag, Germany (May 2006).
Sebastian, M., et al., "Treatment of Non-small Cell Lung Cancer Patients With the Trifunctional Monoclonal Antibody Catumaxomab (Anti-epcam X Anti-cd3): a Phase I Study," Cancer Immunology, Immunotherapy, 56(10):1637-1644, Springer Verlag, Germany (Oct. 2007).
Seimetz, D., et al., "Development and Approval of the Trifunctional Antibody Catumaxomab (Anti-epcam X Anti-cd3) as a Targeted Cancer Immunotherapy," Cancer Treatment Reviews, 36(6):458-467, Elsevier, Netherlands (Oct. 2010).
Selby, M.J., et al., "Anti-CTLA-4 Antibodies of IgG2a Isotype Enhance Antitumor Activity Through Reduction of Intratumoral Regulatory T Cells," Cancer Immunology Research, 1(1):32-42, American Association for Cancer Research, United States (Jul. 2013).
Shields, R. L., et al., "High Resolution Mapping of the Binding Site on Human IgG1 for Fc Gamma RI, Fc Gamma RIII, Fc Gamma RIII, and FcRn and Design of Igg1 Variants With Improved Binding to the Fc Gamma R," The Journal of Biological Chemistry, 276(9):6591-6604, American Society for Biochemistry and Molecular Biology, United States (Mar. 2001).
Simpson, T.R., et al., "Fc-dependent Depletion of Tumor-infiltrating Regulatory T Cells Codefines the Efficacy of Anti-CTLA-4 Therapy Against Melanoma," The Journal of Experimental Medicine, 210(9):1695-1710, Rockefeller University Press, United States (Aug. 2013).
Smith-Gill, S. J., et al., "Contributions of Immunoglobulin Heavy and Light Chains to Antibody Specificity for Lysozyme and Two Haptens," Journal of Immunology, 139(12):4135-4144, American Association of Immunologists, United States (Dec. 1987), Abstract.
Son, J. H., et al., "Humanization of Agonistic Anti-human 4-1BB Monoclonal Antibody Using a Phage-displayed Combinatorial Library," Journal of Immunological Methods, 286(1-2):187-201, Elsevier, Netherlands (Mar. 2004).
Song, M. K., et al., "Light Chain of Natural Antibody Plays a Dominant Role in Protein Antigen Binding," Biochemical and Biophysical Research Communications, 268(2):390-394, Elsevier, United States (Feb. 2000).

Staerz, U. D., and Bevin, M. J., "Hybrid Hybridoma Producing a Bispecific Monoclonal Antibody That Can Focus Effector T-cell Activity," 83(5):1453-1457, National Academy of Sciences, United States (Mar. 1986).
Staerz, U. D., et al., "Hybrid Antibodies Can Target Sites for Attack by T Cells," Nature, 314(6012):628-631, Nature Publishing Group, England (Apr. 1985).
Stroehlein, M.A., et al., "Induction of Anti-tumor Immunity by Trifunctional Antibodies in Patients With Peritoneal Carcinomatosis," Journal of Experimental & Clinical Cancer Research, 28:18, BioMed Central, England (Feb. 2009).
Sugiyama, D., et al., "Anti-CCR4 Mab Selectively Depletes Effector-type FoxP3+CD4+ Regulatory T Cells, Evoking Antitumor Immune Responses in Humans," Proceedings of the National Academy of Sciences of the United States of America, 110(44):17945-17950, National Academy of Sciences, United States (Oct. 2013).
Teerinen, T., et al., "Structure-based Stability Engineering of the Mouse IgG1 Fab Fragment by Modifying Constant Domains," J Mol Biol., 361(4):687-697, Elsevier, England (Aug. 2006).
Teschner, D., et al., "In Vitro Stimulation and Expansion of Human Tumour-reactive CD8+ Cytotoxic T Lymphocytes by Anti-CD3/CD28/CD137 Magnetic Beads," Scandinavian Journal of Immunology, 74(2):155-164, Blackwell Scientific Publications, England (Aug. 2011).
Thakur, A. and Lum, L.G, "Cancer Therapy With Bispecific Antibodies: Clinical Experience," Current Opinion in Molecular Therapeutics, 12(3):340-349, Thomson Reuters (Scientific) Ltd., England (Jun. 2010).
Tosti, G., et al., "Anti-cytotoxic T Lymphocyte Antigen-4 Antibodies in Melanoma," Clinical, Cosmetic and Investigational Dermatology, 6:245-256, Dove Medical Press, New Zealand (Oct. 2013).
Viardot, et al., "Treatment of Patients With Non-Hodgkin Lymphoma With CD19/CD3 Bispecific Antibody Blinautumomab (MT103)," Internet Citation, Dec. 6, 2010 (Dec. 6, 2010), 1 page (http://www.bloodjournal.org/content/116/21/2880?sso-checked=true).
Vinay, D.S. and Kwon, B.S., "4-1BB Signaling Beyond T Cells," Cellular & Molecular Immunology, 8(4):281-284, Nature Publishing Group, China (Jul. 2011).
Wainwright, D.A, et al., "Targeting Tregs in Malignant Brain Cancer: Overcoming IDO," Frontiers in Immunology, 4:116, Frontiers Research Foundation, Switzerland (May 2013).
Wang, X.B., et al., "A New Recombinant Single Chain Trispecific Antibody Recruits T Lymphocytes to Kill Cea (Carcinoma Embryonic Antigen) Positive Tumor Cells in Vitro Efficiently," Journal of Biochemistry, 135(4):555-565, Oxford University Press, England (Apr. 2004).
Wang, Y.Y., et al., "The Variation of CD4+CD25+ Regulatory T Cells in the Periphery Blood and Tumor Microenvironment of Non-small Cell Lung Cancer Patients and the Downregulation Effects Induced by CpG ODN," Targeted Oncology, 6(3):147-154, Springer-Verlag, France (Sep. 2011).
Ward, E. S., et al., "Binding Activities of a Repertoire of Single Immunoglobulin Variable Domains Secreted From *Escherichia Coli*," Nature, 341(6242):544-546, Nature Publishing Group, England (Oct. 1989).
Weiner, L.M., et al., "Monoclonal Antibodies: Versatile Platforms for Cancer Immunotherapy," Nature Reviews. Immunology, 10(5):317-327, Nature Publishing Group, England (May 2010).
Wherry, E.J., "T Cell Exhaustion," Nature Immunology, 12(6):492-499, Nature America Inc., United States (2011).
Wines, B. D., et al., "The IgG Fc Contains Distinct Fc Receptor (FcR) Binding Sites: The Leukocyte Receptors FcvRI and FcvRIIa Bind to a Region in the Fc Distinct from That Recognized by Neonatal FcR and Protein A," Journal of Immunology, 164(10):5313-5318, American Association of Immunologists, United States (May 2000).
Wing, et al., "Mechanism of First -Dose Cytokine-Release Syndrome by Camp ATH 1-H: Involvement of CD16 (FcγRIII) and CDIIa!CD18 (LFA-1) on NK Cells," Journal of Clinical Investigation, 98(12):2819-2826, Dec. 1996).

(56) References Cited

OTHER PUBLICATIONS

Wolf, E., et al., "BiTEs : Bispecific Antibody Constructs With Unique Anti-tumor Activity," Drug Discovery Today, 10(18):1237-1244, Kidlington, Oxford : Irvington, NJ : Elsevier Science Limited, England (Sep. 2005).
Yang, Z. M., et al., "Anti-CD3 scFv-B7.1 Fusion Protein Expressed on the Surface of HeLa Cells Provokes Potent T-lymphocyte Activation and Cytotoxicity," Biochemistry and Cell Biology, 85(2):196-202, Canadian Science Publishing, Canada (Apr. 2007).
Yang, Z.Z., et al., "Attenuation of CD8(+) T-cell function by CD4(+)CD25(+) regulatory T cells in B-cell non-Hodgkin's lymphoma," Cancer Research, 66(20):10145-10152, American Association for Cancer Research, United States (Oct. 2006).
Yang, Z.Z., et al., "Intratumoral CD4+CD25+ Regulatory T-cell-mediated Suppression of Infiltrating CD4+ T Cells in B-cell Non-hodgkin Lymphoma," Blood, 107(9):3639-3646, American Society of Hematology, United States (May 2006).
Yano, et al., Journal of Translational Medicine. 2014;12(1):191 (cited in extended EP Search Report dated Apr. 26, 2019 for corresponding EP application).
Yonezawa, A., et al., "Boosting Cancer Immunotherapy with Anti-CD137 Antibody Therapy," Clinical Cancer Research, 21(14):3113-3120, Denville, United States (Jul. 2015).
Yu, P., et al., "Simultaneous Inhibition of Two Regulatory T-cell Subsets Enhanced Interleukin-15 Efficacy in a Prostate Tumor Model," Proceedings of the National Academy of Sciences of the United States of America, 109(16):6187-6192, National Academy of Sciences, United States (Apr. 2012).
Zalevsky, J., et al., "The Impact of Fc Engineering on an Anti-cd19 Antibody: Increased Fcgamma Receptor Affinity Enhances B-cell Clearing in Nonhuman Primates," Blood, 113(16):3735-3743, American Society of Hematology, United States (Apr. 2009).
Zeidler, R., et al., "Simultaneous Activation of T Cells and Accessory Cells by a New Class of Intact Bispecific Antibody Results in Efficient Tumor Cell Killing," Journal of Immunology, 163(3):1246-1252, American Association of Immunologists, United States (Aug. 1999).
Zeidler, R., et al., "The Fc-region of a New Class of Intact Bispecific Antibody Mediates Activation of Accessory Cells and NK Cells and Induces Direct Phagocytosis of Tumour Cells," British Journal of Cancer, 83(2):261-266, Nature Publishing Group on behalf of Cancer Research UK, England (Jul. 2000).
Zheng, J., et al., "YB-1 Immunization Combined With Regulatory T-cell Depletion Induces Specific T-cell Responses That Protect Against Neuroblastoma in the Early Stage," Acta Biochimica Et Biophysica Sinica, 44(12):1006-1014, Oxford University Press, China (Dec. 2012).
Zhao, H., et al., "A Bispecific Protein Capable of Engaging CTLA-4 and MHCII Protects Non-Obese Diabetic Mice from Autoimmune Diabetes," PLoS ONE 8(5):e63530 (2013).
Alarcon, B., et al., "The CD3-gamma and CD3-delta Subunits of the T Cell Antigen Receptor Can be Expressed Within Distinct Functional TCR/CD3 Complexes," The EMBO Journal, 10(4):903-912(1991).
Alignment of Fc domain sequences of catumaxomab and SEQ ID Nos. 23, 24, 25, and 26, cited in opposition of EP2647707.
Amann, M., et al., "Therapeutic Window of an EpCAM/CD3-specific BiTE Antibody in Mice is Determined by a Subpopulation of EpCAM-expressing Lymphocytes That is Absent in Humans," Cancer Immunology 58(1):95-109(2009).
An, Z., et al., "IgG2m4, an engineered antibody isotype with reduced Fc function," mAbs 1(6):572-579 (2009).
Copy of Annex 1, submitted by the patentee during examination proceedings on Sep. 18, 2015 in Opposition filed against corresponding European Patent No. 2647707.
Aschermann, S., et al., "The other side of immunoglobulin G: suppressor of inflammation," Clinical & Experimental Immunology, 160:161-167 (2010).

Armour, K.L., et al., "Recombinant Human IgG Molecules Lacking Fcgamma Receptor I Binding and Monocyte Triggering Activities," European Journal of Immunology, 29(8):2613-2624(1999).
Asano, R., et al., "Highly Effective Recombinant Format of a Humanized IgG-like Bispecific Antibody for Cancer Immunotherapy With Retargeting of Lymphocytes to Tumor Cells," The Journal of Biological Chemistry, 282(38):27659-27665(2007).
Auerbach, R., et al., "Angiogenesis Assays: Problems and Pitfalls," Cancer Metastasis Reviews, 19(1-2):167-172 (2000).
Baeuerle, P.A and Reinhardt, C. , "Bispecific T-cell Engaging Antibodies for Cancer Therapy," Cancer Research, 69(12):4941-4944 (2009).
Barach, Y. S., et al., "T Cell Coinhibition in Prostate Cancer: New Immune Evasion Pathways and Emerging Therapeutics," Trends in Molecular Medicine, 17(1):47-55(2011).
Bargou, R., et al., "Tumor Regression in Cancer Patients by Very Low Doses of a T Cell-engaging Antibody," Science, 321(5891):974-977(2008).
Bastid, J., et al., "ENTPD1/CD39 is a Promising Therapeutic Target in Oncology," Oncogene, 32(14):1743-1751(2013).
Bates, G. J., et al., "Quantification of Regulatory T Cells Enables the Identification of High-risk Breast Cancer Patients and Those at Risk of Late Relapse," Journal of Clinical Oncology, 24(34):5373-5380(2006).
Bekeredjian-Ding, I and Jego G., "Toll-like Receptors-sentries in the B-cell Response," Immunology, 128(3):311-323(2009).
Bendig, M.M., "Humanization of Rodent Monoclonal Antibodies by CDR Grafting," Methods: a Companion to Methods in Enzymology, 8(2):83-93(1995).
Bhatia, S., et al., "CTLA4 Blockade Enhances the Anti-tumor Activity of Therapy With an Anti-CD3-based Bispecific Antibody," The Journal of Investigative Medicine Midwestern Regional Meeting, 45(7):346A (1997).
Bodelon, G., et al., "Immunoglobulin domains in *Escherichia coli* and other enterobacteria: from pathogenesis to applications in antibody technologies," FEMS Microbiol Rev., 37:204-250 (2013).
Bokemeyer, C., "Catumaxomab—trifunctional Anti-EpCAM Antibody Used to Treat Malignant Ascites," Expert Opinion on Biological Therapy, 10(8):1259-1269(2010).
Borch, T.H., et al., "Reorienting the Immune System in the Treatment of Cancer by Using Anti-PD-1 and Anti-PD-L1 Antibodies," Drug Discovery Today, 20(9):1127-1134(2015).
Brennen, F. R., et al., "Safety and immunotoxicity assessment of immunomodulatory monoclonal antibodies," mAbs 2(3):233-255 (2010).
Brown, M., et al., "Tolerance of Single, but Not Multiple, Amino Acid Replacements in Antibody VH CDR 2: a Means of Minimizing B Cell Wastage From Somatic Hypermutation?," Journal of Immunology, 156(9):3285-3291 (1996).
Buszko, M., et al., "Differential Depletion of Total T Cells and Regulatory T Cells and Prolonged Allotransplant Survival in CD3ε Humanized Mice Treated With Polyclonal Anti Human Thymocyte Globulin," PLoS One, 12(3):e0173088(2017).
Campoli, M., et al., "Immunotherapy of Malignant Disease With Tumor Antigen (TA)-specific Monoclonal Antibodies: Does its Therapeutic Efficacy Require Cooperation With TA-specific CTL?," Clinical Cancer Research, 16(1):11-20(2010).
Chandramohan, V., et al., "Antibody, T-cell and Dendritic Cell Immunotherapy for Malignant Brain Tumors," Future Oncology, 9(7):977-990(2013).
Chelius, D., et al., "Structural and functional characterization of the trifunctional antibody catumaxomab," mAbs 2(3):309-319 (2010).
Chen, S., et al., "Bispecific Antibodies in Cancer Immunotherapy," Human Vaccines & Immunotherapeutics, 12(10):2491-2500(2016).
Cheng, L., et al., "Interleukin-6 Induces Gr-1+CD11b+ Myeloid Cells to Suppress CD8+ T Cell-mediated Liver Injury in Mice," PLoS One, 6(3):e17631(2011).
Chernajovsky, Y. and Nissim, A., editors, "Historical Development of Monoclonal Antibody Therapeutics," Therapeutic Antibodies. Handbook of Experimental Pharmacology, 181, 7 pages (2008).
Christiansen, J and Rajasekaran, A.K., "Biological Impediments to Monoclonal Antibody-based Cancer Immunotherapy," Molecular Cancer Therapeutics, 3(11):1493-1501 (2004).

(56) References Cited

OTHER PUBLICATIONS

Clayton, A. H. A., et al., "Unligated Epidermal Growth Factor Receptor Forms Higher Order Oligomers within Microclusters on A431 Cells That are Sensitive to Tyrosine Kinase Inhibitor Binding," Biochem., 46:4589-4597 (2007).
Curiel, T.J., et al., "Specific Recruitment of Regulatory T Cells in Ovarian Carcinoma Fosters Immune Privilege and Predicts Reduced Survival," Nature Medicine, 10(9):942-949(2004).
Dall'Acqua, W. F., et al., "Increasing the Affinity of a Human IgG1 for the Neonatal Fc Receptor: Biological Consequences," J Immunol., 169:5171-5180 (2002).
Dall'Acqua, W.F., et al., "Modulation of the Effector Functions of a Human IgG1 Through Engineering of its Hinge Region," Journal of Immunology, 177(2):1129-1138(2006).
D'Arena, G., et al., "Regulatory T-cell Number is Increased in Chronic Lymphocytic Leukemia Patients and Correlates With Progressive Disease," Leukemia Research, 35(3):363-368(2011).
Das, D. and Suresh, M. R., "Producing Bispecific and Bifunctional Antibodies," Methods in Molecular Medicine 109:329-346 (2005).
De Gast, G.C., et al., "CD8 T Cell Activation After Intravenous Administration of CD3 X CD19 Bispecific Antibody in Patients With Non-hodgkin Lymphoma," Cancer Immunology, Immunotherapy, 40(6):390-396(1995).
De Vos Van Steenwijk, P.J., et al., "Tumor-infiltrating CD14-positive Myeloid Cells and CD8-positive T-cells Prolong Survival in Patients With Cervical Carcinoma," International Journal of Cancer, 133(12):2884-2894(2013).
Demanet, C., et al., Treatment of murine B Cell lymphoma with bispecific monoclonal antibodies (anti-idiotype xanti-CD3), J Immunol., 147:1091-1097 (1991).
Dillon, T,M., et al., "Structural and Functional Characterization of Disulfide Isoforms of the Human IgG2 Subclass," The Journal of Biological Chemistry, 283(23):16206-16215 (2008).
Drake, C. G., "Combined Immune Checkpoint Blockade," Seminars in Oncology, 42(4):656-662(2015).
Edwards, B. M., et al., "The Remarkable Flexibility of the Human Antibody Repertoire; Isolation of Over One Thousand Different Antibodies to a Single Protein, BLyS," J Mol Biol., 334:103-118 (2003).
El Andaloussi, A., et al., "Prolongation of Survival Following Depletion of CD4+CD25+ Regulatory T Cells in Mice With Experimental Brain Tumors," Journal of Neurosurgery, 105(3):430-437(2006).
English translation of European Patent Application No. 11845786.0, filed Nov. 30, 2011, now European Patent No. 2647707.
English translation of priority Japanese Application No. 2010-266760, filed Nov. 30, 2010, cited by Opponent 3 in opposition case EP2647707 on Mar. 26, 2020 (foreign counterpart case for related U.S. Appl. No. 13/990,088).
European Search Report for European Patent Application No. 18192844.1 dated Dec. 5, 2019.
Fischer, N. and Lé, O., "Bispecific Antibodies: Molecules That Enable Novel Therapeutic Strategies," Pathobiology: Journal of Immunopathology, Molecular and Cellular Biology, 74(1):3-14(2007).
French, J.D., et al., "Tumor-associated Lymphocytes and Increased FoxP3+ Regulatory T Cell Frequency Correlate With More Aggressive Papillary Thyroid Cancer," The Journal of Clinical Endocrinology and Metabolism, 95(5):2325-2333(2010).
Furness, A. J., et al., "Impact of Tumour Microenvironment and Fc Receptors on the Activity of Immunomodulatory Antibodies," Trends in Immunology, 35(7):290-298(2014).
Gajewski, T.F., et al., "Innate and Adaptive Immune Cells in the Tumor Microenvironment," Nature Immunology, 14(10):1014-1022(2013).
Gerber, A.L., et al., "High Expression of FOXP3 in Primary Melanoma is Associated With Tumour Progression," British Journal of Dermatology, 170(1):103-109(2014).
Gobert, M., et al., "Regulatory T Cells Recruited Through CCL22/CCR4 are Selectively Activated in Lymphoid Infiltrates Surrounding Primary Breast Tumors and Lead to an Adverse Clinical Outcome," Cancer Research, 69(5):2000-2009(2009).
Goldstein, M. J., et al., "Adoptive Cell Therapy for Lymphoma With CD4 T Cells Depleted of CD137-expressing Regulatory T Cells," Cancer Research, 72(5):1239-1247(2012).
Graca, L., editor, "The Immune Synapse as a Novel Target for Therapy," Progress in Inflammation Research, 59-61 (2008).
Gunasekaran, K., et al., "Enhancing Antibody Fc Heterodimer Formation Through Electrostatic Steering Effects: Applications to Bispecific Molecules and Monovalent IgG," Journal of Biological Chemistry, 285(25):19637-19646 (2010).
Gura, T., "Systems for Identifying New Drugs are Often Faulty," Science, 278(5340):1041-1042 (1997).
Haagen, I. A., et al., "Evaluation of Fcγ receptor mediated T-cell activation by two purified CD3 x CD19 bispecific monoclonal antibodies with hybrid Fc domains," Therapeutic Immunology 1:279-287 (1994).
Haagen, I. A., et al., "Interaction of human monocyte Fc gamma receptors with rat IgG2b. A new indicator for the Fc gamma RIIa (R-II31) polymorphism," The Journal of Immunology 154:1852-1860 (1995).
Hamid, O and Carvajal, R.D., "Anti-programmed Death-1 and Anti-programmed Death-ligand 1 Antibodies in Cancer Therapy," Expert Opinion on Biological Therapy, 13(6):847-861(2013).
Háusler, S. F. M., et al., "Anti-CD39 and anti-CD73 antibodies A1 and 7G2 improve targeted therapy in ovarian cancer by blocking adenosine-dependent immune evasion," Am J Transl Res., 6(2):129-139 (2014).
Hezareh, M., et al., "Effector Function Activities of a Panel Mutants of a Broadly Neutralizing Antibody against Human Immunodeficiency Virus Type 1," Journal of Virology 75(24):12161-12168 (2001).
Hinton, P.R., et al., "An Engineered Human IgG1 Antibody With Longer Serum Half-life," Journal of Immunology, 176(1):346-356 (2006).
Hoseini, S. S., et al., "Immunotherapy of hepatocellular carcinoma using chimeric antigen receptors and bispecific antibodies," Cancer Letters 399:44-52 (2017).
Hiraoka, N., et al., "Prevalence of FOXP3+ Regulatory T Cells Increases During the Progression of Pancreatic Ductal Adenocarcinoma and its Premalignant Lesions," Clinical Cancer Research, 12(18):5423-5434(2006).
Hornig, N., et al., "Combination of a Bispecific Antibody and Costimulatory Antibody-ligand Fusion Proteins for Targeted Cancer Immunotherapy," Journal of Immunotherapy, 35(5):418-429(2012).
Hornig, N., et al., "Evaluating Combinations of Costimulatory Antibody-ligand Fusion Proteins for Targeted Cancer Immunotherapy," Cancer Immunology, Immunotherapy, 62(8):1369-1380(2013).
Review of InvivoGen—Immunoglobulin G (2011).
Ishiguro, T., et al., "An anti-glypican 3/CD3 bispecific T cell-redirecting antibody for treatment of solid tumors," Sci Transl Med., 9:eaaI4291, 13 pages (2017).
Jacobs, J.F., et al., "Dendritic Cell Vaccination in Combination with anti-CD25 Monoclonal Antibody Treatment: A Phase I/II Study in Metastatic Melanoma Patients," Clinical Cancer Research, 16(20):5067-5078(2010).
Jain R. K., "Barriers to Drug Delivery in Solid Tumors," Scientific American, 271(1):58-65 (1994).
Jefferis, R. and Lund, J., "Interaction sites on human IgG-Fc for FcγR: current models," Immunol Lett., 82:57-65 (2002).
Jure-Kunkel, M., et al., "Synergy Between Chemotherapeutic Agents and CTLA-4 Blockade in Preclinical Tumor Models," Cancer Immunology, Immunotherapy, 62(9):1533-1545(2013).
Kasthuri, R. S., et al., "Role of Tissue Factor in Cancer," J Clin Oncol., 27(29):4834-4838 (2009).
Kawaida, H., et al., "Distribution of CD4(+)CD25 high Regulatory T-cells in Tumor-draining Lymph Nodes in Patients With Gastric Cancer," The Journal of Surgical Research, 124(1):151-157(2005).
Khan, A.R., et al., "Tumor Infiltrating Regulatory T Cells: Tractable Targets for Immunotherapy," International Reviews of Immunology, 29(5):461-484(2010).

(56) References Cited

OTHER PUBLICATIONS

Kim, J., et al., "Anti-CD137 mAb Deletes Both Donor CD4+ and CD8+ T Cells in Acute Graft-versus-host Disease," Immune Network, 11(6):428-430, Korean Association of Immunologists, Korea (Dec. 2011).
King, D. J., "Applications and Engineering of Monoclonal Antibodies," Celltech Therapeutics, 146-147 (2005).
Klein, C., et al., "Progress in Overcoming the Chain Association Issue in Bispecific Heterodimeric IgG Antibodies," mAbs, 4(6):653-663(2012).
Kobayashi, N., et al., "FOXP3+ Regulatory T Cells Affect the Development and Progression of Hepatocarcinogenesis," 13(3):902-911 (2007).
Kono, K., et al., "CD4(+)CD25 high Regulatory T Cells Increase With Tumor Stage in Patients With Gastric and Esophageal Cancers," Cancer Immunology, Immunotherapy, 55(9):1064-1071(2006).
Koristka, S., et al., "Retargeting of Human Regulatory T Cells by Single-chain Bispecific Antibodies," Journal of Immunology, 188(3):1551-1558(2012).
Kufer, P., et al., "A Revival of Bispecific Antibodies," Trends in Biotechnology, 22(5):238-244(2004).
Kumagai et al., "Humanized Bispecific Antibodies That Recognize Lymphocytes and Cancer Cells," Drug Delivery System, 23(5):518-552 (2008).
Kumar, S., et al., "Molecular Cloning and Expression of the Fabs of Human Autoantibodies in *Escherichia coli*," Journal of Biological Chemistry, 275(45):35129-35136 (2000).
Lazar, G.A., et al., "Engineered Antibody Fc Variants With Enhanced Effector Function," Proceedings of the National Academy of Sciences of the United States of America, 103(11):4005-4010(2006).
Little, M., editor, "Recombinant Antibodies for Immunotherapy," Affirmed Therapeutics, 133-134 (2009).
Li, B., et al., "Construction and Characterization of a Humanized Anti-human Cd3 Monoclonal Antibody 1216 With Effective Immunoregulation Functions," Immunology, 116(4):487-498 (2005).
Li, Y., et al., "Phosphorylated Erm is Responsible for Increased T Cell Polarization, Adhesion, and Migration in Patients With Systemic Lupus Erythematosus," Journal of Immunology, 178(3):1938-1947(2007).
Lindhofer, H., et al., "Bispecific Antibodies," Kontermann, R. E Editor, 296-298 (2011).
Link, B. K., et al., " Anti-CD3-Based Bispecific Antibody Designed for Therapy of Human B-Cell Malignancy Can Induce T-Cell Activation by Antigen-Dependent and Antigen-Independent Mechanisms," Int J Cancer, 77:251-256 (1998).
Liotta, F., et al., "Frequency of Regulatory T Cells in Peripheral Blood and in Tumour-infiltrating Lymphocytes Correlates With Poor Prognosis in Renal Cell Carcinoma," BJU International, 107(9):1500-1506(2011).
Liu, R., et al., "Efficient Inhibition of Human B-cell Lymphoma in SCID Mice by Synergistic Antitumor Effect of Human 4-1BB ligand/anti-CD20 Fusion Proteins and Anti-CD3/anti-CD20 Diabodies," Journal of Immunotherapy, 33(5):500-509(2010).
Lloyd, C., et al., "Modelling the human immune response: performance of 10 human antibody repertoire against a broad panel of therapeutically relevant antigens," Protein Eng Des Sel., 22(3):159-168 (2009).
Loffler, A., et al., "A Recombinant Bispecific Single-chain Antibody, CD19 x CD3, Induces Rapid and High Lymphoma-directed Cytotoxicity by Unstimulated T Lymphocytes," Blood, 95(6):2098-2103 (2000).
Mack, M., et al., "A Small Bispecific Antibody Construct Expressed as a Functional Singlechain Molecule With High Tumor Cell Cytotoxicity," Proceedings of the National Academy of Sciences of the United States of America, 92(15):7021-7025 (1995).
Matzku, S. and Stahel, R. A., "Antibodies in Diagnosis and Therapy: Technologies, Mechanisms and Clinical Data" Studies in Medicinal Chemistry, 3:7 (1999).

McDermott, D and Atkins, M., "PD-1 as a Potential Target in Cancer Therapy," Cancer Medicine, 2(5):662-673(2013).
McEarchern, J.A., et al., "Engineered Anti-cd70 Antibody With Multiple Effector Functions Exhibits in Vitro and in Vivo Antitumor Activities," Blood, 109(3):1185-1192(2007).
Melero, I., et al., "Multi-layered Action Mechanisms of CD137 (4-1BB)-targeted Immunotherapies," Trends in Pharmacological Sciences, 29(8):383-390(2008).
Melero, I., et al., "Agonist Antibodies to TNFR Molecules That Costimulate T and NK Cells," Clin Cancer Res., 19(5):1044-1053 (2013).
Merchant, A.M., et al., "An Efficient Route to Human Bispecific IgG," Nature Biotechnology, 16(7):677-681 (1998).
Mezzanzanica, D., et al., "Human Ovarian Carcinoma Lysis by Cytotoxic T Cells Targeted by Bispecific Monoclonal Antibodies: Analysis of the Antibody Components," International Journal of Cancer, 41(4):609-615 (1988).
Milstein, C. and Cuello, A. C., "Hybrid hybridomas and their use in immunohistochemistry," Nature, 305:537-540 (1983).
Molhoj, M., et al., "CD19-/CD3-bispecific Antibodyofthe BiTE Class is Far Superior to Tandem Diabody With Respect to Redirected Tumor Cell Lysis," Molecular Immunology, 44(8):1935-19432007).
Mueller, J. P., et al., "Humanized Porcine VCAM-Specific Monoclonal Antibodies with Chimeric IgG2/G4 Constant Regions Block Human Leukocyte Binding to Porcine Endothelial Cells," Mol Immunol., 34(6):441-452 (1997).
Müller, D., et al., "A Novel Antibody-4-1BBL Fusion Protein for Targeted Costimulation in Cancer Immunotherapy," J Immunother., 31(8):714-722 (2008).
Nakano, K., et al., "Anti-glypican 3 Antibodies Cause Adcc Against Human Hepatocellular Carcinoma Cells," Biochemical and Biophysical Research Communications, 378(2):279-284(2009).
Natsume, A., et al., "Improving Effector Functions of Antibodies for Cancer Treatment: Enhancing ADCC and CDC," Drug Design, Development and Therapy, 3:7-16(2009).
Nelson, D. L. and Cox, M. M., "Principles of Biochemistry," Fifth Edition, Lehninger, Editor, p. 171 (2008).
Nimmerjahn, F and Ravetch, J.V., "Fcgamma Receptors as Regulators of Immune Responses," Nature Reviews, Immunology, 8(1):34-47 (2008).
Nishikawa, W.A., et al., "Perspectives on Clinical Applications of Regulatory T Cells," Inflammation & Immunology, 21(1):66-72 (2013)(with English Translation).
Nitta, T., et al., "Bispecific F(ab')$_2$ monomer prepared with anti-CD3 and anti-tumor monoclonal antibodies is most potent in induction of cytolysis of human T cells," Eur J Immunol., 19:1437-1441 (1989).
Oganesyan, V., et al., "Structural characterization of a human Fc fragment engineered for lack of effector functions," Acta Cryst., D64:700-704 (2008).
Palazón, A., et al., "The HIF-1α Hypoxia Response in Tumor-Infiltrating T Lymphocytes Induces Functional CD137 (4-1BB) for Immunotherapy," Cancer Discov., 2(7):608-623 (2012).
Parren, P. W. H. I., et al., "Induction of T-cell proliferation by recombinant mouse and chimeric mouse/human anti-CD3 monoclonal antibodies," Res Immunol., 142:749-763 (1991).
Pastor, F., et al., "Targeting 4-1BB Costimulation to Disseminated Tumor Lesions With Bispecific Oligonucleotide Aptamers," Molecular Therapy, 19(10):1878-1886(2011).
Paul, W. E., editor, Fundamental Immunology, 3rd Edition, 1993, pp. 292-295 (Year: 1993).
Pavlou, A.K. and Belsey, M.J., "The Therapeutic Antibodies Market to 2008," European Journal of Pharmaceutics and Biopharmaceutics, 59(3):389-396(2005).
Percival-Alwyn, J.L., et al., "Generation of Potent Mouse Monoclonal Antibodies to Self-proteins Using T-cell Epitope "Tags"," mAbs, 7(1):129-137 (2015).
Pere, H., et al., "Comprehensive Analysis of Current Approaches to Inhibit Regulatory T Cells in Cancer," Oncoimmunology, 1(3):326-333(2012).

(56) References Cited

OTHER PUBLICATIONS

Porter, D. L., et al., "Chimeric Antigen Receptor-modified T Cells in Chronic Lymphoid Leukemia," The New England Journal of Medicine, 365(8):725-733(2011).
Postow, M.A., et al., "Nivolumab and Ipilimumab versus Ipilimumab in Untreated Melanoma," The New England Journal of Medicine, 372(21):2006-2017(2015).
Presta, L. G., "Molecular Engineering and Design of Therapeutic Antibodies," Current Opinion in Immunology, 20(4):460-470(2008).
Ravetch, J. V., et al., "Fc Receptors," Annu Rev Immunol., 9:457-492 (1991).
Reichert, J.M., et al., "Monoclonal Antibody Successes in the Clinic," Nature Biotechnology, 23(9):1073-1078(2005).
Remer, M., et al., "Abstract B046: Therapeutic Mechanisms of Anti-4-1bb Antibodies in Cancer: Agonism Versus Regulatory T Cell Depletion," Translating Science into Survival, 4(11 Supl) (2016).
Ridgway, J.B., et al., "'knobs-into-holes' Engineering of Antibody Ch3 Domains for Heavy Chain Heterodimerization," Protein Engineering, 9(7):617-621 (1996).
Routledge, E. G., et al., "A humanized monovalent CD3 antibody which can activate homologous complement," Eur J Immunol., 21:2717-2725 (1991).
Rudikoff, S., et al., "Single amino acid substitution altering antigen-binding specificity," Proc Natl Acad Sci. USA, 79(6):1979-1983 (1982).
Ruf, P., and Lindhofer, H., "Induction of a Long-lasting Antitumor Immunity by a Trifunctional Bispecific Antibody," Blood, 98(8):2526-2534 (2001).
Salfeld, J. G., "Isotype Selection in Antibody Engineering," Nature Biotechnology, 25(12):1369-1372(2007).
Salnikov, A. V., et al., "Targeting of cancer stem cell marker EpCAM by bispecific antibody EpCAMxCD3 inhibits pancreatic carcinoma," J Cell Mol Med., 13(9B):4023-4033 (2009).
Sandin, L. C., "Local CTLA4 blockade Effectively Restrains Experimental Pancreatic Adenocarcinoma Growth in Vivo," Oncoimmunology, 3:e27614 (2014).
Sato, E., et al., "Intraepithelial Cd8+ Tumor-infiltrating Lymphocytes and a High Cd8+/regulatory T Cell Ratio are Associated With Favorable Prognosis in Ovarian Cancer," Proc Natl Acad Sci. USA, 102(51):18538-18543(2005).
Schlereth, B., et al., "T-cell Activation and B-cell Depletion in Chimpanzees Treated With a Bispecific Anti-cd19/anti-cd3 Single-chain Antibody Construct," Cancer Immunology, Immunotherapy, 55(5):503-514(2006).
Sebastian, M., et al., "Treatment of Non-small Cell Lung Cancer Patients With the Trifunctional Monoclonal Antibody Catumaxomab (Anti-epcam X Anti-cd3): a Phase I Study," Cancer Immunology, Immunotherapy, 56(10):1637-1644(2007).
Segal, D. M. and Bast, B. J. E. G., "Production of Bispecific Antibodies," Current Protocols in Immunology, 2.13.1-2.13.16 (1995).
Segal, D. M., et al., "Bispecific Antibodies in Cancer Therapy," Current Opinion in Immunology, 11:558-562 (1999).
Seimetz, D., et al., "Development and Approval of the Trifunctional Antibody Catumaxomab (Anti-epcam X Anti-cd3) as a Targeted Cancer Immunotherapy," Cancer Treatment Reviews, 36(6):458-467 (2010).
Selby, M.J., et al., "Anti-CTLA-4 Antibodies of IgG2a Isotype Enhance Antitumor Activity Through Reduction of Intratumoral Regulatory T Cells," Cancer Immunology Research, 1(1):32-42 (2013).
Sequence Alignments cited in Opposition of European Patent No. 2647707.
Shields, R. L., et al., "High Resolution Mapping of the Binding Site on Human IgG1 for Fc Gamma RI, Fc Gamma RIII, Fc Gamma RIII, and FcRn and Design of Igg1 Variants With Improved Binding to the Fc Gamma R," The Journal of Biological Chemistry, 276(9):6591-6604 (2001).

Simpson, T.R., et al., "Fc-dependent Depletion of Tumor-infiltrating Regulatory T Cells Codefines the Efficacy of Anti-CTLA-4 Therapy Against Melanoma," The Journal of Experimental Medicine, 210(9):1695-1710 (2013).
Smith-Gill, S. J., et al., "Contributions of Immunoglobulin Heavy and Light Chains to Antibody Specificity for Lysozyme and Two Haptens," Journal of Immunology, 139(12):4135-4144 (1987).
Son, J. H., et al., "Humanization of Agonistic Anti-human 4-1BB Monoclonal Antibody Using a Phage-displayed Combinatorial Library," Journal of Immunological Methods, 286(1-2):187-201 (2004).
Song, M. K., et al., "Light Chain of Natural Antibody Plays a Dominant Role in Protein Antigen Binding," Biochemical and Biophysical Research Communications, 268(2):390-394 (2000).
Sporn et al., "Chemoprevention of Cancer," Carcinogenesis, 21(3):525-530 (2000).
Staerz, U. D., and Bevin, M. J., "Hybrid Hybridoma Producing a Bispecific Monoclonal Antibody That Can Focus Effector T-cell Activity," 83(5):1453-1457 (1986).
Staerz, U. D., et al., "Hybrid Antibodies Can Target Sites for Attack by T Cells," Nature, 314(6012):628-631 (1985).
Strauss, G., et al., "Without Prior Stimulation, Tumor-associated Lymphocytes from Malignant Effusions Lyse Autologous Tumor Cells in the Presence of Bispecific Antibody HEA125xOKT3[1]," Clin Cancer Res., 5:171-180 (1999).
Stroehlein, M.A., et al., "Induction of Anti-tumor Immunity by Trifunctional Antibodies in Patients With Peritoneal Carcinomatosis," Journal of Experimental & Clinical Cancer Research, 28:18 (2009).
Strohl, W. R., "Optimization of Fc-mediated effector functions of monoclonal antibodies," Curr Opin Biotechnol., 20:685-691 (2009).
Sugiyama, D., et al., "Anti-CCR4 Mab Selectively Depletes Effector-type FoxP3+CD4+ Regulatory T Cells, Evoking Antitumor Immune Responses in Humans," Proceedings of the National Academy of Sciences of the United States of America, 110(44):17945-17950 (2013).
Suzuki, "Research and Development of Antibody Pharmaceuticals," NIBS Letter 56(4):45-51 (2010), with English translation.
Teerinen, T., et al., "Structure-based Stability Engineering of the Mouse IgG1 Fab Fragment by Modifying Constant Domains," Journal of Molecular Biology, 361(4):687-697 (2006).
Teschner, D., et al., "In Vitro Stimulation and Expansion of Human Tumour-reactive CD8+ Cytotoxic T Lymphocytes by Anti-CD3/CD28/CD137 Magnetic Beads," Scandinavian Journal of Immunology, 74(2):155-164 (2011).
Thakur, A and Lum, L.G, "Cancer Therapy With Bispecific Antibodies: Clinical Experience," Current Opinion in Molecular Therapeutics, 12(3):340-349 (2010).
Topp, E. M., et al., "Antibody transport in cultured tumor cell layers," Journal of Controlled Release, 53(1-3):15-23 (1998).
Tosti, G., et al., "Anti-cytotoxic T Lymphocyte Antigen-4 Antibodies in Melanoma," Clinical, Cosmetic and Investigational Dermatology, 6:245-256 (2013).
Vajdos, F.F et al.,, "Comprehensive Functional Maps of the Antigen-binding Site of an Anti-ErbB2 Antibody Obtained With Shotgun Scanning Mutagenesis," Journal of Molecular Biology, 320(2):415-428 (2002).
Van Loghem, E., et al., "Staphylococcal Protein A and Human IGG Subclasses and Allotypes," Scandinavian Journal of Immunology, 15(3):275-278 (1982).
Viardot, et al., "Treatment of Patients With Non-Hodgkin Lymphoma With CD19/CD3 Bispecific Antibody Blinautumomab (MTI03)," Internet Citation, Dec. 6, 2010 (Dec. 6, 2010), 1 page (http://www.bloodjournal.org/content/116/21/2880?sso-checked=true).
Vinay, D.S and Kwon, B.S., "4-1BB Signaling Beyond T Cells," Cellular & Molecular Immunology, 8(4):281-284 (2011).
Wainwright, D.A, et al., "Targeting Tregs in Malignant Brain Cancer: Overcoming IDO," Frontiers in Immunology, 4:116 (2013).
Wang, X.B., et al., "A New Recombinant Single Chain Trispecific Antibody Recruits T Lymphocytes to Kill Cea (Carcinoma Embryonic Antigen) Positive Tumor Cells in Vitro Efficiently," Journal of Biochemistry, 135(4):555-565 (2004).
Wang, Y.Y., et al., "The Variation of CD4+CD25+ Regulatory T Cells in the Periphery Blood and Tumor Microenvironment of

(56) References Cited

OTHER PUBLICATIONS

Non-small Cell Lung Cancer Patients and the Downregulation Effects Induced by CpG ODN," Targeted Oncology, 6(3):147-154(2011).
Ward, E. S., et al., "Binding Activities of a Repertoire of Single Immunoglobulin Variable Domains Secreted From *Escherichia Coli*," Nature, 341(6242):544-546 (1989).
Weiner, L.M., et al., "Monoclonal Antibodies: Versatile Platforms for Cancer Immunotherapy," Nature Reviews. Immunology, 10(5):317-327 (2010).
Wherry, E.J., "T Cell Exhaustion," Nature Immunology, 12(6):492-499 (2011).
Wines, B. D., et al., "The IgG Fc Contains Distinct Fc Receptor (FcR) Binding Sites: The Leukocyte Receptors FcvRI and FcvRIIa Bind to a Region in the Fc Distinct from That Recognized by Neonatal FcR and Protein A," Journal of Immunology, 164(10):5313-5318 (2000).
Wing et al., "Mechanism of First-Dose Cytokine-Release Syndrome by CampATH 1-H: Involvement of CD16 (FcyRIII) and CDIIa!CD18 (LFA-1) on NK Cells," Journal of Clinical Investigation, 98(12):2819-2826 (1996).
Wolf, E., et al., "BiTEs: Bispecific Antibody Constructs With Unique Anti-tumor Activity," Drug Discovery Today, 10(18):1237-1244 (2005).
Xu, D., et al., "In Vitro Characterization of Five Humanized OKT3 Effector Function Variant Antibodies," Cellular Immunol., 200:16-26 (2000).
Yang, Z. M., et al., "Anti-CD3 scFv-B7.1 Fusion Protein Expressed on the Surface of HeLa Cells Provokes Potent T-lymphocyte Activation and Cytotoxicity," Biochemistry and Cell Biology, 85(2):196-202 (2007).
Yang, Z.Z., et al., "Attenuation of CD8(+) T-cell function by CD4(+)CD25(+) regulatory T cells in B-cell non-Hodgkin's lymphoma," Cancer Research, 66(20):10145-10152 (2006).
Yang, Z.Z., et al., "Intratumoral CD4+CD25+ Regulatory T-cell-mediated Suppression of Infiltrating CD4+ T Cells in B-cell Non-hodgkin Lymphoma," Blood, 107(9):3639-3646 (2006).
Yano, H., et al., "Ipilimumab augments antitumor activity of bispecific antibody-armed T cells," Journal of Translational Medicine 12(1):191 (2014), 11 pages.
Yonezawa, A., et al., "Boosting Cancer Immunotherapy with Anti-CD137 Antibody Therapy," Clinical Cancer Research, 21(14):3113-3120 (2015).
Yu, P., et al., "Simultaneous Inhibition of Two Regulatory T-cell Subsets Enhanced Interleukin-15 Efficacy in a Prostate Tumor Model," Proceedings of the National Academy of Sciences of the United States of America, 109(16):6187-6192 (2012).
Zalevsky, J, et al., "The Impact of Fc Engineering on an Anti-cd19 Antibody: Increased Fcgamma Receptor Affinity Enhances B-cell Clearing in Nonhuman Primates," Blood, 113(16):3735-3743 (2009).
Zeidler, R., et al., "Simultaneous Activation of T Cells and Accessory Cells by a New Class of Intact Bispecific Antibody Results in Efficient Tumor Cell Killing," Journal of Immunology, 163(3):1246-1252 (1999).
Zeidler, R., et al., "The Fc-region of a New Class of Intact Bispecific Antibody Mediates Activation of Accessory Cells and NK Cells and Induces Direct Phagocytosis of Tumour Cells," British Journal of Cancer, 83(2):261-266 (2000).
Zheng, J., et al., "YB-1 Immunization Combined With Regulatory T-cell Depletion Induces Specific T-cell Responses That Protect Against Neuroblastoma in the Early Stage," Acta Biochimica Et Biophysica Sinica, 44(12):1006-1014 (2012).
U.S. Appl. No. 13/990,088, 371(c) date Dec. 19, 2013, Nezu, J., et al., related application.
U.S. Appl. No. 15/578,931, 371(c) date Dec. 1, 2017, Taniguchi, K., et al., related application.
U.S. Appl. No. 15/310,162, 371(c) date Nov. 10, 2016, Igawa, T., et al., related application.
U.S. Appl. No. 15/776,541, 371(c) date May 16, 2018, Igawa, T., et al., related application.
U.S. Appl. No. 15/776,587, 371(c) date May 16, 2018, Tsunenari, T., et al., related application.
U.S. Appl. No. 09/166,750, filed Oct. 5, 1998, Whitlow, M. D., et al.
U.S. Appl. No. 11/572,634, 371 (c) date Jan. 25, 2007, Allan, B., et al.
U.S. Appl. No. 11/879,279, filed Jul. 17, 2007, Kink, J. A., et al.
U.S. Appl. No. 11/520,121, filed Sep. 13, 2006, Presta, L.
U.S. Appl. No. 12/352,632, filed Jan. 13, 2009, Qu, Z., et al.
U.S. Appl. No. 12/896,610, filed Oct. 1, 2010, Lazar, G. A., et al.
U.S. Appl. No. 12/757,801, filed Apr. 9, 2010, McDonagh, C., et al.
U.S. Appl. No. 13/058,492, 371(c) date Feb. 10, 2011, Thudium, K. B., et al.
U.S. Appl. No. 12/524,215, 371(c) date Jul. 23, 2009, Shitara, K., et al.
U.S. Appl. No. 13/502,618, 371(c) date Jul. 9, 2012, McKee, C., et al.
U.S. Appl. No. 172,140, filed Dec. 22, 1993, Bally, M. B., et al.
U.S. Appl. No. 479,752, filed Jun. 7, 1995, Winter, G. P., et al.
U.S. Appl. No. 478,825, filed Jun. 7, 1995, Winter, G. P., et al.
U.S. Appl. No. 10/143,437, filed May 10, 2002, Arathoon, W. R., et al.
U.S. Appl. No. 10/348,651, filed Jan. 21, 2003, Jung, G.
U.S. Appl. No. 12/811,207, 371 (c) date Jun. 29, 2010, Kannan, G., et al.
U.S. Appl. No. 11/728,048, filed Mar. 23, 2007, Davis, J. H., et al.
U.S. Appl. No. 12/224,010, 371(c) date Mar. 31, 2010, Lindhofer, H.
U.S. Appl. No. 12/768,650, filed Apr. 27, 2010, Gurney, A. L., et al.
U.S. Appl. No. 13/642,253, 371(c) date Oct. 24, 2012, Labrijn, A. F., et al.
U.S. Appl. No. 12/593,759, 371(c) date Jan. 6, 2010, Schuurman, J., et al.
U.S. Appl. No. 13/257,112, 371(c) date Nov. 22, 2011, Igawa, T., et al.
U.S. Appl. No. 13/697,683, 371(c) date Jan. 17, 2013, Ho, W.-H., et al.
U.S. Appl. No. 13/092,708, filed Apr. 22, 2011, Scheer, J., et al.
U.S. Appl. No. 10/370,749, filed Feb. 20, 2003, Watkins, J. D., et al.
U.S. Appl. No. 10/982,470, filed Nov. 5, 2004, Presta, L.
U.S. Appl. No. 11/396,495, filed Mar. 31, 2006, Lazar, G. A., et al.
U.S. Appl. No. 11/332,619, filed Jan. 12, 2006, Moore, G. L., et al.
U.S. Appl. No. 12/295,039, 371(c) date Jan. 20, 2009, Igawa, T., et al.
U.S. Appl. No. 13/289,934, filed Nov. 4, 2011, Von Kreudenstein, T. S., et al.
U.S. Appl. No. 13/591,028, filed Aug. 21, 2012, Auer, J., et al.
U.S. Appl. No. 14/217,166, filed Mar. 17, 2014, Chu, S., et al.
U.S. Appl. No. 15/012,414, filed Feb. 1, 2016, Sharp, L. L., et al.
U.S. Appl. No. 13/638,223, 371(c) date Jan. 17, 2013, Kufer, P., et al.
U.S. Appl. No. 13/966,450, filed Aug. 14, 2013, Chang, C.-H., et al.
U.S. Appl. No. 14/128,461, 371(c) date Aug. 13, 2014, Zhu, Y., et al.
U.S. Appl. No. 14/351,654, 371(c) date Apr. 14, 2014, Kuramochi, T., et al.
U.S. Appl. No. 14/574,132, filed Dec. 17, 2014, Chen, X., et al.
U.S. Appl. No. 15/110,414, 371(c) date Jul. 8, 2016, Van Den Brink, E. N., et al.
U.S. Appl. No. 15/302,439, 371(c) date, Oct. 6, 2016, Igawa, T., et al.
Bi, Y., et al., "Treatment of hepatocellular carcinoma with a GPC3-targeted bispecific T cell engager," Oncotarget, 8(32):52866-52876 (2017).
Harada, A., et al., "In vitro toxicological support to establish specification limit for anti-CD3 monospecific impurity in a bispecific T cell engager drug, ERY974," Toxicology in Vitro, 66:104841 (2020), 7 pages.
Ishiguro, T., et al., "An anti-glypican 3/CD3 bispecific T cell-redirecting antibody for treatment of solid tumors," Sci Transl Med., 9:eaal4291 (2017), 13 pages.
Iwata, Y., et al., "Daily ascending dosing in cynomolgus monkeys to mitigate cytokine release syndrome induced by ERY22, surrogate

(56) References Cited

OTHER PUBLICATIONS for T-cell redirecting bispecific antibody ERY974 for cancer immunotherapy," Toxicology and Applied Pharmacology, 379:114657 (2019), 9 pages.

Lejeune, M., et al., "Bispecific, T-Cell-Recruiting Antibodies in B-Cell Malignancies," Frontiers in Immunology, 11(762) (2020), 20 pages.

Runcie, K., et al., "Bi-specific and tri-specific antibodies—the next big thing in solid tumor therapeutics," Molecular Medicine, 24:50 (2018), 15 pages.

Shiraiwa, H., et al., "Engineering a bispecific antibody with a common light chain: Identification and optimization of an anti-CD3 epsilon and anti-GPC3 bispecific antibody, ERY974," Methods, 154:10-20 (2019).

Szoor, A., et al., "T Cell-Activating Mesenchymal Stem Cells as a Biotherapeutic for HCC," Molecular Therapy: Oncolytics, 6:69-79 (2017).

Waaijer, S. J. H., et al., "Preclinical PET imaging of bispecific antibody ERY974 targeting CD3 and glypican 3 reveals that tumor uptake correlates to T cell infiltrate," Journal for ImmunoTherapy of Cancer, 8:e000548 (2020), 10 pages.

Yu, L. and Wang, J., "T cell-redirecting bispecific antibodies in cancer immunotherapy: recent advances," Journal of Cancer Research and Clinical Oncology, 145:941-956 (2019).

Yu, L., et al., "A novel targeted GPC3/CD3 bispecific antibody for the treatment hepatocellular carcinoma," Cancer Biology & Therapy, 21(7):597-603 (2020).

Baeuerle, P. A., et al., "BITE: Teaching antibodies to engage T-cells for cancer therapy," Curr Opino Mol Ther., 11(1):22-30 (2009), submitted by Opponent 2 to European Patent Office on Feb. 18, 2021 in Opposition proceedings of EP2647707.

Beckman, R. A., et al., "Antibody Constructs in Cancer Therapy," Cancer, 189:170-179 (2007).

Bolt, S., et al., "The generation of a humanized, non-mitogenic CD3 monoclonal antibody which retains in vitro immunosuppressive properties," Eur J Immunol., 23:403-411 (1993), submitted by Opponents to European Patent Office in Opposition proceedings of EP2647707, EPO Communication dated Jan. 20, 2021.

Brezski, R. J., et al., "The Origins, Specificity, and Potential Biological Relevance of Human Anti-IgG Hinge Autoantibodies," The Scientific World Journal, 11:1153-1167 (2011).

Brischwein, K., et al., "MT110: A novel bispecific single-chain antibody construct with high efficacy in eradicating established tumors," Mol Immunol., 43:1129-1143 (2006), submitted by Opponent 2 to European Patent Office on Feb. 18, 2021 in Opposition proceedings of EP2647707.

Bugelski, P. J., "Monoclonal antibody-induced cytokine-release syndrome," Expert Rev Clin Immunol., 5(5):499-521 (2009), submitted by Opponents to European Patent Office in Opposition proceedings of EP2647707, EPO Communication dated Jan. 20, 2021.

Carpenter, P. A., et al., "Non-Fc Receptor-Binding Humanized Anti-CD3 Antibodies Induce Apoptosis of Activated Human T Cells," J Immunol., 165:6205-6213 (2000).

Carter, P., "Bispecifc human IgG by design," J Immunol Meth., 248(1-2):7-15 (2001) submitted by Opponents to European Patent Office in Opposition proceedings of EP2647707, EPO Communication dated Jan. 20, 2021.

Carter, P. J., "Potent antibody therapeutics by design," Nat Rev Immunol., 6:343-357 (2006), submitted by Opponents to European Patent Office in Opposition proceedings of EP2647707, EPO Communication dated Jan. 20, 2021.

Céspedes, M., et al., "Mouse models in oncogenesis and cancer therapy," Clin Transl Oncol., 8(5):318-329 (2006).

Dennis, C., "Cancer: Off by a whisker," Nature, 442(7104):739-741 (2006).

European Patent Office Preliminary Decision in Opposition of EP2647707 dated May 13, 2020, 23 pages.

Feucht, J., et al., "T-cell responses against CD19+ pediatric acute lymphoblastic leukemia mediated by bispecific T-cell engager (BiTE) are regulated contrarily by PD-L1 and CD80/CD86 on leukemic blasts," Oncotarget, 7(47):76902-76919 (2016).

Final Office Action dated Jan. 23, 2020 in U.S. Appl. No. 15/578,931, filed Dec. 1, 2017, Taniguchi et al.

Fujimori, K., et al., "A Modeling Analysis of Monoclonal Antibody Percolation Through Tumors: A Binding-Site Barrier," J Nucl Med., 31:1191-1198 (1990).

Hammond, S. A., et al., "Selective Targeting and Potent Control of Tumor Growth Using an EphA2/CD3-Bispecific Single-Chain Antibody Construct," Cancer Res., 67(8):3927-3935 (2007), submitted by Opponent 2 to European Patent Office on Feb. 18, 2021 in Opposition proceedings of EP2647707.

Huang, C., Jr., et al., "Recombinant immunotherapeutics: current state and perspectives regarding the feasibility and market," Appl Microbiol Biotechnol., 87:401-410 (2010).

Köhnke, T., et al., "Increase of PD-L1 expressing B-precursor All cells in a patient resistant to the CD19/CD3-bispecific T cell engager antibody blinatumomab," J Hematol Oncol., 8:111 (2015).

Kontermann, R. E., "Recombinant bispecific antibodies for cancer therapy," Acta Pharmacologica Sinica, 26(1):1-9 (2005), submitted by Opponents to European Patent Office in Opposition proceedings of EP2647707, EPO Communication dated Jan. 20, 2021.

Kontermann, R. E., "Strategies to Extend Plasma Half-Lives of Recombinant Antibodies," BioDrugs, 23(2):93-109 (2009), submitted by Opponent 2 to European Patent Office on Feb. 18, 2021 in Opposition proceedings of EP2647707.

Lutterbuese, R., et al., "Potent tumor killing and inhibition of tumor growth by CEA/CD3-bispecific single chain antibodies that are resistant to inhibition by soluble CEA," Proc Am Assoc Cancer Res., 98:abstract 4106 (2007), submitted by Opponent 2 to European Patent Office on Feb. 18, 2021 in Opposition proceedings of EP2647707.

Lutterbuese, R., et al., "Conversion of Cetuximab and Trastuzumab into T cell-engaging BiTE antibodies creates novel drug candidates with superior anti-tumor activity," Proc Am Assoc Cancer Res., 99:abstract 2402 (2008), submitted by Opponent 2 to European Patent Office on Feb. 18, 2021 in Opposition proceedings of EP2647707.

Representative abstracts showing long-term administration of a variety of anti-cancer antibodies in the prior art, submitted by Opponents to European Patent Office in Opposition proceedings of EP2647707, EPO Communication dated Jan. 20, 2021.

Rother, R. P., et al., "Discovery and development of the complement inhibitor eculizumab for the treatment of paroxysmal nocturnal hemoglobinuria," Nature Biotechnol., 25(11):1256-1264 (2007), submitted by Opponents to European Patent Office in Opposition proceedings of EP2647707, EPO Communication dated Jan. 20, 2021.

Rudnick, S. I. and Adams, G. P., "Affinity and Avidity in Antibody-Based Tumor Targeting," Cancer Biother Radiopharm., 24(2):155-161 (2009).

Saunders, K. O., "Conceptual Approaches to Modulating Antibody Effector Functions and Circulation Half-Life," 10(1296):1-20 (2019)), submitted by Opponents to European Patent Office in Opposition proceedings of EP2647707, EPO Communication dated Jan. 20, 2021.

Schneider, M. A., et al., "In vitro and in vivo properties of a dimeric bispecific single-chain antibody IgG-fusion protein for depletion of CCR2+ target cells in mice," Eur J Immunol., 35:987-995 (2005).

Sequence alignments (comparison of heavy chain constant region), submitted to European Patent Office on Dec. 23, 2020 for Opposition in EP2647707.

Talmadge, J. E., et al., "Murine Models to Evaluate Novel and Conventional Therapeutic Strategies for Cancer," Am J Pathol., 170(3):793-804 (2007).

Thomas, A. K., et al., "A Cell-Based Artificial Antigen-Presenting Cell Coated with Anti-CD3 and CD28 Antibodies Enables Rapid Expansion and Long-Term Growth of CD4 T Lymphocytes," Clin Immunol., 105(3):259-272 (2002), submitted by Opponents to European Patent Office in Opposition proceedings of EP2647707, EPO Communication dated Jan. 20, 2021.

(56) References Cited

OTHER PUBLICATIONS

Thurber, G. M., et al., "Antibody tumor penetration: Transport opposed by systemic and antigen-mediated clearance," Adv Drug Deliv Rev., 60:1421-1434 (2008).
Voskoglou-Nomikos, T., et al., "Clinical Predictive Value of the in Vitro Cell Line, Human Xenograft, and Mouse Allograft Preclinical Cancer Models," Clin Cancer Res., 9:4227-4239 (2003).
Weiner, G. J., et al., "The Role of T Cell Activation in Anti-CD3 x Antitumor Bispecific Antibody Therapy," J Immunol., 152:2385-2392 (1994), submitted by Opponents to European Patent Office in Opposition proceedings of EP2647707, EPO Communication dated Jan. 20, 2021.
Witte, L., et al., "Monoclonal antibodies targeting the VEGF receptor-2 (Flk1/KDR) as an anti-angiogenic therapeutic strategy," Cancer Metastasis Rev., 17:155-161 (1998).
Yu, L., et al., "Interaction between Bevacizumab and Murine VEGF-A: A Reassessment," Invest Ophthalmol Vis Sci., 49:522-527 (2008).
Zhao, X., et al., "Targeting CD37-positive lymphoid malignancies with a novel engineered small modular immunopharmaceutical," Blood, 110:2569-2577 (2007), submitted by Opponents to European Patent Office in Opposition proceedings of EP2647707, EPO Communication dated Jan. 20, 2021.
U.S. Appl. No. 305,856, filed Sep. 14, 1994, Wong et al.
U.S. Appl. No. 988,925, 371(c) date Mar. 9, 1993, Bolt, S. L., et al.
U.S. Appl. No. 08/458,462, filed Jun. 2, 1995, Bluestone, J. A.
U.S. Appl. No. 10/543,323, 371 (c) date Jul. 25, 2005, Hongo et al.
U.S. Appl. No. 11/145,131, filed Jun. 3, 2005, Mach et al.
U.S. Appl. No. 11/579,190, 371(c) date Sep. 18, 2007, Moore et al.
U.S. Appl. No. 11/636,655, filed Dec. 11, 2006, Bolt et al.
U.S. Appl. No. 11/765,353, filed Jun. 19, 2007, Lazar et al.
U.S. Appl. No. 12/866,149, 371(c) date Nov. 22, 2010, Korman et al.
U.S. Appl. No. 13/122,242, 371(c) date Jul. 14, 2011, Kufer et al.
U.S. Appl. No. 13/371,379, filed Feb. 10, 2012, Hilbert.
U.S. Appl. No. 16/083,975, 371 (c) date Sep. 11, 2018, Kinoshita et al.
Baudler, S., et al., "Insulin-Like Growth Factor-1 Controls Type 2 T Cell-Independent B Cell Response," J Immunol., 174:5516-5525 (2005).
Hessell, A. J., et al., "Fc receptor but not complement binding is important in antibody protection against HIV," Nature, 449:101-104 (2007).
International Search Report for PCT/JP2018/048409 dated Mar. 26, 2019, 4 pages.
Kraft, S. and Bieber, T., "FcεRI-Mediated Activation of Transcription Factors in Antigen-Presenting Cells," Int Arch Allergy Immunol., 125:9-15 (2001).
Lutterbuese, R., et al., "T cell-engaging BiTE antibodies specific for EGFR potently eliminate KRAS- and BRAF-mutated colorectal cancer cells," PNAS, 107(28):12605-12610 (2010).
Marmé, A., et al., "Intraperitoneal Bispecific Antibody (HEA125XOKT3) Therapy Inhibits Malignant Ascites Production in Advanced Ovarian Carcinoma," Int J Cancer, 101:183-189 (2002).
U.S. Appl. No. 12/823,838, filed Jun. 25, 2010, Davis et al.
U.S. Appl. No. 13/582,073, 371(c) date Dec. 20, 2012, Kuramochi et al.
U.S. Appl. No. 14/210,178, filed Mar. 13, 2014, Borges et al.
U.S. Appl. No. 15/743,248, 371 (c) date Jan. 9, 2018, Jishage et al.
U.S. Appl. No. 16/099,341,371 (c) date Nov. 6, 2018, Teranishi et al.
U.S. Appl. No. 16/412,701, filed May 15, 2019, Adams et al.
U.S. Appl. No. 16/692,676, filed Nov. 22, 2019, Kuramochi et al.
U.S. Appl. No. 16/936,575, filed Jul. 23, 2020, Teranishi et al.
U.S. Appl. No. 17/367,909, filed Jul. 6, 2021, Nezu et al., related application.
U.S. Appl. No. 17/367,909, filed Jul. 6, 2021, Nezu et al.
Berenbaum, M. C., et al., "Synergy, additivism and antagonism in immunosuppression," Clin exp. Immunol., 28:1-18 (1977).
Bremer, E., "Targeting of the Tumor Necrosis Factor Receptor Superfamily for Cancer Immunotherapy," ISRN Oncol., 2013:371854 (2013).
Gilboa, E., et al., "Use of Oligonucleotide Aptamer Ligands to Modulate the Function of Immune Receptors," Clin Cancer Res., 19(5):1054-1062 (2013).
Hogarth, P. M. and Pietersz, G. A., "Fc receptor-targeted therapies for the treatment of inflammation, cancer and beyond," Nat Rev Drug Discov., 11:311-331 (2012).
Houtenbos, H., et al., "The novel bispecific diabody aCD40/aCD28 strengthens leukaemic dendritic cell-induced T-cell reactivity," Br J Haematol., 142:273-283 (2008).
International Application No. PCT/CN2013/090923 filed Dec. 30, 2013.
Li, F. and Ravetch, J. V., "Apoptotic and antitumor activity of death receptor antibodies require inhibitory Fcγ receptor engagement," PNAS, 109(27):10966-10971 (2012).
Mezzanzanica, D., et al., "Retargeting of human lymphocytes against human ovarian carcinoma cells by bispecific antibodies: from laboratory to clinic," Int J Clin Lab Res., 21:159-164(1991).
Presta, L. G., "Engineering of therapeutic antibodies to minimize immunogenicity and optimize function," Adv Drug Deliv Rev., 58:640-656(2006).
Rath, T., et al., "Fc-fusion proteins and FcRn: structural insights for longer-lasting and more effective therapeutics," Crit Rev Biotechnol., 35(2):235-254 (2015).
Richman, L. P. and Vonderheide, R. H., "Role of Crosslinking for Agonistic CD40 Monoclonal Antibodies as Immune Therapy of Cancer," Cancer Immunol Res., 2(1):19-26 (2014).
Went, P. T., et al., "Frequence EpCam Protein Expression in Human Carcinomas," Hum Pathol., 35(1):122-128 (2004).
Weon, J. L. and Potts, P. R., "The MAGE protein family and cancer," Curr Opin Cell Biol., 37:1-8 (2015).

\* cited by examiner

| Sample name | | Full length | ELISA color development level | | | | | | | |
|---|---|---|---|---|---|---|---|---|---|---|
| | | | CRD1 | CRD1-3 | CRD1-2 | CRD2-4 | CRD2-3 | CRD3-4 | Non |
| Control | M | | 2.123 | 0.093 | 0.067 | 0.085 | 0.863 | 0.081 | 2.258 | 0.055 |
| Control | B | | 2.674 | 1.75 | 2.326 | 2.584 | 0.097 | 0.089 | 0.074 | 0.049 |
| R1 | BB_BBNM001H01-P253/BBNM001_L_01-lam | 1.795 | 0.1235 | 0.473 | 0.865 | 0.0935 | 0.1165 | 0.0875 | 0.065 |
| R2 | BB_BBNM002H01-P253/BBNM002_L_01-lam | 0.2055 | 0.226 | 0.2255 | 0.2015 | 0.1505 | 0.19 | 0.11 | 0.202 |
| R3 | BB_BBNM003H01-P253/BBNM003_L_01-lam | 2.058 | 0.103 | 1.1225 | 1.737 | 0.0875 | 0.0995 | 0.077 | 0.061 |
| R4 | BB_BBNM004H01-P253/BBNM004_L_01-lam | 1.8905 | 0.0635 | 0.7795 | 1.4945 | 0.065 | 0.0585 | 0.056 | 0.051 |
| R5 | BB_BBNM005H01-P253/BBNM005_L_01-lam | 1.8775 | 0.2775 | 1.361 | 1.7045 | 0.25 | 0.274 | 0.161 | 0.216 |
| R6 | BB_BBSM001H01-P253/BBSM001_L_01-ko | 2.157 | 0.42 | 2.3015 | 0.4015 | 2.3375 | 2.5565 | 2.7345 | 0.165 |
| R7 | BB_BBSM002H01-P253/BBSM002_L_01-ko | 1.9165 | 0.61 | 2.2285 | 0.814 | 2.1895 | 2.516 | 2.63 | 0.4435 |
| R8 | BB_BBSM003H01-P253/BBSM003_L_01-ko | 2.088 | 0.738 | 2.254 | 0.5805 | 2.232 | 2.422 | 2.517 | 1.114 |
| R9 | BB_BBSM004H01-P253/BBSM004_L_01-ko | 1.9005 | 1.147 | 2.202 | 0.996 | 2.1185 | 2.6105 | 2.608 | 1.4935 |
| R10 | BB_BBSM005H01-P253/BBSM005_L_01-ko | 2.5885 | 0.211 | 2.464 | 0.222 | 2.4555 | 2.636 | 2.7475 | 0.101 |
| R11 | BB_BBSM006H01-P253/BBSM006_L_01-ko | 2.058 | 1.8175 | 2.4485 | 1.6925 | 2.297 | 2.73 | 2.8825 | 2.0265 |
| R12 | BB_BBSM007H01-P253/BBSM007_L_01-ko | 2.1665 | 1.152 | 2.5955 | 1.127 | 2.3475 | 2.707 | 2.9035 | 1.956 |
| R13 | BB_BBSM004H02-P253/BBSM004_L_02-ko | 0.4745 | 0.6005 | 0.7875 | 0.45 | 0.4545 | 0.555 | 0.2595 | 1.146 |
| R14 | BB_BBSM010H01-P253/BBSM010_L_01-ko | 1.9685 | 1.6375 | 2.4225 | 1.701 | 2.205 | 2.719 | 2.7595 | 2.2055 |
| R15 | BB_BBSM011H01-P253/BBSM011_L_01-ko | 1.254 | 1.3025 | 1.889 | 1.2485 | 1.521 | 2.299 | 1.4745 | 1.94 |
| R16 | BB_BBSM012H01-P253/BBSM012_L_01-ko | 1.929 | 0.2865 | 2.2405 | 0.269 | 2.1695 | 2.543 | 2.6265 | 0.1705 |
| R17 | BB_BBSM014H01-P253/BBSM014_L_01-ko | 1.3375 | 0.197 | 2.052 | 0.169 | 1.9245 | 2.4415 | 2.474 | 0.166 |
| R18 | BB_BBSM015H01-P253/BBSM015_L_01-ko | 2.027 | 0.4 | 2.2945 | 0.4195 | 2.2725 | 2.4905 | 2.655 | 0.3465 |
| R19 | BB_BBSM010H02-P253/BBSM010_L_02-ko | 2.1065 | 2.281 | 2.19 | 2.2045 | 1.898 | 2.0045 | 1.6175 | 2.401 |

FIG. 14-1

| Sample name | | Ratio with respect to Non-Coating | | | | | | | | |
|---|---|---|---|---|---|---|---|---|---|---|
| | | Full length | CRD1 | CRD1-3 | CRD1-2 | CRD2-4 | CRD2-3 | CRD3-4 | Non |
| Control | M | 38.6 | 1.7 | 1.2 | 1.5 | 15.7 | 1.5 | 41.1 | 1.0 |
| Control | B | 54.6 | 35.7 | 47.5 | 52.7 | 2.0 | 1.8 | 1.5 | 1.0 |
| R1 | BB_BBNM001H01-P253/BBNM001_L_01-lam | 27.6 | 1.9 | 7.3 | 13.3 | 1.4 | 1.8 | 1.3 | 1.0 |
| R2 | BB_BBNM002H01-P253/BBNM002_L_01-lam | 1.0 | 1.1 | 1.1 | 1.0 | 0.7 | 0.9 | 0.5 | 1.0 |
| R3 | BB_BBNM003H01-P253/BBNM003_L_01-lam | 33.7 | 1.7 | 18.4 | 28.5 | 1.4 | 1.6 | 1.3 | 1.0 |
| R4 | BB_BBNM004H01-P253/BBNM004_L_01-lam | 37.1 | 1.2 | 15.3 | 29.3 | 1.3 | 1.1 | 1.1 | 1.0 |
| R5 | BB_BBNM005H01-P253/BBNM005_L_01-lam | 8.7 | 1.3 | 6.3 | 7.9 | 1.2 | 1.3 | 0.7 | 1.0 |
| R6 | BB_BBSM001H01-P253/BBSM001_L_01-k0 | 13.1 | 2.5 | 13.9 | 2.4 | 14.2 | 15.5 | 16.6 | 1.0 |
| R7 | BB_BBSM002H01-P253/BBSM002_L_01-k0 | 4.3 | 1.4 | 5.0 | 1.8 | 4.9 | 5.7 | 5.9 | 1.0 |
| R8 | BB_BBSM003H01-P253/BBSM003_L_01-k0 | 1.9 | 0.7 | 2.0 | 0.5 | 2.0 | 2.2 | 2.3 | 1.0 |
| R9 | BB_BBSM004H01-P253/BBSM004_L_01-k0 | 1.3 | 0.8 | 1.5 | 0.7 | 1.4 | 1.7 | 1.7 | 1.0 |
| R10 | BB_BBSM005H01-P253/BBSM005_L_01-k0 | 25.6 | 2.1 | 24.4 | 2.2 | 24.3 | 26.1 | 27.2 | 1.0 |
| R11 | BB_BBSM006H01-P253/BBSM006_L_01-k0 | 1.0 | 0.9 | 1.2 | 0.8 | 1.1 | 1.3 | 1.4 | 1.0 |
| R12 | BB_BBSM007H01-P253/BBSM007_L_01-k0 | 1.1 | 0.6 | 1.3 | 0.6 | 1.2 | 1.4 | 1.5 | 1.0 |
| R13 | BB_BBSM004H02-P253/BBSM004_L_02-k0 | 0.4 | 0.5 | 0.7 | 0.4 | 0.4 | 0.5 | 0.2 | 1.0 |
| R14 | BB_BBSM010H01-P253/BBSM010_L_01-k0 | 0.9 | 0.7 | 1.0 | 0.8 | 1.0 | 1.2 | 1.3 | 1.0 |
| R15 | BB_BBSM011H01-P253/BBSM011_L_01-k0 | 0.6 | 0.7 | 1.0 | 0.6 | 0.8 | 1.2 | 0.8 | 1.0 |
| R16 | BB_BBSM012H01-P253/BBSM012_L_01-k0 | 11.3 | 1.7 | 13.1 | 1.6 | 12.7 | 14.9 | 15.4 | 1.0 |
| R17 | BB_BBSM014H01-P253/BBSM014_L_01-k0 | 8.1 | 1.2 | 12.4 | 1.0 | 11.6 | 14.7 | 14.9 | 1.0 |
| R18 | BB_BBSM015H01-P253/BBSM015_L_01-k0 | 5.8 | 1.2 | 6.6 | 1.2 | 6.6 | 7.2 | 7.7 | 1.0 |
| R19 | BB_BBSM010H02-P253/BBSM010_L_02-k0 | 0.9 | 1.0 | 0.9 | 0.9 | 0.8 | 0.8 | 0.7 | 1.0 |

FIG. 14-2

| Antibody | T cell activation | Epitope |
|---|---|---|
| R1 | + | CRD1-2 |
| R2 | + | N.D. |
| R3 | + | CRD1-2 |
| R4 | + | CRD1-2 |
| R5 | + | CRD1-2 |
| R6 | + | CRD2-3 |
| R7 | − | CRD2-3 |
| R8 | + | N.D. |
| R9 | + | N.D. |
| R10 | + | CRD2-3 |
| R11 | + | N.D. |
| R12 | + | N.D. |
| R13 | + | N.D. |
| R14 | + | N.D. |
| R15 | − | N.D. |
| R16 | + | CRD2-3 |
| R17 | + | CRD2-3 |
| R18 | + | CRD2-3 |
| R19 | + | N.D. |

N.D. Not Determined

FIG. 16

SEQUENCE LISTING

```
<160> NUMBER OF SEQ ID NOS: 125

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
              260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 2
<211> LENGTH: 326
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 377
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

```
Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 4
<211> LENGTH: 327
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

```
<210> SEQ ID NO 5
<211> LENGTH: 330
<212> TYPE: PRT
<213> ORGANISM: Artificial
<220> FEATURE:
<223> OTHER INFORMATION: an artificially synthesized sequence

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 326
<212> TYPE: PRT
<213> ORGANISM: Artificial
<220> FEATURE:
<223> OTHER INFORMATION: an artificially synthesized sequence
```

<400> SEQUENCE: 6

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65              70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 7
<211> LENGTH: 377
<212> TYPE: PRT
<213> ORGANISM: Artificial
<220> FEATURE:
<223> OTHER INFORMATION: an artificially synthesized sequence

<400> SEQUENCE: 7

```
Ala Ser Thr Lys Gly Pro Ser Val Phe Pro Leu Ala Pro Cys Ser Arg
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
370                 375

<210> SEQ ID NO 8
<211> LENGTH: 327
<212> TYPE: PRT
<213> ORGANISM: Artificial
<220> FEATURE:
<223> OTHER INFORMATION: an artificially synthesized sequence

<400> SEQUENCE: 8
```

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 9
<211> LENGTH: 141
<212> TYPE: PRT
<213> ORGANISM: Homo sapiens

<400> SEQUENCE: 9

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
            35                  40                  45
```

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                     85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
                115                 120                 125

Gly Phe Asn Leu Leu Met Thr Leu Arg Leu Trp Ser Ser
    130                 135                 140

<210> SEQ ID NO 10
<211> LENGTH: 179
<212> TYPE: PRT
<213> ORGANISM: Homo sapiens

<400> SEQUENCE: 10

Glu Asp Leu Lys Asn Val Phe Pro Pro Glu Val Ala Val Phe Glu Pro
 1               5                  10                  15

Ser Glu Ala Glu Ile Ser His Thr Gln Lys Ala Thr Leu Val Cys Leu
                 20                  25                  30

Ala Thr Gly Phe Tyr Pro Asp His Val Glu Leu Ser Trp Trp Val Asn
                 35                  40                  45

Gly Lys Glu Val His Ser Gly Val Ser Thr Asp Pro Gln Pro Leu Lys
     50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 11
<211> LENGTH: 173
<212> TYPE: PRT
<213> ORGANISM: Homo sapiens

<400> SEQUENCE: 11

Asp Lys Gln Leu Asp Ala Asp Val Ser Pro Lys Pro Thr Ile Phe Leu
 1               5                  10                  15

Pro Ser Ile Ala Glu Thr Lys Leu Gln Lys Ala Gly Thr Tyr Leu Cys
                 20                  25                  30

Leu Leu Glu Lys Phe Phe Pro Asp Val Ile Lys Ile His Trp Gln Glu
                 35                  40                  45

```
Lys Lys Ser Asn Thr Ile Leu Gly Ser Gln Glu Gly Asn Thr Met Lys
     50                  55                  60

Thr Asn Asp Thr Tyr Met Lys Phe Ser Trp Leu Thr Val Pro Glu Lys
 65                  70                  75                  80

Ser Leu Asp Lys Glu His Arg Cys Ile Val Arg His Glu Asn Asn Lys
                 85                  90                  95

Asn Gly Val Asp Gln Glu Ile Ile Phe Pro Pro Ile Lys Thr Asp Val
            100                 105                 110

Ile Thr Met Asp Pro Lys Asp Asn Cys Ser Lys Asp Ala Asn Asp Thr
        115                 120                 125

Leu Leu Leu Gln Leu Thr Asn Thr Ser Ala Tyr Tyr Met Tyr Leu Leu
    130                 135                 140

Leu Leu Leu Lys Ser Val Val Tyr Phe Ala Ile Ile Thr Cys Cys Leu
145                 150                 155                 160

Leu Arg Arg Thr Ala Phe Cys Cys Asn Gly Glu Lys Ser
                165                 170
```

<210> SEQ ID NO 12
<211> LENGTH: 204
<212> TYPE: PRT
<213> ORGANISM: Homo sapiens

<400> SEQUENCE: 12

```
Lys Gln Leu Asp Ala Asp Val Ser Pro Lys Pro Thr Ile Phe Leu Pro
 1               5                  10                  15

Ser Ile Ala Glu Thr Lys Leu Gln Lys Ala Gly Thr Tyr Leu Cys Leu
             20                  25                  30

Leu Glu Lys Phe Phe Pro Asp Ile Ile Lys Ile His Trp Gln Glu Lys
         35                  40                  45

Lys Ser Asn Thr Ile Leu Gly Ser Gln Glu Gly Asn Thr Met Lys Thr
     50                  55                  60

Asn Asp Thr Tyr Met Lys Phe Ser Trp Leu Thr Val Pro Glu Glu Ser
 65                  70                  75                  80

Leu Asp Lys Glu His Arg Cys Ile Val Arg His Glu Asn Asn Lys Asn
                 85                  90                  95

Gly Ile Asp Gln Glu Ile Ile Phe Pro Pro Ile Lys Thr Asp Val Thr
            100                 105                 110

Thr Val Asp Pro Lys Asp Ser Tyr Ser Lys Asp Ala Asn Asp Val Thr
        115                 120                 125

Thr Val Asp Pro Lys Tyr Asn Tyr Ser Lys Asp Ala Asn Asp Val Ile
    130                 135                 140

Thr Met Asp Pro Lys Asp Asn Trp Ser Lys Asp Ala Asn Asp Thr Leu
145                 150                 155                 160

Leu Leu Gln Leu Thr Asn Thr Ser Ala Tyr Tyr Met Tyr Leu Leu Leu
                165                 170                 175

Leu Leu Lys Ser Val Val Tyr Phe Ala Ile Ile Thr Cys Cys Leu Leu
            180                 185                 190

Gly Arg Thr Ala Phe Cys Cys Asn Gly Glu Lys Ser
        195                 200
```

<210> SEQ ID NO 13
<211> LENGTH: 177
<212> TYPE: PRT
<213> ORGANISM: Homo sapiens

<400> SEQUENCE: 13

Pro Ser Tyr Thr Gly Gly Tyr Ala Asp Lys Leu Ile Phe Gly Lys Gly
1               5                   10                  15

Thr Arg Val Thr Val Glu Pro Arg Ser Gln Pro His Thr Lys Pro Ser
            20                  25                  30

Val Phe Val Met Lys Asn Gly Thr Asn Val Ala Cys Leu Val Lys Glu
        35                  40                  45

Phe Tyr Pro Lys Asp Ile Arg Ile Asn Leu Val Ser Ser Lys Lys Ile
    50                  55                  60

Thr Glu Phe Asp Pro Ala Ile Val Ile Ser Pro Ser Gly Lys Tyr Asn
65                  70                  75                  80

Ala Val Lys Leu Gly Lys Tyr Glu Asp Ser Asn Ser Val Thr Cys Ser
                85                  90                  95

Val Gln His Asp Asn Lys Thr Val His Ser Thr Asp Phe Glu Val Lys
            100                 105                 110

Thr Asp Ser Thr Asp His Val Lys Pro Lys Glu Thr Glu Asn Thr Lys
            115                 120                 125

Gln Pro Ser Lys Ser Cys His Lys Pro Lys Ala Ile Val His Thr Glu
        130                 135                 140

Lys Val Asn Met Met Ser Leu Thr Val Leu Gly Leu Arg Met Leu Phe
145                 150                 155                 160

Ala Lys Thr Val Ala Val Asn Phe Leu Leu Thr Ala Lys Leu Phe Phe
                165                 170                 175

Leu

<210> SEQ ID NO 14
<211> LENGTH: 549
<212> TYPE: DNA
<213> ORGANISM: Homo sapiens

<400> SEQUENCE: 14
atggaacagg ggaagggcct ggctgtcctc atcctggcta tcattcttct tcaaggtact    60
ttggcccagt caatcaaagg aaaccacttg gttaaggtgt atgactatca agaagatggt   120
tcggtacttc tgacttgtga tgcagaagcc aaaaatatca catggtttaa agatgggaag   180
atgatcggct tcctaactga agataaaaaa aaatggaatc tgggaagtaa tgccaaggac   240
cctcgaggga tgtatcagtg taaaggatca cagaacaagt caaaaccact ccaagtgtat   300
tacagaatgt gtcagaactg cattgaacta atgcagccac catatctgg ctttctcttt   360 gctgaaatcg tcagcatttt cgtccttgct gttgggtct acttcattgc tggacaggat   420
ggagttcgcc agtcgagagc ttcagacaag cagactctgt tgcccaatga ccagctctac   480
cagcccctca aggatcgaga agatgaccag tacagccacc ttcaaggaaa ccagttgagg   540
aggaattga                                                           549

<210> SEQ ID NO 15
<211> LENGTH: 182
<212> TYPE: PRT
<213> ORGANISM: Homo sapiens

<400> SEQUENCE: 15

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

```
Glu Ala Lys Asn Ile Thr Trp Phe Lys Asp Gly Lys Met Ile Gly Phe
         50                  55                  60
Leu Thr Glu Asp Lys Lys Trp Asn Leu Gly Ser Asn Ala Lys Asp
 65                  70                  75                  80
Pro Arg Gly Met Tyr Gln Cys Lys Gly Ser Gln Asn Lys Ser Lys Pro
                 85                  90                  95
Leu Gln Val Tyr Tyr Arg Met Cys Gln Asn Cys Ile Glu Leu Asn Ala
            100                 105                 110
Ala Thr Ile Ser Gly Phe Leu Phe Ala Glu Ile Val Ser Ile Phe Val
            115                 120                 125
Leu Ala Val Gly Val Tyr Phe Ile Ala Gly Gln Asp Gly Val Arg Gln
            130                 135                 140
Ser Arg Ala Ser Asp Lys Gln Thr Leu Leu Pro Asn Asp Gln Leu Tyr
145                 150                 155                 160
Gln Pro Leu Lys Asp Arg Glu Asp Gln Tyr Ser His Leu Gln Gly
                165                 170                 175
Asn Gln Leu Arg Arg Asn
            180

<210> SEQ ID NO 16
<211> LENGTH: 516
<212> TYPE: DNA
<213> ORGANISM: Homo sapiens

<400> SEQUENCE: 16
atggaacata gcacgtttct ctctggcctg gtactggcta cccttctctc gcaagtgagc      60
cccttcaaga tacctataga ggaacttgag acagagtgt  ttgtgaattg caataccagc     120
atcacatggg tagagggaac ggtgggaaca ctgctctcag acattacaag actggacctg     180
ggaaaacgca tcctggaccc acgaggaata tataggtgta atgggacaga tatatacaag     240
gacaaagaat ctaccgtgca agttcattat cgaatgtgcc agagctgtgt ggagctggat     300
ccagccaccg tggctggcat cattgtcact gatgtcattg ccactctgct ccttgctttg     360
ggagtcttct gctttgctgg acatgagact ggaaggctgt ctggggctgc cgacacacaa     420
gctctgttga ggaatgacca ggtctatcag cccctccgag atcgagatga tgctcagtac     480
agccaccttg aggaaactg  ggctcggaac aagtga                                516

<210> SEQ ID NO 17
<211> LENGTH: 171
<212> TYPE: PRT
<213> ORGANISM: Homo sapiens

<400> SEQUENCE: 17

Met Glu His Ser Thr Phe Leu Ser Gly Leu Val Leu Ala Thr Leu Leu
  1               5                  10                  15
Ser Gln Val Ser Pro Phe Lys Ile Pro Ile Glu Glu Leu Glu Asp Arg
                 20                  25                  30
Val Phe Val Asn Cys Asn Thr Ser Ile Thr Trp Val Glu Gly Thr Val
             35                  40                  45
Gly Thr Leu Leu Ser Asp Ile Thr Arg Leu Asp Leu Gly Lys Arg Ile
         50                  55                  60
Leu Asp Pro Arg Gly Ile Tyr Arg Cys Asn Gly Thr Asp Ile Tyr Lys
 65                  70                  75                  80
Asp Lys Glu Ser Thr Val Gln Val His Tyr Arg Met Cys Gln Ser Cys
                 85                  90                  95
```

```
Val Glu Leu Asp Pro Ala Thr Val Ala Gly Ile Ile Val Thr Asp Val
            100                 105                 110

Ile Ala Thr Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Ala Gln Tyr
145                 150                 155                 160

Ser His Leu Gly Gly Asn Trp Ala Arg Asn Lys
            165                 170
```

<210> SEQ ID NO 18
<211> LENGTH: 624
<212> TYPE: DNA
<213> ORGANISM: Homo sapiens

<400> SEQUENCE: 18

```
atgcagtcgg gcactcactg gagagttctg ggcctctgcc tcttatcagt tggcgtttgg      60
gggcaagatg gtaatgaaga aatgggtggt attacacaga caccatataa agtctccatc     120
tctggaacca cagtaatatt gacatgccct cagtatcctg gatctgaaat actatggcaa     180
cacaatgata aaacatagg cggtgatgag gatgataaaa acataggcag tgatgaggat     240
cacctgtcac tgaaggaatt ttcagaattg agcaaagtg gttattatgt ctgctacccc     300
agaggaagca aaccagaaga tgcgaacttt tatctctacc tgagggcaag agtgtgtgag     360
aactgcatgg agatggatgt gatgtcggtg gccacaattg tcatagtgga catctgcatc     420
actgggggct gctgctgct ggtttactac tggagcaaga atagaaaggc caaggccaag     480
cctgtgacac gaggagcggg tgctggcggc aggcaaaggg gacaaaacaa ggagaggcca     540
ccacctgttc ccaacccaga ctatgagccc atccggaaag ccagcgggaa cctgtattct     600
ggcctgaatc agagacgcat ctga                                            624
```

<210> SEQ ID NO 19
<211> LENGTH: 207
<212> TYPE: PRT
<213> ORGANISM: Homo sapiens

<400> SEQUENCE: 19

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
```

```
                130                 135                 140
Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 20
<211> LENGTH: 4
<212> TYPE: PRT
<213> ORGANISM: Artificial
<220> FEATURE:
<223> OTHER INFORMATION: an artificially synthesized sequence

<400> SEQUENCE: 20

Gly Gly Gly Ser
1

<210> SEQ ID NO 21
<211> LENGTH: 4
<212> TYPE: PRT
<213> ORGANISM: Artificial
<220> FEATURE:
<223> OTHER INFORMATION: an artificially synthesized sequence

<400> SEQUENCE: 21

Ser Gly Gly Gly
1

<210> SEQ ID NO 22
<211> LENGTH: 5
<212> TYPE: PRT
<213> ORGANISM: Artificial
<220> FEATURE:
<223> OTHER INFORMATION: an artificially synthesized sequence

<400> SEQUENCE: 22

Gly Gly Gly Gly Ser
1               5

<210> SEQ ID NO 23
<211> LENGTH: 5
<212> TYPE: PRT
<213> ORGANISM: Artificial
<220> FEATURE:
<223> OTHER INFORMATION: an artificially synthesized sequence

<400> SEQUENCE: 23

Ser Gly Gly Gly Gly
1               5

<210> SEQ ID NO 24
<211> LENGTH: 6
<212> TYPE: PRT
<213> ORGANISM: Artificial
<220> FEATURE:
<223> OTHER INFORMATION: an artificially synthesized sequence

<400> SEQUENCE: 24

Gly Gly Gly Gly Gly Ser
1               5
```

<210> SEQ ID NO 25
<211> LENGTH: 6
<212> TYPE: PRT
<213> ORGANISM: Artificial
<220> FEATURE:
<223> OTHER INFORMATION: an artificially synthesized sequence

<400> SEQUENCE: 25

Ser Gly Gly Gly Gly Gly
1               5

<210> SEQ ID NO 26
<211> LENGTH: 7
<212> TYPE: PRT
<213> ORGANISM: Artificial
<220> FEATURE:
<223> OTHER INFORMATION: an artificially synthesized sequence

<400> SEQUENCE: 26

Gly Gly Gly Gly Gly Gly Ser
1               5

<210> SEQ ID NO 27
<211> LENGTH: 7
<212> TYPE: PRT
<213> ORGANISM: Artificial
<220> FEATURE:
<223> OTHER INFORMATION: an artificially synthesized sequence

<400> SEQUENCE: 27

Ser Gly Gly Gly Gly Gly Gly
1               5

<210> SEQ ID NO 28
<211> LENGTH: 113
<212> TYPE: PRT
<213> ORGANISM: Artificial
<220> FEATURE:
<223> OTHER INFORMATION: an artificially synthesized sequence

<400> SEQUENCE: 28

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
            20                  25                  30

Gly Val His Trp Ile Arg Gln Pro Pro Gly Lys Gly Leu Glu Trp Met
        35                  40                  45

Gly Ile Ile Tyr Tyr Asp Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Ile Asn Ser Leu Gln Thr Asp Asp Thr Ala Met Tyr Tyr Cys Ala
                85                  90                  95

Arg Ile His Phe Asp Tyr Trp Gly Gln Gly Val Met Val Thr Val Ser
            100                 105                 110

Ser

<210> SEQ ID NO 29
<211> LENGTH: 437
<212> TYPE: PRT
<213> ORGANISM: Artificial
<220> FEATURE:
<223> OTHER INFORMATION: an artificially synthesized sequence

<400> SEQUENCE: 29

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
            20                  25                  30

Gly Val His Trp Ile Arg Gln Pro Pro Gly Lys Gly Leu Glu Trp Met
        35                  40                  45

Gly Ile Ile Tyr Tyr Asp Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Ile Asn Ser Leu Gln Thr Asp Asp Thr Ala Met Tyr Tyr Cys Ala
                85                  90                  95

Arg Ile His Phe Asp Tyr Trp Gly Gln Gly Val Met Val Thr Val Ser
            100                 105                 110

Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Cys Lys Pro Cys Ile Cys Thr Val
210                 215                 220

Pro Glu Val Ser Ser Val Phe Ile Phe Pro Pro Lys Pro Lys Asp Val
225                 230                 235                 240

Leu Thr Ile Thr Leu Thr Pro Lys Val Thr Cys Val Val Val Asp Ile
                245                 250                 255

Ser Lys Asp Asp Pro Glu Val Gln Phe Ser Trp Phe Val Asp Asp Val
            260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
290                 295                 300

Asn Gly Lys Glu Phe Lys Cys Arg Val Asn Ser Ala Ala Phe Pro Ala
305                 310                 315                 320

Pro Ile Glu Lys Thr Ile Ser Lys Thr Lys Gly Arg Pro Lys Ala Pro
                325                 330                 335

Gln Val Tyr Thr Ile Pro Pro Pro Lys Glu Gln Met Ala Lys Asp Lys
            340                 345                 350

Val Ser Leu Thr Cys Met Ile Thr Asp Phe Phe Pro Glu Asp Ile Thr
        355                 360                 365

Val Glu Trp Gln Trp Asn Gly Gln Pro Ala Glu Asn Tyr Lys Asn Thr
370                 375                 380

Gln Pro Ile Met Asp Thr Asp Gly Ser Tyr Phe Val Tyr Ser Lys Leu
385                 390                 395                 400

Asn Val Gln Lys Ser Asn Trp Glu Ala Gly Asn Thr Phe Thr Cys Ser

```
                      405                 410                 415
Val Leu His Glu Gly Leu His Asn His His Thr Glu Lys Ser Leu Ser
            420                 425                 430

His Ser Pro Gly Lys
            435

<210> SEQ ID NO 30
<211> LENGTH: 437
<212> TYPE: PRT
<213> ORGANISM: Artificial
<220> FEATURE:
<223> OTHER INFORMATION: an artificially synthesized sequence

<400> SEQUENCE: 30

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
            20                  25                  30

Gly Val His Trp Ile Arg Gln Pro Pro Gly Lys Gly Leu Glu Trp Met
        35                  40                  45

Gly Ile Ile Tyr Tyr Asp Gly Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Ile Asn Ser Leu Gln Thr Asp Asp Thr Ala Met Tyr Tyr Cys Ala
                85                  90                  95

Arg Ile His Phe Asp Tyr Trp Gly Gln Gly Val Met Val Thr Val Ser
            100                 105                 110

Ser Ala Lys Thr Thr Pro Pro Ser Val Tyr Pro Leu Ala Pro Gly Ser
        115                 120                 125

Ala Ala Gln Thr Asn Ser Met Val Thr Leu Gly Cys Leu Val Lys Gly
    130                 135                 140

Tyr Phe Pro Glu Pro Val Thr Val Thr Trp Asn Ser Gly Ser Leu Ser
145                 150                 155                 160

Ser Gly Val His Thr Phe Pro Ala Val Leu Gln Ser Asp Leu Tyr Thr
                165                 170                 175

Leu Ser Ser Ser Val Thr Val Pro Ser Ser Thr Trp Pro Ser Glu Thr
            180                 185                 190

Val Thr Cys Asn Val Ala His Pro Ala Ser Ser Thr Lys Val Asp Lys
        195                 200                 205

Lys Ile Val Pro Arg Asp Cys Gly Cys Lys Pro Cys Ile Cys Thr Val
    210                 215                 220

Lys Glu Val Ser Lys Val Phe Ile Phe Pro Pro Lys Pro Lys Asp Val
225                 230                 235                 240

Leu Thr Ile Thr Leu Thr Pro Lys Val Thr Cys Val Val Val Asp Ile
                245                 250                 255

Ser Lys Asp Asp Pro Glu Val Gln Phe Ser Trp Phe Val Asp Asp Val
            260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
    290                 295                 300

Asn Gly Lys Glu Phe Lys Cys Arg Val Asn Ser Ala Ala Phe Pro Ala
305                 310                 315                 320

Pro Ile Glu Lys Thr Ile Ser Lys Thr Lys Gly Arg Pro Lys Ala Pro
```

```
                    325                 330                 335
Gln Val Tyr Thr Ile Pro Pro Lys Glu Gln Met Ala Lys Asp Lys
            340                 345                 350
Val Ser Leu Thr Cys Met Ile Thr Asp Phe Phe Pro Glu Asp Ile Thr
            355                 360                 365
Val Glu Trp Gln Trp Asn Gly Gln Pro Ala Glu Asn Tyr Lys Asn Thr
            370                 375                 380
Gln Pro Ile Met Asp Thr Asp Gly Ser Tyr Phe Val Tyr Ser Lys Leu
385                 390                 395                 400
Asn Val Gln Lys Ser Asn Trp Glu Ala Gly Asn Thr Phe Thr Cys Ser
            405                 410                 415
Val Leu His Glu Gly Leu His Asn His His Thr Glu Lys Ser Leu Ser
            420                 425                 430
His Ser Pro Gly Lys
            435

<210> SEQ ID NO 31
<211> LENGTH: 437
<212> TYPE: PRT
<213> ORGANISM: Artificial
<220> FEATURE:
<223> OTHER INFORMATION: an artificially synthesized sequence

<400> SEQUENCE: 31

Gln Val Gln Leu Lys Glu Ala Gly Pro Gly Leu Val Gln Pro Thr Gln
1               5                   10                  15
Thr Leu Ser Leu Thr Cys Thr Val Ser Gly Phe Ser Leu Thr Ser Asp
            20                  25                  30
Gly Val His Trp Ile Arg Gln Pro Pro Gly Lys Gly Leu Glu Trp Met
            35                  40                  45
Gly Ile Ile Tyr Tyr Asp Gly Gly Thr Asp Tyr Asn Ser Ala Ile Lys
            50                  55                  60
Ser Arg Leu Ser Ile Ser Arg Asp Thr Ser Lys Ser Gln Val Phe Leu
65                  70                  75                  80
Lys Ile Asn Ser Leu Gln Thr Asp Asp Thr Ala Met Tyr Tyr Cys Ala
            85                  90                  95
Arg Ile His Phe Asp Tyr Trp Gly Gln Gly Val Met Val Thr Val Ser
            100                 105                 110
Ser Ala Lys Thr Thr Pro Pro Ser Val Tyr Pro Leu Ala Pro Gly Ser
            115                 120                 125
Ala Ala Gln Thr Asn Ser Met Val Thr Leu Gly Cys Leu Val Lys Gly
            130                 135                 140
Tyr Phe Pro Glu Pro Val Thr Val Thr Trp Asn Ser Gly Ser Leu Ser
145                 150                 155                 160
Ser Gly Val His Thr Phe Pro Ala Val Leu Gln Ser Asp Leu Tyr Thr
            165                 170                 175
Leu Ser Ser Ser Val Thr Val Pro Ser Ser Thr Trp Pro Ser Glu Thr
            180                 185                 190
Val Thr Cys Asn Val Ala His Pro Ala Ser Ser Thr Lys Val Asp Lys
            195                 200                 205
Lys Ile Val Pro Arg Asp Cys Gly Cys Lys Pro Cys Ile Cys Glu Pro
            210                 215                 220
Asn Glu Val Glu Asp Val Phe Ile Phe Pro Pro Lys Pro Lys Asp Val
225                 230                 235                 240
Leu Thr Ile Thr Leu Thr Pro Lys Val Thr Cys Val Val Val Asp Ile
```

```
            245                 250                 255
Ser Lys Asp Asp Pro Glu Val Gln Phe Ser Trp Phe Val Asp Val
            260                 265                 270

Glu Val His Thr Ala Gln Thr Gln Pro Arg Glu Glu Gln Phe Asn Ser
        275                 280                 285

Thr Phe Arg Ser Val Ser Glu Leu Pro Ile Met His Gln Asp Trp Leu
    290                 295                 300

Asn Gly Lys Glu Phe Lys Cys Arg Val Asp Ser Ala Ala Phe Pro Ala
305                 310                 315                 320

Pro Ile Glu Lys Thr Ile Ser Lys Thr Lys Gly Arg Pro Lys Ala Pro
                325                 330                 335

Gln Val Tyr Thr Ile Pro Pro Lys Glu Gln Met Ala Lys Asp Lys
                340                 345                 350

Val Ser Leu Thr Cys Met Ile Thr Asp Phe Phe Pro Glu Asp Ile Thr
            355                 360                 365

Val Glu Trp Gln Trp Asn Gly Gln Pro Ala Glu Asn Tyr Lys Asn Thr
        370                 375                 380

Gln Pro Ile Met Asp Thr Asp Gly Ser Tyr Phe Val Tyr Ser Lys Leu
385                 390                 395                 400

Asn Val Gln Lys Ser Asn Trp Glu Ala Gly Asn Thr Phe Thr Cys Ser
                405                 410                 415

Val Leu His Glu Gly Leu His Asn His His Thr Glu Lys Ser Leu Ser
                420                 425                 430

His Ser Pro Gly Lys
            435

<210> SEQ ID NO 32
<211> LENGTH: 213
<212> TYPE: PRT
<213> ORGANISM: Artificial
<220> FEATURE:
<223> OTHER INFORMATION: an artificially synthesized sequence

<400> SEQUENCE: 32

Asp Ile Val Leu Thr Gln Ser Pro Thr Thr Ile Ala Ala Ser Pro Gly
1               5                   10                  15

Glu Lys Val Thr Ile Thr Cys Arg Ala Ser Ser Ser Val Ser Tyr Met
                20                  25                  30

Tyr Trp Tyr Gln Gln Lys Ser Gly Ala Ser Pro Lys Leu Trp Ile Tyr
            35                  40                  45

Asp Thr Ser Lys Leu Ala Ser Gly Val Pro Asn Arg Phe Ser Gly Ser
        50                  55                  60

Gly Ser Gly Thr Ser Tyr Ser Leu Ala Ile Asn Thr Met Glu Thr Glu
65                  70                  75                  80

Asp Ala Ala Thr Tyr Tyr Cys Gln Gln Trp Ser Ser Thr Pro Leu Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
```

```
                        165                 170                 175
Thr Leu Thr Leu Thr Lys Asp Glu Tyr Glu Arg His Asn Ser Tyr Thr
                180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 33
<211> LENGTH: 119
<212> TYPE: PRT
<213> ORGANISM: Artificial
<220> FEATURE:
<223> OTHER INFORMATION: an artificially synthesized sequence

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 34
<211> LENGTH: 443
<212> TYPE: PRT
<213> ORGANISM: Artificial
<220> FEATURE:
<223> OTHER INFORMATION: an artificially synthesized sequence

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125
```

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
    195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
    275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
    355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
    435                 440

<210> SEQ ID NO 35
<211> LENGTH: 443
<212> TYPE: PRT
<213> ORGANISM: Artificial
<220> FEATURE:
<223> OTHER INFORMATION: an artificially synthesized sequence

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Gln Gly
             100                 105                 110

Thr Leu Val Thr Val Ser Ser Ala Lys Thr Thr Pro Pro Ser Val Tyr
         115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Glu Pro Asn Glu Val Glu Asp Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asp
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 36
<211> LENGTH: 214
<212> TYPE: PRT

<213> ORGANISM: Artificial
<220> FEATURE:
<223> OTHER INFORMATION: an artificially synthesized sequence

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 443
<212> TYPE: PRT
<213> ORGANISM: Artificial
<220> FEATURE:
<223> OTHER INFORMATION: an artificially synthesized sequence

<400> SEQUENCE: 37

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
            20                  25                  30

His Ala Trp Ser Trp Ile Arg Gln Phe Pro Gly Asn Lys Leu Glu Trp
        35                  40                  45

Met Gly Tyr Ile Ser Tyr Ser Gly Ile Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Gly Asp Thr Ser Thr Tyr Tyr Cys
                85                  90                  95

Ala Arg Ser Leu Ala Arg Thr Thr Ala Met Asp Tyr Trp Gly Gln Gly
            100                 105                 110

Thr Ser Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
            210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 38
<211> LENGTH: 443
<212> TYPE: PRT
<213> ORGANISM: Artificial
<220> FEATURE:
<223> OTHER INFORMATION: an artificially synthesized sequence

<400> SEQUENCE: 38

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
            20                  25                  30

```
His Ala Trp Ser Trp Ile Arg Gln Phe Pro Gly Asn Lys Leu Glu Trp
            35                  40                  45

Met Gly Tyr Ile Ser Tyr Ser Gly Ile Thr Thr Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Gly Asp Thr Ser Thr Tyr Tyr Cys
                85                  90                  95

Ala Arg Ser Leu Ala Arg Thr Thr Ala Met Asp Tyr Trp Gly Gln Gly
                100                 105                 110

Thr Ser Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
            210                 215                 220

Pro Cys Ile Cys Thr Val Lys Glu Val Ser Lys Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
            370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440
```

```
<210> SEQ ID NO 39
<211> LENGTH: 450
<212> TYPE: PRT
<213> ORGANISM: Artificial
<220> FEATURE:
<223> OTHER INFORMATION: an artificially synthesized sequence

<400> SEQUENCE: 39
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Ala Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Cys Thr Leu Pro Pro Ser Arg
            340                 345                 350

Asp Glu Leu Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro

```
            370                 375                 380
Glu Asn Asn Tyr Lys Thr Thr Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro His His His His His His
            435                 440                 445

His His
    450

<210> SEQ ID NO 40
<211> LENGTH: 446
<212> TYPE: PRT
<213> ORGANISM: Artificial
<220> FEATURE:
<223> OTHER INFORMATION: an artificially synthesized sequence

<400> SEQUENCE: 40

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Ser Ser Ala Ser Thr Lys Gly Pro Ser Val Phe Pro Leu Ala Pro Ser
    115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Asn Phe Gly Thr
            180                 185                 190

Gln Thr Tyr Thr Cys Asn Val Asp His Lys Pro Ser Asn Thr Lys Val
        195                 200                 205

Asp Lys Thr Val Glu Arg Lys Ser Cys Val Glu Cys Pro Pro Cys Pro
    210                 215                 220

Ala Pro Pro Ala Ala Ala Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Gln Phe Asn Trp Tyr Val
            260                 265                 270

Asp Gly Val Glu Val His Asn Ala Lys Thr Lys Pro Arg Glu Glu Gln
```

```
                275                 280                 285
Phe Ala Ser Thr Phe Arg Val Ser Val Leu Thr Val His Gln
290                 295                 300

Asp Trp Leu Asn Gly Lys Glu Tyr Lys Cys Lys Val Ser Asn Lys Gly
305                 310                 315                 320

Leu Pro Ala Pro Ile Glu Lys Thr Ile Ser Lys Thr Lys Gly Gln Pro
                325                 330                 335

Arg Glu Pro Gln Val Cys Thr Leu Pro Pro Ser Arg Glu Glu Met Thr
                340                 345                 350

Lys Asn Gln Val Ser Leu Trp Cys Leu Val Lys Gly Phe Tyr Pro Ser
                355                 360                 365

Asp Ile Ala Val Glu Trp Glu Ser Asn Gly Gln Pro Glu Asn Asn Tyr
                370                 375                 380

Lys Thr Thr Pro Pro Met Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
                420                 425                 430

Ser Leu Ser Leu Ser Pro His His His His His His
                435                 440                 445
```

```
<210> SEQ ID NO 41
<211> LENGTH: 447
<212> TYPE: PRT
<213> ORGANISM: Artificial
<220> FEATURE:
<223> OTHER INFORMATION: an artificially synthesized sequence

<400> SEQUENCE: 41

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

Ser Ser Ala Ser Thr Lys Gly Pro Ser Val Phe Pro Leu Ala Pro Cys
            115                 120                 125

Ser Arg Ser Thr Ser Glu Ser Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Lys Thr Tyr Thr Cys Asn Val Asp His Lys Pro Ser Asn Thr Lys Val
```

```
                195                 200                 205
Asp Lys Arg Val Glu Ser Lys Tyr Gly Pro Cys Pro Cys Pro
210                 215                 220

Ala Pro Glu Ala Ala Gly Gly Pro Ser Val Phe Leu Phe Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
                275                 280                 285

Gln Phe Ala Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Cys Thr Leu Pro Pro Ser Gln Glu Glu Met
                340                 345                 350

Thr Lys Asn Gln Val Ser Leu Trp Cys Leu Val Lys Gly Phe Tyr Pro
                355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
                420                 425                 430

Lys Ser Leu Ser Leu Ser Leu His His His His His His His
                435                 440                 445

<210> SEQ ID NO 42
<211> LENGTH: 449
<212> TYPE: PRT
<213> ORGANISM: Artificial
<220> FEATURE:
<223> OTHER INFORMATION: an artificially synthesized sequence

<400> SEQUENCE: 42

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
                20                  25                  30

Gly Val His Trp Ile Arg Gln Pro Pro Gly Lys Gly Leu Glu Trp Met
            35                  40                  45

Gly Ile Ile Tyr Tyr Asp Gly Thr Asp Tyr Asn Ser Ala Ile Lys
        50                  55                  60

Ser Arg Leu Ser Ile Ser Arg Asp Thr Ser Lys Ser Gln Val Phe Leu
65                  70                  75                  80

Lys Ile Asn Ser Leu Gln Thr Asp Asp Thr Ala Met Tyr Tyr Cys Ala
                85                  90                  95

Arg Ile His Phe Asp Tyr Trp Gly Gln Gly Val Met Val Thr Val Ser
                100                 105                 110

Ser Ala Ser Thr Lys Gly Pro Ser Val Phe Pro Leu Ala Pro Ser Ser
```

```
            115                 120                 125
Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Cys
            340                 345                 350

Glu Leu Thr Lys Asn Gln Val Ser Leu Ser Cys Ala Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Val Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Asp Tyr Lys Asp Asp Asp Asp
        435                 440                 445

Lys

<210> SEQ ID NO 43
<211> LENGTH: 445
<212> TYPE: PRT
<213> ORGANISM: Artificial
<220> FEATURE:
<223> OTHER INFORMATION: an artificially synthesized sequence

<400> SEQUENCE: 43

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
            20                  25                  30
```

```
Gly Val His Trp Ile Arg Gln Pro Gly Lys Gly Leu Glu Trp Met
            35                  40                  45
Gly Ile Ile Tyr Tyr Asp Gly Thr Asp Tyr Asn Ser Ala Ile Lys
 50                  55                  60
Ser Arg Leu Ser Ile Ser Arg Asp Thr Ser Lys Ser Gln Val Phe Leu
 65                  70                  75                  80
Lys Ile Asn Ser Leu Gln Thr Asp Asp Thr Ala Met Tyr Tyr Cys Ala
                 85                  90                  95
Arg Ile His Phe Asp Tyr Trp Gly Gln Gly Val Met Val Thr Val Ser
                100                 105                 110
Ser Ala Ser Thr Lys Gly Pro Ser Val Phe Pro Leu Ala Pro Ser Ser
            115                 120                 125
Lys Ser Thr Ser Gly Gly Thr Ala Ala Leu Gly Cys Leu Val Lys Asp
            130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Asn Phe Gly Thr Gln
            180                 185                 190
Thr Tyr Thr Cys Asn Val Asp His Lys Pro Ser Asn Thr Lys Val Asp
                195                 200                 205
Lys Thr Val Glu Arg Lys Ser Cys Val Glu Cys Pro Pro Cys Pro Ala
            210                 215                 220
Pro Pro Ala Ala Ala Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
Asp Val Ser His Glu Asp Pro Glu Val Gln Phe Asn Trp Tyr Val Asp
                260                 265                 270
Gly Val Glu Val His Asn Ala Lys Thr Lys Pro Arg Glu Glu Gln Phe
            275                 280                 285
Ala Ser Thr Phe Arg Val Val Ser Val Leu Thr Val Val His Gln Asp
            290                 295                 300
Trp Leu Asn Gly Lys Glu Tyr Lys Cys Lys Val Ser Asn Lys Gly Leu
305                 310                 315                 320
Pro Ala Pro Ile Glu Lys Thr Ile Ser Lys Thr Lys Gly Gln Pro Arg
                325                 330                 335
Glu Pro Gln Val Tyr Thr Leu Pro Pro Ser Arg Cys Glu Met Thr Lys
                340                 345                 350
Asn Gln Val Ser Leu Ser Cys Ala Val Lys Gly Phe Tyr Pro Ser Asp
            355                 360                 365
Ile Ala Val Glu Trp Glu Ser Asn Gly Gln Pro Glu Asn Asn Tyr Lys
370                 375                 380
Thr Thr Pro Pro Met Leu Asp Ser Asp Gly Ser Phe Phe Leu Val Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
                420                 425                 430
Leu Ser Leu Ser Pro Asp Tyr Lys Asp Asp Asp Lys
            435                 440                 445
```

```
<210> SEQ ID NO 44
<211> LENGTH: 446
<212> TYPE: PRT
<213> ORGANISM: Artificial
<220> FEATURE:
<223> OTHER INFORMATION: an artificially synthesized sequence

<400> SEQUENCE: 44

Gln Val Gln Leu Lys Glu Ala Gly Pro Gly Leu Val Gln Pro Thr Gln
1               5                   10                  15

Thr Leu Ser Leu Thr Cys Thr Val Ser Gly Phe Ser Leu Thr Ser Asp
            20                  25                  30

Gly Val His Trp Ile Arg Gln Pro Pro Gly Lys Gly Leu Glu Trp Met
        35                  40                  45

Gly Ile Ile Tyr Tyr Asp Gly Thr Asp Tyr Asn Ser Ala Ile Lys
    50                  55                  60

Ser Arg Leu Ser Ile Ser Arg Asp Thr Ser Lys Ser Gln Val Phe Leu
65              70                  75                  80

Lys Ile Asn Ser Leu Gln Thr Asp Asp Thr Ala Met Tyr Tyr Cys Ala
                85                  90                  95

Arg Ile His Phe Asp Tyr Trp Gly Gln Gly Val Met Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Ala Ala Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Ala Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Cys Glu Met Thr
            340                 345                 350

Lys Asn Gln Val Ser Leu Ser Cys Ala Val Lys Gly Phe Tyr Pro Ser
        355                 360                 365
```

```
Asp Ile Ala Val Glu Trp Glu Ser Asn Gly Gln Pro Glu Asn Asn Tyr
    370                 375                 380
Lys Thr Thr Pro Pro Val Leu Asp Ser Asp Gly Ser Phe Phe Leu Val
385                 390                 395                 400
Ser Arg Leu Thr Val Asp Lys Ser Arg Trp Gln Glu Gly Asn Val Phe
                405                 410                 415
Ser Cys Ser Val Met His Glu Ala Leu His Asn His Tyr Thr Gln Lys
                420                 425                 430
Ser Leu Ser Leu Ser Leu Asp Tyr Lys Asp Asp Asp Lys
                435                 440                 445

<210> SEQ ID NO 45
<211> LENGTH: 222
<212> TYPE: PRT
<213> ORGANISM: Artificial
<220> FEATURE:
<223> OTHER INFORMATION: an artificially synthesized sequence

<400> SEQUENCE: 45

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
                20                  25                  30
Glu Met His Trp Ile Arg Gln Pro Gly Gln Gly Leu Glu Trp Ile
            35                  40                  45
Gly Ala Ile Asp Pro Lys Thr Gly Asp Thr Ala Tyr Ser Gln Lys Phe
    50                  55                  60
Lys Gly Arg Val Thr Leu Thr Ala Asp Lys Ser Thr Ser Thr Ala Tyr
65                  70                  75                  80
Met Glu Leu Ser Ser Leu Thr Ser Glu Asp Thr Ala Val Tyr Tyr Cys
                85                  90                  95
Thr Arg Phe Tyr Ser Tyr Thr Tyr Trp Gly Gln Gly Thr Leu Val Thr
            100                 105                 110
Val Ser Ser Arg Thr Val Ala Ala Pro Ser Val Phe Ile Phe Pro Pro
        115                 120                 125
Ser Asp Glu Gln Leu Lys Ser Gly Thr Ala Ser Val Val Cys Leu Leu
    130                 135                 140
Asn Asn Phe Tyr Pro Arg Glu Ala Lys Val Gln Trp Lys Val Asp Asn
145                 150                 155                 160
Ala Leu Gln Ser Gly Asn Ser Gln Glu Ser Val Thr Glu Gln Asp Ser
                165                 170                 175
Lys Asp Ser Thr Tyr Ser Leu Ser Ser Thr Leu Thr Leu Ser Lys Ala
            180                 185                 190
Asp Tyr Glu Lys His Lys Val Tyr Ala Cys Glu Val Thr His Gln Gly
        195                 200                 205
Leu Ser Ser Pro Val Thr Lys Ser Phe Asn Arg Gly Glu Cys
    210                 215                 220

<210> SEQ ID NO 46
<211> LENGTH: 213
<212> TYPE: PRT
<213> ORGANISM: Artificial
<220> FEATURE:
<223> OTHER INFORMATION: an artificially synthesized sequence

<400> SEQUENCE: 46

Asp Ile Val Leu Thr Gln Ser Pro Thr Thr Ile Ala Ala Ser Pro Gly
1               5                   10                  15
```

-continued

```
Glu Lys Val Thr Ile Thr Cys Arg Ala Ser Ser Val Ser Tyr Met
                 20                  25                  30

Tyr Trp Tyr Gln Gln Lys Ser Gly Ala Ser Pro Lys Leu Trp Ile Tyr
             35                  40                  45

Asp Thr Ser Lys Leu Ala Ser Gly Val Pro Asn Arg Phe Ser Gly Ser
 50                  55                  60

Gly Ser Gly Thr Ser Tyr Ser Leu Ala Ile Asn Thr Met Glu Thr Glu
 65                  70                  75                  80

Asp Ala Ala Thr Tyr Tyr Cys Gln Gln Trp Ser Ser Thr Pro Leu Thr
                 85                  90                  95

Phe Gly Ser Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
             115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 47
<211> LENGTH: 441
<212> TYPE: PRT
<213> ORGANISM: Artificial
<220> FEATURE:
<223> OTHER INFORMATION: an artificially synthesized sequence

<400> SEQUENCE: 47

Gln Val Gln Leu Lys Glu Ala Gly Pro Gly Leu Val Gln Pro Thr Gln
 1               5                  10                  15

Thr Leu Ser Leu Thr Cys Thr Val Ser Gly Phe Ser Leu Thr Ser Asp
                 20                  25                  30

Gly Val His Trp Ile Arg Gln Pro Pro Gly Lys Gly Leu Glu Trp Met
             35                  40                  45

Gly Ile Ile Tyr Tyr Asp Gly Thr Asp Tyr Asn Ser Ala Ile Lys
 50                  55                  60

Ser Arg Leu Ser Ile Ser Arg Asp Thr Ser Lys Ser Gln Val Phe Leu
 65                  70                  75                  80

Lys Ile Asn Ser Leu Gln Thr Asp Asp Thr Ala Met Tyr Tyr Cys Ala
                 85                  90                  95

Arg Ile His Phe Asp Tyr Trp Gly Gln Gly Val Met Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160
```

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Cys
            340                 345                 350

Glu Leu Thr Lys Asn Gln Val Ser Leu Ser Cys Ala Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Val Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro
            435                 440

<210> SEQ ID NO 48
<211> LENGTH: 450
<212> TYPE: PRT
<213> ORGANISM: Artificial
<220> FEATURE:
<223> OTHER INFORMATION: an artificially synthesized sequence

<400> SEQUENCE: 48

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Ala Ala Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Ala Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Cys Thr Leu Pro Pro Ser Arg
            340                 345                 350

Asp Glu Leu Thr Lys Asn Gln Val Ser Leu Trp Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn Arg
            420                 425                 430

Tyr Thr Gln Lys Ser Leu Ser Leu Ser Pro His His His His His His
        435                 440                 445

His His
    450

<210> SEQ ID NO 49
<211> LENGTH: 116
<212> TYPE: PRT
<213> ORGANISM: Artificial
<220> FEATURE:
```

```
<223> OTHER INFORMATION: an artificially synthesized sequence

<400> SEQUENCE: 49

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser
        115

<210> SEQ ID NO 50
<211> LENGTH: 444
<212> TYPE: PRT
<213> ORGANISM: Artificial
<220> FEATURE:
<223> OTHER INFORMATION: an artificially synthesized sequence

<400> SEQUENCE: 50

Glu Val Gln Leu Val Glu Ser Gly Gly Gly Leu Val Gln Pro Gly Lys
1               5                   10                  15

Ser Leu Lys Leu Ser Cys Glu Ala Ser Gly Phe Thr Phe Ser Gly Tyr
            20                  25                  30

Gly Met His Trp Val Arg Gln Ala Pro Gly Arg Gly Leu Glu Ser Val
        35                  40                  45

Ala Tyr Ile Thr Ser Ser Ile Asn Ile Lys Tyr Ala Asp Ala Val
    50                  55                  60

Lys Gly Arg Phe Thr Val Ser Arg Asp Asn Ala Lys Asn Leu Leu Phe
65                  70                  75                  80

Leu Gln Met Asn Ile Leu Lys Ser Glu Asp Thr Ala Met Tyr Tyr Cys
                85                  90                  95

Ala Arg Phe Asp Trp Asp Lys Asn Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

```
Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Ala Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Cys Glu Leu Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 51
<211> LENGTH: 214
<212> TYPE: PRT
<213> ORGANISM: Artificial
<220> FEATURE:
<223> OTHER INFORMATION: an artificially synthesized sequence

<400> SEQUENCE: 51

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Asn Lys Leu Ala Asp Gly Val Pro Ser Arg Phe Ser Gly
    50                  55                  60

Ser Gly Ser Gly Arg Asp Ser Ser Phe Thr Ile Ser Ser Leu Glu Ser
65                  70                  75                  80

Glu Asp Ile Gly Ser Tyr Tyr Cys Gln Gln Tyr Tyr Asn Tyr Pro Trp
                85                  90                  95

Thr Phe Gly Pro Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 115
<212> TYPE: PRT
<213> ORGANISM: Artificial
<220> FEATURE:
<223> OTHER INFORMATION: an artificially synthesized sequence

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 53
<211> LENGTH: 443
<212> TYPE: PRT
<213> ORGANISM: Artificial
<220> FEATURE:
<223> OTHER INFORMATION: an artificially synthesized sequence

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
```

```
                100             105             110
Val Ser Ser Ala Ser Thr Lys Gly Pro Ser Val Phe Pro Leu Ala Pro
            115             120             125

Ser Ser Lys Ser Thr Ser Gly Gly Thr Ala Ala Leu Gly Cys Leu Val
130             135             140

Lys Asp Tyr Phe Pro Glu Pro Val Thr Val Ser Trp Asn Ser Gly Ala
145             150             155             160

Leu Thr Ser Gly Val His Thr Phe Pro Ala Val Leu Gln Ser Ser Gly
                165             170             175

Leu Tyr Ser Leu Ser Ser Val Val Thr Val Pro Ser Ser Ser Leu Gly
            180             185             190

Thr Gln Thr Tyr Ile Cys Asn Val Asn His Lys Pro Ser Asn Thr Lys
        195             200             205

Val Asp Lys Lys Val Glu Pro Lys Ser Cys Asp Lys Thr His Thr Cys
    210             215             220

Pro Pro Cys Pro Ala Pro Glu Ala Ala Gly Gly Pro Ser Val Phe Leu
225             230             235             240

Phe Pro Pro Lys Pro Lys Asp Thr Leu Met Ile Ser Arg Thr Pro Glu
                245             250             255

Val Thr Cys Val Val Val Asp Val Ser His Glu Asp Pro Glu Val Lys
            260             265             270

Phe Asn Trp Tyr Val Asp Gly Val Glu Val His Asn Ala Lys Thr Lys
        275             280             285

Pro Arg Glu Glu Gln Tyr Ala Ser Thr Tyr Arg Val Val Ser Val Leu
    290             295             300

Thr Val Leu His Gln Asp Trp Leu Asn Gly Lys Glu Tyr Lys Cys Lys
305             310             315             320

Val Ser Asn Lys Ala Leu Pro Ala Pro Ile Glu Lys Thr Ile Ser Lys
                325             330             335

Ala Lys Gly Gln Pro Arg Glu Pro Gln Val Tyr Thr Leu Pro Pro Ser
            340             345             350

Arg Asp Glu Leu Thr Lys Asn Gln Val Ser Leu Thr Cys Leu Val Lys
        355             360             365

Gly Phe Tyr Pro Ser Asp Ile Ala Val Glu Trp Glu Ser Asn Gly Gln
    370             375             380

Pro Glu Asn Asn Tyr Lys Thr Thr Pro Pro Val Leu Asp Ser Asp Gly
385             390             395             400

Ser Phe Phe Leu Tyr Ser Lys Leu Thr Val Asp Lys Ser Arg Trp Gln
                405             410             415

Gln Gly Asn Val Phe Ser Cys Ser Val Met His Glu Ala Leu His Asn
            420             425             430

His Tyr Thr Gln Lys Ser Leu Ser Leu Ser Pro
        435             440

<210> SEQ ID NO 54
<211> LENGTH: 219
<212> TYPE: PRT
<213> ORGANISM: Artificial
<220> FEATURE:
<223> OTHER INFORMATION: an artificially synthesized sequence

<400> SEQUENCE: 54

Asp Ile Val Met Thr Gln Ser Pro Leu Ser Leu Pro Val Thr Pro Gly
1               5               10              15

Glu Pro Ala Ser Ile Ser Cys Arg Ser Ser Gln Ser Leu Val His Ser
```

```
            20                  25                  30
Asn Arg Asn Thr Tyr Leu His Trp Tyr Gln Gln Lys Pro Gly Gln Ala
         35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 55
<211> LENGTH: 20
<212> TYPE: DNA
<213> ORGANISM: Artificial
<220> FEATURE:
<223> OTHER INFORMATION: an artificially synthesized sequence

<400> SEQUENCE: 55
cgcaacgcaa ttaatgtgag                                              20

<210> SEQ ID NO 56
<211> LENGTH: 21
<212> TYPE: DNA
<213> ORGANISM: Artificial
<220> FEATURE:
<223> OTHER INFORMATION: an artificially synthesized sequence

<400> SEQUENCE: 56
tgagttccac gacaccgtca c                                            21

<210> SEQ ID NO 57
<211> LENGTH: 18
<212> TYPE: DNA
<213> ORGANISM: Artificial
<220> FEATURE:
<223> OTHER INFORMATION: an artificially synthesized sequence

<400> SEQUENCE: 57
gcgtcacact ttgctatg                                                18

<210> SEQ ID NO 58
<211> LENGTH: 328
<212> TYPE: PRT
<213> ORGANISM: Artificial
```

<220> FEATURE:
<223> OTHER INFORMATION: an artificially synthesized sequence

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Gly Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn Arg Tyr Thr
305                 310                 315                 320

Gln Lys Ser Leu Ser Leu Ser Pro
                325

<210> SEQ ID NO 59
<211> LENGTH: 107
<212> TYPE: PRT
<213> ORGANISM: Homo sapiens

<400> SEQUENCE: 59

Arg Thr Val Ala Ala Pro Ser Val Phe Ile Phe Pro Pro Ser Asp Glu
1               5                   10                  15

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 60
<211> LENGTH: 106
<212> TYPE: PRT
<213> ORGANISM: Homo sapiens

<400> SEQUENCE: 60

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

```
<210> SEQ ID NO 61
<211> LENGTH: 120
<212> TYPE: PRT
<213> ORGANISM: Artificial
<220> FEATURE:
<223> OTHER INFORMATION: an artificially synthesized sequence

<400> SEQUENCE: 61

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Thr His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Glu Tyr Ser Ser Ser Ser Asp Tyr Trp Gly Gln
            100                 105                 110

Gly Thr Met Val Thr Val Ser Ser
```

<210> SEQ ID NO 62
<211> LENGTH: 124
<212> TYPE: PRT
<213> ORGANISM: Artificial
<220> FEATURE:
<223> OTHER INFORMATION: an artificially synthesized sequence

<400> SEQUENCE: 62

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile His Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Asn Pro Ser Ile Ala Ala Arg Pro Gly Ala Phe Asp
            100                 105                 110

Ile Trp Gly Gln Gly Thr Met Val Thr Val Ser Ser
            115                 120

<210> SEQ ID NO 63
<211> LENGTH: 120
<212> TYPE: PRT
<213> ORGANISM: Artificial
<220> FEATURE:
<223> OTHER INFORMATION: an artificially synthesized sequence

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Thr His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Glu Tyr Ser Ser Ser Ser Asp Tyr Trp Gly Gln
            100                 105                 110

Gly Thr Met Val Thr Val Ser Ser
            115                 120

<210> SEQ ID NO 64
<211> LENGTH: 120
<212> TYPE: PRT
<213> ORGANISM: Artificial
<220> FEATURE:
<223> OTHER INFORMATION: an artificially synthesized sequence

<400> SEQUENCE: 64

Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Ser Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asp Thr Asn Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Thr Gly Tyr Ser Ser Pro Asp Tyr Trp Gly Gln
            100                 105                 110

Gly Thr Pro Val Thr Val Ser Ser
        115                 120

<210> SEQ ID NO 65
<211> LENGTH: 117
<212> TYPE: PRT
<213> ORGANISM: Artificial
<220> FEATURE:
<223> OTHER INFORMATION: an artificially synthesized sequence

<400> SEQUENCE: 65

Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gly Thr Gly Asp Leu Asp Tyr Trp Gly Gln Gly Thr Leu
            100                 105                 110

Val Thr Val Ser Ser
        115

<210> SEQ ID NO 66
<211> LENGTH: 119
<212> TYPE: PRT
<213> ORGANISM: Artificial
<220> FEATURE:
<223> OTHER INFORMATION: an artificially synthesized sequence

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Trp Tyr Ser Tyr Met Leu Arg Met Asp Tyr Trp Gly Gln Gly
                100                 105                 110

Thr Leu Val Thr Val Ser Ser
            115
```

<210> SEQ ID NO 67
<211> LENGTH: 120
<212> TYPE: PRT
<213> ORGANISM: Artificial
<220> FEATURE:
<223> OTHER INFORMATION: an artificially synthesized sequence

<400> SEQUENCE: 67

```
Gln Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Ala Met Tyr His Pro Ser Phe Asn Tyr Trp Gly Gln
                100                 105                 110

Gly Thr Leu Val Thr Val Ser Ser
            115                 120
```

<210> SEQ ID NO 68
<211> LENGTH: 124
<212> TYPE: PRT
<213> ORGANISM: Artificial
<220> FEATURE:
<223> OTHER INFORMATION: an artificially synthesized sequence

<400> SEQUENCE: 68

```
Gln Val Gln Leu Gln Glu Ser Gly Pro Gly Leu Val Lys Pro Ser Glu
  1               5                  10                  15

Thr Leu Ser Leu Thr Cys Ala Val Ser Gly Tyr Ser Ile Ser Ser Gly
                 20                  25                  30

Tyr Tyr Trp Gly Trp Ile Arg Gln Pro Pro Gly Lys Gly Leu Glu Trp
             35                  40                  45

Ile Gly Ser Ile Tyr His Ser Gly Ser Thr Tyr Tyr Asn Pro Ser Leu
         50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gln His Ser Phe Thr Arg Tyr Tyr Gly Tyr Tyr Tyr Phe Asp
                100                 105                 110
```

Tyr Trp Gly Gln Gly Thr Thr Val Thr Val Ser Ser
            115                 120

<210> SEQ ID NO 69
<211> LENGTH: 120
<212> TYPE: PRT
<213> ORGANISM: Artificial
<220> FEATURE:
<223> OTHER INFORMATION: an artificially synthesized sequence

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Trp Tyr Tyr Tyr Pro Ala Leu Asp Tyr Trp Gly Gln
            100                 105                 110

Gly Thr Leu Val Thr Val Ser Ser
            115                 120

<210> SEQ ID NO 70
<211> LENGTH: 118
<212> TYPE: PRT
<213> ORGANISM: Artificial
<220> FEATURE:
<223> OTHER INFORMATION: an artificially synthesized sequence

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Met Asp Tyr Trp Met Leu Pro Asp Val Trp Gly Gln Gly Thr
            100                 105                 110

Leu Val Thr Val Ser Ser
        115

<210> SEQ ID NO 71
<211> LENGTH: 120
<212> TYPE: PRT
<213> ORGANISM: Artificial
<220> FEATURE:
<223> OTHER INFORMATION: an artificially synthesized sequence -continued

<400> SEQUENCE: 71

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Lys Trp Tyr Tyr Pro Ala Leu Asp Tyr Trp Gly Gln Gly
            100                 105                 110

Gly Thr Leu Val Thr Val Ser Ser
        115                 120
```

<210> SEQ ID NO 72
<211> LENGTH: 119
<212> TYPE: PRT
<213> ORGANISM: Artificial
<220> FEATURE:
<223> OTHER INFORMATION: an artificially synthesized sequence

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Ser Tyr Trp Met Lys Trp Asp Tyr Trp Gly Gln Gly
            100                 105                 110

Thr Leu Val Thr Val Ser Ser
        115
```

<210> SEQ ID NO 73
<211> LENGTH: 123
<212> TYPE: PRT
<213> ORGANISM: Artificial
<220> FEATURE:
<223> OTHER INFORMATION: an artificially synthesized sequence

<400> SEQUENCE: 73

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45
```

Ser Ser Ile Ser Pro Ser Gly Gln Ser Thr Tyr Tyr Arg Arg Glu Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Trp Tyr Phe Asp Tyr
                100                 105                 110

Trp Gly Gln Gly Thr Leu Val Thr Val Ser Ser
            115                 120

<210> SEQ ID NO 74
<211> LENGTH: 120
<212> TYPE: PRT
<213> ORGANISM: Artificial
<220> FEATURE:
<223> OTHER INFORMATION: an artificially synthesized sequence

<400> SEQUENCE: 74

Gln Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Lys Trp Tyr Tyr Tyr Pro Ala Leu Asp Tyr Trp Gly Gln
                100                 105                 110

Gly Thr Leu Val Thr Val Ser Ser
            115                 120

<210> SEQ ID NO 75
<211> LENGTH: 119
<212> TYPE: PRT
<213> ORGANISM: Artificial
<220> FEATURE:
<223> OTHER INFORMATION: an artificially synthesized sequence

<400> SEQUENCE: 75

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ser Tyr Tyr Tyr Tyr Lys Met Asp Val Trp Gly Gln Gly
                100                 105                 110

```
Thr Thr Val Thr Val Ser Ser
        115
```

<210> SEQ ID NO 76
<211> LENGTH: 119
<212> TYPE: PRT
<213> ORGANISM: Artificial
<220> FEATURE:
<223> OTHER INFORMATION: an artificially synthesized sequence

<400> SEQUENCE: 76

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Pro Ser Tyr Tyr Pro Trp Met Asp Tyr Trp Gly Gln Gly
            100                 105                 110

Thr Leu Val Thr Val Ser Ser
        115
```

<210> SEQ ID NO 77
<211> LENGTH: 118
<212> TYPE: PRT
<213> ORGANISM: Artificial
<220> FEATURE:
<223> OTHER INFORMATION: an artificially synthesized sequence

<400> SEQUENCE: 77

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Tyr Tyr Met Phe Met Asp Leu Trp Gly Gln Gly Thr
            100                 105                 110

Leu Val Thr Val Tyr Ser
        115
```

<210> SEQ ID NO 78
<211> LENGTH: 119
<212> TYPE: PRT
<213> ORGANISM: Artificial
<220> FEATURE:
<223> OTHER INFORMATION: an artificially synthesized sequence

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Tyr Gly Leu His Met Phe Asp Tyr Trp Gly Gln Gly
            100                 105                 110

Thr Leu Val Thr Val Ser Ser
            115

<210> SEQ ID NO 79
<211> LENGTH: 127
<212> TYPE: PRT
<213> ORGANISM: Artificial
<220> FEATURE:
<223> OTHER INFORMATION: an artificially synthesized sequence

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Thr Lys Ser Ser Lys Ser Arg Gly Lys Arg Tyr Tyr Arg
            100                 105                 110

Tyr Met Asp Val Trp Gly Gln Gly Thr Thr Val Thr Val Ser Ser
            115                 120                 125

<210> SEQ ID NO 80
<211> LENGTH: 111
<212> TYPE: PRT
<213> ORGANISM: Artificial
<220> FEATURE:
<223> OTHER INFORMATION: an artificially synthesized sequence

<400> SEQUENCE: 80

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

```
Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Trp Val Phe Gly Gly Gly Thr Lys Leu Thr Val Leu
            100                 105                 110

<210> SEQ ID NO 81
<211> LENGTH: 110
<212> TYPE: PRT
<213> ORGANISM: Artificial
<220> FEATURE:
<223> OTHER INFORMATION: an artificially synthesized sequence

<400> SEQUENCE: 81

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Ala Asn Asn
                 20                  25                  30

Phe Val Ser Trp Phe Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
         50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Arg Ser Leu
                 85                  90                  95

Ser Ala Gly Val Phe Gly Gly Gly Thr Lys Val Thr Val Leu
            100                 105                 110

<210> SEQ ID NO 82
<211> LENGTH: 111
<212> TYPE: PRT
<213> ORGANISM: Artificial
<220> FEATURE:
<223> OTHER INFORMATION: an artificially synthesized sequence

<400> SEQUENCE: 82

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Phe Val Ser Trp Tyr Gln Gln His Pro Gly Lys Ala Pro Lys Leu
             35                  40                  45

Met Ile Tyr Asp Val Ser Lys Arg Pro Ser Gly Val Ser Thr Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Asn Ser Tyr Thr Thr Ser
                 85                  90                  95

Ser Thr Arg Trp Met Phe Gly Gly Gly Thr Lys Val Thr Val Leu
            100                 105                 110

<210> SEQ ID NO 83
<211> LENGTH: 111
<212> TYPE: PRT
```

<213> ORGANISM: Artificial
<220> FEATURE:
<223> OTHER INFORMATION: an artificially synthesized sequence

<400> SEQUENCE: 83

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Trp Val Phe Gly Gly Gly Thr Lys Leu Thr Val Leu
            100                 105                 110

<210> SEQ ID NO 84
<211> LENGTH: 111
<212> TYPE: PRT
<213> ORGANISM: Artificial
<220> FEATURE:
<223> OTHER INFORMATION: an artificially synthesized sequence

<400> SEQUENCE: 84

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Val Tyr
            20                  25                  30

Asp Tyr Val Ser Trp Tyr Gln Gln Phe Pro Gly Lys Ala Pro Lys Leu
        35                  40                  45

Met Ile Tyr Asp Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Cys Ser Tyr Ser Gly Thr
                85                  90                  95

Asp Ile Arg Trp Leu Phe Gly Gly Gly Thr Lys Leu Thr Val Leu
            100                 105                 110

<210> SEQ ID NO 85
<211> LENGTH: 107
<212> TYPE: PRT
<213> ORGANISM: Artificial
<220> FEATURE:
<223> OTHER INFORMATION: an artificially synthesized sequence

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Ser Phe Pro Leu
            85                  90                  95

Thr Phe Gly Gly Gly Thr Lys Val Glu Ile Lys
            100                 105

<210> SEQ ID NO 86
<211> LENGTH: 107
<212> TYPE: PRT
<213> ORGANISM: Artificial
<220> FEATURE:
<223> OTHER INFORMATION: an artificially synthesized sequence

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
            85                  90                  95

Thr Phe Gly Gly Gly Thr Lys Val Glu Ile Lys
            100                 105

<210> SEQ ID NO 87
<211> LENGTH: 107
<212> TYPE: PRT
<213> ORGANISM: Artificial
<220> FEATURE:
<223> OTHER INFORMATION: an artificially synthesized sequence

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Ser Ile Pro Leu
            85                  90                  95

Thr Phe Gly Gly Gly Thr Lys Val Glu Ile Lys
            100                 105

<210> SEQ ID NO 88
<211> LENGTH: 107
<212> TYPE: PRT
<213> ORGANISM: Artificial
<220> FEATURE:
<223> OTHER INFORMATION: an artificially synthesized sequence

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Ser Phe Pro Leu
                85                  90                  95

Thr Phe Gly Gly Gly Thr Lys Val Glu Ile Lys
            100                 105

<210> SEQ ID NO 89
<211> LENGTH: 107
<212> TYPE: PRT
<213> ORGANISM: Artificial
<220> FEATURE:
<223> OTHER INFORMATION: an artificially synthesized sequence

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Asn Phe Pro Leu
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial
<220> FEATURE:
<223> OTHER INFORMATION: an artificially synthesized sequence

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Ser Arg Phe Pro Leu
                85                  90                  95

Thr Phe Gly Gly Gly Thr Lys Val Glu Ile Lys
            100                 105

<210> SEQ ID NO 91
<211> LENGTH: 107
<212> TYPE: PRT
<213> ORGANISM: Artificial
<220> FEATURE:
<223> OTHER INFORMATION: an artificially synthesized sequence

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Gly Phe Pro Leu
                85                  90                  95

Thr Phe Gly Gly Gly Thr Lys Val Glu Ile Lys
            100                 105

<210> SEQ ID NO 92
<211> LENGTH: 107
<212> TYPE: PRT
<213> ORGANISM: Artificial
<220> FEATURE:
<223> OTHER INFORMATION: an artificially synthesized sequence

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Ser Arg Phe Pro Leu
                85                  90                  95

Thr Phe Gly Gly Gly Thr Lys Val Glu Ile Lys
            100                 105

<210> SEQ ID NO 93
<211> LENGTH: 107
<212> TYPE: PRT
<213> ORGANISM: Artificial
<220> FEATURE:
<223> OTHER INFORMATION: an artificially synthesized sequence

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Val Tyr Arg Ser Pro Leu
                85                  90                  95

Thr Phe Gly Gly Gly Thr Lys Val Glu Ile Lys
            100                 105

<210> SEQ ID NO 94
<211> LENGTH: 107
<212> TYPE: PRT
<213> ORGANISM: Artificial
<220> FEATURE:
<223> OTHER INFORMATION: an artificially synthesized sequence

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Val Arg His Pro Pro
                85                  90                  95

Thr Phe Gly Gly Gly Thr Lys Val Glu Ile Lys
            100                 105

<210> SEQ ID NO 95
<211> LENGTH: 107
<212> TYPE: PRT
<213> ORGANISM: Artificial
<220> FEATURE:
<223> OTHER INFORMATION: an artificially synthesized sequence

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Leu
                85                  90                  95

Thr Phe Gly Gly Gly Thr Lys Val Glu Ile Lys
            100                 105

<210> SEQ ID NO 96
<211> LENGTH: 107
<212> TYPE: PRT
<213> ORGANISM: Artificial
<220> FEATURE:
<223> OTHER INFORMATION: an artificially synthesized sequence

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Thr Ser Phe Pro Leu
                85                  90                  95

Thr Phe Gly Gly Gly Thr Lys Val Glu Ile Lys
            100                 105

<210> SEQ ID NO 97
<211> LENGTH: 107
<212> TYPE: PRT
<213> ORGANISM: Artificial
<220> FEATURE:
<223> OTHER INFORMATION: an artificially synthesized sequence

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Asn Ser Phe Pro Leu
                85                  90                  95

Thr Phe Gly Gly Gly Thr Lys Val Glu Ile Lys
            100                 105

<210> SEQ ID NO 98
<211> LENGTH: 107
<212> TYPE: PRT
<213> ORGANISM: Artificial
<220> FEATURE:
<223> OTHER INFORMATION: an artificially synthesized sequence

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Val Tyr Ser Ser Pro Leu
            85                  90                  95

Thr Phe Gly Gly Gly Thr Lys Val Glu Ile Lys
            100                 105

<210> SEQ ID NO 99
<211> LENGTH: 328
<212> TYPE: PRT
<213> ORGANISM: Artificial
<220> FEATURE:
<223> OTHER INFORMATION: an artificially synthesized sequence

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 100
<211> LENGTH: 399
<212> TYPE: PRT
<213> ORGANISM: Artificial
<220> FEATURE:
<223> OTHER INFORMATION: an artificially synthesized sequence

<400> SEQUENCE: 100

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
                20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln Asp Ile Glu Gly Arg Met Asp Pro Lys Ser Cys Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

Arg Thr Pro Glu Val Thr Cys Val Val Val Asp Val Ser His Glu Asp
210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
        275                 280                 285

Thr Ile Ser Lys Ala Lys Gly Gln Pro Arg Glu Pro Gln Val Tyr Thr
290                 295                 300
```

```
Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
        355                 360                 365

Ser Arg Trp Gln Gln Gly Asn Val Phe Ser Cys Ser Val Met His Glu
    370                 375                 380

Ala Leu His Asn His Tyr Thr Gln Lys Ser Leu Ser Leu Ser Pro
385                 390                 395

<210> SEQ ID NO 101
<211> LENGTH: 449
<212> TYPE: PRT
<213> ORGANISM: Artificial
<220> FEATURE:
<223> OTHER INFORMATION: an artificially synthesized sequence

<400> SEQUENCE: 101

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
            275                 280                 285

His Asn Ala Lys Thr Lys Pro Arg Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro

<210> SEQ ID NO 102
<211> LENGTH: 216
<212> TYPE: PRT
<213> ORGANISM: Artificial
<220> FEATURE:
<223> OTHER INFORMATION: an artificially synthesized sequence

<400> SEQUENCE: 102

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
```

```
                180             185             190
Val Tyr Ala Cys Glu Val Thr His Gln Gly Leu Ser Ser Pro Val Thr
            195                 200             205

Lys Ser Phe Asn Arg Gly Glu Cys
            210                 215

<210> SEQ ID NO 103
<211> LENGTH: 444
<212> TYPE: PRT
<213> ORGANISM: Artificial
<220> FEATURE:
<223> OTHER INFORMATION: an artificially synthesized sequence

<400> SEQUENCE: 103

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Glu His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Phe Pro Ala Pro Ile Glu Lys Thr Ile Ser
```

|  | 325 |  |  |  | 330 |  |  |  | 335 |  |  |
|---|---|---|---|---|---|---|---|---|---|---|---|

Lys Ala Lys Gly Gln Pro Arg Glu Pro Gln Val Tyr Thr Leu Pro Pro
           340                    345                   350

Ser Arg Asp Glu Leu Thr Lys Asn Gln Val Ser Leu Thr Cys Leu Val
        355                    360                365

Lys Gly Phe Tyr Pro Ser Asp Ile Ala Val Glu Trp Glu Ser Asn Gly
    370                    375                380

Gln Pro Glu Asn Asn Tyr Lys Thr Thr Pro Pro Val Leu Asp Ser Asp
385                  390                    395                400

Gly Ser Phe Phe Leu Tyr Ser Lys Leu Thr Val Asp Lys Ser Arg Trp
        405                    410                415

Gln Gln Gly Asn Val Phe Ser Cys Ser Val Met His Glu Ala Leu His
           420                    425                430

Asn His Tyr Thr Gln Lys Ser Leu Ser Leu Ser Pro
           435                    440

<210> SEQ ID NO 104
<211> LENGTH: 214
<212> TYPE: PRT
<213> ORGANISM: Artificial
<220> FEATURE:
<223> OTHER INFORMATION: an artificially synthesized sequence

<400> SEQUENCE: 104

Ser Tyr Glu Leu Thr Gln Pro Pro Ser Val Ser Val Ser Pro Gly Gln
1                   5                    10                15

Thr Ala Ser Ile Thr Cys Ser Gly Asp Asn Ile Gly Asp Gln Tyr Ala
           20                    25                30

His Trp Tyr Gln Gln Lys Pro Gly Gln Ser Pro Val Leu Val Ile Tyr
        35                    40                45

Gln Asp Lys Asn Arg Pro Ser Gly Ile Pro Glu Arg Phe Ser Gly Ser
50                  55                    60

Asn Ser Gly Asn Thr Ala Thr Leu Thr Ile Ser Gly Thr Gln Ala Met
65                  70                    75                80

Asp Glu Ala Asp Tyr Tyr Cys Ala Thr Tyr Thr Gly Phe Gly Ser Leu
           85                    90                95

Ala Val Phe Gly Gly Gly Thr Lys Leu Thr Val Leu Gln Gln Pro Lys
           100                 105              110

Ala Ala Pro Ser Val Thr Leu Phe Pro Pro Ser Ser Glu Glu Leu Gln
        115                 120              125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150               155                160

Val Glu Thr Thr Thr Pro Ser Lys Gln Ser Asn Asn Lys Tyr Ala Ala
           165                 170              175

Ser Ser Tyr Leu Ser Leu Thr Pro Glu Gln Trp Lys Ser His Arg Ser
        180                 185              190

Tyr Ser Cys Gln Val Thr His Glu Gly Ser Thr Val Glu Lys Thr Val
           195                 200              205

Ala Pro Thr Glu Cys Ser
       210

<210> SEQ ID NO 105
<211> LENGTH: 163
<212> TYPE: PRT

<213> ORGANISM: Homo sapiens

<400> SEQUENCE: 105

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln

<210> SEQ ID NO 106
<211> LENGTH: 39
<212> TYPE: PRT
<213> ORGANISM: Homo sapiens

<400> SEQUENCE: 106

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys
        35

<210> SEQ ID NO 107
<211> LENGTH: 41
<212> TYPE: PRT
<213> ORGANISM: Homo sapiens

<400> SEQUENCE: 107

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
            20                  25                  30

Cys Ser Ser Thr Ser Asn Ala Glu Cys
        35                  40

<210> SEQ ID NO 108
<211> LENGTH: 31
<212> TYPE: PRT
<213> ORGANISM: Homo sapiens

<400> SEQUENCE: 108

Asp Cys Thr Pro Gly Phe His Cys Leu Gly Ala Gly Cys Ser Met Cys

```
                1               5                   10                  15
            Glu Gln Asp Cys Lys Gln Gly Gln Glu Leu Thr Lys Lys Gly Cys
                            20                  25                  30

<210> SEQ ID NO 109
<211> LENGTH: 69
<212> TYPE: PRT
<213> ORGANISM: Homo sapiens

<400> SEQUENCE: 109

Lys Asp Cys Cys Phe Gly Thr Phe Asn Asp Gln Lys Arg Gly Ile Cys
1               5                   10                  15

Arg Pro Trp Thr Asn Cys Ser Leu Asp Gly Lys Ser Val Leu Val Asn
            20                  25                  30

Gly Thr Lys Glu Arg Asp Val Val Cys Gly Pro Ser Pro Ala Asp Leu
        35                  40                  45

Ser Pro Gly Ala Ser Ser Val Thr Pro Pro Ala Pro Ala Arg Glu Pro
    50                  55                  60

Gly His Ser Pro Gln
65

<210> SEQ ID NO 110
<211> LENGTH: 94
<212> TYPE: PRT
<213> ORGANISM: Homo sapiens

<400> SEQUENCE: 110

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys
                85                  90

<210> SEQ ID NO 111
<211> LENGTH: 63
<212> TYPE: PRT
<213> ORGANISM: Homo sapiens

<400> SEQUENCE: 111

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys
    50                  55                  60

<210> SEQ ID NO 112
<211> LENGTH: 141
<212> TYPE: PRT
<213> ORGANISM: Homo sapiens
```

<400> SEQUENCE: 112

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
            20                  25                  30

Cys Ser Ser Thr Ser Asn Ala Glu Cys Asp Cys Thr Pro Gly Phe His
        35                  40                  45

Cys Leu Gly Ala Gly Cys Ser Met Cys Glu Gln Asp Cys Lys Gln Gly
    50                  55                  60

Gln Glu Leu Thr Lys Lys Gly Cys Lys Asp Cys Cys Phe Gly Thr Phe
65                  70                  75                  80

Asn Asp Gln Lys Arg Gly Ile Cys Arg Pro Trp Thr Asn Cys Ser Leu
                85                  90                  95

Asp Gly Lys Ser Val Leu Val Asn Gly Thr Lys Glu Arg Asp Val Val
            100                 105                 110

Cys Gly Pro Ser Pro Ala Asp Leu Ser Pro Gly Ala Ser Ser Val Thr
        115                 120                 125

Pro Pro Ala Pro Ala Arg Glu Pro Gly His Ser Pro Gln
    130                 135                 140

<210> SEQ ID NO 113
<211> LENGTH: 72
<212> TYPE: PRT
<213> ORGANISM: Homo sapiens

<400> SEQUENCE: 113

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
            20                  25                  30

Cys Ser Ser Thr Ser Asn Ala Glu Cys Asp Cys Thr Pro Gly Phe His
        35                  40                  45

Cys Leu Gly Ala Gly Cys Ser Met Cys Glu Gln Asp Cys Lys Gln Gly
    50                  55                  60

Gln Glu Leu Thr Lys Lys Gly Cys
65                  70

<210> SEQ ID NO 114
<211> LENGTH: 100
<212> TYPE: PRT
<213> ORGANISM: Homo sapiens

<400> SEQUENCE: 114

Asp Cys Thr Pro Gly Phe His Cys Leu Gly Ala Gly Cys Ser Met Cys
1               5                   10                  15

Glu Gln Asp Cys Lys Gln Gly Gln Glu Leu Thr Lys Lys Gly Cys Lys
            20                  25                  30

Asp Cys Cys Phe Gly Thr Phe Asn Asp Gln Lys Arg Gly Ile Cys Arg
        35                  40                  45

Pro Trp Thr Asn Cys Ser Leu Asp Gly Lys Ser Val Leu Val Asn Gly
    50                  55                  60

Thr Lys Glu Arg Asp Val Val Cys Gly Pro Ser Pro Ala Asp Leu Ser
65                  70                  75                  80

Pro Gly Ala Ser Ser Val Thr Pro Pro Ala Pro Ala Arg Glu Pro Gly
            85                  90                  95

His Ser Pro Gln
        100

<210> SEQ ID NO 115
<211> LENGTH: 115
<212> TYPE: PRT
<213> ORGANISM: Artificial
<220> FEATURE:
<223> OTHER INFORMATION: an artificially synthesized sequence

<400> SEQUENCE: 115

Gln Val Gln Leu Val Gln Ser Gly Ala Glu Val Lys Pro Gly Ala
1               5                  10                  15

Ser Val Lys Val Ser Cys Lys Ala Ser Gly Tyr Thr Phe Thr Asp Tyr
                20                  25                  30

Glu Met His Trp Ile Arg Gln Pro Gly Gln Gly Leu Glu Trp Ile
            35                  40                  45

Gly Ala Ile Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 116
<211> LENGTH: 112
<212> TYPE: PRT
<213> ORGANISM: Artificial
<220> FEATURE:
<223> OTHER INFORMATION: an artificially synthesized sequence

<400> SEQUENCE: 116

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Val His Ser
                20                  25                  30

Asn Arg Asn Thr Tyr Leu His Trp Tyr Gln Gln Lys Pro Gly Gln Ala
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

<210> SEQ ID NO 117
<211> LENGTH: 328
<212> TYPE: PRT
<213> ORGANISM: Artificial
<220> FEATURE:
<223> OTHER INFORMATION: an artificially synthesized sequence

<400> SEQUENCE: 117

Ala Ser Thr Lys Gly Pro Ser Val Phe Pro Leu Ala Pro Ser Ser Lys

```
              1               5                  10                    15
Ser Thr Ser Gly Gly Thr Ala Ala Leu Gly Cys Leu Val Lys Asp Tyr
              20                  25                    30

Phe Pro Glu Pro Val Thr Val Ser Trp Asn Ser Gly Ala Leu Thr Ser
              35                  40                    45

Gly Val His Thr Phe Pro Ala Val Leu Gln Ser Ser Gly Leu Tyr Ser
              50                  55                    60

Leu Ser Ser Val Val Thr Val Pro Ser Ser Leu Gly Thr Gln Thr
65                  70                  75                    80

Tyr Ile Cys Asn Val Asn His Lys Pro Ser Asn Thr Lys Val Asp Lys
                  85                  90                    95

Lys Val Glu Pro Lys Ser Cys Asp Lys Thr His Thr Cys Pro Pro Cys
              100                 105                   110

Pro Ala Pro Glu Leu Arg Gly Gly Pro Lys Val Phe Leu Phe Pro Pro
              115                 120                   125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                   160

Tyr Val Asp Gly Val Glu Val His Asn Ala Lys Thr Lys Pro Arg Glu
                  165                 170                   175

Glu Gln Tyr Ala Ser Thr Tyr Arg Val Val Ser Val Leu Thr Val Leu
              180                 185                   190

His Gln Asp Trp Leu Asn Gly Lys Glu Tyr Lys Cys Lys Val Ser Asn
              195                 200                   205

Lys Ala Leu Pro Ala Pro Ile Glu Lys Thr Ile Ser Lys Ala Lys Gly
              210                 215                   220

Gln Pro Arg Glu Pro Gln Val Tyr Thr Leu Pro Pro Ser Arg Asp Glu
225                 230                 235                   240

Leu Thr Lys Asn Gln Val Ser Leu Thr Cys Leu Val Lys Gly Phe Tyr
                  245                 250                   255

Pro Ser Asp Ile Ala Val Glu Trp Glu Ser Asn Gly Gln Pro Glu Asn
              260                 265                   270

Asn Tyr Lys Thr Thr Pro Pro Tyr Leu Asp Ser Asp Gly Ser Phe Phe
                  275                 280                   285

Leu Tyr Ser Lys Leu Thr Val Asp Lys Ser Arg Trp Gln Gln Gly Asn
              290                 295                   300

Val Phe Ser Cys Ser Val Met His Glu Ala Leu His Asn His Tyr Thr
305                 310                 315                   320

Gln Glu Ser Leu Ser Leu Ser Pro
                  325

<210> SEQ ID NO 118
<211> LENGTH: 107
<212> TYPE: PRT
<213> ORGANISM: Artificial
<220> FEATURE:
<223> OTHER INFORMATION: an artificially synthesized sequence

<400> SEQUENCE: 118

Arg Thr Val Ala Ala Pro Ser Val Phe Ile Phe Pro Pro Ser Asp Glu
1               5                   10                    15

Gln Leu Lys Ser Gly Thr Ala Ser Val Val Cys Leu Leu Asn Asn Phe
              20                  25                    30

Tyr Pro Arg Glu Ala Lys Val Gln Trp Lys Val Asp Asn Ala Leu Gln
```

-continued

```
            35                  40                  45
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 119
<211> LENGTH: 328
<212> TYPE: PRT
<213> ORGANISM: Artificial
<220> FEATURE:
<223> OTHER INFORMATION: an artificially synthesized sequence

<400> SEQUENCE: 119

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Arg Gly Gly Pro Lys Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
```

```
                290                 295                 300
Val Phe Ser Cys Ser Val Met His Glu Ala Leu His Asn Arg Tyr Thr
305                 310                 315                 320

Gln Lys Ser Leu Ser Leu Ser Pro
                325

<210> SEQ ID NO 120
<211> LENGTH: 116
<212> TYPE: PRT
<213> ORGANISM: Artificial
<220> FEATURE:
<223> OTHER INFORMATION: an artificially synthesized sequence

<400> SEQUENCE: 120

Glu Val Gln Val Val Glu Ser Asp Gly Gly Leu Val Gln Pro Gly Arg
1               5                   10                  15

Ser Leu Lys Leu Pro Cys Ala Ala Ser Gly Phe Thr Phe Ser Asp Tyr
                20                  25                  30

Tyr Met Ala Trp Val Arg Gln Ala Pro Thr Lys Gly Leu Glu Trp Val
            35                  40                  45

Ala Ser Ile Ser Tyr Asp Gly Ser Ser Thr Tyr Tyr Arg Asp Ser Val
50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Gly Arg His Ser Ser Tyr Phe Asp Tyr Trp Gly Gln Gly Val Met Val
            100                 105                 110

Thr Val Ser Ser
        115

<210> SEQ ID NO 121
<211> LENGTH: 106
<212> TYPE: PRT
<213> ORGANISM: Artificial
<220> FEATURE:
<223> OTHER INFORMATION: an artificially synthesized sequence

<400> SEQUENCE: 121

Asp Ile Glu Leu Thr Gln Ser Pro Ala Leu Ala Val Ser Pro Gly Glu
1               5                   10                  15

Arg Val Thr Ile Ser Cys Arg Ala Ser Asp Ser Val Ser Thr Leu Met
                20                  25                  30

His Trp Tyr Gln Gln Lys Pro Gly Gln Gln Pro Lys Leu Leu Ile Tyr
            35                  40                  45

Leu Ala Ser His Leu Glu Ser Gly Val Pro Ala Arg Phe Ser Gly Ser
    50                  55                  60

Gly Ser Gly Thr Asp Phe Thr Leu Thr Ile Asp Pro Val Glu Ala Asp
65                  70                  75                  80

Asp Thr Ala Thr Tyr Tyr Cys Gln Gln Ser Trp Asn Asp Pro Trp Thr
                85                  90                  95

Phe Gly Gly Gly Thr Lys Leu Glu Leu Lys
            100                 105

<210> SEQ ID NO 122
<211> LENGTH: 121
<212> TYPE: PRT
<213> ORGANISM: Artificial sequence
<220> FEATURE:
```

<223> OTHER INFORMATION: an artificially synthesized sequence

<400> SEQUENCE: 122

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
            115                 120
```

<210> SEQ ID NO 123
<211> LENGTH: 109
<212> TYPE: PRT
<213> ORGANISM: Artificial sequence
<220> FEATURE:
<223> OTHER INFORMATION: an artificially synthesized sequence

<400> SEQUENCE: 123

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105
```

<210> SEQ ID NO 124
<211> LENGTH: 120
<212> TYPE: PRT
<213> ORGANISM: Artificial sequence
<220> FEATURE:
<223> OTHER INFORMATION: an artificially synthesized sequence

<400> SEQUENCE: 124

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Thr His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
```

```
                50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ala Pro Glu Tyr Ser Ser Ser Asp Tyr Trp Gly Gln
                100                 105                 110

Gly Thr Met Val Thr Val Ser Ser
            115                 120

<210> SEQ ID NO 125
<211> LENGTH: 117
<212> TYPE: PRT
<213> ORGANISM: Artificial sequence
<220> FEATURE:
<223> OTHER INFORMATION: an artificially synthesized sequence

<400> SEQUENCE: 125

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
             35                  40                  45

Gly Trp Ile Asn Pro Asn Ser Gly Gly Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Gly Ile Gly Asn His Asp Tyr Trp Gly Gln Gly Thr Leu
                100                 105                 110

Val Thr Val Ser Ser
            115
```

IMMUNOACTIVATING ANTIGEN-BINDING MOLECULE

CROSS-REFERENCE TO RELATED APPLICATIONS

This application is a U.S. National Phase of PCT Application No. PCT/JP2015/060794, filed Apr. 7, 2015, which claims the benefit of Japanese Patent Application No. 2014-078457, filed Apr. 7, 2014, and Japanese Patent Application No. 2014-264589, filed Dec. 26, 2014, each of which is incorporated herein by reference.

TECHNICAL FIELD

The present invention relates to a novel cancer treatment method that uses a bispecific antibody.

BACKGROUND ART

Cancer is one of the major causes of death in the world. With the exception of certain carcinomas, a cancer is often inoperable at the time it is found, and the outcome of treatment using chemotherapeutic agents, which is the main therapeutic method, is not necessarily good. Heterogeneity of cancer cells per se is not the only factor that makes cancer treatment difficult, and the tumor microenvironment has been suggested to play a major role (Non-patent Document 1). Recently, a possibility of curing unresectable malignant melanoma and such with an anti-CTLA-4 antibody which attenuates suppressor T cells has been suggested (Non-patent Document 2). This suggests that tumor immunostimulation may form the basis for designing new cancer treatment strategies.

It is understood that T cells which have important roles in tumor immunity become activated by two signals: 1) binding of a T cell receptor (TCR) to an antigenic peptide presented by major histocompatibility complex (MHC) class I molecules and activation of TCR; and 2) binding of a costimulator on the surface of T cells to the ligands on antigen-presenting cells and activation of the costimulator. Furthermore, activation of molecules belonging to the tumor necrosis factor (TNF) superfamily and the TNF receptor superfamily, such as CD137(4-1BB) on the surface of T cells, has been described to be important for T cell activation (Non-patent Document 3).

Molecules such as CD137, CD137L, CD40, CD40L, OX40, OX40L, CD27, CD70, HVEM, LIGHT, RANK, RANKL, CD30, CD153, GITR, and GITRL are included in the TNF superfamily and the TNF receptor superfamily. CD137 has been reported to be expressed not only on the surface of T cells, but also on the surface of other immune cells such as dendritic cells (DC), B cells, NK cells, and neutrophils (Non-patent Document 4).

CD137 agonist antibodies have already been demonstrated to show anti-tumor effects, and this has been shown experimentally to be mainly due to activation of CD8-positive T cells and NK cells (Non-patent Document 5). However, side effects due to non-specific hepatotoxicity of CD137 agonist antibodies have been a problem clinically and non-clinically, and development of pharmaceutical agents has not advanced (Non-patent Documents 6 and 7). The main cause of the side effects has been suggested to involve binding to the Fcγ receptor via the antibody constant region (Non-patent Document 8). Furthermore, it has been reported that for agonist antibodies targeting receptors that belong to the TNF receptor superfamily to exert an agonist activity in vivo, antibody crosslinking by Fcγ receptor-expressing cells (FcγRII-expressing cells) is necessary (Non-patent Document 9). More specifically, medicinal effects of CD137 agonist antibodies, which are anti-tumor effects, and side effects including hepatotoxicity both involve binding of the antibodies to Fcγ receptors. Therefore, if binding of the antibodies to Fcγ receptors is enhanced, medicinal effects are expected to improve but hepatotoxic side effects will also increase, and if binding of the antibodies to Fcγ receptors is reduced, side effects will be reduced but medicinal effects may become reduced as well, and CD137 agonist antibodies whose medicinal effects are separated from side effects have not been reported so far. Furthermore, the antitumor effects of CD137 agonist antibodies per se are not strong at all, and it is desirable to avoid toxicity and at the same time increase medicinal effects further.

Bispecific antibodies are characterized in that they have at least two binding domains, and their molecular morphology is already well known to those skilled in the art. Among them, molecules in which one of the two binding domains binds specifically to a cancer surface antigen and the second binding domain binds to a T cell surface antigen CD3 have also been constructed (Non-patent Document 10). Such bispecific single-chain antibodies have been shown to exert an antitumor effect by activating T cells in a cancer antigen-dependent manner.

Glypican 3 (GPC3) is a protein that belongs to the glypican family, i.e., a group of heparan sulfate proteoglycans bound to cell surface via glycosylphosphatidylinositol (Non-patent Document 11). Glypicans play an important role in cell proliferation, differentiation, and migration. GPC3 is expressed in 70% or more of hepatoma tissues obtained by surgical excision or biopsy, and is hardly or not at all expressed in neighboring nonneoplastic hepatic lesions and most adult tissues (Non-patent Documents 12 and 13). Furthermore, patients with high expression of hepatoma tissue GPC3 have been reported to have a poor prognosis (Non-patent Document 14), and GPC3 is considered to be a promising target molecule for hepatoma.

PRIOR ART DOCUMENTS

Non-Patent Documents

[Non-patent Document 1] Hanahan, Cell, 2011, 144, 646-74

[Non-patent Document 2] Prieto, Clin Cancer Res. 2012, 18, 2039-47

[Non-patent Document 3] Summers, Nat. Rev. Immunol., 2012, 12, 339-51

[Non-patent Document 4] Vinay, Cell Biol Int., 2009, 33, 453-65

[Non-patent Document 5] Houot, Blood. 2009, 114, 3431-8

[Non-patent Document 6] Ascierto, Semin Oncol., 2010, 37, 508-16

[Non-patent Document 7] Dubrot, Cancer Immunol. Immunother., 2010, 59, 1223-33

[Non-patent Document 8] Schabowsky, Vaccine, 2009, 28, 512-22

[Non-patent Document 9] Li, Proc Natl Acad Sci USA. 2013, 110(48), 19501-6

[Non-patent Document 10] Brandl, Cancer Immunol. Immunother., 2007, 56, 1551-63

[Non-patent Document 11] Filmus, J. Clin. Invest., 2001, 108, 497-501

[Non-patent Document 12] Zhu-Zu-W, Gut, 2001, 48, 558-564

[Non-patent Document 13] Yamauchi, Mod. Pathol., 2005, 18, 1591-1598
[Non-patent Document 14] Yorita, Liver Int., 2010, 1, 120-131

SUMMARY OF THE INVENTION

Problems to be Solved by the Invention

The present invention was achieved in view of the above circumstances. An objective of the present invention is to provide antigen-binding molecules that have an agonist activity against the TNF superfamily or the TNF receptor superfamily, which avoid toxicity while activating immune cells and exhibiting an excellent anti-tumor effect. Another objective of the present invention is to provide pharmaceutical compositions comprising the antigen-binding molecule as an active ingredient or methods for treating cancer using the pharmaceutical composition.

Means for Solving the Problems

The present inventors discovered that even though antigen-binding molecules having only the TNF superfamily-binding domain or only the TNF receptor superfamily-binding domain do not have an immune cell-activating effect, antigen-binding molecules having a cancer-specific antigen-binding domain and a TNF superfamily-binding domain or a cancer-specific antigen-binding domain and a TNF receptor superfamily-binding domain activate immune cells by exerting an agonist activity against factors belonging to the TNF superfamily or the TNF receptor superfamily only in the presence of cancer-specific antigen-expressing cells, and avoid side effects such as hepatotoxicity while maintaining an anti-tumor activity. Furthermore, the present inventors discovered that by using the antigen-binding molecules in combination with antigen-binding molecules having a cancer-specific antigen-binding domain and a T cell receptor complex-binding domain, side effects can be avoided and antitumor activity can be increased, and thereby completed the present invention.

More specifically, the present invention provides the following:
[1] an antigen-binding molecule comprising:
  (1) a cancer-specific antigen-binding domain; and
  (2) a tumor necrosis factor (TNF) superfamily-binding domain or a tumor necrosis factor (TNF) receptor superfamily-binding domain:
[2] the antigen-binding molecule of [1], further comprising an FcRn-binding domain;
[3] the antigen-binding molecule of [2], wherein the FcRn-binding domain is an antibody Fc region having decreased Fcγ receptor-binding activity;
[4] the antigen-binding molecule of any one of [1] to [3], wherein the TNF superfamily-binding domain or the TNF receptor superfamily-binding domain is a CD137-binding domain;
[5] the antigen-binding molecule of any one of [1] to [4], which is a bispecific antibody;
[6] a pharmaceutical composition comprising as an active ingredient the antigen-binding molecule of any one of [1] to [5];
[7] the pharmaceutical composition of [6], which is a cytotoxicity-inducing composition;
[8] the pharmaceutical composition of [6], which is a composition for use in the treatment of cancer;
[9] a pharmaceutical composition comprising a combination of a first antigen-binding molecule of any one of [1] to [5], and a second antigen-binding molecule that comprises:
  (1) a cancer-specific antigen-binding domain; and
  (2) a T cell receptor complex-binding domain:
[10] the pharmaceutical composition of [9], wherein the second antigen-binding molecule is an antigen-binding molecule that further comprises an FcRn-binding domain;
[11] the pharmaceutical composition of [10], wherein the FcRn-binding domain is an antibody Fc region having decreased Fcγ receptor-binding activity,
[12] the pharmaceutical composition of any one of [9] to [11], wherein the T cell receptor complex-binding domain is a T cell receptor-binding domain;
[13] the pharmaceutical composition of any one of [9] to [11], wherein the T cell receptor complex-binding domain is a CD3-binding domain;
[14] the pharmaceutical composition of any one of [9] to [13], wherein the second antigen-binding molecule is a bispecific antibody;
[15] the pharmaceutical composition of any one of [9] to [14], wherein the first antigen-binding molecule and the second antigen-binding molecule are mixed;
[16] the pharmaceutical composition of any one of [9] to [14], wherein the first antigen-binding molecule and the second antigen-binding molecule are used concomitantly;
[17] the pharmaceutical composition of any one of [9] to [14], wherein the first antigen-binding molecule and the second antigen-binding molecule are administered simultaneously;
[18] the pharmaceutical composition of any one of [9] to [14], wherein the first antigen-binding molecule and the second antigen-binding molecule are administered separately;
[19] the pharmaceutical composition of any one of [9] to [18], which is a cytotoxicity-inducing composition;
[20] the pharmaceutical composition of any one of 191 to [18], which is a composition for use in the treatment of cancer;
[21] a pharmaceutical composition comprising as an active ingredient a first antigen-binding molecule that comprises:
  (1) a cancer-specific antigen-binding domain; and
  (2) a tumor necrosis factor (TNF) superfamily-binding domain or a tumor necrosis factor (TNF) receptor superfamily-binding domain, for concomitant use with a second antigen-binding molecule that comprises:
  (1) a cancer-specific antigen-binding domain; and
  (2) a T cell receptor complex-binding domain;
[22] the pharmaceutical composition of [21], which is a cytotoxicity-inducing composition;
[23] the pharmaceutical composition of [21], which is a composition for use in the treatment of cancer;
[24] the pharmaceutical composition of any one of [21] to [23], wherein the first antigen-binding molecule and/or the second antigen-binding molecule is an antigen-binding molecule that further comprises an FcRn-binding domain;
[25] the pharmaceutical composition of [24], wherein the FcRn-binding domain is an antibody Fc region having decreased Fcγ receptor-binding activity;
[26] the pharmaceutical composition of any one of [21] to [25], wherein the TNF superfamily-binding domain or the TNF receptor superfamily-binding domain is a CD137-binding domain or a CD40-binding domain;

[27] the pharmaceutical composition of any one of [2] to [26], wherein the T cell receptor complex-binding domain is a T cell receptor-binding domain;

[28] the pharmaceutical composition of any one of [21] to [26], wherein the T cell receptor complex-binding domain is a CD3-binding domain;

[29] the pharmaceutical composition of any one of [21] to [28], wherein the first antigen-binding molecule and/or the second antigen-binding molecule is a bispecific antibody;

[30] the pharmaceutical composition of any one of [21] to [29], which is administered simultaneously with the second antigen-binding molecule;

[31] the pharmaceutical composition of any one of [21] to [29], which is administered separately from the second antigen-binding molecule;

[32] a pharmaceutical composition comprising as an active ingredient a second antigen-binding molecule that comprises:
 (1) a cancer-specific antigen-binding domain; and
 (2) a T cell receptor complex-binding domain,
for concomitant use with a first antigen-binding molecule that comprises:
 (1) a cancer-specific antigen-binding domain; and
 (2) a tumor necrosis factor (TNF) superfamily-binding domain or a tumor necrosis factor (TNF) receptor superfamily-binding domain:

[33] the pharmaceutical composition of [32], which is a cytotoxicity-inducing composition;

[34] the pharmaceutical composition of [32], which is a composition for use in the treatment of cancer;

[35] the pharmaceutical composition of any one of [32] to [34], wherein the first antigen-binding molecule and/or the second antigen-binding molecule is an antigen-binding molecule that further comprises an FcRn-binding domain;

[36] the pharmaceutical composition of [35], wherein the FcRn-binding domain is an antibody Fc region having decreased Fcγ receptor-binding activity;

[37] the pharmaceutical composition of any one of [32] to [36], wherein the T cell receptor complex-binding domain is a T cell receptor-binding domain;

[38] the pharmaceutical composition of any one of [32] to [36], wherein the T cell receptor complex-binding domain is a CD3-binding domain;

[39] the pharmaceutical composition of any one of [32] to [38], wherein the TNF superfamily-binding domain or the TNF receptor superfamily-binding domain is a CD137-binding domain or a CD40-binding domain;

[40] the pharmaceutical composition of any one of [32] to [39], wherein the first antigen-binding molecule and/or the second antigen-binding molecule is a bispecific antibody;

[41] the pharmaceutical composition of any one of [32] to [40], which is administered simultaneously with the first antigen-binding molecule;

[42] the pharmaceutical composition of any one of [32] to [40], which is administered separately from the first antigen-binding molecule;

[43] a method for inducing cytotoxicity, suppressing cell proliferation, activating immunity against a cancer cell or a cancer cell-comprising tumor tissue, or treating or preventing cancer, which comprises the step of administering the antigen-binding molecule of any one of [1] to [5] or the pharmaceutical composition of any one of [6] to [42];

[44] the antigen-binding molecule of any one of [1] to [5] or the pharmaceutical composition of any one of [6] to [42], for use in inducing cytotoxicity, suppressing cell proliferation, activating immunity against a cancer cell or a cancer cell-comprising tumor tissue, or treating or preventing cancer;

[45] use of the antigen-binding molecule of any one of [1] to [5] in production of the pharmaceutical composition of any one of [6] to [42]; and

[46] a method for producing the pharmaceutical composition of any one of [6] to [42], which comprises the step of using the antigen-binding molecule of any one of [1] to [5].

Furthermore, the present invention relates to methods for treating or preventing cancer, which comprises administering an antigen-binding molecule of the present invention or a pharmaceutical composition of the present invention to a patient in need of treatment. The present invention also relates to a kit for use in the method of the present invention, which comprises an antigen-binding molecule of the present invention. The present invention also relates to the use of an antigen-binding molecule of the present invention in producing a pharmaceutical composition for inducing cytotoxicity (for example, a pharmaceutical composition for treating or preventing cancer). Furthermore, the present invention relates to antigen-binding molecules of the present invention or pharmaceutical compositions of the present invention for use in methods of the present invention.

BRIEF DESCRIPTION OF THE DRAWINGS

FIG. 14-1 shows the results of ELISA for assessing the binding of anti-human CD137 antibodies to fragmented human CD137-Fc fusion proteins. In the figure, "Non" indicates the level of ELISA color development in wells that have not been immobilized with the antigen (Non-Coating).

FIG. 14-2 shows the values (ratios relative to the level in Non-Coating) obtained by dividing the levels of ELISA color development of each sample shown in FIG. 14-1 by the level of ELISA color development in Non-Coating (Non) wells (binding to wells that have not been immobilized with the antigen).

FIG. 16 shows the T cell activation effect and binding profile of anti-human CD137 antibodies.

MODE FOR CARRYING OUT THE INVENTION

Figure 1:
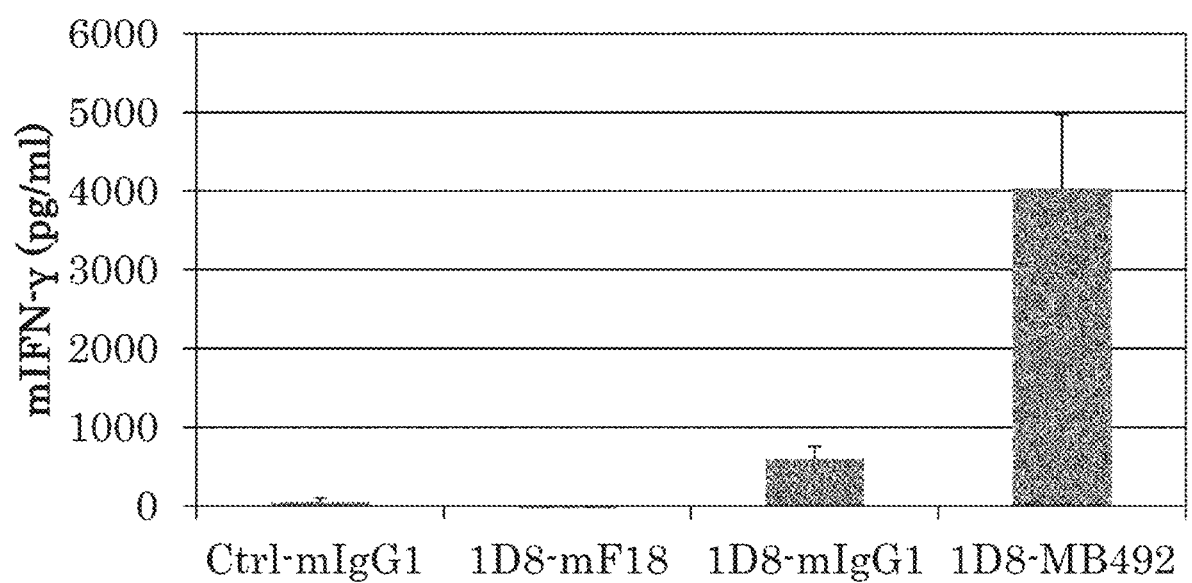
FIG. 1 presents a graph showing results of assessing the effect of anti-mouse CD137 antibodies on T cell activation by IFN-γ ELISA. Ctrl mIgG1 indicates the negative control mouse IgG1 antibody.

The following definitions are provided in order to facilitate understanding of the invention described herein.

Antigen-Binding Molecules

In the present invention, "antigen-binding molecules" are not particularly limited as long as they are molecules that comprise a "binding domain" of the present invention, and they may further comprise a peptide or protein having a length of about five amino acids or more. The peptide and protein are not limited to those derived from a living organism, and for example, they may be a polypeptide produced from an artificially designed sequence. They may also be any of a naturally-occurring polypeptide, synthetic polypeptide, recombinant polypeptide, and such.

A favorable example of an antigen-binding molecule of the present invention is an antigen-binding molecule that comprises an FcRn-binding domain contained in an antibody Fc region. As a method for extending the blood half-life of a protein administered to a living body, the method of adding an FcRn-binding domain of an antibody to the protein of interest and utilizing the function of FcRn-mediated recycling is well known.

In the present invention, the "FcRn-binding domain" is not particularly limited as long as it has binding activity to FcRn, and examples include antibody variable regions, Fab and antibody Fc regions whose antigens are FcRn, and fragments thereof. A preferred embodiment of the present invention includes antibody Fc regions or fragments containing an FcRn-binding region of an Fc region. Herein, for example, an Fc region derived from a naturally-occurring IgG may be used as the "Fc region". A naturally-occurring IgG means a polypeptide that comprises the same amino acid sequence as an IgG found in nature, and belongs to a class of antibodies substantially encoded by immunoglobulin gamma genes. A naturally-occurring human IgG means, for example, a naturally-occurring human IgG1, a naturally-occurring human IgG2, a naturally-occurring human IgG3, or a naturally-occurring human IgG4. Naturally-occurring IgGs also include mutants and such that naturally generate therefrom. A plurality of allotype sequences that result from genetic polymorphism have been described in Sequences of Proteins of Immunological Interest, NIH Publication No. 91-3242 for the human IgG1, human IgG2, human IgG3, and human IgG4 antibody constant region, and any of the sequences may be used in the present invention. In particular, the amino acid sequence of positions 356 to 358 according to EU numbering may be DEL or EEM for the human IgG1 sequence.

Existing antibody Fc regions are, for example. IgA1. IgA2, IgD, IgE, IgG1, IgG2, IgG3, IgG4, and IgM-type Fc regions. For example, an Fc region derived from a naturally-occurring human IgG antibody can be used as the antibody Fc region of the present invention. Fc regions derived from a constant region of a naturally-occurring IgG, or more specifically, a constant region derived from a naturally-occurring human IgG1 (SEQ ID NO: 1), a constant region derived from a naturally-occurring human IgG2 (SEQ ID NO: 2), a constant region derived from a naturally-occurring human IgG3 (SEQ ID NO: 3), and a constant region derived from a naturally-occurring human IgG4 (SEQ ID NO: 4), can be used as an Fc region of the present invention. Mutants and such that naturally generate therefrom are also included in the naturally-occurring IgG constant regions.

Such antibody Fc regions can be suitably obtained, for example, by partial digestion of antibodies such as monoclonal antibodies using a protease such as pepsin, then adsorption of the resulting fragments onto a protein A column or a protein G column, and subsequent elution using an appropriate elution buffer and such. The protease is not particularly limited as long as it can digest an antibody such as a monoclonal antibody by appropriately establishing the enzyme reaction conditions such as pH, and examples include pepsin and ficin.

Figure 13:
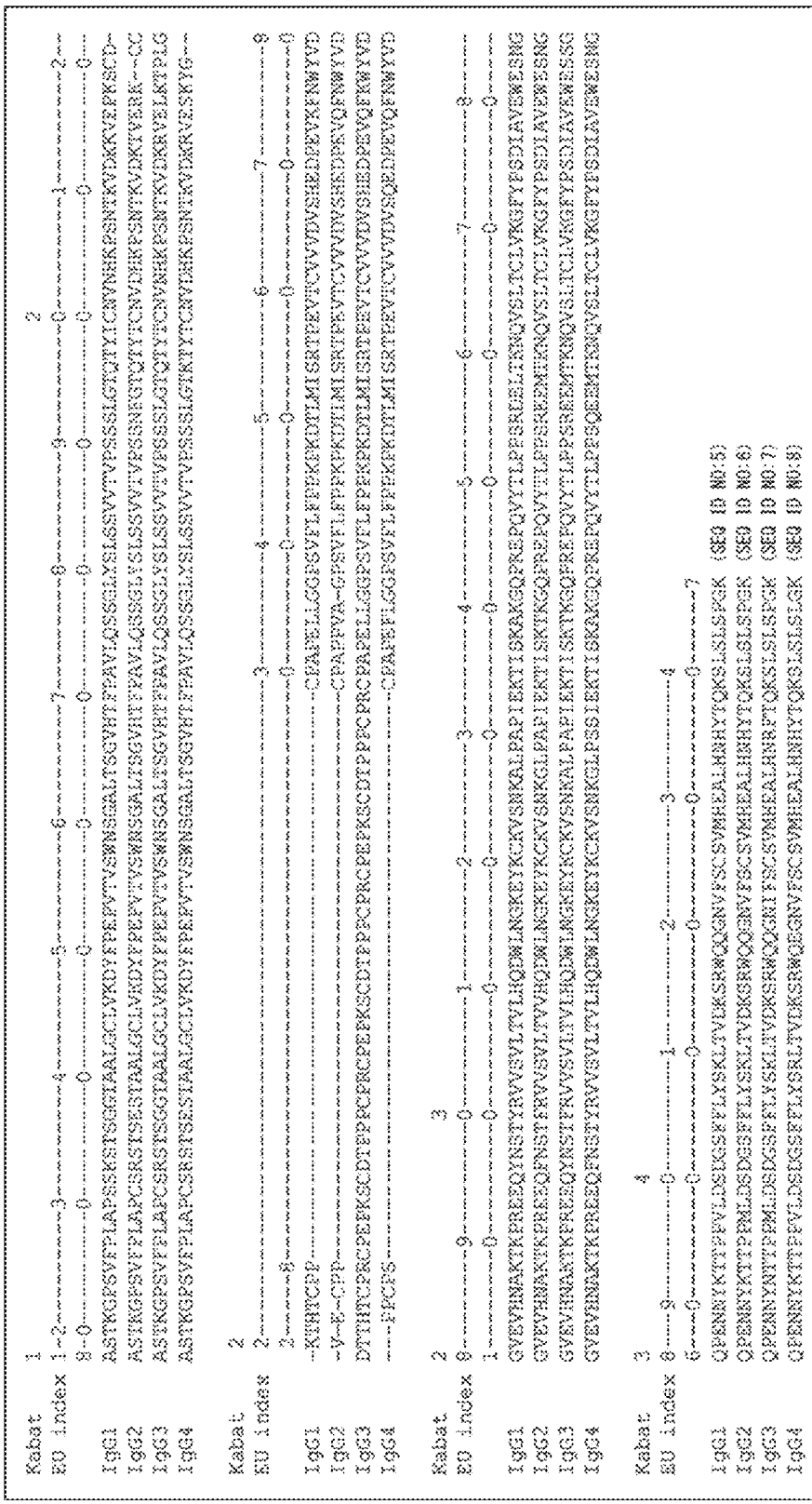
FIG. 13 shows the relationship between the amino acid residues constituting the Fc regions of IgG1, IgG2, IgG3, and IgG4, and Kabat's EU numbering (herein, it is also called the EU INDEX).

The isotype of an antibody is determined by the structure of the constant region. The constant region of isotypes IgG1, IgG2, IgG3, and IgG4 is called Cγ1, Cγ2, Cγ3, and Cγ4, respectively. The amino acid sequences of polypeptides constituting the Fc regions of human Cγ1, Cγ2, Cγ3, and Cγ4 are exemplified in SEQ ID NOs: 5, 6, 7, and 8. The relationship between amino acid residues constituting each of these amino acid sequences and Kabat's EU numbering (herein, also referred to as EU INDEX) is shown in FIG. 13.

An Fc region refers to a region that excludes F(ab')$_2$ which contains two light chains and two heavy chains containing part of the constant region between the CH1 domain and the CH2 domain such that the disulfide bonds between the chains are formed between the two heavy chains. Fc regions forming the antigen-binding molecules disclosed herein can be obtained suitably by partially digesting the IgG1, IgG2, IgG3, or IgG4 monoclonal antibodies or the like using a protease such as pepsin, and then re-eluting fractions adsorbed to the protein A column. The protease is not particularly limited as long as it can digest a full-length antibody in a restrictive manner to produce F(ab')$_2$ by appropriately establishing the enzyme reaction conditions such as pH. Such proteases include, for example, pepsin and ficin.

A domain with decreased Fcγ receptor-binding activity is particularly preferred as the FcRn-binding domain of the present invention. Here, an Fcγ receptor (herein, also denoted as Fcγ receptor, FcγR, or FcgR) refers to a receptor that can bind to the Fc region of IgG1, IgG2. IgG3, or IgG4, and includes all members belonging to the family of proteins substantially encoded by Fcγ receptor genes. In humans, this family includes, but is not limited to, FcγRI (CD64) including isoforms FcγRIa, FcγRIb, and FcγRIc; FcγRII (CD32) including isoforms FcγRIIa (including allotypes H131 (type H) and R131 (type R), FcγRIIb (including FcγRIIb-1 and FcγRIIb-2), and FcγRIIc; and FcγRIII (CD16) including isoforms FcγRIIIa (including allotypes V158 and F158) and FcγRIIIb (including allotypes FcγRIIIb-NA1 and FcγRIIIb-NA2); as well as any undiscovered human FcγRs, and FcγR isoforms or allotypes. FcγRs include, but are not limited to, those derived from humans, mice, rats, rabbits, and monkeys, and may be derived from any organism. Mouse FcγRs include, but are not limited to, FcγRI (CD64), FcγRII (CD32), FcγRIII (CD16), and FcγRIII-2 (CD16-2), as well as any undiscovered mouse FcγRs, and FcγR isoforms or allotypes. Suitable examples of such Fcγ receptors include human FcγRI (CD64), FcγRIIa (CD32), FcγRIIb (CD32), FcγRIIa (CD16) and/or FcγRIIIb (CD16).

Activating receptors which carry an immunoreceptor tyrosine-based activation motif (ITAM) and inhibitory receptors which carry an immunoreceptor tyrosine-based inhibitory motif (ITIM) are present among FcγRs. FcγRs are categorized into activating FcγRs: FcγRI, FcγRIIa R, FcγRIIa H, FcγRIIIa, and FcγRIIIb, and inhibitory FcγR: FcγRIIb.

The polynucleotide sequence and amino acid sequence of FcγRI are shown in NM_000566.3 and NP_000557.1, respectively; the polynucleotide sequence and amino acid sequence of FcγRIIa are shown in BC020823.1 and AAH20823.1, respectively; the polynucleotide sequence and amino acid sequence of FcγRIIb are shown in BC146678.1 and AAI46679.1, respectively; the polynucleotide sequence and amino acid sequence of FcγRIIIa are shown in BC033678.1 and AAH33678.1, respectively; and the polynucleotide sequence and amino acid sequence of FcγRIIIb are shown in BC128562.1 and AAI28563.1, respectively (RefSeq accession number). There are two types of gene polymorphisms for FcγRIIa where the amino acid at position 131 of FcγRIIa is substituted into histidine (type H) or arginine (type R) (J. Exp. Med, 172, 19-25, 1990). Furthermore, there are two types of gene polymorphisms for FcγRIIb, where the amino acid at position 232 of FcγRIIb is substituted with isoleucine (type I) or threonine (type T) (Arthritis. Rheum. 46: 1242-1254 (2002)). In addition, there are two types of gene polymorphisms for FcγRIIIa, where the amino acid at position 158 of FcγRIIIa is substituted with valine (type V) or phenylalanine (type F) (J. Clin. Invest. 100(5): 1059-1070 (1997)). There are also two types of gene polymorphisms for FcγRIIIb, which are type NA1 and type NA2 (J. Clin. Invest. 85: 1287-1295 (1990)).

Whether the binding activity to an Fcγ receptor is decreased can be confirmed by well-known methods such as FACS, ELISA format, screening by Amplified Luminescent Proximity Homogeneous Assay (ALPHA), surface plasmon resonance (SPR)-based BIACORE method, and others (Proc. Natl. Acad. Sci. USA (2006) 103(11), 4005-4010).

ALPHA screening is performed with ALPHA technology which uses two beads, a donor and an acceptor bead, based on the following principle. Luminescent signals are detected only when molecules bound to donor beads interact biologically with molecules bound to the acceptor beads, and the two beads are in close proximity to each other. The laser-excited photosensitizer within the donor beads converts ambient oxygen to excited-state singlet oxygen. Singlet oxygen is dispersed around the donor beads; and when it reaches the adjacent acceptor beads, a chemiluminescent reaction is induced within the beads, and light is ultimately emitted. When molecules bound to the donor beads do not interact with molecules bound to the acceptor beads, the chemiluminescent reaction does not take place because singlet oxygen produced by the donor beads does not reach the acceptor beads.

For example, when an antigen-binding molecule contains an antibody Fc region as the FcRn-binding domain, an antigen-binding molecule having a wild-type Fc region and an antigen-binding molecule having a mutant Fc region produced by adding amino acid mutations to change the binding to an Fcγ receptor are prepared, a biotinylated antigen-binding molecule is bound to the donor beads, and an Fcγ receptor tagged with glutathione S transferase (GST) is bond to the acceptor beads. In the presence of an antigen-binding molecule having a mutant Fc region, the antigen-binding molecule having a wild-type Fc region interacts with the Fcγ receptor and produces 520-620 nm signals. When the antigen-binding molecule having a mutant Fc region is untagged, it competes with the antigen-binding molecule having a wild-type Fc region for interaction with the Fcγ receptor. The relative binding affinity can be determined by quantifying the decrease in fluorescence observed as a result of the competition. Biotinylation of antigen-binding molecules using Sulfo-NHS-biotin and such is well known. As a method for tagging an Fcγ receptor with GST, the method of expressing the Fcγ receptor and GST in a cell carrying a vector that can express a fusion gene produced by fusing a polynucleotide encoding the Fcγ receptor in frame with a GST-encoding polynucleotide, and purifying it using a glutathione column can be appropriately adopted. The obtained signals are suitably analyzed, for example, by fitting them into a one-site competition model that utilizes a non-linear regression analysis with software such as GRAPHPAD PRISM (GraphPad, San Diego).

One of the substances (ligand) observed for interaction is immobilized onto a gold thin film on a sensor chip, and by shining light from the reverse side of the sensor chip so that total reflection takes place at the interface between the gold thin film and glass, a portion with reduced reflection intensity is formed in part of the reflected light (SPR signal). The other substance (analyte) observed for interaction is made to flow over the sensor chip surface; and when the ligand binds to the analyte, the mass of the immobilized ligand molecule increases and the refractive index of the solvent on the sensor chip surface changes. The position of the SPR signal shifts as a result of this change in the refractive index (reversely, the signal position returns if this binding dissociates). The Biacore system shows the amount of shift mentioned above, or more specifically the time variable of mass, by plotting the change in mass on the sensor chip surface on the vertical axis as the measurement data (sensorgram). Kinetic parameters such as association rate constant (ka) and dissociation rate constant (kd) are determined from the curve in the sensorgram, and the affinity (KD) is determined from the ratio of these constants. In the BIACORE method, a method for measuring inhibition is also suitably used. An example of the method for measuring inhibition is described in Proc. Natl. Acad. Sci USA (2006) 103 (11): 4005-4010.

Herein, "decreased Fcγ receptor-binding activity" means that, for example, based on the above-described analytical method, the binding activity of the test antigen-binding molecule is 50% or less, preferably 45% or less, 40% or less, 35% or less, 30% or less, 20% or less, 15% or less, or particularly preferably 10% or less, 9% or less, 8% or less, 7% or less, 6% or less, 5% or less, 4% or less, 3% or less. 2% or less, or 1% or less as compared to the binding activity of the control antigen-binding molecule containing an Fc region.

For the control antigen-binding molecule, antigen-binding molecules having, for example, a domain comprising an Fc region of a monoclonal IgG, IgG2. IgG3, or IgG4 antibody may be suitably used. The structures of the Fc regions are shown in SEQ ID NO: 1 (A is added to the N terminus of RefSeq Accession No. AAC82527.1), SEQ ID NO: 2 (A is added to the N terminus of RefSeq Accession No. AAB59393.1), SEQ ID NO: 3 (A is added to the N terminus of RefSeq Accession No. CAA27268.1), and SEQ ID NO: 4 (A is added to the N terminus of RefSeq Accession No. AAB59394.1). Further, when an antigen-binding molecule containing a mutant of an Fc region of a particular antibody isotype is used as the test substance, the effect of a mutation possessed by the mutant on the Fcγ receptor-binding activity is tested by using as a control an antigen-binding molecule having an Fc region of an antibody of that particular isotype. In this way, antigen-binding molecules containing an Fc region mutant whose binding activity toward the Fcγ receptor verified to be decreased are suitably produced.

Examples of such mutants include mutants with a 231A-238S deletion (WO 2009/011941), or C226S, C229S, P238S, (C220S) (J. Rheumatol (2007) 34, 11), C226S, C229S (Hum. Antibod. Hybridomas (1990) 1(1), 47-54), C226S, C229S, E233P, L234V, or L235A (Blood (2007) 109, 1185-1192) mutants, where the amino acids are specified by EU numbering.

That is, suitable examples include antigen-binding molecules having an Fc region in which any of the amino acids at positions 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, and 332 specified according to EU numbering has been substituted in the amino acids constituting the Fc region of an antibody of a specific isotype. The isotype of the antibody from which the Fc region originates is not particularly limited, and the Fc region derived from an IgG1. IgG2. IgG3, or IgG4 monoclonal antibody can be used appropriately, and the Fc region derived from a naturally-occurring human IgG1 antibody is suitably used.

For example, an antigen-binding molecule having an Fc region that comprises any substitution specified below based on EU numbering from among amino acids constituting the IgG1 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue before the substitution):

(a) L234F, L235E, P331S
(b) C226S, C229S, P238S
(c) C226S, C229S
(d) C226S, C229S, E233P, L234V, L235A:

or an Fc region lacking the amino acid sequence of positions 231 to 238 from among amino acids constituting the IgG1 antibody Fc region may be appropriately used.

Furthermore, antigen-binding molecules having an Fc region that comprises any substitution specified below based on EU numbering from among amino acids constituting the IgG2 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue before the substitution):

(e) H268Q, V309L, A330S. P331S
(f) V234A
(g) G237A
(h) V234A, G237A
(i) A235E, G237A
(j) V234A. A235E, G237A may be appropriately used.

Furthermore, antigen-binding molecules having an Fc region that comprises any substitution specified below based on EU numbering from among amino acids constituting the IgG3 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue before the substitution):

(k) F241A
(l) D265A
(m) V264A may be appropriately used.

Furthermore, antigen-binding molecules having an Fc region that comprises any substitution specified below based on EU numbering from among amino acids constituting the IgG4 antibody Fc region (wherein the number indicates the position of the amino acid residue specified according to EU numbering, the one-letter amino acid code positioned before the number indicates the amino acid residue before the substitution, and the one-letter amino acid code positioned after the number indicates the amino acid residue before the substitution):

(n) L235A, G237A, E318A
(o) L235E
(p) F234A, L235A may be appropriately used.

Other preferred examples include antigen-binding molecules having an Fc region in which any of the amino acids at positions 233, 234, 235, 236, 237, 327, 330, and 331 specified according to EU numbering in the amino acids constituting the Fc region of a naturally-occurring human IgG1 antibody is substituted with amino acids of corresponding EU numbering in the corresponding IgG2 or IgG4.

Other preferred examples suitably include antigen-binding molecules having an Fc region in which any one or more of the amino acids at positions 234, 235, and 297 specified according to EU numbering in the amino acids constituting the Fc region of a naturally-occurring human IgG1 antibody are substituted by other amino acids. The type of amino acid present after substitution is not particularly limited, and an antigen-binding molecule having an Fc region in which any one or more of the amino acids at positions 234, 235, and 297 are substituted with alanine is particularly preferred.

Other preferred examples suitably include antigen-binding molecules having an Fc region in which the amino acid at position 265 specified according to EU numbering in the amino acids constituting an IgG1 antibody Fc region is substituted by another amino acid. The type of amino acid present after substitution is not particularly limited, and an antigen-binding molecule having an Fc region in which the amino acid at position 265 is substituted with alanine is particularly preferred.

The "cancer-specific antigen-binding domain", "tumor necrosis factor (TNF) superfamily-binding domain", "tumor necrosis factor (TNF) receptor superfamily-binding domain", and "T cell receptor complex-binding domain" (hereinafter, the four binding domains are collectively referred to as antigen-binding domains) included in the antigen-binding molecules of the present invention refer to regions that bind specifically to the whole or a portion of their respective antigens which are cancer-specific antigens, factors belonging to the TNF superfamily, factors belonging to the TNF receptor superfamily, or T cell receptor complex; and an example of the binding domain is a region that comprises the antigen-binding region of an antibody. When the molecular weight of the antigen is large, the antigen-binding region of the antibody can bind only to a specific portion of the antigen. This specific portion is called an epitope. The antigen-binding domain is provided by one or more variable domains of an antibody. Preferably, an antigen-binding domain comprises an antibody light chain variable region (VL) and an antibody heavy chain variable region (VH). Suitable examples of such antigen-binding domains include "single chain Fv (scFv)", "single chain antibody", "Fv", "single chain Fv 2 (scFv2)". "Fab", "F(ab')$_2$", and such.

Herein, a "cancer-specific antigen" refers to an antigen expressed by cancer cells, which enables one to distinguish between cancer cells and healthy cells; and for example, it includes antigens that are expressed as cells become malignant, or abnormal sugar chains that appear on protein molecules or cell surface when cells become cancerous. Specific examples include ALK receptor (pleiotrophin receptor); pleiotrophin; KS 1/4 pancreas carcinoma antigen; ovarian carcinoma antigen (CA125); prostatic acid phosphate; prostate-specific antigen (PSA); melanoma-associated antigen p97; melanoma antigen gp75; high molecular weight melanoma antigen (HMW-MAA); prostate-specific membrane antigen; carcinoembryonic antigen (CEA); polymorphic epithelial mucin antigen; human milk fat globule antigen; colorectal tumor-associated antigens such as CEA, TAG-72, CO17-1A, GICA 19-9, CTA-1, and LEA; Burkitt's lymphoma antigen-38.13; CD19; human B-lymphoma antigen-CD20; CD33; melanoma-specific antigens such as ganglioside GD2, ganglioside GD3, ganglioside GM2, and ganglioside GM3; tumor-specific transplantation type cell-surface antigen (TSTA); virus-induced tumor antigens including T antigen and envelope antigens of DNA tumor viruses and RNA tumor viruses; CEA of colon; oncofetal antigens such as 5T4 oncofetal trophoblast glycoprotein and bladder tumor oncofetal antigen; α-fetoprotein; differentiation antigens such as human lung carcinoma antigens L6 and L20; antigens of fibrosarcoma; human leukemia T cell antigen-Gp37; neoglycoprotein; sphingolipids; breast cancer antigens such as EGFR (epidermal growth factor receptor); NY-BR-16; NY-BR-16 and HER2 antigen (p185HER2); polymorphic epithelial mucin (PEM); malignant human lymphocyte antigen-APO-1; differentiation antigens such as I antigen found in fetal erythrocytes; primary endoderm I antigen found in adult erythrocytes; preimplantation embryos; I(Ma) found in gastric cancer; M18 and M39 found in mammary epithelium; SSEA-1, VEP8, VEP9, My1, and VIM-D5 found in myeloid cells; D156-22 found in colorectal cancer; TRA-1-85 (blood group H); SCP-1 found in testis and ovarian cancer; C14 found in colon cancer; F3 found in lung cancer; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric cancer antigen; CO-514 (blood group Lea) found in adenocarcinomas; NS-10 found in adenocarcinomas; CO-43 (blood group Leb); G49 found in EGF receptor of A431 cells; MH2 (blood group ALeb/Ley) found in colon cancer; 19.9 found in colon cancer; gastric cancer mucins; T5A7 found in myeloid cells; R24 found in melanoma; 4.2. GD3, D1.1, OFA-1. GM2, OFA-2, GD2, and M1:22:25:8 found in embryonal carcinoma cells as well as SSEA-3 and SSEA-4 found in 4 to 8-cell stage embryos; subcutaneous T cell lymphoma antigen; MART-1 antigen; sialyl Tn (STn) antigen; colon cancer antigen NY-CO-45; lung cancer antigen NY-LU-12 variant A; adenocarcinoma antigen ART1; paraneoplastic associated brain-testis-cancer antigen (onconeuronal antigen MA2; paraneoplastic neuronal antigen); Neuro-oncological ventral antigen 2 (NOVA2); hemocyte carcinoma antigen gene 520; tumor-associated antigen CO-029; tumor-associated antigens MAGE-C1 (cancer/testis antigen CT7). MAGE-B1 (MAGE-XP antigen), MAGE-B2 (DAM6), MAGE-2, MAGE-4a, MAGE-4b and MAGE-X2; Cancer-Testis Antigen (NY-EOS-1); YKL-40, fragments of any of the aforementioned polypeptides, or structures produced by modification thereof (for example, the above-mentioned modified phosphate group or sugar chain); EpCAM; EREG; CA19-9; CA15-3; sialyl SSEA-1(SLX); HER2; PSMA; CEA; and CLEC12A. Cancer-specific antigens which become targets of the cancer-specific antigen-binding domains of the present invention are, in particular, preferably those expressed on cell surface, and examples of such cancer-specific antigens include CD19, CD20, EGFR, HER2, EpCAM, and EREG.

Furthermore, as factors belonging to the "TNF superfamily" or the "TNF receptor superfamily", ligands having a trimeric structure and receptors with a trimeric structure to which the ligands bind, which contribute to activation of various immune cells are known (Nat. Rev. Immunol., 2012, 12, 339-51). Examples of factors belonging to the TNF superfamily or the TNF receptor superfamily include CD137, CD137L, CD40, CD40L, OX40, OX40L, CD27, CD70, HVEM, LIGHT, RANK, RANKL, CD30, CD153, GITR, and GITRL. Preferred factors include, for example, CD137 and CD40. A more preferred factor is, for example, CD137.

Furthermore, the "T cell-receptor complex" may be a T cell receptor itself, or an adaptor molecule constituting a T cell-receptor complex together with a T cell receptor. CD3 is suitable as an adaptor molecule.

For the T cell receptor, an epitope to which the T cell receptor binding domain binds may be a variable region or a constant region, but an epitope present in the constant region is preferred. Examples of the constant region sequence include the T cell receptor α chain of RefSeq Accession No. CAA26636.1 (SEQ ID NO: 9), the T cell receptor β chain of RefSeq Accession No. C25777 (SEQ ID NO: 10), the T cell receptor γ1 chain of RefSeq Accession No. A26659 (SEQ ID NO: 11), the T cell receptor γ2 chain of RefSeq Accession No. AAB63312.1 (SEQ ID NO: 12), and the T cell receptor δ chain of RefSeq Accession No. AAA61033.1 (SEQ ID NO: 13).

In the present invention, when the "CD3-binding domain" is used as the T cell receptor complex-binding domain, the CD3-binding domain may be provided by one or more antibody variable domains. Preferably, the CD3-binding domain includes a light chain variable region (VL) and a heavy chain variable region (VH) of the CD3 antibody. Suitable examples of such CD3-binding domains include "single chain Fv (scFv)", "single chain antibody", "Fv", "single chain Fv 2 (scFv2)", "Fab", "F(ab')$_2$", and such.

The CD3-binding domain of the present invention may be those that bind to any epitope as long as the epitope exists in the γ-chain, δ-chain, or ε-chain sequence constituting human CD3. In the present invention, preferably, a CD3-binding domain that comprises a light chain variable region (VL) of a CD3 antibody and a heavy chain variable region (VH) of a CD3 antibody, and which binds to an epitope present in the extracellular region of the ε chain of the human CD3 complex, is suitably used. For such CD3-binding domain, a CD3-binding domain comprising the light chain variable region (VL) and heavy chain variable region (VH) of the OKT3 antibody (Proc. Natl. Acad. Sci. USA (1980) 77, 4914-4917) or various known CD3 antibodies is suitably used. A CD3-binding domain derived from a CD3 antibody that has the desired properties and is obtained by immunizing a desired animal with the γ-chain, δ-chain, or ε-chain constituting the human CD3 by the above-mentioned method may be appropriately used. Human antibodies and appropriately humanized antibodies as described below may be suitably used as the CD3 antibody that serves as the origin for the CD3-binding domain. For the structure of the CD3-constituting γ-chain, δ-chain, or ε-chain, their polynucleotide sequences are shown in SEQ ID NOs: 14 (NM_000073.2), 16 (NM_000732.4), and 18 (NM_000733.3), and their polypeptide sequences are shown in SEQ ID NOs: 15 (NP_000064.1), 17 (NP_000723.1), and 19 (NP_000724.1) (the RefSeq accession number is shown in parentheses).

A preferred embodiment of the "antigen-binding molecule" of the present invention includes an antibody comprising an antibody variable region of the present invention.

Examples of the antibodies provided by the present invention include the following antibodies:

[1] an antibody comprising the amino acid sequence of SEQ ID NO: 66 as the heavy-chain variable region and the amino acid sequence of SEQ ID NO: 85 as the light-chain variable region;

[2] an antibody comprising the amino acid sequence of SEQ ID NO: 67 as the heavy-chain variable region and the amino acid sequence of SEQ ID NO: 86 as the light-chain variable region;

[3] an antibody comprising the amino acid sequence of SEQ ID NO: 70 as the heavy-chain variable region and the amino acid sequence of SEQ ID NO: 89 as the light-chain variable region;

[4] an antibody comprising the amino acid sequence of SEQ ID NO: 76 as the heavy-chain variable region and the amino acid sequence of SEQ ID NO: 95 as the light-chain variable region;

[5] an antibody comprising the amino acid sequence of SEQ ID NO: 77 as the heavy-chain variable region and the amino acid sequence of SEQ ID NO: 96 as the light-chain variable region;

[6] an antibody comprising the amino acid sequence of SEQ ID NO: 78 as the heavy-chain variable region and the amino acid sequence of SEQ ID NO: 97 as the light-chain variable region;

[7] the antibody of any one of [1] to [6], which comprises the amino acid sequence of SEQ ID NO: 99 as the heavy-chain constant region and the amino acid sequence of SEQ ID NO: 59 or the amino acid sequence of SEQ ID NO: 60 as the light-chain constant region;

[8] an antibody that has an activity equivalent to that of the antibody of any one of [1] to [7]; and

[9] an antibody that binds to the same epitope as the epitope bound by the antibody of any one of [1] to 171.

In the antibody of [8], an "equivalent activity" refers to a CD137 agonist activity that is 70% or more, preferably 80% or more, and more preferably 90% or more of the binding activity of the antibody of any one of [1] to [7].

The present invention also provides the antibody of [9] which binds to the same epitope as the epitope bound by the anti-CD137 antibody disclosed in this invention. Such an antibody can be obtained, for example, by the method below.

Whether a test antibody shares a common epitope with a certain antibody can be assessed based on competition between the two antibodies for the same epitope. The competition between antibodies can be detected by a cross-blocking assay or the like. For example, the competitive ELISA assay is a preferred cross-blocking assay. Specifically, in a cross-blocking assay, the CD137 protein used to coat the wells of a microtiter plate is pre-incubated in the presence or absence of a candidate competitor antibody, and then an anti-CD137 antibody of the present invention is added thereto. The quantity of the anti-CD137 antibody of the present invention bound to the CD137 protein in the wells is indirectly correlated with the binding ability of a candidate competitor antibody (test antibody) that competes for the binding to the same epitope. That is, the greater the affinity of the test antibody for the same epitope, the lower the amount of the anti-CD137 antibody of the present invention bound to the CD137 protein-coated wells, and the higher the amount of the test antibody bound to the CD137 protein-coated wells.

The quantity of the antibody bound to the wells can be readily determined by labeling the antibody in advance. For example, a biotin-labeled antibody can be measured using an avidin/peroxidase conjugate and an appropriate substrate. In particular, a cross-blocking assay that uses an enzyme label such as peroxidase is called a "competitive ELISA assay". The antibody can be labeled with other labeling substances that enable detection or measurement. Specifically, radiolabels, fluorescent labels, and such are known.

Furthermore, when the test antibody has a constant region derived from a species different from that of the anti-CD137 antibody of the present invention, the amount of antibody bound to the wells can be measured by using a labeled antibody that recognizes the constant region of that antibody. Alternatively, if the antibodies are derived from the same species but belong to different classes, the amount of the antibodies bound to the wells can be measured using antibodies that distinguish individual classes.

If a candidate antibody can block binding of an anti-CD137 antibody by at least 20%, preferably by at least 20% to 50%, and even more preferably, by at least 50%, as compared to the binding activity obtained in a control experiment performed in the absence of the candidate competing antibody, the candidate competing antibody is either an antibody that binds substantially to the same epitope or an antibody that competes for binding to the same epitope as that by an anti-CD137 antibody of the present invention.

A preferred example of an antibody that binds to the same epitope as the epitope bound by the antibody of any one of [1] to [7] includes, for example, an antibody that recognizes a region comprising the SPCPPNSFSSAGGQRTCDI-CRQCKGVFRTRKE CSSTSNAECDCTPGFHCL-GAGCSMCEQDCKQGQELTKKGC sequence (SEQ ID NO: 113) in the CD137 protein. A further example includes an antibody that recognizes a region comprising the DCTPGFHCLGAGCSMCEQDCKQGQELTKKGC sequence (SEQ ID NO: 108) in the CD137 protein.

An anticancer antigen/anti-human CD137 bispecific antibody that exhibits the desired antitumor effects can be provided by modifying the above-mentioned anti-human CD137 antibody into a bispecific antibody with a cancer-specific antigen antibody (for example, an anti-human GPC3 antibody), and evaluating its cancer-specific antigen-dependent CD137 agonist ability.

As a non-limiting embodiment of the present invention, a bispecific antibody comprising a cancer-specific antigen-binding domain and a human CD137-binding domain is provided.

Examples of a bispecific antibody provided by the present invention include the following antibodies:

[i] a bispecific antibody comprising the amino acid sequence of SEQ ID NO: 122 (heavy chain variable region) and the amino acid sequence of SEQ ID NO: 123 (light chain variable region) as the human CD137-binding domain;

[ii] a bispecific antibody comprising the amino acid sequence of SEQ ID NO: 124 (heavy chain variable region) and the amino acid sequence of SEQ ID NO: 82 (light chain variable region) as the human CD137-binding domain;

[iii] a bispecific antibody comprising the amino acid sequence of SEQ ID NO: 125 (heavy chain variable region) and the amino acid sequence of SEQ ID NO: 84 (light chain variable region) as the human CD137-binding domain; and

[iv] an antibody that binds to the same epitope as the epitope bound by the bispecific antibody of any one of [i] to [iii].

Depending on the target cancer antigen, those skilled in the art can appropriately select a heavy chain variable region sequence and a light chain variable region sequence that bind to the cancer antigen as the heavy chain variable region and the light chain variable region to be included in the cancer-specific antigen-binding domain.

The present invention also provides the bispecific antibody of [iv] which binds to the same epitope as the epitope bound by the anti-cancer-specific antigen/anti-human CD137 bispecific antibody disclosed in this invention. Such an antibody can be obtained, for example, by the method below.

Whether a test antibody shares a common epitope with a certain antibody can be assessed based on competition between the two antibodies for the same epitope. The competition between antibodies can be detected by a cross-blocking assay or the like. For example, the competitive ELISA assay is a preferred cross-blocking assay. Specifically, in a cross-blocking assay, the CD137 protein used to coat the wells of a microtiter plate is pre-incubated in the presence or absence of a candidate competitor antibody, and then an anti-CD137 antibody of the present invention is added thereto. The amount of the anti-CD137 antibody of the present invention bound to the CD137 protein in the wells is indirectly correlated with the binding ability of a candidate competitor antibody (test antibody) that competes for the binding to the same epitope. That is, the greater the affinity of the test antibody for the same epitope, the lower the amount of the anti-CD137 antibody of the present invention bound to the CD137 protein-coated wells, and the higher the amount of the test antibody bound to the CD137 protein-coated wells.

The amount of the antibody bound to the wells can be readily determined by labeling the antibody in advance. For example, a biotin-labeled antibody can be measured using an avidin/peroxidase conjugate and an appropriate substrate. In particular, a cross-blocking assay that uses enzyme labels such as peroxidase is called a "competitive ELISA assay". The antibody can be labeled with other labeling substances that enable detection or measurement. Specifically, radiolabels, fluorescent labels, and such are known.

Furthermore, when the test antibody has a constant region derived from a species different from that of the anti-CD137 antibody of the present invention, the amount of antibody bound to the wells can be measured by using a labeled antibody that recognizes the constant region of that antibody. Alternatively, if the antibodies are derived from the same species but belong to different classes, the amount of the antibodies bound to the wells can be measured using antibodies that distinguish individual classes.

If a candidate antibody can block binding of an anti-CD137 antibody by at least 20%, preferably by at least 20% to 50%, and even more preferably, by at least 50%, as compared to the binding activity obtained in a control experiment performed in the absence of the candidate competing antibody, the candidate competing antibody is either an antibody that binds substantially to the same epitope or an antibody that competes for binding to the same epitope as an anti-CD137 antibody of the present invention.

In another embodiment, the ability of a test antibody to competitively or cross competitively bind with another antibody can be appropriately determined by those skilled in the art using a standard binding assay such as BIAcore analysis or flow cytometry known in the art.

Methods for determining the spatial conformation of an epitope include, for example, X ray crystallography and two-dimensional nuclear magnetic resonance (see, Epitope Mapping Protocols in Methods in Molecular Biology, G. E. Morris (ed.). Vol. 66 (1996)).

Favorable examples of a bispecific antibody that binds to the same epitope as the human CD137 epitope bound by the bispecific antibody of any one of [i] to [iii] include bispecific antibodies that recognize a region comprising the SPCPPNSFSSAGGQRTCD ICRQCKGVFRTRKECSSTS-NAECDCTPGFHCLGAGCSMCEQDCKQGQELTKKGC sequence (SEQ ID NO: 113), a region comprising the DCTPGFHCLGAGCSMCEQDC KQGQELTKKGC sequence (SEQ ID NO: 108), a region comprising the LQDPCSNC PAGTFCDNNRNQICSPCPPNSFS-SAGGQRTCDICRQCKGVFRTRKECSSTSNAEC sequence (SEQ ID NO: 11), or a region comprising the LQDPCSNCPAGTFCDNNRN QICSPCPPNSFS-SAGGQRTC sequence (SEQ ID NO: 106) in the human CD137 protein. More preferable examples include bispecific antibodies that recognize a region comprising the LQDPCSNCPAGTFCDNNRNQICSPCPPNSFS-SAGGQRTCDICRQCK GVFRTRKECSSTSNAEC sequence (SEQ ID NO: 111) or a region comprising the LQDPCSNCPAGTFCDNNRNQICSPCPPNSFS-SAGGQRTC sequence (SEQ ID NO: 106) in the human CD137 protein.

A bispecific antibody comprising a cancer-specific antigen-binding domain and a human CD40-binding domain is provided as a non-limiting embodiment of the present invention.

Depending on the targeted cancer antigen, those skilled in the art can appropriately select a heavy chain variable region sequence and a light chain variable region sequence that bind to the cancer antigen for the heavy chain variable region and the light chain variable region to be included in the cancer-specific antigen-binding domain.

Binding Activity of Antibodies

The antigen-binding activity of an antibody can be measured using known means (Antibodies A Laboratory Manual. Ed Harlow, David Lane, Cold Spring Harbor Laboratory, 1988). For example, an enzyme linked immunosorbent assay (ELISA), an enzyme immunoassay (EIA), a radioimmunoassay (RIA), FACS, ALPHA screen (Amplified Luminescent Proximity Homogeneous Assay), surface plasmon resonance (SPR)-based BIACORE method, or a fluoroimmunoassay can be used. Methods for assaying the binding activity of an antibody towards an antigen expressed by a cell include, for example, the methods described on pages 359 to 420 in "Antibodies: A Laboratory Manual".

In particular, methods that use a flow cytometer can be suitably used as a method for measuring the binding between an antigen expressed on the surface of cells suspended in buffer or the like and an antibody against the antigen. Flow cytometers that are used include, for example, FACSCanto™ II, FACSAria™, FACSArray™, FACSVantage™ SE, and FACSCalibur™ (the above are from BD Biosciences); and EPICS ALTRA HyPerSort Cytomics FC 500, EPICS XL-MCL ADC EPICS XL ADC, and Cell Lab Quanta/Cell Lab Quanta SC (the above are all from Beckman Coulter).

An example of a suitable method for measuring the binding activity of a test CD137 antibody toward an antigen includes the method of reacting CD137-expressing cells with a test antibody, and then staining this with an FITC-labeled secondary antibody that recognizes the test antibody, and subsequently taking measurements using FACSCalibur (BD), and analyzing the obtained fluorescence intensity using the CELL QUEST Software (BD).

Antibody

Herein, an "antibody" refers to a naturally occurring immunoglobulin or an immunoglobulin produced by partial or complete synthesis. Antibodies can be isolated from natural sources such as naturally-occurring plasma and serum, or culture supernatants of antibody-producing hybridoma cells. Alternatively, antibodies can be partially or completely synthesized using techniques such as genetic recombination. Suitable examples of the antibodies include antibodies of an immunoglobulin isotype or subclass of such isotype. Known human immunoglobulins include those of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing antibodies having the desired binding activity are known to those skilled in the art, and the antibodies may be obtained as polyclonal or monoclonal antibodies. Monoclonal antibodies derived from mammals may be suitably produced as the antibodies of the present invention. Such mammalian-derived monoclonal antibodies include antibodies produced by hybridomas and antibodies produced by host cells transformed with an expression vector carrying an antibody gene by genetic engineering techniques.

There is no particular limitation on the mammal to be immunized for obtaining antibodies. It is preferable to select the mammal by considering its compatibility with the parent cells to be used in cell fusion for hybridoma production. In general, rabbits, monkeys, and rodents such as mice, rats, and hamsters are suitably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with Phosphate-Buffered Saline (PBS), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein; and there is no need to purify the antigen for immunization.

In order to prepare a monoclonal antibody of the present invention using DNA immunization, first, a DNA expressing an antigen protein is administered to an animal to be immunized. The antigen protein-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized.

After immunizing a mammal as described above, an increase in the titer of an antigen-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used: P3(P3x63Ag8.653) (J. Immunol. (1979) 123 (4), 1548-1550): P3x63Ag8U.1 (Current Topics in Microbiology and Immunology (1978)81, 1-7); NS-1 (C. Eur. J. Immunol. (1976)6 (7), 511-519); MPC-11 (Cell (1976) 8 (3). 405-415); SP2/0 (Nature (1978) 276 (5685), 269-270); FO (J. Immunol. Methods (1980) 35 (1-2), 1-21); S194/5.XX0.BU.1 (J. Exp. Med. (1978) 148 (1), 313-323); R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73; 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immunocytes to myeloma cells may be arbitrarily set, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) pre-warmed to about 37° C. is added thereto at a concentration of generally 30% to 60% (w/v). The mixed solution is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Culture is continued in the above medium using the HAT medium for a period of time sufficient to kill cells other than the desired hybridomas (non-fused cells). Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Culture is continued in the above medium using the HAT medium for a period of time sufficient to kill cells other than the desired hybridomas (non-fused cells). Specifically, desired hybridomas can be selected by culture for generally several days to several weeks. Then, hybridomas producing the desired antibody are screened and singly cloned by conventional limiting dilution methods.

Screening and single cloning of desired antibodies can be suitably performed by screening methods based on known antigen-antibody reaction. For example, a desired antibody can be selected by screening using fluorescence activated cell sorting (FACS). FACS is a system that enables measurement of the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, cells that express the antigen bound by the produced antibody are first prepared. Preferred cells used for screening are mammalian cells that are forced to express the antigen. By using mammalian cells that are used as the host cell but have not been transformed as a control, the activity of an antibody to bind to the cell-surface antigen can be selectively detected. Specifically, hybridomas producing a desired monoclonal antibody can be obtained by selecting hybridomas that produce an antibody which binds to cells forced to express the antigen but not to the host cell.

Alternatively, cells expressing the antigen of interest are immobilized and the activity of an antibody to bind to the antigen-expressing cells can be assessed based on the principle of ELISA. For example, antigen-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium. The hybridomas can be stored in liquid nitrogen for a long period.

The above hybridomas are cultured by a conventional method, and desired monoclonal antibodies can be obtained from the culture supernatants. Alternatively, the hybridomas are administered to and grown in compatible mammals, and monoclonal antibodies can be obtained from the ascites. The former method is suitable for obtaining antibodies with high purity.

Antibodies that are encoded by antibody genes cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

Generally, to obtain a cDNA encoding the antibody variable region (V region), total RNA is first extracted from hybridomas. For example, the following methods can be used as methods for extracting mRNAs from cells:
the guanidine ultracentrifugation method (Biochemistry (1979) 18(24), 5294-5299), and
the AGPC method (Anal. Biochem. (1987) 162(1), 156-159).

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Corporation) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into E. coli or such. After colony selection, the desired recombinant vector can be prepared from the colony-forming E. coli. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ2b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5' RACE cDNA library construction kit is used as a 5'-side primer.

Immunoglobulins composed of a combination of heavy and light chains may be reshaped using the thus amplified PCR products. A desired antibody can be selected by screening using the antigen-binding activity of a reshaped immunoglobulin as an indicator. The screening can be carried out, for example, by the following steps:
(1) contacting a desired antigen-expressing cell with an antibody comprising the V region encoded by a cDNA obtained from a hybridoma;
(2) detecting the binding of the antibody to the antigen-expressing cell; and
(3) selecting an antibody that binds to the antigen-expressing cell.

Methods for detecting the binding of an antibody to the antigen-expressing cells are known. Specifically, the binding of an antibody to the antigen-expressing cells can be detected by the above-described techniques such as FACS. Fixed samples of the antigen-expressing cells may be appropriately used to assess the binding activity of an antibody.

For antibody screening methods that use the binding activity as an indicator, panning methods that use phage vectors can also be used suitably. Screening methods using phage vectors are advantageous when the antibody genes are obtained from a polyclonal antibody-expressing cell population as heavy-chain and light-chain subclass libraries. Genes encoding the heavy-chain and light-chain variable regions can be linked by an appropriate linker sequence to form a single-chain Fv (scFv). Phages expressing scFv on their surface can be produced by inserting an scFv-encoding gene into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, a "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA that encodes a desired antibody constant region (C region). A chimeric antibody expression vector is constructed by fusing in-frame two genes digested with the same combination of restriction enzymes.

To produce a monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. The signal sequence is cleaved from the carboxyl terminus of the expressed polypeptide, and the resulting antibody can be secreted to the outside of cells. Then, appropriate host cells are transformed with the expression vector, and recombinant cells expressing the antibody-encoding DNA can be obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors inserted with the H chain and L chain. Alternatively, host cells can be transformed with a single expression vector into which DNAs encoding the H and L chains are inserted (see WO 94/11523).

There are many known combinations of host cells and expression vectors for antibody preparation by introducing isolated antibody genes into appropriate hosts. All these expression systems are applicable to isolation of the cancer-specific antigen-binding domains of the present invention, tumor necrosis factor receptor superfamily (TNFRSF) and T cell receptor complex-binding domain.

Appropriate eukaryotic cells used as host cells include animal cells, plant cells, and fungal cells. Specifically, the animal cells include, for example, the following cells: (1) mammalian cells: CHO, COS, myeloma, baby hamster kidney (BHK), HeLa, Vero, or such; (2) amphibian cells: *Xenopus oocytes*, or such; and (3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:
  yeasts: the *Saccharomyces* genus such as *Saccharomyces cerevisiae*, and the *Pichia* genus such as *Pichia pasloris*; and
  filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Bio/Technology (1994) 12 (7), 699-702).

When an antigen-binding molecule described herein is administered to human, an antigen-binding domain derived from a genetically recombinant antibody that has been artificially modified to reduce the heterologous antigenicity against human and such, can be appropriately used as the various binding domains in the molecule when domains comprising an antibody variable region are used. Such genetically recombinant antibodies include, for example, humanized antibodies. These modified antibodies are appropriately produced by known methods.

An antibody variable region used to produce the various binding domains of antigen-binding molecules described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced into another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585. WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the phage display method, techniques that use a cell-free translation system, techniques for displaying antigen-binding molecules on the surface of viruses or cells, and techniques that use emulsions are also known as techniques for obtaining human antibodies by panning using human antibody libraries. For example, the ribosome display method where a complex is formed between the translated protein and mRNA via the ribosome by removing the stop codon and such, the cDNA display method or the mRNA display method where a genetic sequence and the translated protein are covalently linked using a compound such as puromycin, the CIS display method where a complex is formed between the gene and the translated protein using a nucleic acid-binding protein, or such may be used as techniques of using a cell-free translation system. For the technique of presenting antigen-binding molecules on the surface of cells or viruses, besides the phage display method, the *E. coli* display method, Gram-positive bacteria display method, yeast display method, mammalian cell display method, virus display method, and such may be used. As a technique that uses emulsions, the in vitro virus display method which involves incorporating genes and translation-related molecules into an emulsion, and such may be used. These methods are already publicly known (Nat Biotechnol. 2000 December; 18(12):1287-92; Nucleic Acids Res. 2006; 34(19): e127; Proc Natl Acad Sci USA. 2004 Mar. 2; 101(9):2806-10; Proc Natl Acad Sci USA. 2004 Jun. 22; 101(25):9193-8; Protein Eng Des Sel. 2008 April; 21(4): 247-55; Proc Natl Acad Sci U S A. 2000 Sep. 26; 97(20): 10701-5; MAbs. 2010 September-October; 2(5):508-18; and Methods Mol Biol. 2012, 911:183-98).

In the present invention, "specific" means a condition where one of the molecules involved in specific binding does not show any significant binding to molecules other than a single or a number of binding partner molecules. Furthermore. "specific" is also used when an antigen-binding domain is specific to a particular epitope among multiple epitopes contained in an antigen. When an epitope bound by an antigen-binding domain is contained in multiple different antigens, antigen-binding molecules containing the antigen-binding domain can bind to various antigens that have the epitope.

"Epitope" means an antigenic determinant in an antigen, and refers to an antigen site to which various binding domains in antigen-binding molecules disclosed herein bind. Thus, for example, an epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues that form the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance spectroscopy, site-specific spin labeling, and electron paramagnetic resonance spectroscopy, but are not limited thereto. See, for example, Epitope Mapping Protocols in Methods in Molecular Biology (1996), Vol. 66, Morris (ed.).

Examples of a method for assessing the binding of an epitope in a cancer-specific antigen by a test antigen-binding molecule are shown below. According to the examples below, methods for assessing the binding of an epitope in a target antigen by another binding domain can also be appropriately conducted.

For example, whether a test antigen-binding molecule that comprises an antigen-binding domain for a cancer-specific antigen recognizes a linear epitope in the antigen molecule can be confirmed for example as mentioned below. For example, a linear peptide comprising an amino acid sequence forming the extracellular domain of a cancer-specific antigen is synthesized for the above purpose. The peptide can be synthesized chemically, or obtained by genetic engineering techniques using a region in a cDNA of a cancer-specific antigen encoding the amino acid sequence that corresponds to the extracellular domain. Then, a test antigen-binding molecule containing an antigen-binding domain for a cancer-specific antigen is assessed for its binding activity towards a linear peptide comprising the extracellular domain-constituting amino acid sequence. For example, an immobilized linear peptide can be used as an antigen to evaluate the binding activity of the antigen-binding molecule towards the peptide by ELISA. Alternatively, the binding activity towards a linear peptide can be assessed based on the level at which the linear peptide inhibits binding of the antigen-binding molecule to cancer-specific antigen-expressing cells. The binding activity of the antigen-binding molecule towards the linear peptide can be demonstrated by these tests.

Whether the above-mentioned test antigen-binding molecule containing an antigen-binding domain towards an antigen recognizes a conformational epitope can be confirmed as below. For example, an antigen-binding molecule that comprises an antigen-binding domain for a cancer-specific antigen strongly binds to cancer-specific antigen-expressing cells upon contact, but does not substantially bind to an immobilized linear peptide comprising an amino acid sequence forming the extracellular domain of the cancer-specific antigen. Herein, "does not substantially bind" means that the binding activity is 80% or less, generally 50% or less, preferably 30% or less, and particularly preferably 15% or less compared to the binding activity to antigen-expressing cells.

Methods for assaying the binding activity of a test antigen-binding molecule comprising an antigen-binding domain to antigen-expressing cells include, for example, the methods described in Antibodies A Laboratory Manual (Ed Harlow, David Lane. Cold Spring Harbor Laboratory (1988) 359-420). Specifically, the assessment can be performed based on the principle of ELISA or fluorescence activated cell sorting (FACS) using antigen-expressing cells as antigen.

In the ELISA format, the binding activity of a test antigen-binding molecule comprising an antigen-binding domain towards antigen-expressing cells can be assessed quantitatively by comparing the levels of signals generated by enzymatic reaction. Specifically, a test antigen-binding molecule is added to an ELISA plate onto which antigen-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody-binding titer for antigen-expressing cells can be determined to compare the binding activity of the test antigen-binding molecule towards antigen-expressing cells.

The binding of a test antigen-binding molecule to an antigen expressed on the surface of cells suspended in buffer or the like can be detected using a flow cytometer. Known flow cytometers include, for example, the following devices:
FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Suitable methods for assaying the binding activity of the above-mentioned test antigen-binding molecule comprising an antigen-binding domain towards an antigen include, for example, the method below. First, antigen-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the antigen-binding molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to the cells. That is, the binding activity of a test antigen-binding molecule, which is represented by the quantity of the test antigen-binding molecule bound, can be measured by determining the Geometric Mean value.

Whether a test antigen-binding molecule comprising an antigen-binding domain of the present invention shares a common epitope with another antigen-binding molecule can be assessed based on competition between the two molecules for the same epitope. The competition between antigen-binding molecules can be detected by a cross-blocking assay or the like. For example, the competitive ELISA assay is a preferred cross-blocking assay.

Specifically, in a cross-blocking assay, the antigen coating the wells of a microtiter plate is pre-incubated in the presence or absence of a candidate competitor antigen-binding molecule, and then a test antigen-binding molecule is added thereto. The quantity of test antigen-binding molecule bound to the antigen in the wells indirectly correlates with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the antigen-coated wells.

The quantity of the test antigen-binding molecule bound to the wells via the antigen can be readily determined by labeling the antigen-binding molecule in advance. For example, a biotin-labeled antigen-binding molecule can be measured using an avidin/peroxidase conjugate and appropriate substrate. In particular, a cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding of a test antigen-binding molecule comprising an antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or to compete for binding to the same epitope.

When the structure of an epitope bound by a test antigen-binding molecule comprising an antigen-binding domain of the present invention is already identified, whether the test and control antigen-binding molecules share a common epitope can be assessed by comparing the binding activities of the two antigen-binding molecules towards a peptide prepared by introducing amino acid mutations into the peptide forming the epitope.

As a method for measuring such binding activities, for example, the binding activities of test and control antigen-binding molecules towards a linear peptide into which a mutation is introduced are measured by comparison in the above ELISA format. Besides the ELISA methods, the binding activity towards the mutant peptide bound to a column can be determined by passing the test and control antigen-binding molecules through the column, and then quantifying the antigen-binding molecule eluted in the eluate. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, cells expressing an antigen targeted by an antigen-binding domain and cells expressing an antigen having an epitope introduced with a mutation are prepared. The test and control antigen-binding molecules are added to a cell suspension prepared by suspending these cells in an appropriate buffer such as PBS. Then, the cell suspension is appropriately washed with a buffer, and an FITC-labeled antibody that can recognize the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 µg/ml to 10 ng/ml. The fluorescence intensity determined by analysis using the CELL QUEST Software (BD), i.e., the Geometric Mean value, reflects the quantity of the labeled antibody bound to the cells. That is, the binding activities of the test and control antigen-binding molecules, which are represented by the quantity of the labeled antibody bound, can be measured by determining the Geometric Mean value.

An "antigen-binding molecule" of the present invention comprises both heavy and light chains which form an "antibody variable region" of this invention within a single polypeptide chain; however, it may be an antibody fragment lacking a constant region. Examples of such antibody fragments include a diabody (Db), an scFv, a single-chain antibody, an sc(Fv)$_2$, and an sc(Fab')$_2$.

Db is a dimer composed of two polypeptide chains (Holliger P et al., Proc. Natl. Acad. Sci. USA 90: 6444-6448 (1993); EP404,097; WO93/11161). In each polypeptide chain, an L-chain variable region (VL) and an H-chain variable region (VH) are linked by a linker short enough so that these two regions on the same chain cannot associate with each other, for example, a linker of about five residues.

Because the linker between VL and VH is too short for formation of a single chain variable region fragment, VL and VH encoded on the same polypeptide chain dimerize to form two antigen-binding sites.

Furthermore, herein, the terms "scFv", "single-chain antibody", and "sc(Fv)$_2$" all refer to an antibody fragment of a single polypeptide chain that contains variable regions derived from the heavy and light chains, but not the constant region. In general, a single-chain antibody also contains a polypeptide linker between the VH and VL domains, which enables formation of a desired structure that is thought to allow antigen binding. The single-chain antibody is discussed in detail by Pluckthun in "The Pharmacology of Monoclonal Antibodies, Vol. 113, Rosenburg and Moore, eds., Springer-Verlag, New York, 269-315 (1994)". See also International Patent Publication WO 1988/001649; U.S. Pat. Nos. 4,946,778 and 5,260,203. In a particular embodiment, the single-chain antibody can be bispecific and/or humanized.

scFv is an antigen-binding domain in which VH and VL forming Fv are linked together by a peptide linker (Proc. Natl. Acad. Sci. U.S.A. (1988) 85(16), 5879-5883). VH and VL can be retained in close proximity by the peptide linker.

sc(Fv)$_2$ is a single-chain antibody in which four variable regions of two VL and two VH are linked by linkers such as peptide linkers to form a single chain (J Immunol. Methods (1999) 231(1-2), 177-189). The two VH and two VL may be derived from different monoclonal antibodies. Such sc(Fv)$_2$ preferably includes, for example, a bispecific sc(Fv)$_2$ that recognizes two types of epitopes present in a single antigen as disclosed in the Journal of Immunology (1994) 152(11), 5368-5374. sc(Fv)$_2$ can be produced by methods known to those skilled in the art. For example, sc(Fv)$_2$ can be produced by linking scFv by a linker such as a peptide linker.

Herein, the form of an antigen-binding domain forming an sc(Fv)$_2$ include an antibody in which the two VH units and two VL units are arranged in the order of VH, VL, VH, and VL ([VH]-linker-[VL]-linker-[VH]-linker-[VL]) beginning from the N terminus of a single-chain polypeptide. The order of the two VH units and two VL units is not limited to the above form, and they may be arranged in any order. Example order of the form is listed below.

[VL]-linker-[VH]-linker-[VH]-linker-[VL]
[VH]-linker-[VL]-linker-[VL]-linker-[VH]
[VH]-linker-[VH]-linker-[VL]-linker-[VL]
[VL]-linker-[VL]-linker-[VH]-linker-[VH]
[VL]-linker-[VH]-linker-[VL]-linker-[VH]

The molecular form of sc(Fv)$_2$ is also described in detail in WO2006/132352. According to these descriptions, those skilled in the art can appropriately prepare desired sc(Fv)$_2$ to produce the antigen-binding molecules disclosed herein.

Herein, the term "variable fragment (Fv)" refers to the minimum unit of an antibody-derived antigen-binding domain composed of a pair of the antibody light chain variable region (VL) and antibody heavy chain variable region (VH). In 1988. Skerra and Pluckthun found that homogeneous and active antibodies can be prepared from the E. coli periplasm fraction by inserting an antibody gene downstream of a bacterial signal sequence and inducing expression of the gene in E. coli (Science (1988) 240(4855), 1038-1041). In the Fv prepared from the periplasm fraction, VH associates with VL in a manner so as to bind to an antigen.

Furthermore, the antigen-binding molecule of the present invention may be conjugated with a carrier polymer such as PEG or an organic compound such as an anticancer agent. Alternatively, a glycosylation sequence can be inserted to suitably add a sugar chain for the purpose of producing a desired effect.

The linkers to be used for linking the variable regions of an antibody comprise arbitrary peptide linkers that can be introduced by genetic engineering, synthetic linkers, and linkers disclosed in, for example. Protein Engineering, 9(3). 299-305, 1996. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids. When sc(Fv)$_2$ contains three peptide linkers, their length may be all the same or different.

For example, such peptide linkers include:

```
Ser

Gly•Ser

Gly•Gly•Ser

Ser•Gly•Gly

Gly•Gly•Gly•Ser         (SEQ ID NO: 20)

Ser•Gly•Gly•Gly         (SEQ ID NO: 21)

Gly•Gly•Gly•Gly•Ser     (SEQ ID NO: 22)

Ser•Gly•Gly•Gly•Gly     (SEQ ID NO: 23)

Gly•Gly•Gly•Gly•Gly•Ser (SEQ ID NO: 24)

Ser•Gly•Gly•Gly•Gly•Gly (SEQ ID NO: 25)

Gly•Gly•Gly•Gly•Gly•Gly•Ser (SEQ ID NO: 26)

Ser•Gly•Gly•Gly•Gly•Gly•Gly (SEQ ID NO: 27)

(Gly•Gly•Gly•Gly•Ser)   (SEQ ID NO: 22))n (Ser•Gly•Gly•Gly•Gly)   (SEQ ID NO: 23))n
``` where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl] sulfone (BSOCOES),
and bis[2-(sulfosuccinimidoxycarbonyloxy)ethyl] sulfone (sulfo-BSOCOES).
These crosslinking agents are commercially available.

In general, three linkers are required to link four antibody variable regions together. The linkers to be used may be of the same type or different types.

Furthermore, "Fab" is composed of a single light chain, and a CH1 domain and variable region from a single heavy chain. The heavy chain of Fab molecule cannot form disulfide bonds with another heavy chain molecule.

"F(ab')$_2$" or "Fab'" is produced by treating an immunoglobulin (monoclonal antibody) with a protease such as pepsin and papain, and refers to an antibody fragment generated by digesting an immunoglobulin (monoclonal antibody) at near the disulfide bonds present between the hinge regions in each of the two H chains. For example, papain cleaves IgG upstream of the disulfide bonds present between the hinge regions in each of the two H chains to generate two homologous antibody fragments, in which an L chain comprising VL (L-chain variable region) and CL (L-chain constant region) is linked to an H-chain fragment comprising VH (H-chain variable region) and CHγ1 (γ1 region in an H-chain constant region) via a disulfide bond at their C-terminal regions. Each of these two homologous antibody fragments is called Fab'.

"F(ab')$_2$" contains two light chains and two heavy chains comprising the constant region of a CH1 domain and a portion of a CH2 domain so that disulfide bonds are formed between the two heavy chains. The F(ab')$_2$ constituting an antigen-binding molecule disclosed herein can be preferably obtained as below. A full-length monoclonal antibody or such comprising a desired antigen-binding domain is partially digested with a protease such as pepsin, and then Fc fragments are removed by adsorption onto a Protein A column. The protease is not particularly limited, as long as it can digest the full-length antibody in a restrictive manner to produce F(ab')$_2$ under an appropriately established enzyme reaction condition such as pH. Such proteases include, for example, pepsin and ficin.

A preferred embodiment of the "antigen-binding molecule" of the present invention includes a multispecific antibody. When using an Fc region with decreased Fcγ receptor-binding activity as the Fc region of a multispecific antibody, an Fc region derived from a multispecific antibody may also be used appropriately. For the multispecific antibodies of the present invention, in particular, bispecific antibodies are preferred.

For association of multispecific antibodies, one can apply the technique of introducing charge repulsion at the interface of the second constant region of the antibody H chain (CH2) or the third constant region of the H chain (CH3) to suppress undesired associations between H chains (WO2006/106905).

In the technique of suppressing unintended association between H chains by introducing charge repulsion at the interface of CH2 or CH3, examples of the amino acid residues that are contacted at the interface of other constant regions of the H chain include the region facing the residue at position 356 (EU numbering), the residue at position 439 (EU numbering), the residue at position 357 (EU numbering), the residue at position 370 (EU numbering), the residue at position 399 (EU numbering), and the residue at position 409 (EU numbering) in the CH3 region.

More specifically, for example, for an antibody comprising two types of H chain CH3 regions, the antibody can be made so that one to three pairs of amino acid residues selected from the amino acid residue pairs shown below in (1) to (3) in the first H chain CH3 region have the same charge: (1) amino acid residues at positions 356 and 439 (EU numbering) which are amino acid residues contained in the H chain CH3 region; (2) amino acid residues at positions 357 and 370 (EU numbering) which are amino acid residues contained in the H chain CH3 region; and (3) amino acid residues at positions 399 and 409 (EU numbering) which are amino acid residues contained in the H chain CH3 region.

Furthermore, the antibody can be made so that one to three pairs of amino acid residues corresponding to the amino acid residue pairs shown above in (1) to (3) having the same type of charge in the first H chain CH3 region, which are amino acid residue pairs selected from the amino acid residue pairs shown above in (1) to (3) in the second H chain CH3 region which differs from the first H chain CH3 region, have a charge opposite to the corresponding amino acid residues in the aforementioned first H chain CH3 region.

The respective amino acid residues of (1) to (3) mentioned above are positioned close to each other when associated. For the desired H chain CH3 region or H chain constant region, those skilled in the art can find sites corresponding to the above-mentioned amino acid residues of (1) to (3) by homology modeling and such using commercially available software, and amino acid residues of these sites can be subjected to modifications as appropriate.

In the above-mentioned antibodies, "amino acid residues having a charge" are preferably selected, for example, from amino acid residues contained in either one of groups (a) and (b) below:

(a) glutamic acid (E) and aspartic acid (D); and
(b) lysine (K), arginine (R), and histidine (H).

Regarding the above-mentioned antibodies, "having the same type of charge" means, for example, that two or more amino acid residues all have amino acid residues included in either one of the above-mentioned groups (a) and (b). The phrase "having the opposite charge" means that, for example, when at least one of the two or more amino acid residues has an amino acid residue included in either one of the above-mentioned groups (a) and (b), the remaining amino acid residue(s) will have an amino acid residue included in the other group.

In a preferred embodiment of the above-mentioned antibody, the first H chain CH3 region and the second H chain CH3 region may be cross-linked by a disulfide bond.

In the present invention, the amino acid residue to be subjected to alteration is not limited to an amino acid residue of the constant region or variable region of the antibody described above. With regard to polypeptide mutants or heteromultimers, those skilled in the art can find amino acid residues that form the interface through homology modeling and such using commercially available software, and can subject the amino acid residues at those sites to alterations so that association is regulated.

Other known techniques can also be used for the association of multispecific antibodies of the present invention. Polypeptides with different amino acids having an Fc region can be efficiently associated with each other by substituting an amino acid side chain present in one of the H chain variable regions of the antibody with a larger side chain (knob), and substituting an amino acid side chain present in the corresponding variable region of the other H chain with a smaller side chain (hole), to allow placement of the knob within the hole (WO 1996/027011; Ridgway J B et al., Protein Engineering (1996) 9, 617-621; Merchant A M et al. Nature Biotechnology (1998) 16, 677-681; and US20130336973).

In addition, other known techniques can also be used to form multispecific antibodies of the present invention. Association of polypeptides having different sequences can be induced efficiently by complementary association of CH3s, using a strand-exchange engineered CH3 domain produced by changing part of CH3 in one of the H chains of an antibody into its corresponding IgA-derived sequence, and introducing into the complementary portion of the CH3 in the other H chain its corresponding IgA-derived sequence (Protein Engineering Design & Selection, 23; 195-202, 2010). This known technique can also be used to efficiently form multispecific antibodies of interest.

In addition, the following techniques and such may be used for the formation of multispecific antibodies: techniques for antibody production using association of antibody CH1 and CL, and association of VH and VL as described in WO 2011/028952, WO2014/018572, and Nat Biotechnol. 2014 February; 32(2): 191-8; techniques for producing bispecific antibodies using separately prepared monoclonal antibodies in combination (Fab Arm Exchange) as described in WO2008/119353 and WO2011/131746; techniques for regulating association between antibody heavy chain CH3s as described in WO2012/058768 and WO2013/063702; techniques for producing bispecific antibodies composed of two types of light chains and one type of heavy chain as described in WO2012/023053; techniques for producing bispecific antibodies using two bacterial cell strains that individually express one of the chains of an antibody comprising a single H chain and a single L chain as described by Christoph et al. (Nature Biotechnology Vol. 31, p 753-758 (2013)).

An embodiment of multispecific antibody formation includes methods for obtaining bispecific antibodies by mixing two types of monoclonal antibodies in the presence of a reducing agent to cleave the disulfide bonds in the core hinge region, followed by re-association for heterodimerization (FAE) as described above. Meanwhile, introduction of electrostatic interactions at the interacting interface of the CH3 region (WO2006/106905) can induce even more efficient heterodimerization during the re-association (WO2015/046467). In FAE using naturally-occurring IgG, re-association takes place randomly; and thus theoretically, bispecific antibodies can only be obtained at 50% efficiency; however, in this method, bispecific antibodies can be produced in high yield.

Alternatively, even when a multispecific antibody of interest cannot be formed efficiently, a multispecific antibody of the present invention can be obtained by separating and purifying the multispecific antibody of interest from the produced antibodies. For example, a method has been reported that enables purification of two types of homologous forms and the heterologous antibody of interest by ion exchange chromatography, by conferring a difference in the isoelectric points by introducing amino acid substitutions into the variable regions of the two types of H chains (WO2007114325). To date, as a method for purifying heterologous forms, a method using Protein A to purify a heterodimerized antibody comprising a mouse IgG2a H chain that binds to Protein A and a rat IgG2b H chain that does not bind to Protein A has been reported (WO98050431 and WO95033844). Furthermore, the heterodimerized antibody per se can be purified efficiently using a Protein A column by changing the interaction between each of the H chains and Protein A, by using H chains in which amino acid residues at the IgG-Protein A binding site, positions 435 and 436 (EU numbering), are substituted with amino acids that yield a different binding strength to Protein A such as Tyr, His, or such.

Alternatively, a common L chain that can confer binding ability to a plurality of different H chains can be obtained and used as the common L chain of a multispecific antibody. Efficient expression of a multispecific IgG can be achieved by introducing the genes of such a common L chain and a plurality of different H chains into cells and expressing the IgG (Nature Biotechnology (1998) 16, 677-681). A method for selecting a common L chain that shows strong binding ability to any different H chains can also be used when selecting a common H chain (WO 2004/065611).

Furthermore, an Fc region whose C-terminal heterogeneity has been improved can be appropriately used as an Fc region of the present invention. More specifically, Fc regions lacking glycine at position 446 and lysine at position 447, as specified by EU numbering, in the amino acid sequences of two polypeptides constituting an Fc region derived from IgG1, IgG2, IgG3, or IgG4, are provided.

A plurality, such as two or more, of these techniques can be used in combination. Furthermore, these techniques can be appropriately and separately applied to the two H chains to be associated. Furthermore, these techniques can be used in combination with the above-mentioned Fc region of which Fcγ receptor-binding activity has been decreased. Furthermore, an antigen-binding molecule of the present invention may be a molecule produced separately based on an antigen-binding molecule subjected to the above-described modifications so as to have the same amino acid sequence.

An antigen-binding molecule (first antigen-binding molecule) of the present invention may comprise (1) the cancer-specific antigen-binding domain mentioned above and (2) a tumor necrosis factor (TNF) superfamily-binding domain or a tumor necrosis factor (TNF) receptor superfamily-binding domain, and its structure is not limited. By comprising these two binding domains, the first antigen-binding molecule specifically activates cells that express a molecule belonging to the TNF superfamily or the TNF receptor superfamily, and which express a cancer-specific antigen or are cells contained in tumor tissues comprising these cells, and induces excellent (specific) cytotoxic effects against these cancer-specific antigen-expressing cells or tumor tissues containing these cells. A cancer-specific antigen-binding domain, TNF superfamily-binding domain, and TNF receptor superfamily-binding domain of the present invention can be appropriately selected using a cancer-specific antigen or an antigen belonging to the TNF superfamily or the TNF receptor superfamily described above, respectively. These binding domains can be linked directly by peptide bonds or bound via linkers.

Antigen-binding molecules of the present invention may further comprise an FcRn-binding domain. When using an antibody Fc region described above as the FcRn-binding domain, it is preferably an Fc region with decreased Fcγ receptor-binding activity. Reducing the activity to bind to an Fcγ receptor enables suppression of side effects produced by immunostimulation such as cytokine release caused by the crosslinking between Fcγ receptor-expressing cells and cells that express factors belonging to the TNF receptor superfamily.

Antigen-binding molecules of the present invention can be produced using known methods described above. For example, when (1) F(ab')$_2$ as a cancer-specific antigen-binding domain. (2) F(ab')$_2$ as a TNF superfamily-binding domain or a TNF receptor superfamily-binding domain, and (3) a domain comprising an Fc region with decreased Fcγ receptor-binding activity as the FcRn-binding domain are used, and when the antigen-binding domains described in (1) and (2) and the Fc region-containing domain described in (3) are directly linked by peptide bonds, the linked polypeptides will form an antibody structure. Such antibodies can be produced by purification from the afore-mentioned hybridoma culture medium, and also by purifying antibodies from the culture medium of desired host cells that stably carry polynucleotides encoding polypeptides constituting the antibody.

In addition to the linkers exemplified above, linkers with peptide tags such as His tag, HA tag, myc tag, and FLAG tag may also be suitably used as the linkers to be employed when connecting each of the domains via linkers. Furthermore, hydrogen bonding, disulfide bonding, covalent bonding, ionic interaction, or the property of mutual binding as a result of combination thereof may be suitably used. For example, the affinity between antibody CH1 and CL may be used, and Fc regions derived from the above-described multispecific antibodies may also be used for heterologous Fc region association.

In the present invention, a first antigen-binding molecule can be used in combination with a second antigen-binding molecule.

As in the case with the first antigen-binding molecule, the structure of a second antigen-binding molecule is not limited and it may comprise:
(1) a cancer-specific antigen-binding domain, and
(2) a T cell receptor complex-binding domain;
and it can be obtained by methods similar to those for the first antigen-binding molecule. Furthermore, as long as the second antigen-binding molecule contains a cancer-specific antigen-binding domain and a T cell receptor complex-binding domain, its structure does not have to be the same as that of the first antigen-binding molecule. The cancer-specific antigen bound by the cancer-specific antigen-binding domain of the first antigen-binding molecule and the cancer-specific antigen bound by the cancer-specific antigen-binding domain of the second antigen-binding molecule may be the same or different, but they are preferably the same cancer-specific antigen. When the cancer-specific antigens are the same, the epitopes to which the first and second antigen-binding molecules bind may be the same or different. Use of these first and second antigen-binding molecules in combination yields an excellent cytotoxic activity. The cancer-specific antigen-binding domain and T cell receptor complex-binding domain in the second antigen-binding domain can be appropriately selected, respectively, from the above-mentioned cancer-specific antigens or antigens belonging to T cell receptor complexes.

Similarly to the first antigen-binding molecule, the second antigen-binding molecule of the present invention may further comprise an FcRn-binding domain. When an antibody Fc region described above is used as the FcRn-binding domain, an Fc region with decreased Fcγ receptor-binding activity is preferred, as in the case of the first antigen-binding molecule. Reducing the activity to bind to an Fcγ receptor enables suppression of side effects produced by immunostimulation such as cytokine release caused by the crosslinking between Fcγ receptor-expressing cells and T cell receptor complex-expressing cells and/or cells that express factors belonging to the TNF receptor superfamily.

The present invention also relates to polynucleotides encoding the antigen-binding molecules of the present invention, and they can be incorporated into arbitrary expression vectors. Suitable hosts can be transformed with the expression vectors to produce cells that express the antigen-binding molecules. Antigen-binding molecules encoded by the polynucleotides can be obtained by culturing cells that express the antigen-binding molecules, and collecting expression products from the culture supernatant. That is, the present invention relates to vectors comprising a polynucleotide that encodes an antigen-binding molecule of the present invention, cells carrying such a vector, and methods for producing antigen-binding molecules, which comprise culturing the cells and collecting antigen-binding molecules from the culture supernatant. These can be obtained by techniques similar to those for recombinant antibodies mentioned above.

Pharmaceutical Compositions

From another viewpoint, the present invention provides pharmaceutical compositions comprising the above-described first antigen-binding molecule as the active ingredient. Furthermore, the present invention relates to pharmaceutical compositions that induce cytotoxicity (cytotoxicity-inducing therapeutic agents), cell proliferation inhibitors, and anticancer agents, which comprise the antigen-binding molecule as an active ingredient. Pharmaceutical compositions of the present invention can be used as agents for treating cancer or agents for preventing cancer. The cytotoxicity-inducing therapeutic agents, cell proliferation inhibitors, and anticancer agents of the present invention are preferably administered to subjects suffering from cancer, or subjects who may undergo relapse.

Furthermore, in the present invention, cytotoxicity-inducing therapeutic agents, cell proliferation inhibitors and anticancer agents that comprise the first antigen-binding molecule as an active ingredient described above can be presented as methods for inducing cytotoxicity, methods for suppressing cell proliferation, methods for activating immunity against cancer cells or tumor tissues containing cancer cells, or methods for preventing or treating cancer, which comprise the step of administering the antigen-binding molecule to a subject; or they can be presented as use of the antigen-binding molecules in producing pharmaceutical compositions for inducing cytotoxicity, cell proliferation inhibitors, and anticancer agents. Alternatively, they can be presented as antigen-binding molecules for use in inducing cytotoxicity, suppressing cell proliferation, activating immunity against cancer cells or tumor tissues containing cancer cells, or treating or preventing cancer.

In the present invention, "comprising the antigen-binding molecule as an active ingredient" means containing the antigen-binding molecule as a major active component, and does not limit the content of the antigen-binding molecule.

Furthermore, pharmaceutical compositions, or pharmaceutical compositions for inducing cytotoxicity, cell proliferation inhibitors, and anticancer agents of the present invention (hereinafter, referred to as pharmaceutical compositions or such) can be used in combination with the above-described second antigen-binding molecules. Use of a second antigen-binding molecule in combination with a pharmaceutical composition or such containing a first antigen-binding molecule can strengthen the cytotoxic actions against the antigen-expressing cells. Here, "use of a second antigen-binding molecule in combination" may refer to the case of mixing a second antigen-binding molecule into a pharmaceutical composition or such containing a first antigen-binding molecule, or the case where a second antigen-binding molecule is included in a pharmaceutical composition or such that is different from the pharmaceutical composition or such containing a first antigen-binding molecule. Their dosage forms may be the same or different. Furthermore, when the first antigen-binding molecule and the second antigen-binding molecule are included in different pharmaceutical compositions or such, these pharmaceutical compositions or such may be administered simultaneously or separately to the subject. In addition, these pharmaceutical compositions or such may be provided as a kit.

In the present invention, a first antigen-binding molecule or a pharmaceutical composition comprising a first antigen-binding molecule as an active ingredient can be used as a pharmaceutical composition for strengthening the cytotoxic activity or enhancing the induction of cytotoxic activity by concomitantly using it with a second antigen-binding molecule or a pharmaceutical composition or such comprising a second antigen-binding molecule as an active ingredient. Furthermore, a second antigen-binding molecule or a pharmaceutical composition comprising a second antigen-binding molecule as an active ingredient can be used as a pharmaceutical composition for strengthening the cytotoxic activity or enhancing the induction of cytotoxic activity by concomitantly using it with a first antigen-binding molecule or a pharmaceutical composition or such comprising a first antigen-binding molecule as an active ingredient.

Herein, "concomitant use" includes the case where a pharmaceutical composition or such comprising a first antigen-binding molecule as an active ingredient and a pharmaceutical composition or such comprising a second antigen-binding molecule as an active ingredient are simultaneously administered to a subject, and the case where they are separately administered to a subject. Their dosage forms may be the same or different. Furthermore, these pharmaceutical compositions or such may be provided as a kit.

Furthermore, the present invention provides a method that utilizes the effects produced by concomitant use of a first antigen-binding molecule described above or a pharmaceutical composition or such comprising this antigen-binding molecule as an active ingredient and a second antigen-binding molecule or a pharmaceutical composition or such comprising the second antigen-binding molecule as an active ingredient to enhance the cytotoxic activity or anti-tumor effect of the second antigen-binding molecule or a pharmaceutical composition or such comprising the second antigen-binding molecule as an active ingredient by the first antigen-binding molecule or a pharmaceutical composition or such comprising the first antigen-binding molecule as an active ingredient. Furthermore, the present invention provides a method for strengthening the cytotoxic activity or antitumor effect of a first antigen-binding molecule or a pharmaceutical composition or such comprising a first antigen-binding molecule as an active ingredient with a second antigen-binding molecule or a pharmaceutical composition or such comprising a second antigen-binding molecule as an active ingredient.

Furthermore, pharmaceutical compositions or such of the present invention can be used by combining multiple types of a first antigen-binding molecule and/or a second antigen-binding molecule as necessary. For example, by using a cocktail of a plurality of antigen-binding molecules of the present invention that bind to the same antigen, one can enhance the cytotoxic action against cells expressing the antigen.

If necessary, the antigen-binding molecules of the present invention may be encapsulated in microcapsules (microcapsules made from hydroxymethylcellulose, gelatin, poly[m-ethylmethacrylate], and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for preparing agents as sustained-release agents are known, and these can be applied to the antigen-binding molecules of the present invention (J. Biomed. Mater. Res. (1981) 15, 267-277; Chemtech. (1982) 12, 98-105; U.S. Pat. No. 3,773, 719; European Patent Application (EP) Nos. EP58481 and EP133988; Biopolymers (1983) 22, 547-556).

The pharmaceutical compositions, cell proliferation-suppressing agents, or anticancer agents of the present invention may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections. For example, pharmaceutical compositions, therapeutic agents for inducing cellular cytotoxicity, cell proliferation-suppressing agents, or anticancer agents of the present invention can be administered locally or systemically by injection. Furthermore, appropriate administration methods can be selected according to the patient's age and symptoms. The administered dose can be selected, for example, from the range of 0.0001 mg to 1,000 mg per kg of body weight for each administration. Alternatively, the dose can be selected, for example, from the range of 0.001 mg/body to 100,000 mg/body per patient. However, the dose of a pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such.

Furthermore, the present invention provides methods of inducing damage to cells expressing a cancer-specific antigen or to tumor tissues containing cells expressing a cancer-specific antigen and methods for suppressing proliferation of these cells or these tumor tissues, by contacting cells that express the certain cancer-specific antigen to a first antigen-binding molecule or to a first antigen-binding molecule as well as a second antigen-binding molecule of the present invention which binds to the cancer specific antigen. The cells bound by an antigen-binding molecule of the present invention that binds to the cancer-specific antigen are not particularly limited as long as they are cells that express the cancer-specific antigens. Suitable examples of the preferred cancer antigen-expressing cells of the present invention are specifically, cells of ovarian cancer, prostate cancer, breast cancer, uterine cancer, hepatic cancer, lung cancer, pancreatic cancer, gastric cancer, bladder cancer, and colorectal cancer.

In the present invention, "contact" is carried out, for example, by adding an antigen-binding molecule of the present invention that binds to the cancer antigen to a solution of cancer antigen-expressing cells cultured in vitro. In this case, a form suitable for use of the added antigen-binding molecule may be a solution, or a solid or such obtained by freeze-drying, and the like. When added as an aqueous solution, an aqueous solution containing purely the antigen-binding molecule of the present invention alone may be used, or a solution containing surfactants, excipients, coloring agents, perfumes, preservatives, stabilizers, buffers, suspending agents, isotonization agents, binders, disintegrants, lubricants, fluidity promoting agents, flavoring agents, and such described above may be used. The concentration used for the addition is not particularly limited, but a suitable final concentration in the culture solution is preferably in the range of 1 pg/ml to 1 g/ml, more preferably 1 ng/ml to 1 mg/ml, and even more preferably 1 µg/ml to 1 mg/ml.

Furthermore, in another embodiment, "contact" of the present invention is carried out by administering an antigen-binding molecule of the present invention that binds to a cancer antigen to a non-human animal with cells expressing the cancer-specific antigen transplanted into their bodies, and to an animal having cancer cells that intrinsically express the cancer-specific antigens. The method of administration may be oral or parenteral, and parenteral administration is particularly preferred. Specific examples of the administration method include administration by injection, transnasal administration, transpulmonary administration, and transdermal administration. Examples of administration by injection include intravenous injection, intramuscular injection, intraperitoneal injection, and subcutaneous injection. A pharmaceutical composition of the present invention or a pharmaceutical composition for inducing cytotoxicity, a cell proliferation inhibitor, and an anticancer agent can be administered systemically or locally, for example, through administration by injection. The method of administration can be selected appropriately according to the age and symptoms of the test animal. When administered as an aqueous solution, an aqueous solution containing purely the antigen-binding molecule of the present invention alone may be used, or a solution containing surfactants, excipients, coloring agents, perfumes, preservatives, stabilizers, buffers, suspending agents, isotonization agents, binders, disintegrants, lubricants, fluidity promoting agents, flavoring agents, and such described above may be used. The dose can be selected, for example, from the range of 0.0001 mg to 1000 mg per kilogram body weight for a single administration. Alternatively, for example, the dose may be selected from the range of 0.001 mg/body to 100000 mg/body per patient. However, the dose of the antigen-binding molecule of the present invention is not limited to these doses.

The following method is suitably used as a method for evaluating or measuring cytotoxicity induced in cells expressing a cancer-specific antigen bound by the cancer specific antigen-binding domain constituting an antigen-binding molecule of the present invention, as a result of contacting the antigen-binding molecule with the cells. Examples of a method for evaluating or measuring the cytotoxic activity in vitro include methods for measuring cytotoxic T cell activity, and such. Whether an antigen-binding molecule of the present invention has T cell cytotoxicity can be measured by known methods (for example, Current protocols in Immunology, Chapter 7. Immunologic studies in humans, Editor, John E. Coligan et al., John Wiley & Sons, Inc., (1993) and the like). For activity measurements, an antigen-binding molecule with an antigen-binding domain that binds to an antigen which differs from the antigen bound in the present invention and is an antigen not expressed in the cells used for the examination can be used as a control and in the same manner as the antigen-binding molecule of the present invention, and the activity can be determined to be present when the antigen-binding molecule of the present invention shows a stronger cytotoxic activity than that of the antigen-binding molecule used as a control.

To evaluate or measure cytotoxic activity in vivo, for example, cells expressing an antigen bound by a cancer-specific antigen-binding domain that constitutes an antigen-binding molecule of the present invention are intradermally or subcutaneously transplanted into a non-human test animal, and then a test antigen-binding molecule is intravenously or intraperitoneally administered daily or with an interval of few days, starting from the day of transplantation or the following day. Tumor size is measured daily and the difference in the change of tumor size can be defined as the cytotoxic activity. In a similar manner to the in vitro evaluation, a control antigen-binding molecule is administered, and an antigen-binding molecule of the present invention can be determined as exhibiting cytotoxic activity based on the finding that the tumor size in the group subjected to administration of an antigen-binding molecule of the present invention is significantly smaller than the tumor size in the group subjected to administration of the control antigen-binding molecule.

As a method for evaluating or measuring the suppressive effect on proliferation of cells expressing an antigen bound by a cancer-specific antigen-binding domain that constitutes an antigen-binding molecule of the present invention by contact with the antigen-binding molecule, a method of measuring the uptake of isotope-labeled thymidine into cells, or the MTT method may be suitably used. As a method for evaluating or measuring the cell proliferation-suppressing activity in vivo, the same method as that described above for evaluating or measuring cytotoxic activity in vivo may be suitably used.

The present invention also provides kits for use in the methods of the present invention, which comprise an antigen-binding molecule of the present invention or an antigen-binding molecule produced by a production method of the present invention. Additionally, the kit may include in its package, a pharmaceutically acceptable carrier, solvent, and instructions describing the method of use.

The present invention also relates to an antigen-binding molecule of the present invention or an antigen-binding molecule produced by a production method of the present invention for use in a method of the present invention.

Those skilled in the art will naturally understand that optional combinations of one or more of the embodiments described herein are included in the present invention, as long as they are not technically inconsistent based on common technical knowledge of those skilled in the art.

All prior art references cited herein are incorporated by reference into this description.

EXAMPLES

Herein below, the present invention will be specifically described with reference to the Examples, but the scope of the present invention is not to be construed as being limited thereto.

Reference Example 1

Construction of Antibody Expression Vectors, and Expression and Purification of Antibodies Synthesis of full-length genes encoding the nucleotide sequences of the H chain and L chain of the antibody variable regions was carried out by production methods known to those skilled in the art using Assemble PCR and such. Introduction of amino acid substitutions was carried out by methods known to those skilled in the art using PCR or such. The obtained plasmid fragment was inserted into an animal cell expression vector, and the H-chain expression vector and L-chain expression vector were produced. The nucleotide sequence of the obtained expression vectors was determined by methods known to those skilled in the art. The produced plasmids were transiently introduced into the HEK293H cell line derived from human embryonic kidney cancer cells (Invitrogen) or into FreeStyle293 cells (Invitrogen) for antibody expression. The obtained culture supernatant was collected, and then passed through a 0.22 μm MILLEX(R)-GV filter (Millipore), or through a 0.45 μm MILLEX(R)-GV filter (Millipore) to obtain the culture supernatant. The antibodies were purified from the obtained culture supernatant by methods known to those skilled in the art using rProtein A Sepharose Fast Flow (GE Healthcare) or Protein G Sepharose 4 Fast Flow (GE Healthcare). For the concentration of the purified antibodies, their absorbance at 280 nm was measured using a spectrophotometer. From the obtained value, the antibody concentration was calculated using the extinction coefficient determined by methods such as PACE (Protein Science 1995; 4: 2411-2423).

Reference Example 2

Method for Preparing Mouse Fcγ Receptor (mFcγR) and Method for Analyzing the Interaction Between a Modified Antibody and mFcγR Extracellular domains of mouse FcγRs were prepared by the following method. First, genes of FcγR extracellular domains were synthesized by a method well known to those skilled in the art. In so doing, the sequence of each FcγR was produced based on the information registered at NCBI. Specifically, mFcγRI was produced based on the sequence of NCBI Reference Sequence: NP_034316.1; mFcγRII was produced based on the sequence of NCBI Reference Sequence: NP_034317.1 mFcγRIII was produced based on the sequence of NCBI Reference Sequence: NP_034318.2; and mFcγRIV was produced based on the sequence of NCBI Reference Sequence: NP_653142.2. A His tag was attached to the C terminus of these sequences. Each of the obtained gene fragments was inserted into an animal cell expression vector to construct expression vectors. The constructed expression vector was transiently introduced into human embryonic kidney cancer cell-derived FreeStyle293 cells (Invitrogen) to express the proteins of interest. The obtained culture supernatant was collected, and then passed through a 0.22 μm filter to obtain the culture supernatant. The obtained culture supernatants were purified in principle by the following four steps: step 1—ion exchange column chromatography, step 2—affinity column chromatography for His tag (HisTrap HP), step 3—gel filtration column chromatography (Superdex200), and step 4—aseptic filtration. The ion exchange column chromatography of step 1 was carried out using Q Sepharose HP for mFcγRI, using SP Sepharose FF for mFcγRII and mFcγRIV, and using SP Sepharose HP for mFcγRIII. While the solvent used in step 3 and the subsequent step was D-PBS(−), D-PBS(−) containing 0.1 M Arginine was used for mFcγRIII. The absorbance at 280 nm was measured for the purified proteins using a spectrophotometer. From the obtained values, the concentrations of the purified proteins were calculated using the extinction coefficients determined using methods such as PACE (Protein Science 1995; 4: 2411-2423). The interaction between each modified antibody and the Fcγ receptor prepared as mentioned above was analyzed using Biacore T100 (GE Healthcare), Biacore T200 (GE Healthcare), Biacore A100, and Biacore 4000. The running buffer used was HBS-EP+(GE Healthcare) and the measurement temperature was set to 25° C. The chip used was: a Series S Sensor Chip CM5 (GE Healthcare) or Series S Sensor Chip CM4 (GE Healthcare) to which Protein L (ACTIGEN or BioVision) was immobilized by the amine coupling method. Antibodies of interest were captured onto these sensor chips, and mFcγR diluted with the running buffer was allowed to interact with them. The amount bound by the antibodies was measured and compared between the antibodies. However, since the amount of mFcγR bound depends on the amount of the captured antibody, the comparison was carried out on corrected values obtained by dividing the amount of bound mFcγR by the amount of each antibody captured. Furthermore, 10 mM glycine-HCl, pH 1.5 was reacted to wash out the captured antibody from the sensor chips, and the sensor chip was regenerated and used repeatedly. Kinetic analyses for calculating the KD values of each altered antibody to FcγR were performed according to the method below. First, antibodies of interest were captured onto the above-mentioned sensor chips, and mFcγR diluted with the running buffer was allowed to interact with them. As for the obtained sensorgrams, the measurement results were processed by global fitting according to a 1:1 Langumuir binding model using Biacore Evaluation Software to calculate the association rate constant ka (L/mol/s) and the dissociation rate constant kd (1/s). From those values, the dissociation constant KD (mol/L) was determined.

Reference Example 3

Experimental Animals and Cell Lines

The experimental animals used were female C57BL/6 mice (Charles River Laboratories Japan. Inc.) or female Balb/c mice (Charles River Laboratories Japan, Inc.). They were bred in a breeding room under constant conditions (temperature: 20° C. to 26° C.; lighting: 12-hour light-dark cycle) with ad libitum access to feed and water. The human GPC3 gene was integrated into the chromosome of the mouse lung cancer cell line LLC (ATCC No. CRL-1642) by a method well known to those skilled in the art to obtain an LLC-GPC3 cell line that expresses human GPC3 in high levels. The expression level of human GPC3 ($2.3 \times 10^5$/cell) was determined using the QIFI kit (Dako) by the manufacturer's recommended method. Similarly, the human GPC3 gene was integrated into the mouse colorectal cancer cell line CT-26 (ATCC No. CRL-2638) to obtain the high expression CT26-GPC3 cell line (expression level: $3.1 \times 10^5$/cell). To maintain the human GPC3 gene, these recombinant cell lines were cultured in ATCC-recommended media by adding Geneticin (GIBCO) at 400 g/ml for LLC-GPC3 and 200 μg/ml for CT26-GPC3. After culturing, these cells were detached using 2.5 g/L trypsin-1 mM EDTA (nacalai tesque), and then used for each of the experiments.

Example 1

Preparation of Anti-CD137 Mouse Antibodies and Assessment of Agonist Activity 1-1. Preparation of Anti-Mouse CD137 Mouse Antibody and Assessment of mFcγR Binding 1D8VH (SEQ ID NO: 28), a variable region against mouse CD137 disclosed in WO2005/017148, which was used as the antibody H-chain variable region, and 1D8VH-mIgG 1 (SEQ ID NO: 29) having the H-chain constant region of a naturally-occurring mouse IgG1, which was used as the antibody H-chain constant region, were prepared according to the method of Reference Example 1. 1D8VH-mF18 (SEQ ID NO: 30) was produced by introducing into 1D8VH-mIgG1 a modification of substituting Lys for Pro at position 235 (EU numbering) and a modification of substituting Lys for Ser at position 239 (EU numbering), which are modifications that eliminate FcγR binding as described in WO2012/133782. Furthermore, 1D8VH-MB492 (SEQ ID NO: 31) was produced by introducing into 1D8VH-mIgG1 modifications (T230E, V231P, P232N, S238E, S239D, N324D) that enhance mFcgRII binding. 1D8VL disclosed in WO2005/017148 was used as the antibody L-chain variable region, and 1 D8VL-mk0 (SEQ ID NO: 32) which has the constant region of the mouse K chain was used as the L-chain constant region. They were expressed and purified according to the method of Reference Example 1 to obtain 1D8VH-mIgG1/1D8VL-mk0, 1D8VH-mF18/1D8VL-mk0, and 1D8VH-MB492/1 D8VL-mk0. Herein below, these antibodies will be denoted as 1D8-mIgG1, 1D8-mF18, and 1D8-MB492 for simplicity.

Furthermore, to measure mFcγR binding of each constant region, H237-mIgG1 (SEQ ID NO: 34) and H237-MB492 (SEQ ID NO: 35) which have the variable region H237 of the anti-human interleukin 6 receptor antibody (SEQ ID NO: 33) described in WO2009/125825 were prepared as the H-chain variable region. MRAL-k0 (SEQ ID NO: 36) which is the L chain of tocilizumab was used as the antibody L chain. Expression and purification were performed according to the method of Reference Example 1 to obtain H237-mIgG1/MRAL-k0 and H237-MB492/MRAL-k0. Similarly, mPM1H-mIgG1 (SEQ ID NO: 37) and mPMIH-mF18 (SEQ ID NO: 38) were produced, which have the variable region (mPM1H) of mouse PM-1, a mouse antibody that binds to human IL6R (Sato, Cancer Res., 1993, 53, 851-856), as the antibody H chain variable region. MRAL-k0 was used as the antibody L chain. Expression and purification were carried out according to the method of Reference Example 1 to obtain mPM1H-mIgG1/MRAL-k0 and mPM1H-mF18/MRAL-k0.

The ability of mPMIH-mIgG1/MRAL-k0 and mPM1H-mF18/MRAL-k0 to bind mFcγRII and mFcγRIII was assessed according to the method of Reference Example 2. Naturally-occurring mouse IgG1 (mIgG1) does not bind to mFcγRI or mFcγRIV, and binds only to mFcγRII and mFcγRIII among the four types of mouse FcγR (Nimmerjahn, 2005, Science, 310, 1510-1512). Therefore, introduction of modifications that decrease mFcγR binding into naturally-occurring mIgG1 was expected to provide variants having decreased binding to mFcγRII and mFcγRIII, and thus reduced binding to all mFcγRs. The results are shown in Table 1.

TABLE 1

| Name of the constant region | Amount of binding (RU) | |
|---|---|---|
| | mFcγRII | mFcγRIII |
| mIgG1 | 202.1 | 450 |
| mF18 | 1.01 | 2.75 |

The above-mentioned results demonstrated that the constant region mF18 is a variant having remarkably reduced mFcγR binding.

Similarly, Table 2 shows the results of assessing H237-mIgG1/MRAL-k0 and H237-MB492/MRAL-k0 for the binding towards mFcγRII and mFcγRIII.

TABLE 2

| Name of the constant region | KD (M) | | Relative binding activity | |
|---|---|---|---|---|
| | mFc γ RII | mFc γ RIII | mFc γ RII | mFc γ RIII |
| mIgG1 | 2.10E−07 | 2.82E−07 | 1.0 | 1.0 |
| MB492 | 3.38E−10 | 2.58E−08 | 621.5 | 10.9 |

"Relative binding activity" in the table indicates the binding activity of MB492 when the binding activity of the naturally-occurring mIgG1 towards each mFcγR is defined as 1. The above-mentioned results showed that MB492 is a variant with 621.5-fold increase in mFcγRII binding and 10.9-fold increase in mFcγRIII binding in comparison to mIgG1.

1-2. Assessment of the In Vitro CD137 Agonist Effect of Anti-Mouse CD137 Antibodies.

Spleen was collected from naive female C57BL/6 mice. Cells were suspended in 10% FBS-containing RPMI1640 medium supplemented with 0.5 μg/ml ionomycin and 10 ng/ml PHORBOL 12-MYRISTATE 13-ACETATE (PMA), and they were seeded into a 96-well plate at a density of $2 \times 10^5$ cells/100 μl/well. Anti-mouse CD137 antibodies were added to these wells at 3 μg/ml, and the cells were cultured under the conditions of 37° C. and 5% $CO_2$ for 3 days. The culture supernatant was collected, and the concentration of mouse IFN-γ contained in the supernatant was determined by ELISA to assess the activation of spleen-derived T cells. ELISA was performed by following the instructions provided by the kit manufacturer (PeproTech).

As a result (FIG. 1), among the prepared anti-mouse CD137 mouse IgG1 antibodies, the antibody (1D8-mF18) having extremely decreased FcγR binding did not show the activity, and the antibody (1D8-mIgG1) having a wild-type Fc showed T cell activation. Furthermore, the specific activity of the antibody (I D8-MB492) having an enhanced binding ability towards FcγRIIB was increased by approximately eight-fold compared to that of the wild-type Fc antibody.

Figure 2:
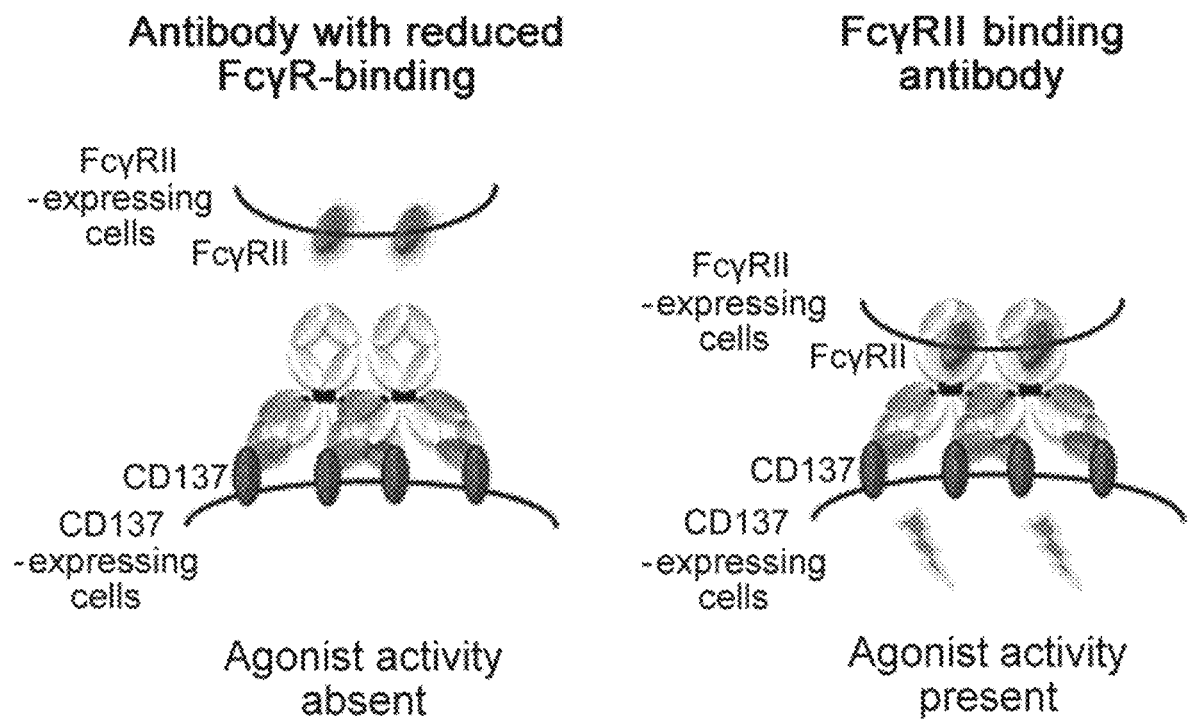
FIG. 2 presents a diagram that conceptually demonstrates the T cell activation effect of an anti-mouse CD137 antibody in various molecular forms.

This revealed that, in a similar manner to agonist antibodies against other TNFRSF as described in Proc Natl Acad Sci USA. 2013, 110(48), 19501-6, in order for anti-CD137 antibodies to exert an agonist activity, the antibodies must bind to FcγRII, and the anti-CD137 antibodies bound to CD137-expressing T cells must crosslink with FcγRII-expressing cells (FIG. 2). FcγRII is expressed in many immune cells and phagocytes such as B cells. Therefore, the agonist activity by anti-CD137 antibodies may take place systemically, and thereby causes side effects.

Example 2

Figure 3:
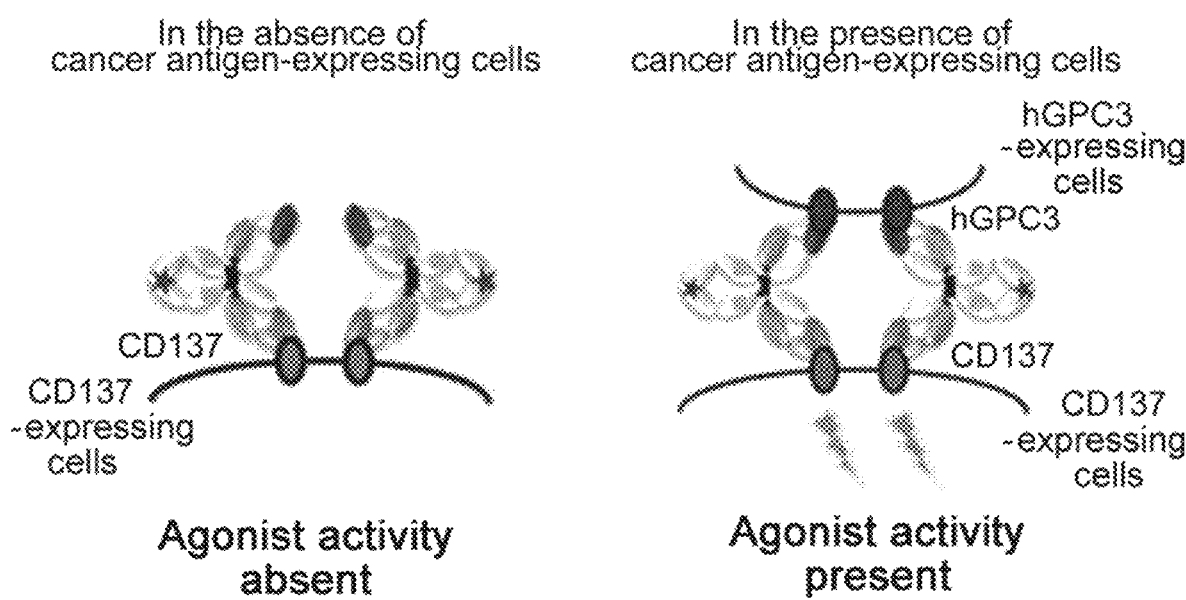
FIG. 3 presents a diagram that conceptually demonstrates the GPC3 antigen-dependent T cell activation effect of an anti-human GPC3/anti-mouse CD137 bispecific antibody.

Preparation of Anti-Human GPC3/Anti-Mouse CD137 Bispecific Antibodies and Assessment of their Agonist Activities 2-1. Concept of a Cancer Antigen-Dependent Agonist Antibody Based on Cancer Antigen- and CD137-Bispecific Antibodies According to the examination in Example 1, since agonist activity by common anti-CD137 antibodies takes place systemically, antitumor effects and side effects in normal tissues (such as T cell activation) have been considered to be inseparable. Therefore, the present inventors conceived that use of bispecific antibodies against a cancer antigen and CD137 may enable exhibition of the agonist activity by an anti-CD137 antibody only in cancer tissues where the cancer antigen is present by crosslinking CD137-expressing T cells and cancer antigen-expressing cells (such as cancer cells) via the bispecific antibodies (FIG. 3).

2-1. Preparation of Anti-Human GPC3/Anti-Mouse CD137 Bispecific Antibodies (GPC3 ERY22-1D8, GPC3 ERY22-G2-1D8, and GPC3 ERY22-G4-1D8)

Three types of anti-human GPC3/anti-mouse CD137 bispecific antibodies having the constant region of human IgG1, IgG2, or IgG4, were prepared respectively. For these molecules, the CrossMab technique reported by Schaefer et al. (Schaefer, Proc. Natl. Acad. Sci., 2011, 108, 11187-11192) was used to regulate the association between the H and L chains and efficiently obtain the bispecific antibodies. More specifically, these molecules were produced by exchanging the VH and VL domains of Fab against human GPC3 described in WO2012/073985. For promotion of heterologous association, the Knobs-into-Holes technology was used for the constant region of the antibody H chain. The Knobs-into-Holes technology is a technique that enables preparation of heterodimerized antibodies of interest through promotion of the heterodimerization of H chains by substituting an amino acid side chain present in the CH3 region of one of the H chains with a larger side chain (Knob) and substituting an amino acid side chain in the CH3 region of the other H chain with a smaller side chains (Hole) so that the knob will be placed into the hole (Burmeister, Nature, 1994, 372, 379-383). Hereinafter, the constant region into which the Knob modification has been introduced will be indicated as Kn, and the constant region into which the Hole modification has been introduced will be indicated as Hl. Furthermore, the modifications described in WO2011/108714 were used to reduce the Fcγ binding. Specifically, the IgG1 type and the IgG4 type were introduced with modifications of substituting Ala for the amino acids at positions 234, 235, and 297 (EU numbering). The IgG2 type was introduced with modifications of substituting Ala for the amino acids at positions 234, 237, and 297. Gly at position 446 and Lys at position 447 (EU numbering) were removed from the C termini of the antibody H chains. In order to further facilitate purification after antibody expression, a histidine tag was added to the C terminus of the anti-human GPC3 H chain, and a FLAG tag was added to the C terminus of the anti-mouse CD137 H chain. The anti-human GPC3 H chains prepared by introducing the above-mentioned modifications were GC33(2)H-G1dKnHS (SEQ ID NO: 39), GC33(2)H-G2dmKnHS (SEQ ID NO: 40), and GC33(2)H-G4dKnHS (SEQ ID NO: 41). The anti-mouse CD137 H chains prepared were 1D8VH-G1 dHIFS (SEQ ID NO: 42). 1D8VH-G2dmHIFS (SEQ ID NO: 43), and 1D8VH-G4dHIFS (SEQ ID NO: 44). In GC33(2)H-G2dmKnHS and 1D8VH-G2dmHIFS having the IgG2-type constant region, only the CH1 domain and the first half of the hinge region are of the IgG1 type. Specifically, they contain, compared to the CH1 sequence of naturally-occurring human IgG2, Ser at position 131, Lys at position 133, and Gly at positions 137 and 138; and the hinge region contains Ser at position 219 (EU numbering). The antibody L chains GC33(2)L-k0 (SEQ ID NO: 45) and 1D8VL-k0 (SEQ ID NO: 46) were commonly used on the anti-human GPC3 side and the anti-mouse CD137 side, respectively. The antibodies having the combinations shown in Table 3 were expressed to obtain the bispecific antibodies of interest. These antibodies were expressed by transient expression in FreeStyle293 cells (Invitrogen) according to "1-1". The obtained culture supernatant was added to an Anti-FLAG M2 column (Sigma), and the column was washed, followed by elution with 0.1 mg/mL FLAG peptide (Sigma). The antibody-containing fraction was added to a HisTrap HP column (GE Healthcare), and the column was washed, followed by elution using an imidazole concentration gradient. The antibody-containing fraction was concentrated using an ultrafiltration membrane, and then the concentrated solution was added to Superdex 200 column (GE Healthcare). Only the monomeric antibodies in the eluate were collected to obtain the purified antibodies.

TABLE 3

| Antibody name | H-chain gene 1 | L-chain gene 1 | H-chain gene 2 | L-chain gene 2 |
|---|---|---|---|---|
| GPC3 ERY22-1D8 | GC33(2)H-G1dKnHS | GC33(2)L-k0 | 1D8VH-G1dHlFS | 1D8VL-k0 |
| GPG3 ERY22-G2-1D8 | GC33(2)H-G2dmKnHS | GC33(2)L-k0 | 1D8VH-G2dmHlFS | 1D8VL-k0 |
| GPC3 ERY22-G4-1D8 | GC33(2)H-G4dKnHS | GC33(2)L-k0 | 1D8VH-G4dHlFS | 1D8VL-k0 |

2-2. Assessment of the In Vitro GPC3-Dependent CD137 Agonistic Effect of Anti-Human GPC3/Anti-Mouse CD137 Bispecific Antibodies The mouse T cell line CTLL-2 (ATCC Cat. No. TIB-214) was suspended in 10% FBS-containing RPMI1640 medium supplemented with 0.5 µg/ml ionomycin and 10 ng/ml PMA, and the cells were seeded into a 96-well plate at a density of $2 \times 10^4$ cells/100 µl/well. The human GPC3-expressing mouse lung cancer cell line LLC-GPC3 (Reference Example 3) was suspended in the same medium, and this was seeded into the same 96-well plate at a density of $2 \times 10^4$ cells/100 µl/well. Furthermore, suspensions each containing the same number of CTLL-2 or LLC-GPC3 cells were prepared, and then the cells were seeded into a 96-well plate at a density of $4 \times 10^4$ cells/100 µl/well. To the wells, an anti-human GPC3/anti-mouse CD137 bispecific human IgG1 type antibody having extremely reduced FcγR binding (GPC3 ERY22-1D8), or an anti-human GPC3 monospecific human IgG-type antibody (GC33(2)-hG1S comprising GC33(2) H2-G1dS and GC33(2)L2-k0) was added at a concentration of 5 µg/ml, and the cells were cultured under the conditions of 37° C. and 5% CO$_2$ for 24 hours. The culture supernatant was collected, and the mouse IFN-γ concentration in the supernatant was measured by ELISA to assess the CTLL-2 activation. ELISA was performed by following the instructions provided by the kit manufacturer (PeproTech).

Figure 4:
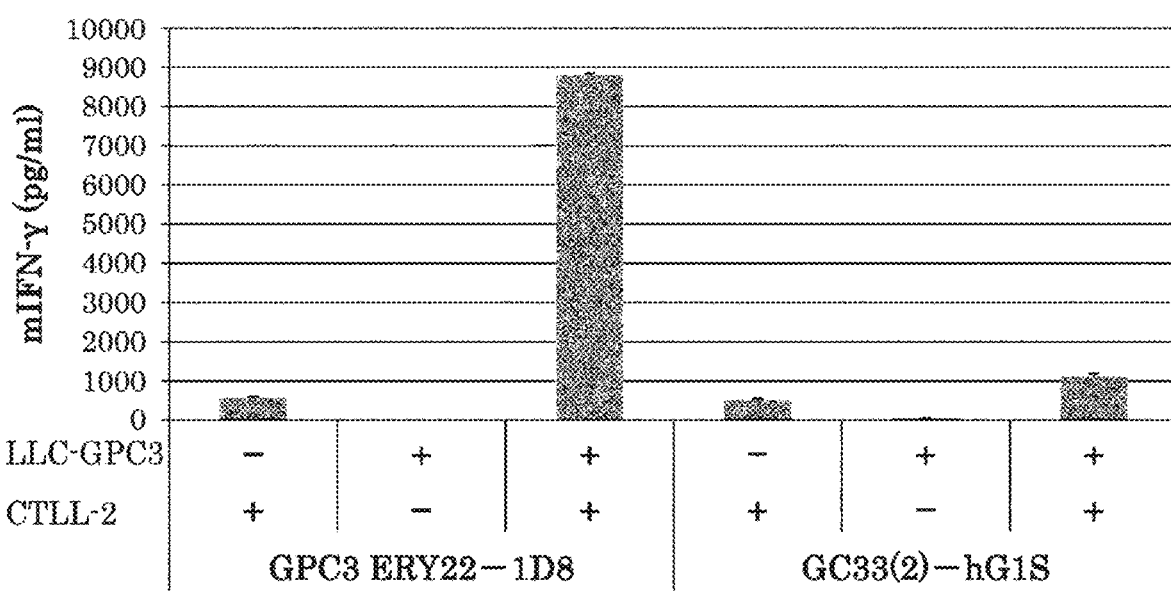
FIG. 4 presents a graph showing the result of assessing the GPC3 antigen-dependent T cell activation effect of an anti-human GPC3/anti-mouse CD137 bispecific antibody using IFN-γ ELISA.

As a result, mouse IFN-γ was found to highly accumulate only under conditions where both LLC-GPC3 and CTLL-2 cells were present (FIG. 4). Based on this result, it was thought that T cell activation occurred in accordance with the association of CD137 on T cells mediated by a plurality of the bispecific antibodies bound to GPC3-expressing cells (FIG. 3).

Figure 5:
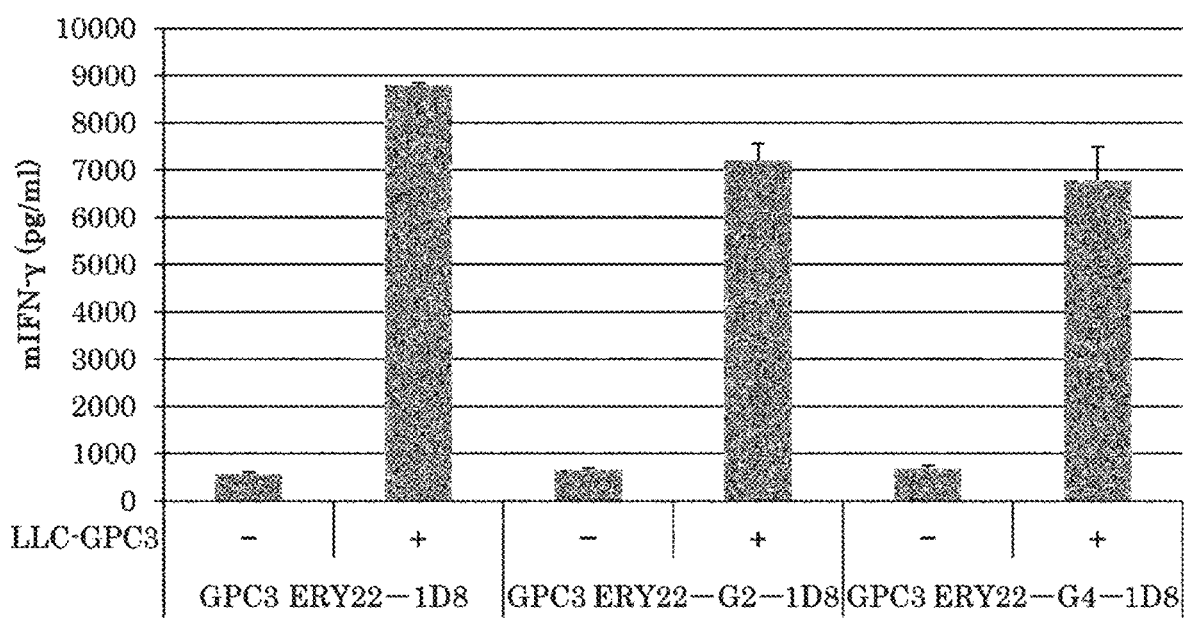
FIG. 5 presents a graph showing the result of assessing the influence of changes in the antibody constant regions of an anti-human GPC3/anti-mouse CD137 bispecific antibody on the GPC3 antigen-dependent T cell activation effect using IFN-γ ELISA.

Furthermore. FIG. 5 shows the activity of bispecific antibodies whose Fc portion has been changed to that of the human IgG2 type (GPC3 ERY22-G2-1D8) or human IgG4 type (GPC3 ERY22-G4-1D8) which has extremely decreased FcγR binding. Changing the antibody subclass did not result in any significant changes in the CD137 agonist activity.

From these results, it was confirmed that bispecific antibodies with reduced FcγR binding against a cancer antigen (GPC3 in the present Examples) and CD137 are able to exhibit an agonist activity upon association of CD137 on T cells only when cancer antigen-expressing cells (cancer cells and such) are present. More specifically, T cells are not activated in normal tissues where the cancer antigen is absent, and thus, side effects may be reduced or avoided.

Example 3

The T Cell Activation-Enhancing Effect by a Mixture of an Anti-Human GPC3/Anti-Mouse CD137 Bispecific Antibody and an Anti-Human GPC3/Anti-Mouse CD3 Bispecific Antibody 3-1. Concept While anti-CD137 agonist antibodies are known to exert an anti-tumor effect by activating T cells, this effect is known to be low when the anti-CD137 agonist antibodies are used as a single agent. Therefore, to enhance the ability of anti-cancer antigen/anti-CD137 bispecific antibodies to activate T cells, and thereby exert a stronger antitumor effect, concomitant use with an agent that similarly activates T cells was examined. Anti-cancer antigen/anti-CD3 bispecific antibodies can redirect T cells to the cancer antigen, and exert a T cell-mediated cytotoxic activity against cancer cells. However, the antitumor effect of the anti-cancer antigen/anti-CD3 bispecific antibodies is also not necessarily high when they are used as single agents. Therefore, concomitant use of an anti-cancer antigen/anti-CD137 bispecific antibody and an anti-cancer antigen/anti-CD3 bispecific antibody was examined to see whether synergistic T cell-activating ability and antitumor effect can be demonstrated.

3-2. Preparation of GPC3 ERY22-3-1 D8 and GPC3 ERY22-3-2C11

An anti-human GPC3/anti-mouse CD137 bispecific antibody, GPC3 ERY22-3-1D8, and an anti-human GPC3/anti-mouse CD3 bispecific antibody, GPC3 ERY22-3-2C11, were prepared. GPC3 ERY22-3-1D8 was produced by adding modifications that are known to those skilled in the art to further simplify purification to the constant region of the GPC3 ERY22-1D8 bispecific antibody prepared in Example 2-1. Specifically, GC33(2)H-G1dKnHSG3 (SEQ ID NO: 48) was prepared by adding the H435R modification for simplifying purification, which is known to those skilled in the art, to the anti-human GPC3 H-chain constant region gene GC33(2)H-G1dKnHS. Along with this, 1D8VH-G1dHIS (SEQ ID NO: 47) was prepared by removing the FLAG tag from the anti-mouse CD137 H-chain constant region gene 1D8VH-G1dHIFS. Furthermore, 2C1 VH-G1dHIS (SEQ ID NO: 50) was prepared by using the sequence of 2C11VH (SEQ ID NO: 49) as the H-chain variable region of the anti-mouse CD3 antibody. Antibody L chains GC33(2)L-k0, 1D8VL-k0, and 2C1 IVL-k0 (SEQ ID NO: 51) were used for the anti-humanGPC3 side, the anti-mouse CD137 side, and the anti-mouse CD3 side, respectively. The antibodies having the combinations shown in Table 4 were expressed to obtain the bispecific antibodies of interest. These antibodies were expressed by transient expression in FreeStyle293 cells according to Reference Example 1. The obtained culture supernatant was added to a MabSelect SuRe column (GE Healthcare), and the column was washed, followed by elution with 50 mM acetic acid. The antibody-containing fraction was added to a HisTrap HP column (GE Healthcare) or a Ni Sepharose FF column (GE Healthcare), and the column was washed, followed by elution with imidazole. The antibody-containing fraction was concentrated using an ultrafiltration membrane. Then, the concentrated solution was added to a Superdex 200 column (GE Healthcare). Only the monomeric antibodies in the eluate were collected to obtain the purified antibodies.

TABLE 4

| Antibody name | H-chain gene 1 | L-chain gene 1 | H-chain gene 2 | L-chain gene 2 |
|---|---|---|---|---|
| GPC3 ERY22-3-1D8 | GC33(2)H-G1dKnHSG3 | GC33(2)L-k0 | 1D8VH-G1dHlS | 1D8VL-k0 |
| GPC3 ERY22-3-2C11 | GC33(2)H-G1dKnHSG3 | GC33(2)L-k0 | 2C11VH-G1dHlS | 2C11VL-k0 |

Furthermore, GC33(2)-G1dS, which has decreased FcγR binding and is also an anti-human GPC3 antibody, was prepared as a comparative control. GC33(2)-G1dS is a naturally-occurring anti-human GPC3 antibody prepared without using the CrossMab technique, and has a constant region with decreased FcγR binding. Specifically, GC33(2) H2-G1dS (SEQ ID NO: 53), which has GC33(2)H2 (SEQ ID NO: 52) as the antibody H-chain variable region and has G1d introduced with L234A, L235A, and N297A as the antibody H-chain constant region, was prepared. GC33(2) L2-k0 (SEQ ID NO: 54) was used as the antibody L chain. Expression and purification were preformed according to the method of Reference Example 1 to obtain GC33(2)H2-G1dS/GC33(2)L2-k0. Hereinafter, for simplicity, the antibody will be denoted as GC33(2)-G1dS.

3-3. Assessment of the In Vitro T Cell Activation-Enhancing Effect by a Mixture of an Anti-Human GPC3/Anti-Mouse CD137 Bispecific Antibody and an Anti-Human GPC3/Anti-Mouse CD3 Bispecific Antibody Spleen was collected from naive female C57BL/6 mice. Cells were suspended in 10% FBS-containing RPMI1640 medium supplemented with 10 ng/ml mouse IL2 at a density of $4 \times 10^6$ cells/ml. Furthermore, the human GPC3-expressing mouse colorectal cancer cell line CT26-GPC3 (Reference Example 3) was suspended in the same medium at a density of $4 \times 10^5$ cells/ml. Equal amounts of each cell suspension were mixed, and the mixture was seeded into a 96-well plate at 100 μl/well. Some of the wells were further added with 0.5 μg/ml ionomycin and 10 ng/ml PMA. To this, an anti-human GPC3/anti-mouse CD137 bispecific antibody with extremely reduced FcγR binding (GPC3 ERY22-1D8) and an anti-human GPC3/anti-mouse CD3 bispecific antibody with extremely reduced FcγR binding (GPC3 ERY22-2C11:GPC3 ERY22-3-2C11 in which the H435R modification has been restored to its original state) were added at a concentration of 3 μg/ml, and the cells were cultured under the conditions of 37° C. and 5% $CO_2$ for 24 hours. The culture supernatant was collected, and the concentration of mouse IFN-γ contained in the supernatant was measured by ELISA to assess the activation of T cells contained in the spleen cells. ELISA was performed by following the instructions provided by the kit manufacturer (PeproTech).

Figure 6:
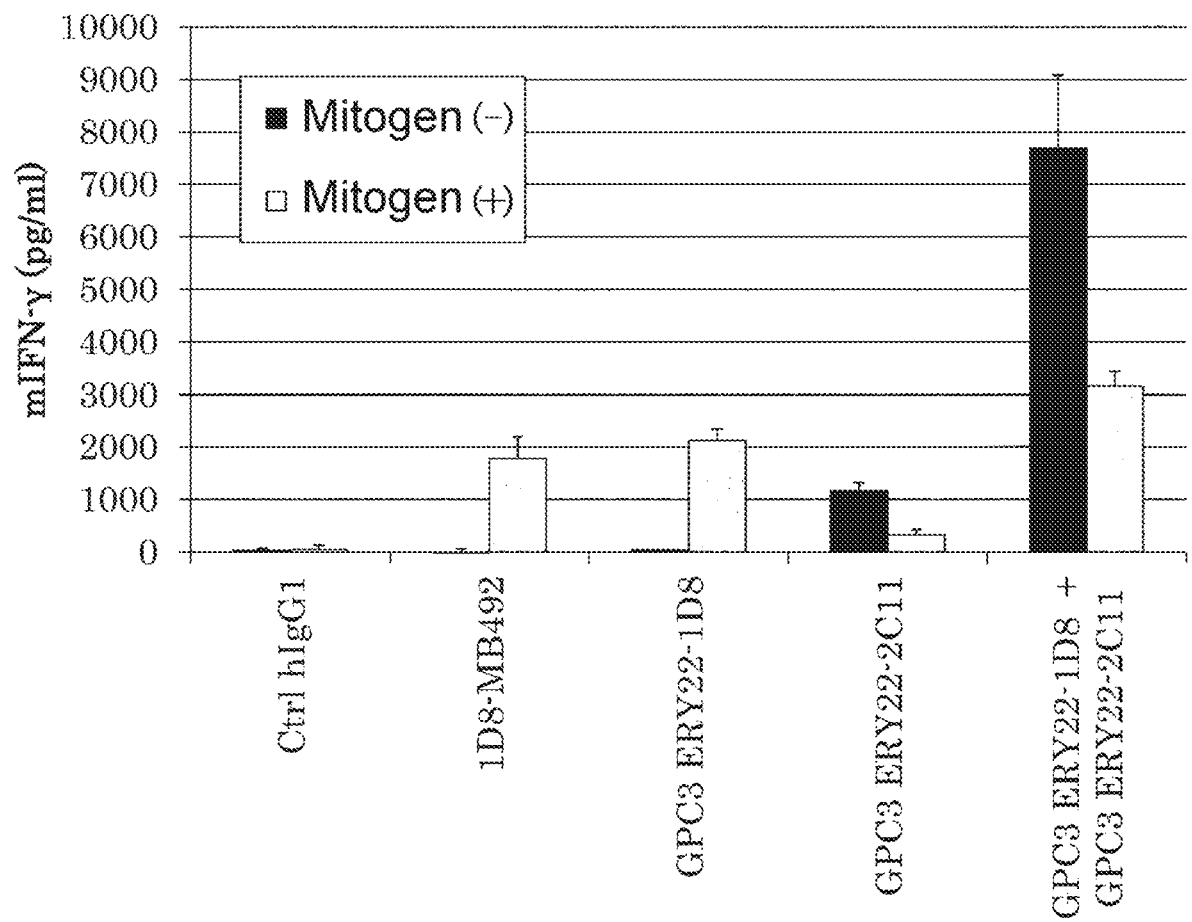
FIG. 6 presents a graph showing the result of assessing the effect of enhancing T cell activation produced by a mixture of an anti-human GPC3/anti-mouse CD137 bispecific antibody and an anti-human GPC3/anti-mouse CD3 bispecific antibody using IFN-γ ELISA. Ctrl hIgG1 indicates the negative control human IgG1 antibody (Alexis Corporation).

As a result (FIG. 6), 1D8-MB492 and GPC3 ERY22-1D8 showed an IFN-γ-inducing activity when added with ionomycin and PMA. This was assumed to be a result of CD137 induction in spleen T cells due to stimulation by mitogen and such. Furthermore, IFN-γ was found to highly accumulate in the mixture containing GPC3 ERY22-1D8 and GPC3 ERY22-2C11. This suggests that simultaneous stimulation of CD3 and CD137 strongly elicits T cell activation.

Example 4

Antitumor Effect of Anti-Human GPC3/Anti-Mouse CD137 Bispecific Antibodies and their Effect in Reducing Liver Toxicity 4-1. Comparison of the Drug Efficacy of Anti-Human GPC3/Anti-Mouse CD137 Bispecific Antibodies and Anti-Mouse CD137 Antibodies The recombinant mouse colorectal cancer cell line CT26-GPC3 which expresses human GPC3 (Reference Example 3) was placed into Hanks' Balanced Salt Solution (HBSS) at $5 \times 10^6$ cells/mL, and 200 μL of this ($1 \times 10^6$ cells) was transplanted subcutaneously into the abdomen of BALB/c mice (female, 7-weeks old, Charles River Laboratories Japan Inc.). The animals were randomly divided into five groups of five individuals each, and then the antibodies were administered by intravenous injection through the tail vein three days, seven days, ten days, and 17 days after transplantation. The anti-human GPC3/mouse CD137 bispecific antibody (GPC3 ERY22-3-1D8) was made into 0.75 mg/mL and 0.15 mg/mL preparations using a solvent (an aqueous solution containing 150 mM NaCl and 20 mM His-HCl (pH 6.0) that has been passed through a 0.22 μm filter), and this was administered at 10 mL/kg (7.5 mg/kg and 1.5 mg/kg, respectively). The anti-mouse CD137 antibody (1D8-MB492) was made into 1.5 mg/mL and 0.3 mg/mL preparations using a solvent, and this was administered at 10 mL/kg (15 mg/kg and 3 mg/kg, respectively). Percentage of tumor growth-inhibition (%) was assessed from the tumor volume calculated using the equation below.

Tumor volume (mm$^3$)=major axis (mm)×minor axis (mm)×minor axis (mm)/2 Percentage of tumor growth inhibition (%)=[1−(T−T0)/(C−C0)]×100

Figure 7:
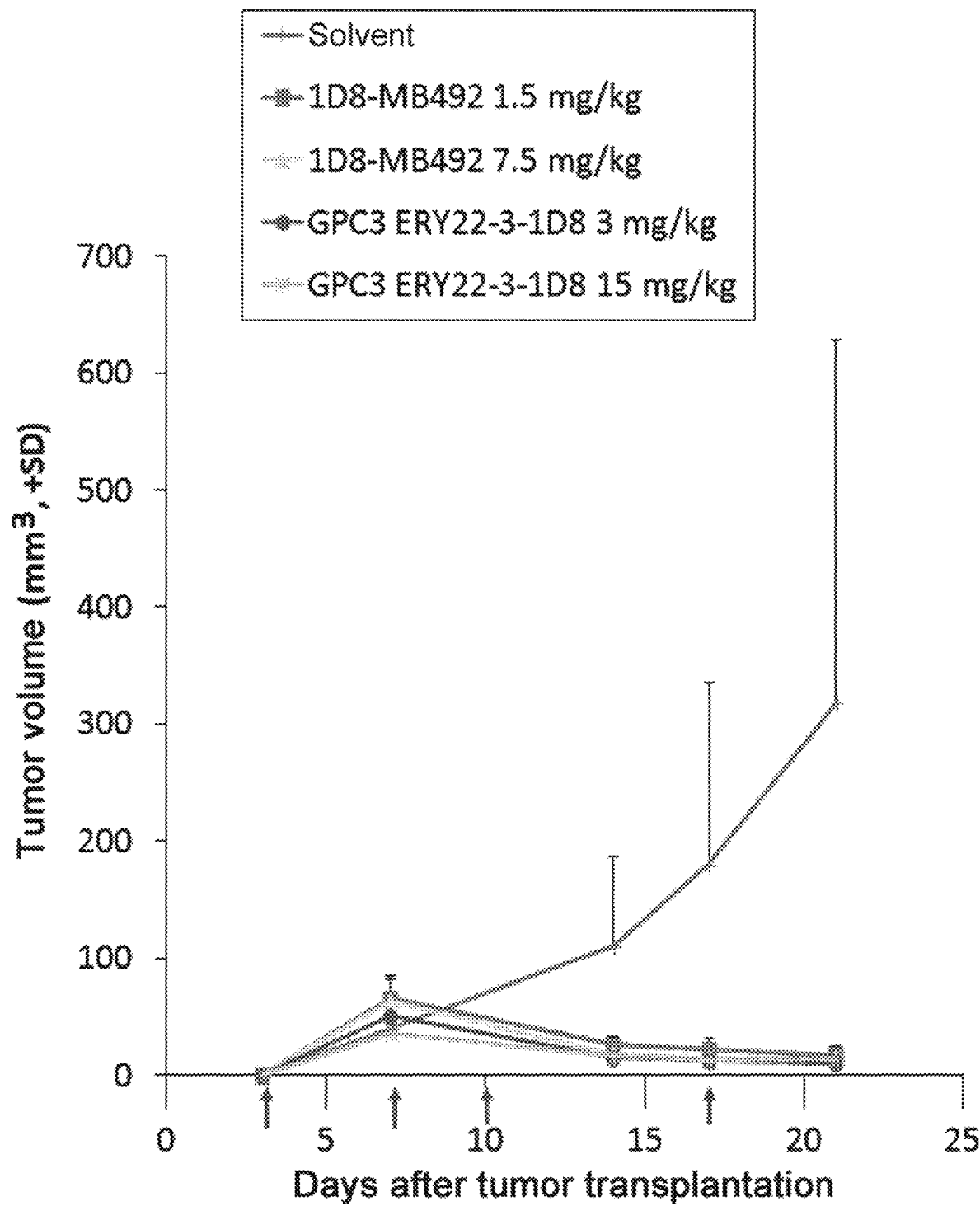
FIG. 7 presents a graph showing the antitumor effect of an anti-human GPC3/mouse CD137 bispecific antibody and an anti-mouse CD137 antibody on a syngeneic CT26 tumor mouse model. The arrows indicate the time when the antibodies were administered.
Figure 8:
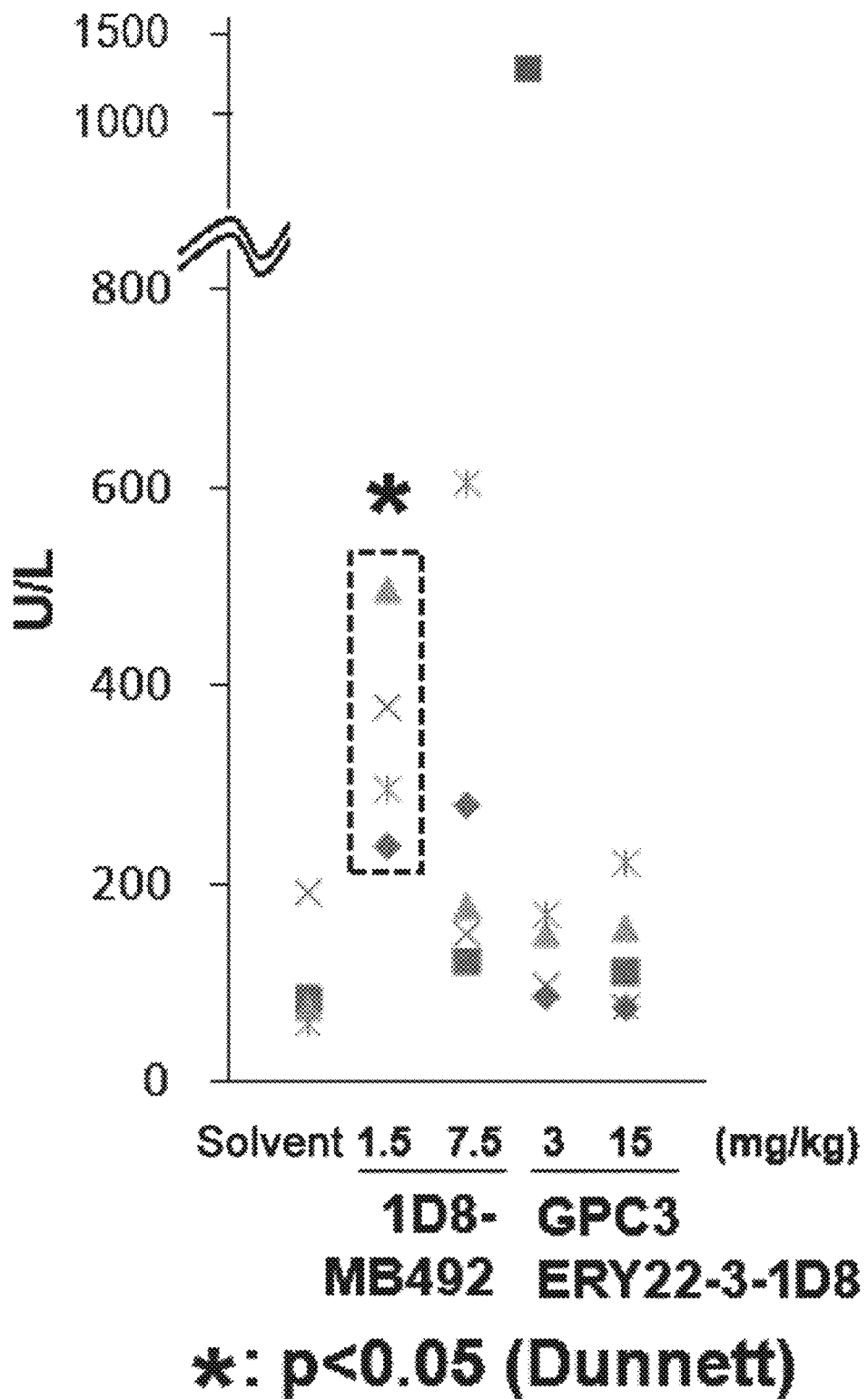
FIG. 8 presents a graph showing the influence of an anti-human GPC3/mouse CD137 bispecific antibody and an anti-mouse CD137 antibody on aspartate aminotransferase (AST) in the blood of a syngeneic CT26 tumor mouse model.
Figure 9:
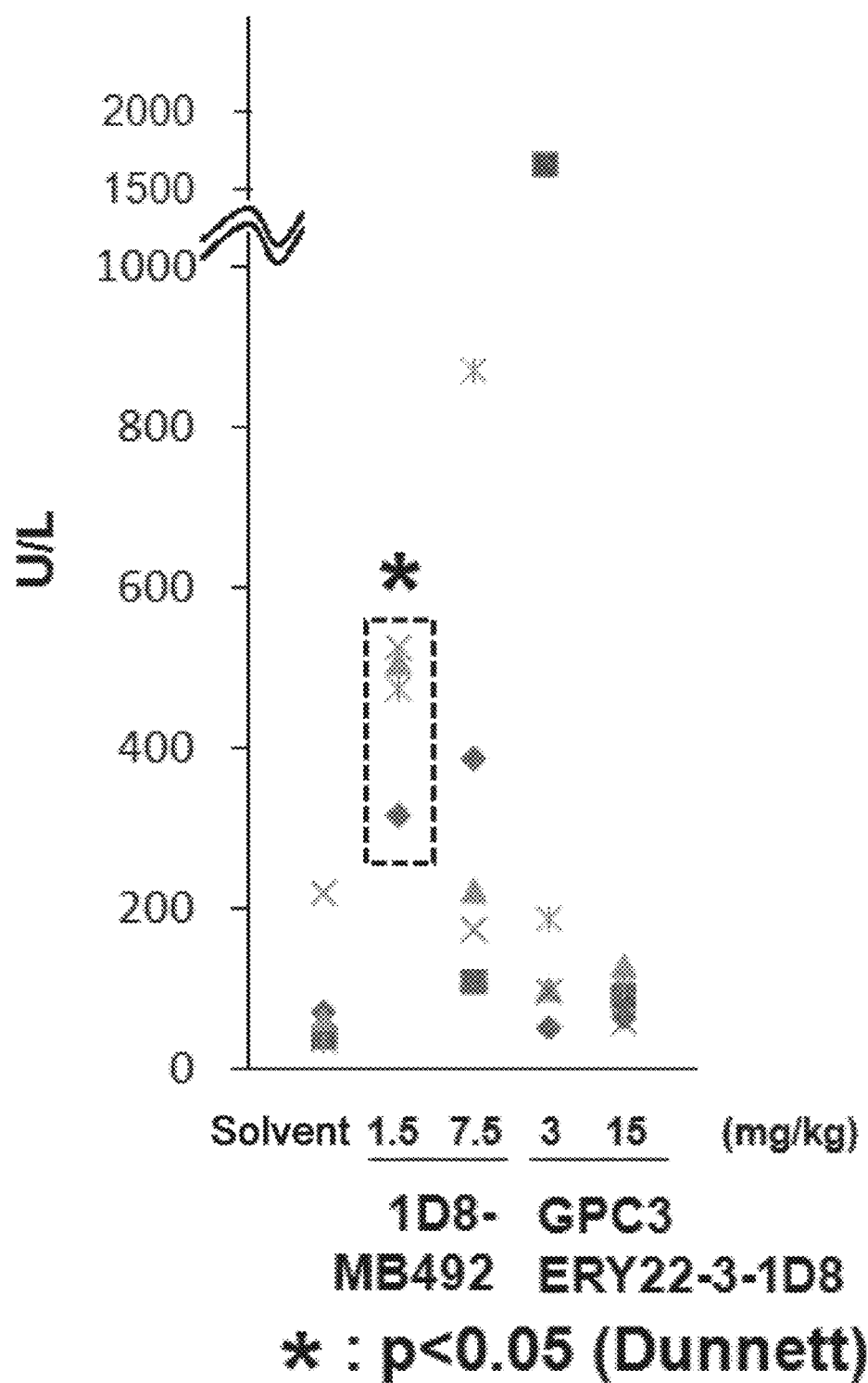
FIG. 9 presents a graph showing the influence of an anti-human GPC3/mouse CD137 bispecific antibody and an anti-mouse CD137 antibody on alanine aminotransferase (ALT) in the blood of a syngeneic CT26 tumor mouse model.
Figure 10:
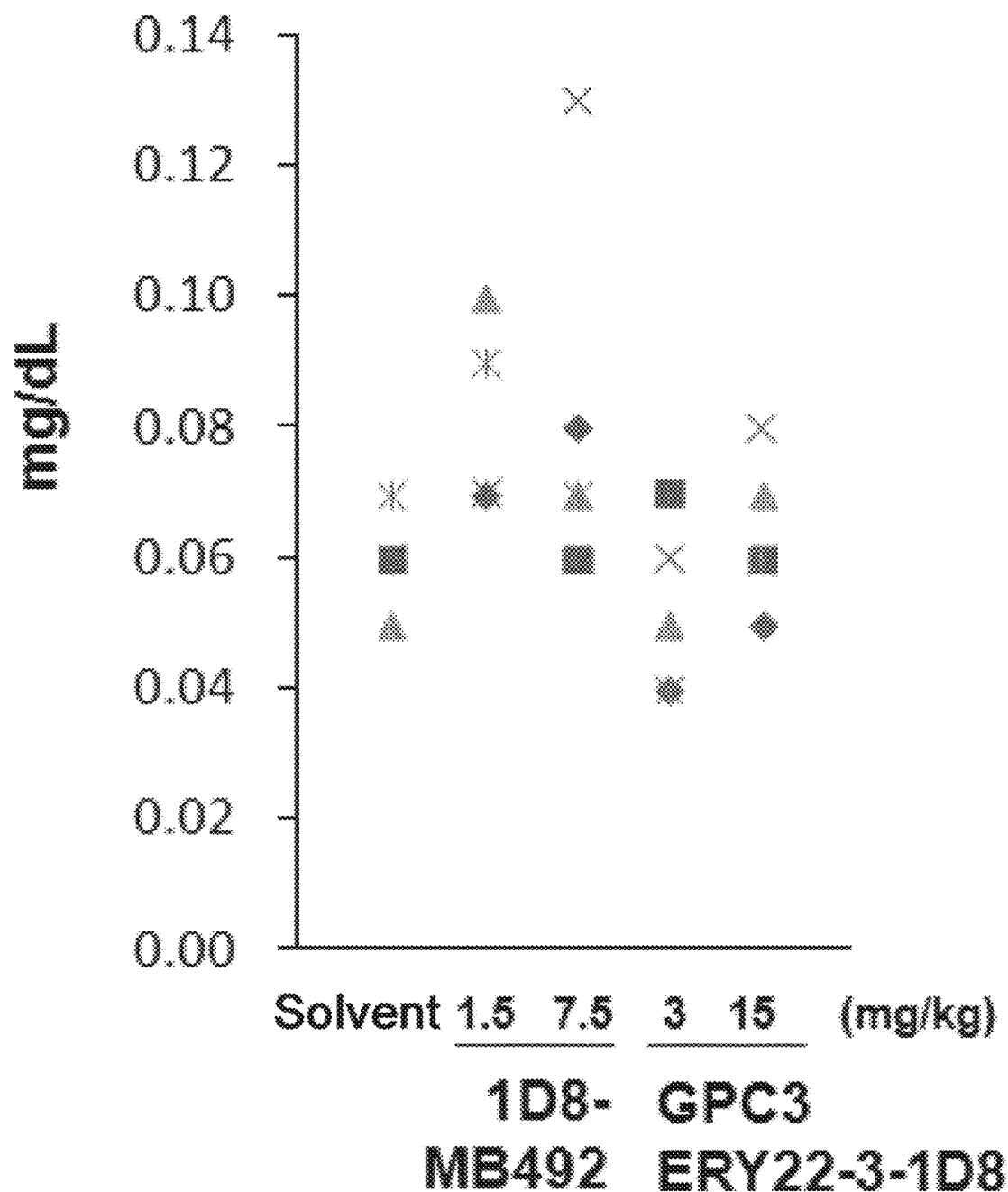
FIG. 10 presents a graph showing the influence of an anti-human GPC3/mouse CD137 bispecific antibody and an anti-mouse CD137 antibody on total bilirubin in the blood of a syngeneic CT26 tumor mouse model.
Figure 11:
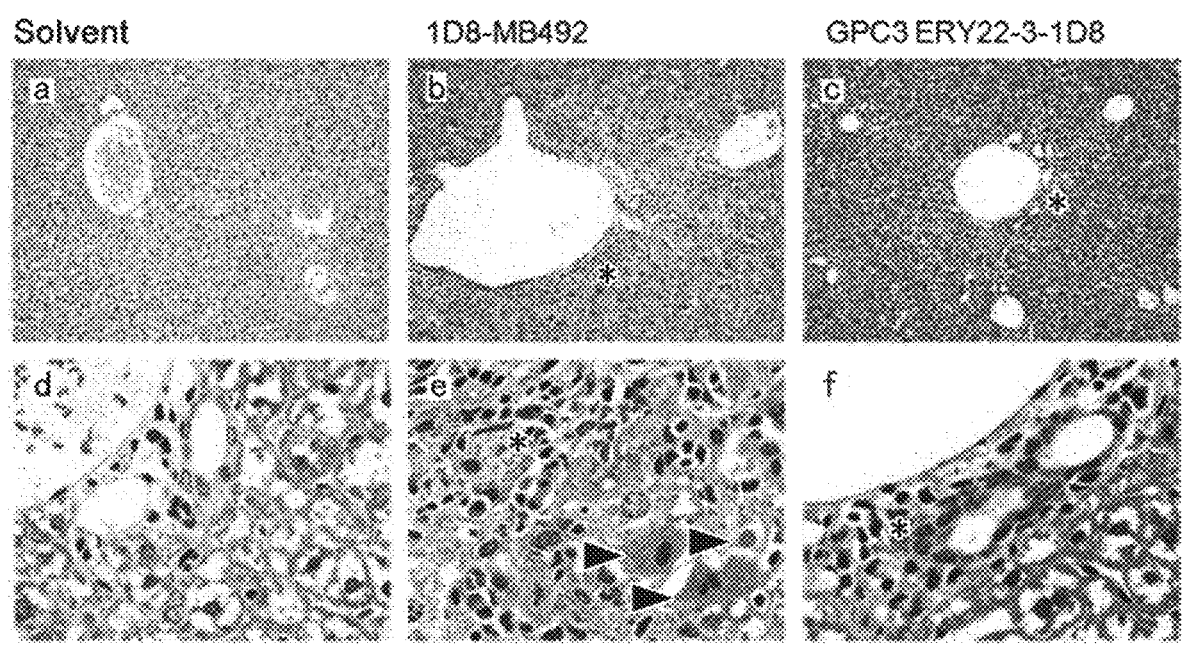
FIG. 11 shows photographs of hepatic histopathological findings in a syngeneic CT26 tumor mouse model by an anti-human GPC3/mouse CD137 bispecific antibody and an anti-mouse CD137 antibody. The photographs are hematoxylin-eosin stained histopathological images of liver sections from a representative mouse, where a and d show the results of administering the solvent, b and e show the results of administering 1D8-MB492, and c and f show the results of administering GPC3 ERY22-3-1D8. The arrow heads indicate the degenerated or necrotic liver cells, and * indicates finding of inflammation.

T: Average tumor volume of each group on each assay date
T0: Average tumor volume of each group on the first day of administration
C: Average tumor volume of the control group on each assay date
C0: Average tumor volume of the control group on the first day of administration As shown in FIG. 7, all groups subjected to antibody administration showed strong antitumor effects with 95% or higher tumor growth inhibition. More specifically, the anti-human GPC3/mouse CD137 bispecific antibodies were shown to have strong antitumor effects similar to those of the anti-mouse CD137 antibodies, and also exhibit strong antitumor effects when CD137 is activated in a cancer antigen-dependent manner.

4-2. Attenuation of Liver Damage by Anti-Human GPC3/Mouse CD137 Bispecific Antibodies in the CT26-GPC3 Subcutaneous Transplant Model At the end of the drug efficacy tests for antibody administration, the animals were euthanized by exsanguination under anesthesia, and plasma was isolated. The plasma was used to measure aspartate amino transferase (AST; JSCC Transferable method), alanine amino transferase (ALT: JSCC Transferable method), and total bilirubin (TBIL; enzyme method) on an automatic analyzer TBA-120FR (Toshiba Medical Systems Corporation). The liver was collected during autopsy, fixed in a 10% neutrally-buffered formalin solution to prepare a tissue preparation of paraffin-embedded thin-tissue sections (hematoxylin-eosin (HE)) by following general methods, and histopathologically observed under a light microscope. Statistical analysis was carried out by performing a non-parametric Dunnett's multiple comparison test with the control group.

As a result, as shown in FIGS. 8 to 11, in the anti-mouse CD137 antibody (1D8-MB492)-administered group, AST, ALT, and TBIL in blood was found to increase or show an increasing trend at all doses; and histopathologically, slight to mild liver damage such as degeneration/necrosis and inflammation of liver cells was found in all examples. On the other hand, in the anti-human GPC3/mouse CD137 bispecific antibody (GPC3 ERY22-3-1D8)-administered group, changes that are thought to be caused by liver damage could not be found with regard to AST, ALT, and TBIL in blood. Histopathologically, slight degeneration/necrosis or inflammation of liver cells was found in two to three cases out of five in each dosage group, and hepatic disorder was decreased. In one case in the group subjected to administration of the same antibody at 3 mg/kg, remarkable increases of AST and ALT in blood were observed while there was no change in blood TBIL. Since findings suggestive of liver damage were not found from histopathological observation of the liver, the source of the enzymes was judged not to attribute to liver damage.

From the above-mentioned results, the anti-human GPC3/anti-mouse CD137 bispecific antibody GPC3 ERY22-3-1D8 was shown to have a strong antitumor effect without inducing severe liver damage such as those reported so far with general anti-CD137 agonist antibodies. More specifically, bispecific antibodies with reduced FcγR binding against a cancer antigen and CD137 were believed to exert a cancer antigen-dependent CD137 agonist activity, and by activating T cells only in tumors without activation of T cells in normal tissues, exert a cytotoxic activity selectively against cancer cells while avoiding side effects such as cytotoxicity and cytokine release.

Example 5

Antitumor Effect by Concomitant Use of an Anti-Human GPC3/Anti-Mouse CD137 Bispecific Antibody and an Anti-Human GPC3/Anti-Mouse CD3 Bispecific Antibody The mouse lung cancer cell line LLC-GPC3 which expresses human GPC3 (Reference Example 3) was suspended in HBSS at $5 \times 10^6$ cells/mL, and 200 μL of this ($1 \times 10^6$ cells) was transplanted subcutaneously to the abdomen of C57BL/6N mice (female, 6-weeks old. Charles River Laboratories Japan Inc.). Ten days after transplantation, based on the data on tumor volume and body weight, the animals were divided into five groups of five individuals each unbiased, and then the antibodies were administered by intravenous injection through the tail vein ten days, 14 days, and 17 days after transplantation. An anti-human GPC3/mouse CD137 bispecific antibody (GPC3 ERY22-3-1D8) was made into a 0.5 mg/mL preparation using a solvent (an aqueous solution containing 150 mM NaCl and 20 mM His-HCl (pH 6.0) that has been passed through a 0.22 μm filter), and this was administered at 10 mL/kg (5 mg/kg). An anti-human GPC3/mouse CD3 bispecific antibody (GPC3 ERY22-3-2C11) was made into a 0.45 mg/mL preparation using the solvent, and this was administered at 10 mL/kg (4.5 mg/kg). Furthermore, a group administered with two types of antibodies concomitantly was prepared. Percentage of tumor growth-inhibition (%) was assessed from the tumor volume calculated using the equation below.

$$\text{Tumor volume (mm}^3\text{)} = \text{major axis (mm)} \times \text{minor axis (mm)} \times \text{minor axis (mm)}/2$$
$$\text{Percentage of tumor growth inhibition (\%)} = [1-(T-T0)/(C-C0)] \times 100$$

T: Average tumor volume of each group on each assay date

T0: Average tumor volume of each group on the first day of administration

C: Average tumor volume of the control group on each assay date

Figure 12:
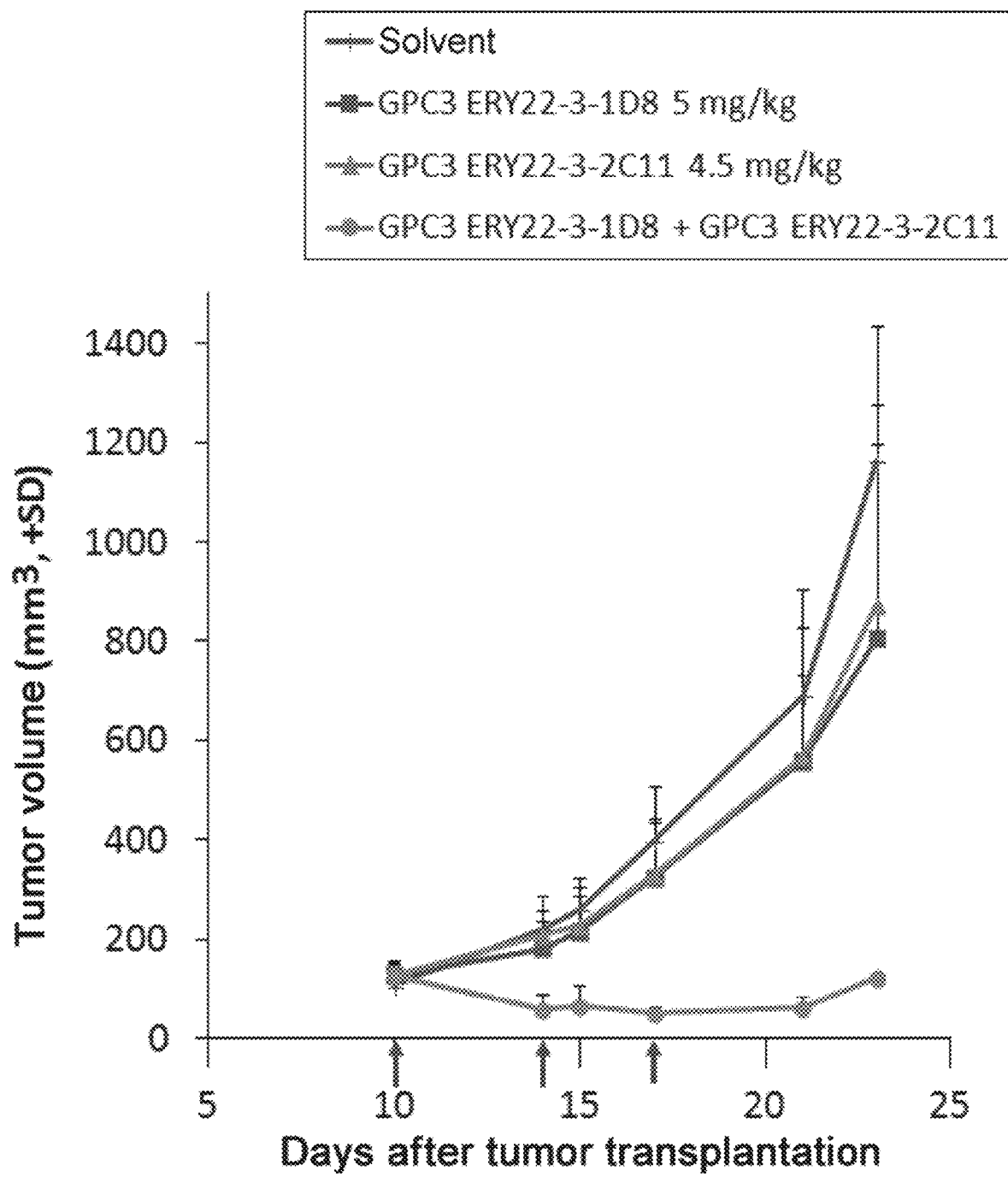
FIG. 12 presents a graph demonstrating the antitumor effect of concomitant use of an anti-human GPC3/mouse CD137 bispecific antibody and an anti-human GPC3/mouse CD3 bispecific antibody on a syngeneic LLC tumor mouse model. The arrows show the time when the antibodies were administered.

C0: Average tumor volume of the control group on the first day of administration As shown in FIG. 12, the percentage of tumor growth inhibition 23 days after tumor transplantation was 36% for the group administered with an anti-human GPC3/mouse CD137 bispecific antibody alone, and 29% for the group administered with an anti-human GPC3/mouse CD3 bispecific antibody alone, but the group administered with these two antibodies concomitantly showed 100% inhibition, and a synergistic effect of the concomitant use was clearly observed.

At the end of the drug efficacy tests, analysis of the liver function parameters (AST, ALT, and TBIL) in plasma and histopathological analysis of liver tissue sections by HE staining were carried out by methods similar to those of "4-2". Changes suggesting liver damage were not observed in any of the administration groups.

Accordingly, it was shown that concomitant use of a bispecific antibody against a cancer antigen and CD137 and a bispecific antibody against a cancer antigen and CD3 results in simultaneous association of CD137 and CD3 specifically and locally at the tumor and exerts a strong T cell-activating ability, which could not be achieved by singular stimulation of each of the antibodies as observed in the in vitro experiments, and thereby achieves a strong antitumor effect that also could not be exerted by their single agents in vivo.

Example 6

Acquisition of Human CD137-Binding Antibodies from a Human Antibody Library Using a Phage Display Technique 6-1. Preparation of a Naive Human Antibody Phage Display Library According to methods known to those skilled in the art, poly A RNA prepared from human PBMC and commercially available human poly A RNA and such were used as a template to construct a human antibody phage display library comprising a plurality of phages displaying the Fab domains of human antibody sequences that are different from each other.

6-2. Acquisition of Human CD137-Binding Antibodies from a Naive Human Antibody Library by Bead Panning Antibodies that show antigen-binding activities were selected by screening from the naive human antibody phage display library constructed in Example 6-1. More specifically, phages presenting antibodies that show a binding activity towards antigens captured by the beads were collected. Biotinylated human CD137 was used as the antigen. Specifically, panning was performed using the antigen fixed onto magnetic beads. NeutrAvidin-coated beads (Sera-Mag SpeedBeads NeutrAvidin-coated) or Streptavidin-coated beads (Dynabeads M-280 Streptavidin) were used as the magnetic beads.

First, phages produced from *Escherichia coli* carrying the constructed phagemids for phage display were purified by a common method. Then, a phage library suspension that has been dialyzed against TBS was obtained. Next, BSA was added to the phage library suspension to make a final concentration of 4%.

Then, 250 pmol of biotinylated human CD137 was added to the prepared phage library suspension to contact the phage library suspension with human CD137 at room temperature for 60 minutes. Next, BSA-blocked magnetic beads were added to the phage library suspension, and the human CD137-phage complexes were allowed to bind to the magnetic beads at room temperature for 15 minutes. The beads were washed once with TBS. Then, 0.5 ml of 1 mg/mL trypsin solution was added to the beads, the beads were suspended at room temperature for 15 minutes, and the beads were immediately separated using a magnetic stand to collect a phage suspension. The collected phage suspension was added to 10 mL of the *E. coli* strain ER2738 in the logarithmic growth phase (OD600=0.4 to 0.7). The *E. coli* was gently stirred and incubated at 37° C. for one hour to allow phages to infect the *E. coli*. The infected *E. coli* was seeded on a plate (225 mm×225 mm). Then, phages were collected from the culture medium of the seeded *E. coli* to prepare a phage library suspension.

In the second round of panning, phages capable of binding to human CD137 were enriched. 100 pmol of the biotinylated human CD137 was added to the obtained phage library suspension and the phage library suspension was contacted with human CD137 at room temperature for 60 minutes. Next, BSA-blocked magnetic beads were added to the phage library suspension, and the human CD137-phage complexes were allowed to bind the magnetic beads at room temperature for 15 minutes. The beads were washed three times with TBST (TBS containing 0.1% Tween20), and twice with TBS. Thereafter. 0.5 mL of 1 mg/mL trypsin solution was added to the beads. The beads were suspended at room temperature for 15 minutes and immediately separated using a magnetic stand to collect a phage suspension. The collected phage suspension was added to 10 mL of the *E. coli* strain ER2738 in the logarithmic growth phase (OD600=0.4 to 0.7). The *E. coli* was gently stirred and incubated at 37° C. for one hour to allow the phages to infect the *E. coli*. The infected *E. coli* was seeded on a plate (225 mm×225 mm). Then, phages were collected from the culture medium of the seeded *E. coli* to prepare a phage library suspension.

Panning for obtaining antibodies capable of binding to human CD137 was repeated three times with the same procedure. A fourth panning was performed using 40 pmol of biotinylated human CD137.

6-3. Construction of a Synthetic Human Antibody Phage Display Library

A synthetic human antibody phage display library was constructed by a method known to those skilled in the art using ten types of heavy-chain germline sequences and seven types of light chain germline sequences. The frequency of appearance in the human B cell repertoire and physicochemical properties in the variable region family were used as indicators to select VH1-2, VH1-69, VH3-23, VH3-66, VH3-72, VH4-59, VH4-61, VH4-b, VH5-51, VH6-1, Vκ1-39, Vκ2-28, Vκ3-20, Vλ1-40, Vλ1-44, Vλ2-14, and Vλ3-21 for use as the germline sequences. The antigen-recognition sites of the synthetic antibody library were diversified by mimicking the human B-cell antibody repertoires.

6-4. Acquisition of Human CD137-Binding Antibodies from a Synthetic Human Antibody Library by Bead Panning Antibodies showing an antigen-binding activity were selected by screening from the synthetic human antibody phage display library constructed in Example 6-3. More specifically, phages presenting antibodies that show binding activity towards antigens captured by the beads were collected. Biotinylated human CD137 was used as the antigen.

Phages produced from *E. coli* carrying the constructed phagemids for phage display were purified by a common method. A phage population was precipitated from the *E. coli* culture medium used for the phage production by adding 2.5 M NaCl/10% PEG. Then, the precipitate was diluted with TBS to prepare a phage library suspension. Next, BSA was added to the phage library suspension to make a final concentration of 4%. Panning was carried out using antigen-immobilized magnetic beads. The magnetic beads used were NeutrAvidin-coated beads (Sera-Mag SpeedBeads NeutrAvidin-coated) or Streptavidin-coated beads (Dynabeads M-280 Streptavidin).

Then, 250 pmol of biotinylated human CD137 was added to the prepared phage library suspension to place the phage library suspension in contact with human CD137 at room temperature for 60 minutes. Next, BSA-blocked magnetic beads were added to the phage library suspension, and the human CD137-phage complexes were allowed to bind to the magnetic beads at room temperature for 15 minutes. The beads were washed once with TBS. Then. 0.5 mL of 1 mg/mL trypsin solution was added to the beads, and the beads were suspended at room temperature for 15 minutes and immediately separated using a magnetic stand to collect a phage suspension. The collected phage suspension was added to 10 mL of the *E. coli* stain ER2738 in the logarithmic growth phase (OD600=0.4 to 0.7). The *E. coli* was stirred and incubated at 37° C. for one hour to allow the phages to infect the *E. coli*. The infected *E. coli* was seeded on a plate (225 mm×225 mm). Then, phages were collected from the culture medium of the seeded *E. coli* to prepare a phage library suspension.

In the second round of panning, phages capable of binding to human CD137 were enriched. 100 pmol of biotinylated human CD137 was added to the obtained phage library suspension, and the phage library suspension was contacted with human CD137 at room temperature for 60 minutes. Next, BSA-blocked magnetic beads were added to the phage library suspension, and the human CD137-phage complexes were allowed to bind to the magnetic beads for 15 minutes at room temperature. The beads were washed three times with TBST, and twice with TBS. Then, 0.5 mL of 1 mg/mL trypsin solution was added to the beads, and the beads were suspended at room temperature for 15 minutes and immediately separated using a magnetic stand to collect a phage suspension. The collected phage suspension was added to 10 mL of the *E. coli* strain ER2738 in the logarithmic growth phase (OD600=0.4 to 0.7). The *E. coli* was gently stirred and incubated at 37° C. for one hour to allow the phages to infect the *E. coli*. The infected *E. coli* was seeded on a plate (225 mm×225 mm). Then, phages were collected from the culture medium of the seeded *E. coli* to prepare a phage library suspension.

Panning for obtaining antibodies capable of binding to human CD137 was repeated three times with the same procedure. A fourth panning was performed using 40 pmol of biotinylated human CD137.

6-5. Assessment of the Human CD137-Binding Property by Phage ELISA

From single colonies of *E. coli* obtained by the panning method described in the Examples above, phage-containing culture supernatants were collected by following a conventional method (Methods Mol. Biol. 2002, 178: 133-145).

TBS-supplemented phages were subjected to ELISA by the procedure below. StreptaWell 96 microtiter plates (Roche) were coated using 100 μL of TBS containing the biotin-labeled antigen (biotinylated human CD137) at room temperature for one hour. After each well of the plate was washed with TBST (TBS containing 0.1% Tween20) to remove the antigen that did not bind to the plate, the wells were blocked with 250 μL of 2% SkimMilk-TBS for one hour or more. 2% SkimMilk-TBS was removed, and then the prepared phages were added to each well. The plates were allowed to stand at room temperature for one hour to achieve the binding of antibody-displaying phages to the antigen in each of the wells. After each well was washed with TBST, an HRP-conjugated anti-M13 antibody (Amersham Pharmacia Biotech) diluted with TBS was added to the wells and the plates were incubated for one hour. After TBST washes, the TMB single solution (ZYMED) was added to each well. The chromogenic reaction in the solution of each well was stopped by adding sulfuric acid. Then, the developed color was assessed by measuring the absorbance at 450 nm.

From among the 192 clones subjected to phage ELISA, a plurality of antibodies that have human CD137-binding activity were identified. The results of phage ELISA are shown in Table 5.

TABLE 5

| Library | Naive library | Synthetic library |
| --- | --- | --- |
| Number of panning rounds | 4 | 4 |
| Number of clones subjected to ELISA | 96 | 96 |
| Number of positive clones (absorbance > 0.2, absorbance ratio with/without antigen > 2) | 59 | 78 |
| Number of positive clone sequences | 12 | 17 |

6-6. Sequence Analysis of Antibodies that Bind to Biotinylated Human CD137

From clones assessed to have a specific binding activity towards human CD137 as a result of the phage ELISA described in Example 6-5, the nucleotide sequences of genes amplified using specific primer pairs (SEQ ID NOs: 55 and 56 for the naive human antibody libraries, and SEQ ID NOs: 57 and 56 for the synthetic human antibody libraries) were analyzed. The result of the analysis confirmed the presence of multiple types of antibody sequences having human CD137-binding activity.

6-7. Preparation of Human CD137-Binding Antibodies

From the clones obtained in Example 6-6, which have been assessed to have binding activity towards biotin-labeled human CD137, the heavy-chain and light-chain variable region sequences of five clones derived from the naive human antibody library (R1 to R5) and 14 clones derived from the synthetic human antibody library (R6 to R19) were linked with the heavy-chain antibody constant region (SEQ ID NO: 58 which is a sequence produced by modifying the human IgG1 constant region), or the light chain kappa constant region sequence (SEQ ID NO: 59) or lambda constant region sequence (SEQ ID NO: 60), and then each were inserted into plasmids for animal expression. The heavy-chain and light-chain variable region sequences of each of the clones are shown in Table 6.

TABLE 6

| Clone name | SEQ ID NO of the heavy-chain variable region | SEQ ID NO of the light-chain variable region |
| --- | --- | --- |
| R1 | 61 | 80 |
| R2 | 62 | 81 |
| R3 | 63 | 82 |
| R4 | 64 | 83 |
| R5 | 65 | 84 |
| R6 | 66 | 85 |
| R7 | 67 | 86 |
| R8 | 68 | 87 |
| R9 | 69 | 88 |
| R10 | 70 | 89 |
| R11 | 71 | 90 |
| R12 | 72 | 91 |
| R13 | 73 | 92 |
| R14 | 74 | 93 |
| R15 | 75 | 94 |
| R16 | 76 | 95 |
| R17 | 77 | 96 |
| R18 | 78 | 97 |
| R19 | 79 | 98 |

Each of the antibodies was expressed and purified by the method described in Reference Example 1. Furthermore, with the objective of enhancing the in vitro T cell-activating effect of anti-human CD137 antibodies, genes in which a VH region shown in Table 6 is linked with the constant region (SEQ ID NO: 99) that has enhanced binding to human FcγRIIB were produced, the genes were inserted into a plasmid vector for expression in animal cells, and antibodies were expressed and purified by a similar method so as to make their combination of variable regions as the combinations shown in Table 6.

Example 7

Epitope Analysis of Anti-Human CD137 Antibodies 7-1. Preparation of Fragmented Human CD137-Fc Fusion Proteins and Antibody Preparation For analyzing the epitope of the obtained anti-human CD137 antibodies, fusion proteins comprising a fragmented human CD137 and an antibody Fc region were prepared, where the fragmented human CD137 were divided into domains based on a structure common to the TNFRSF and structures formed by Cys-Cys called CRD by referring to J Exp Med. 2014 Jun. 30; 211(7): 1433-48 (Table 7). The fragmented human CD137-Fc fusion protein was inserted into a plasmid vector for expression in animal cells by a method known to those skilled in the art by obtaining each gene fragment by PCR from the polynucleotide encoding the full-length human CD137-Fc fusion protein (SEQ ID NO: 100) so as to contain an amino acid sequence shown in Table 7. The fragmented human CD137-Fc fusion protein was purified in the same manner as antibodies, by the method described in Reference Example 1. Furthermore, as a control for ELISA, antibodies were obtained by the method described in Reference Example 1 by incorporating into a plasmid vector for expression in animal cells, genes encoding an antibody (SEQ ID NO: 101 for the H chain, and SEQ ID NO: 102 for the L chain) produced by changing the H chain constant region of the anti-human CD137 antibody described in WO2005/035584A1 (abbreviated as B) into a constant region removed of C-terminal Gly and Lys in the human IgG1 H-chain constant region, and encoding an antibody (SEQ ID NO: 103 for the H chain, and SEQ ID NO: 104 for the L chain) produced by changing the constant region of the anti-human CD137 antibody described in WO2012/145183A3 (abbreviated as M) into a constant region with enhanced binding to human FcγRIIB.

buffer (TBS containing 0.1% Tween20, TaKaRa). Next, 150 µL of blocking buffer (TBS containing 2% BSA) was added to each well, and this was allowed to stand for one hour or more. The blocking buffer was removed by tilting, and each well was washed three times with Wash Buffer in a similar manner to an earlier step. Then, 50 µL of an antibody solution prepared in advance by dilution with TBS to 10 µg/mL or 5 µg/mL was added to each well. This was subjected to a speed of 600 rpm or so for one hour at room temperature to bind the antibody to the immobilized antigen. After removing the antibody solution by tilting, each well

TABLE 7

| Name of the fragmented human CD137 | Amino acid sequence of the fragmented human CD137 | Domains that are included | SEQ ID NO |
|---|---|---|---|
| Full length | LQDPCSNCPAGTFCDNNRNQICSPCPPNSFSSAGGQRTCDICRQCKGVFRTRKECSST SNAECDCTPGFHCLGAGCSMCEQDCKQQQELTKKGCKDCCFGTGNDQKRGICRPWTNC SLDGKSVLVNGTKERDVVCGPSPADLSPGASSVTPPAPAREPGHSPQ | CRD1, 2, 3, 4 | 105 |
| CRD1 | LQDPCSNCPAGTFCDNNRNQICSPCPPNSFSSAGGQRTC | CRD1 | 106 |
| CRD2 | SPCPPNSFSSAGGQRTCDICRQCKGVFRTRKECSSTSNAEC | CRD2 | 107 |
| CRD3 | DCTPGFHCLGAGCSMCEQDCKQGQELTKKGC | CRD3 | 108 |
| CRD4 | KDCCFGTFNDQKRGICRPWTNCSLDGKSVLVNGTKERDVVCGPSPADLSPGASSVTPP APAREPGHSPQ | CRD4 | 109 |
| CRD1-3 | LQDPCSNCPAGTFCDNNRNQICSPCPPNSFSSAGGQRTCDICRQCKGVFRTRKECSST SNAECDCTPGFHCLGAGCSMCEQDCKQGQELTKKGC | CRD1, 2, 3 | 110 |
| CRD1-2 | LQDPCSNCPAGTFCDNNRNQICSPCPPNSFSSAGGQRTCDICRQCKGVFRTRKECSST SNAEC | CRD1, 2 | 111 |
| CRD2-4 | SPCPPNSFSSAGGQRTCDICRQCKGVFRTRKECSSTSNAECDCTPGFHCLGAGCSMCE QDCKQGQELTKKGCKDCCFGTFNDQKRGICRPWTNCSLDGKSVLVNGTKERDVVCGPS PADLSPGASSVTPPAPAREPGHSPQ | CRD2, 3, 4 | 112 |
| CRD2-3 | SPCPPNSFSSAGGQRTCDICRQCKGVFRTRKECSSTSNAECDCTPGFHCLGAGCSMCE QDCKQGQELTKKGC | CRD2, 3 | 113 |
| CRD3-4 | DCTPGFHCLGAGCSMCEQDCKQGQELTKKGCKDCCFGTFNDQKRGICRPWTNCSLDGK SVLVNGTKERDVVCGPSPADLSPGASSVTPPAPAREPGHSPQ | CRD3, 4 | 114 |

7-2-1. Epitope Analysis Using the Fragmented Human CD137-Fc Fusion Proteins

The fragmented human CD137-Fc fusion proteins prepared in Example 7-1 were used to evaluate binding by ELISA to determine which of the sites on human CD137 are bound by the antibodies (which use SEQ ID NO: 99 as the heavy chain constant region) obtained in Example 6 described above. For example, in the case of an antibody that binds to domain 1, such an antibody is predicted to bind to domain 1-containing fragmented human CD137-Fc fusion proteins, but not to fragmented human CD137-Fc fusion proteins that do not contain domain 1.

7-2-2. ELISA Method

Fragmented human CD137-Fc fusion proteins were diluted to 2 µg/mL in an aqueous sodium carbonate solution adjusted to pH9.6. Fifty µL of a diluted fragmented human CD137-Fc fusion protein was added individually to each well of a Nunc MaxiSorp flat-bottom 96 well plate (Nunc). This was allowed to stand at 4° C. overnight or longer, and then the plate was allowed to stand at room temperature for one hour so that the plate has the same temperature as the room temperature. The solution containing the fragmented human CD137-Fc fusion protein was removed by tilting, and each well was washed three times with 300 µL of Wash was washed three times with Wash Buffer in a similar manner to an earlier step. 100 µL of a secondary antibody solution produced by 1000-fold dilution with TBS containing 0.1% Tween20 was added to each well. For the secondary antibody, ANTIBODY ALKALINE PHOSPHATASE CONJUGATE HUMAN IMMUNOGLOBULIN ABSORBED Goat Anti-Human Kappa Alkaline Phosphate from BIOSOURCE was used in the case of antibodies carrying a Kappa chain, and Human Lambda Light Chain Antibody; Goat anti-Human Lambda Light Chain Antibody Alkaline Phosphatase Conjugated from BETHYL LABORATORIES INC. was used in the case of antibodies carrying a Lambda chain. After one hour of reaction by incubation at room temperature, the antibody solution was removed by tilting, and each well was washed three times with Wash Buffer in a similar manner to an earlier step. Color development was performed using the BluePhos Microwell kit from KPL. After the chromogenic reaction was stopped using the AP stop solution from KPL, the absorbance was measured at 620 nm on an absorptiometer. The results are shown in FIG. 14. As shown in FIG. 14, each antibody showed a different value of color development towards its respective fragmented human CD137-Fc fusion protein, and binds to a different portion of human CD137-Fc. Furthermore, the obtained antibodies were shown to be different from the existing antibodies B and M.

Example 8

Assessment of Anti-Human CD137 Antibodies for their In Vitro T Cell-Activating Effect T cells were expansively cultured from commercially available PBMC (AllCells) using Dynabeads Human T-Activator CD3/CD28 (Gibco, 11132D). Human T cells were suspended at a density of $4 \times 10^5$ cells/ml in RPMI1640 medium containing 10% FBS, 60 U/ml human IL2, 0.5 μg/ml ionomycin, 10 ng/ml PMA, and a specific concentration of penicillin and streptomycin. Furthermore, the human B cell lymphoma cell line Raji was suspended in the same medium at a density of $4 \times 10^5$ cells/ml. These cell suspensions were mixed in equal quantities, and they were seeded onto a 96-well plate at 100 μl/well. The human CD137-binding antibodies obtained in Example 6 (R1 to R19; antibodies used were the same as in ELISA described in Example 7) were added at a concentration of 5 μg/ml, and the cells were cultured under the conditions of 37° C. and 5% $CO_2$ for three days. The culture supernatant was collected, and the concentration of human IFN-γ in the supernatant was measured by ELISA to assess the activation of human T cells. ELISA was performed by following the instructions provided by the ELISA kit manufacturer (PeproTech).

Figure 15:
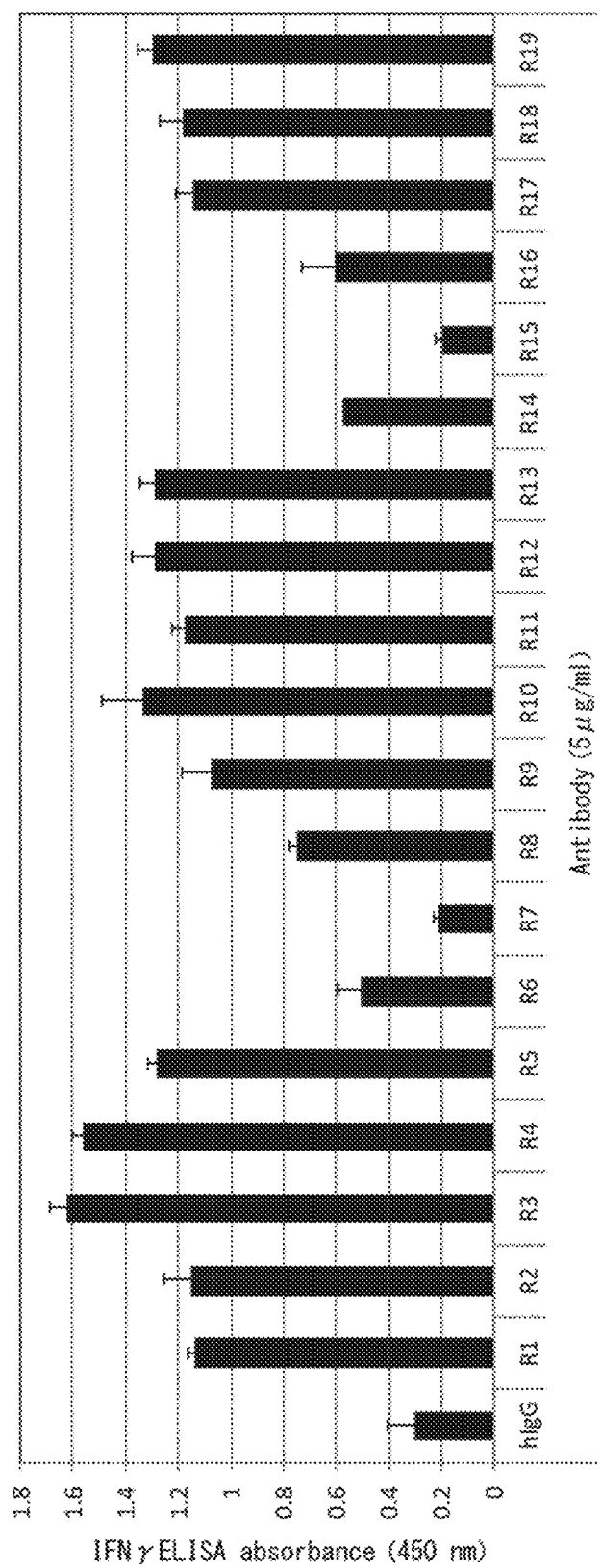
FIG. 15 presents a graph showing the IFNγ-inducing activity of anti-human CD137 antibodies.

As a result (FIG. 15), compared to the control human IgG (Allexis, 804-133-C100: hIgG in FIG. 15), clones other than R7 and R15 all showed an IFN-γ-inducing activity. These antibodies having an IFN-γ-inducing activity were assessed to be agonist antibodies against CD137.

The characteristics of the obtained antibodies are summarized in FIG. 16. Many antibodies that recognize epitopes different from those of the anti-human CD137 antibodies B and M shown in the above-described Examples were obtained. These anti-human CD137 antibodies were modified into bispecific antibodies with a GC33 antibody (anti-human GPC3 antibody), and assessed for their cancer antigen (GPC3)-dependent CD137 agonist ability. This can provide anti-human GPC3/anti-human CD137 bispecific antibodies that exert the desired antitumor effects.

Example 9

Preparation of an Anti-Human GPC3/Anti-Mouse CD40 Bispecific Antibody (GPC3 FAE-FGK45)

The anti-human GPC3/anti-mouse CD40 bispecific antibody GPC3 FAE-FGK45 carrying the human IgG1 constant regions was produced by the procedure below. For the anti-mouse CD40 side, FGK45VH6 (SEQ ID NO: 120) was used for the heavy-chain variable region, and FGK45VL4 (SEQ ID NO: 121) was used for the light-chain variable region. In this case, F760nG3P17 (SEQ ID NO: 119) and k0 (SEQ ID NO: 118) were used for the heavy-chain and light-chain constant regions, respectively. The anti-human GPC3 side of the antibodies shared the heavy-chain variable region H0000 (SEQ ID NO: 115) and light-chain variable region GL4 (SEQ ID NO: 116) in common. In this case, the heavy chain constant region F760nN17 (SEQ ID NO: 117) which has been modified so that there is heterologous association between the two heavy chains and Fcγ receptor-binding is reduced, and the light chain constant region k0 (SEQ ID NO: 118) were used for the constant regions. These antibodies were expressed using the following method. Cells of the human embryonic kidney cell-derived FreeStyle 293-F strain (Invitrogen) were suspended in the FreeStyle 293 Expression Medium (Invitrogen), and seeded at a cell density of $1.33 \times 10^6$ cells/mL. The prepared plasmids were introduced into the cells by a lipofection method. The cells were cultured for four days in a $CO_2$ incubator (37° C., 8% $CO_2$, 90 rpm) and from the culture supernatants, antibodies were purified using the rProtein A Sepharose™ Fast Flow (Amersham Biosciences) or Protein G Sepharose 4 Fast Flow (GE HEALTHCARE) by a method known to those skilled in the art. Absorbance at 280 nm of the purified antibody solutions was measured using a spectrophotometer. Concentrations of the purified antibodies were calculated from the determined values using an extinction coefficient calculated by the PACE method (Protein Science (1995) 4: 2411-2423). Each of the purified homologous forms were mixed using the combinations shown in Table 8 to prepare the bispecific antibodies of interest using techniques known to those skilled in the art (WO2015/046467).

TABLE 8

| No | Clone name | Antibody 1 | Antibody 2 |
|---|---|---|---|
| 1 | GPC3 FAE–FGK45 | H0000/<br>GL4-F760nN17 | FGK45VH6/<br>FGK45VL4-F760nG3P17 |

Example 10

Assessment of the In Vitro Splenocyte Activation-Enhancing Effect by a Mixture of an Anti-Human GPC3/Anti-Mouse CD40 Bispecific Antibody and an Anti-Human GPC3/Anti-Mouse CD3 Bispecific Antibody Spleen was removed from naive female Balb/c mice, and its cells were suspended at a density of $4 \times 10^6$ cells/ml in a medium prepared by adding mouse IL2 at 10 ng/ml to a RPMI1640 medium containing 10% FBS, 0.5 μg/ml ionomycin, and 10 ng/ml PMA. The mouse colorectal cancer cell line CT26-GPC3 that expresses human GPC3 (Reference Example 3) was also suspended in the same medium at a density of $4 \times 10^5$ cells/ml. These two cell suspensions were mixed in equal quantities, and this was seeded into a 96-well plate at 100 μl/well. An anti-human GPC3/anti-mouse CD40 bispecific antibody with extremely reduced FcγR binding (GPC3 ERY22-FGK45) was added at a concentration of 3 μg/ml, and an anti-human GPC3/anti-mouse CD3 bispecific antibody with extremely reduced FcγR binding (GPC3 ERY22-2C11) was added at 1 μg/ml, and the cells were cultured under conditions of 37° C. and 5% $CO_2$ for 72 hours. The culture supernatant was collected, and the mouse IFN-γ concentration in the supernatant was measured by ELISA to assess the activation of T cells contained in the splenocytes. ELISA was performed by following the instructions provided by the ELISA kit manufacturer (PeproTech).

Figure 17:
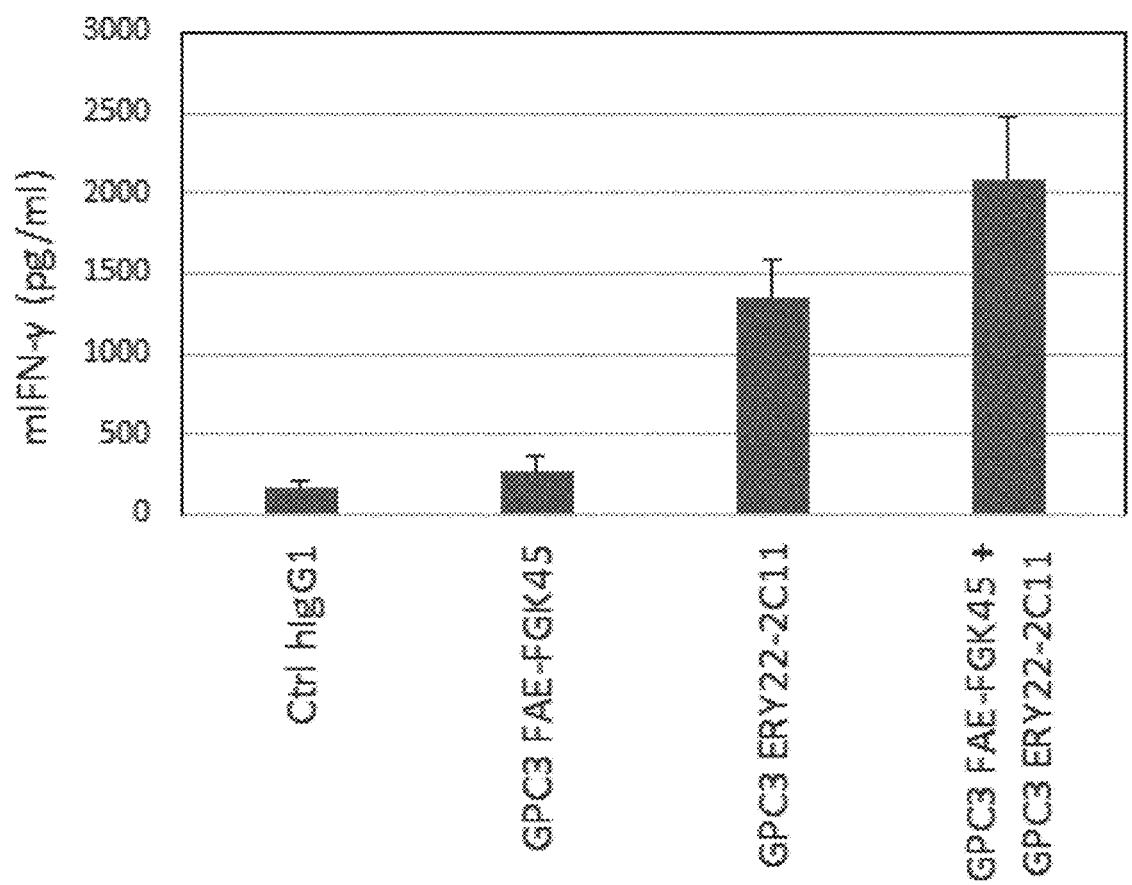
FIG. 17 presents a graph showing the results of assessing the effect of enhancing T cell activation produced by a mixture of an anti-human GPC3/anti-mouse CD40 bispecific antibody and an anti-human GPC3/anti-mouse CD3 bispecific antibody using IFN-γ ELISA. Ctrl hIgG1 indicates the negative control human IgG1 antibody.

As a result (FIG. 17), while GPC3 ERY22-2C11 shows IFN-γ-inducing activity as a single agent, GPC3 ERY22-FGK45 as a single agent hardly showed any activity. However, a mixture of GPC3 ERY22-FGK45 and GPC3 ERY22-2C11 showed high accumulation of IFN-γ. This suggests that applying CD3 stimulation and CD40 stimulation simultaneously to various immune cell mixtures results in strong activation of T cells.

Example 11

Preparation of Anti-Human GPC3/Anti-Human CD137 Bispecific Antibodies and Assessment of their Agonist Activities 11-1. Preparation of Anti-Human GPC3/Anti-Human CD137 Bispecific Antibodies The anti-human GPC3/anti-human CD137 bispecific antibodies carrying human IgG1 constant regions were produced by the following procedure. The sequences (R3 and R5) confirmed to bind to human CD137 in Example 7, were modified using primers designed to cause random changes in the amino acids of the heavy-chain CDR3. The variable region sequences are shown in Table 9. In this case, when modified from R3 and R5, a sequence produced by adding Gly-Lys (also written as "GK") to the C terminus of the F760nG3P17 sequence constructed in Example 9 and the lambda constant region sequence (SEQ ID NO: 60) were used for the heavy-chain constant region and light-chain constant region, respectively. The anti-human GPC3 side of the antibodies shared the heavy-chain variable region H0000 (SEQ ID NO: 115) and light-chain variable region GL4 (SEQ ID NO: 116) in common. In this case, the heavy chain constant region F760nN17 (SEQ ID NO: 117) which has been modified so that there is heterologous association between the two heavy chains and which has reduced Fcγ receptor binding, and the light chain constant region k0 (SEQ ID NO: 118) were used for the constant regions. These antibodies were expressed using the method below. Cells of the human embryonic kidney cell-derived FreeStyle 293-F strain (Invitrogen) were suspended in the FreeStyle 293 Expression Medium (Invitrogen), and plated at a cell density of $1.33 \times 10^6$ cells/mL. The prepared plasmids were introduced into the cells by a lipofection method. The cells were cultured for four days in a $CO_2$ incubator (37° C., 8% $CO_2$, 90 rpm), and from the culture supernatants, antibodies were purified using the rProtein A Sepharose™ Fast Flow (Amersham Biosciences) or Protein G Sepharose 4 Fast Flow (GE HEALTHCARE) by a method known to those skilled in the art. Absorbance at 280 nm of the purified antibody solutions was measured using a spectrophotometer. Concentrations of the purified antibodies were calculated from the determined values using an extinction coefficient calculated by the PACE method (Protein Science (1995) 4: 2411-2423). For the anti-human CD137 antibodies (derived from R3 and R5), calculations were carried out using E1%=14. As shown in Table 9, the anti-human GPC antibody and homologous forms of each of the human CD137 antibodies purified in the same manner as in Example 9 were mixed to prepare the bispecific antibodies of interest using techniques known to those skilled in the art (WO2015/046467).

Figure 18:
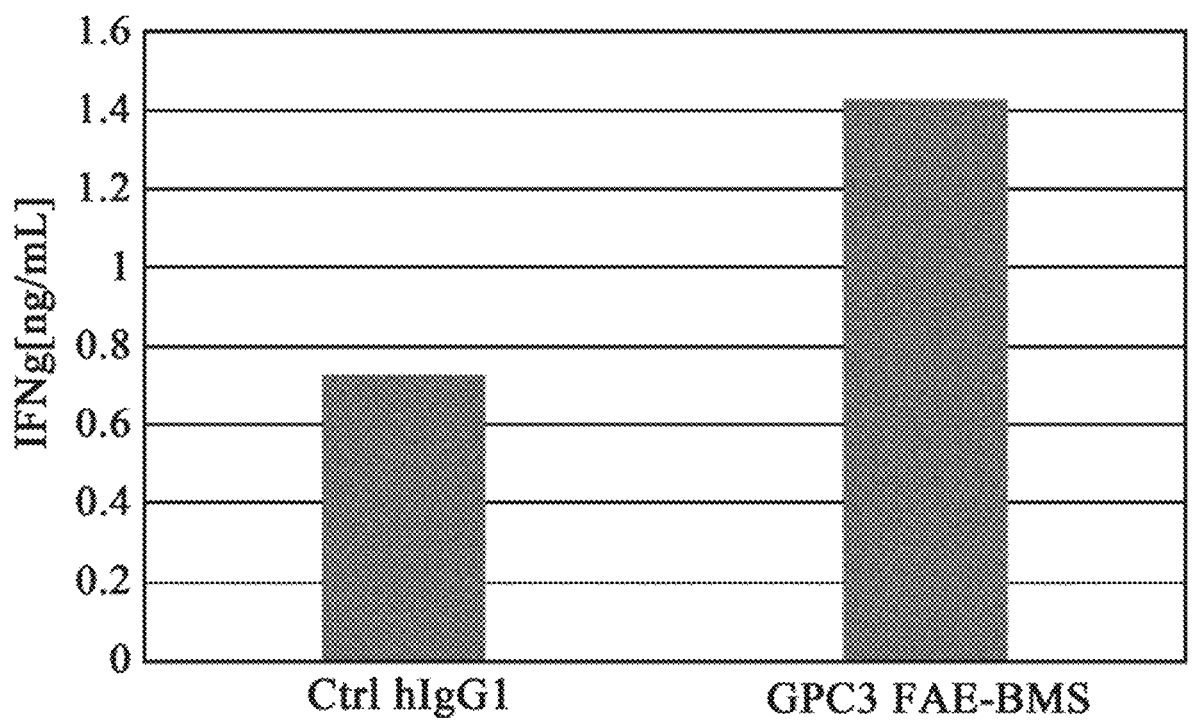
FIG. 18 presents a graph showing the results of assessing the T cell activation effect of the anti-human GPC3/anti-human CD137 bispecific antibody GPC3 FAE-BMS using IFN-γ ELISA. Ctrl hIgG1 indicates the negative control human IgG1 antibody.

11-2. Assessment of the In Vitro GPC3-Dependent CD137 Agonist Effect of an Anti-Human GPC3/Anti-Human CD137 Bispecific Antibody T cells were expansively cultured from commercially available PBMC (AllCells) using Dynabeads Human T-Activator CD3/CD28 (Gibco. 11132D). Human T cells were suspended at a density of $4 \times 10^5$ cells/ml in RPMI1640 medium containing 10% FBS, 60 U/ml human IL2, 0.5 µg/ml ionomycin, 10 ng/ml PMA, and a specified concentration of penicillin-streptomycin. Furthermore, the mouse colorectal cancer cell line CT26-GPC3 which expresses human GPC3 (Reference Example 3) was suspended in the same medium at a density of $4 \times 10^5$ cells/ml. These two cell suspensions were mixed in equal quantities, and this was seeded into a 96-well plate at 100 µl/well. Control human IgG (Allexis, 804-133-C100: Ctrl hIgG1 in FIG. 18) or GPC3 FAE-BMS prepared in preceding Example 11-1 (anti-human GPC3/anti-human CD137 bispecific antibody with extremely reduced FcγR binding) was added to this at a concentration of 10 µg/ml, and the cells were cultured under the conditions of 37° C. and 5% $CO_2$ for three days. The culture supernatant was collected, and the human IFN-γ concentration in the supernatant was measured by ELISA to assess the activation of T cells. ELISA was performed by following the instructions provided by the ELISA kit manufacturer (PeproTech).

As a result (FIG. 18), the anti-human GPC3/anti-human CD137 bispecific antibody showed an IFN-γ-inducing activity. This suggests that in human T cells as well, CD137 stimulation results in strong activation of the T cells, similarly to when mouse T cells were used in Example 2.

Figure 19:
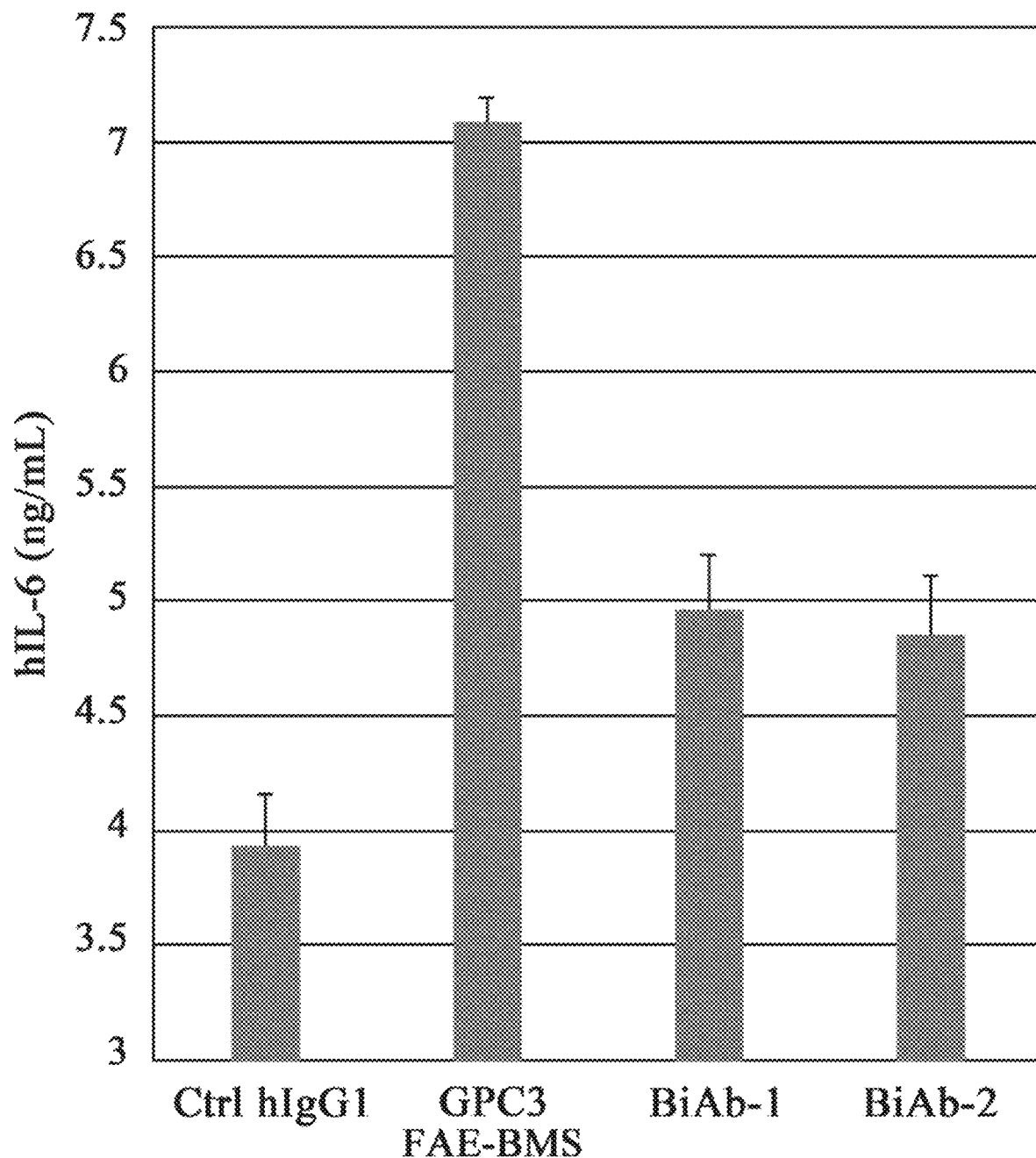
FIG. 19 presents a graph showing the results of assessing the CD137-mediated agonist activity of various anti-human GPC3/anti-human CD137 bispecific antibodies by the level of production of IL-6 which activates B cells. Ctrl hIgG1 indicates the negative control human IgG1 antibody.

11-3. Assessment of the In Vitro GPC3-Dependent CD137 Agonist Effect of an Anti-Human GPC3/Anti-Human CD137 Bispecific Antibody Human CD137 is also expressed in B cell line HDML-2, and the CD137 agonist activity can also be measured using HDML-2. Cells of the human B cell cancer cell line HDML-2 were suspended at a density of $8 \times 10^5$ cells/ml in RPMI1640 medium containing 20% FBS, and a specified concentration of penicillin-streptomycin. Furthermore, the mouse colorectal cancer cell line CT26-GPC3 which expresses human GPC3 (Reference Example 3) was suspended in the same medium at a density of $4 \times 10^5$ cells/ml. These cell suspensions were mixed in equal quantities, and this was seeded into a 96-well plate at 100 µl/well. Control human IgG (Allexis, 804-133-C100: Ctrl hIgG1 in FIG. 19) or anti-human GPC3/anti-human CD137 bispecific antibody with extremely reduced FcγR binding, which was prepared in preceding Example 11-1, was added to this at a concentration of 10 µg/ml and the cells were cultured under the conditions of 37° C. and 5% $CO_2$ for three days. The culture supernatant was collected, and the human IL-6 concentra-

TABLE 9

| | Human CD137 antibody | | | | Human GPC3 antibody |
|---|---|---|---|---|---|
| Sample name | Heavy-chain variable region | SEQ ID NO of the heavy-chain variable region | Light-chain variable region | SEQ ID NO of the light-chain variable region | Heavy chain and light chain (described in Example 9) |
| GPC3 FAE-BMS | BH | 1 2 2 | BL | 1 2 3 | H0000/ GL4-F760nN17 |
| BiAb-1 | 1150313C04 | 1 2 4 | BBNM003L01 | 8 2 | H0000/ GL4-F760nN17 |
| BiAb-2 | 2150313B04 | 1 2 5 | BBNM005L01 | 8 4 | H0000/ GL4-F760nN17 | tion in the supernatant was measured by ELISA to assess the activation of B cells. ELISA was performed by following the instructions provided by the ELISA kit manufacturer (Pepro-Tech).

As a result (FIG. 19), the anti-human GPC3/anti-human CD137 bispecific antibody showed IL-6-inducing activity. This showed that with human B cell lines as well, CD137 stimulation can be assessed in a similar manner to when mouse T cells were used in Example 2 and when human T cells were used in Example 11-2.

Examples 11-2 and 11-3 showed that similar to the results shown in Examples 2 to 5 performed with mouse CD137, the bispecific antibodies have an agonist activity towards human CD137, and that human CD137 can be expected to have effects similar to those with mouse CD137.

INDUSTRIAL APPLICABILITY

The present invention provides novel antigen-binding molecules or pharmaceutical compositions that are highly safe, have excellent antitumor activity, and do not have toxicity resulting from normal tissue injury or a cytokine storm in a cancer antigen-independent manner. Pharmaceutical compositions comprising an antigen-binding molecule of the present invention as the active ingredient active immune cells in a cancer antigen-dependent manner, and bring about cytotoxic actions that target various cells including cancer cells. This enables treatment or prevention of various cancers. The present invention can provide not only highly safe treatments, but also reduced physical burden and great convenience, which are desirable for patients.

The invention claimed is:

1. A bispecific antibody comprising:
   (1) a single cancer-specific antigen-binding Fab domain;
   (2) a single CD137 binding Fab domain; and
   (3) an FcRn-binding domain which is a variant antibody Fc region having decreased Fcγ receptor-binding activity compared to the corresponding native Fc region.

2. A pharmaceutical composition comprising as an active ingredient the bispecific antibody of claim 1.

3. A pharmaceutical composition comprising a combination of a first bispecific antibody of claim 1, and a second antibody that comprises:
   (1) a single cancer-specific antigen-binding Fab domain; and
   (2) a single CD3-binding Fab domain.

4. The pharmaceutical composition of claim 3, wherein the second antibody further comprises an FcRn-binding domain.

5. The pharmaceutical composition of claim 4, wherein the FcRn-binding domain is a variant antibody Fc region having decreased Fcγ receptor-binding activity compared to the corresponding native Fc region.

6. The bispecific antibody of claim 1, wherein the single cancer-specific antigen-binding Fab domain binds to Glypican 3.

7. The bispecific antibody of claim 1, wherein the antibody Fc region having decreased Fcγ receptor-binding activity is a variant IgG2 Fc region.

8. The bispecific antibody of claim 1, wherein the antibody Fc region having decreased Fcγ receptor-binding activity is a variant IgG4 Fc region.

* * * * *